(12) United States Patent
Ohmoto et al.

(10) Patent No.: US 7,008,938 B2
(45) Date of Patent: Mar. 7, 2006

(54) BENZENE-FUSED HETERORING DERIVATIVES AND PHARMACEUTICAL AGENTS COMPRISING THE SAME AS ACTIVE INGREDIENT

(75) Inventors: Kazuyuki Ohmoto, Osaka (JP); Iori Itagaki, Nagano (JP)

(73) Assignee: Nokia Corporation, Espoo (FI)

( * ) Notice: Subject to any disclaimer, the term of this patent is extended or adjusted under 35 U.S.C. 154(b) by 145 days.

(21) Appl. No.: 10/901,263

(22) Filed: Jul. 29, 2004

(65) Prior Publication Data

US 2005/0009755 A1 Jan. 13, 2005

Related U.S. Application Data

(62) Division of application No. 10/181,713, filed as application No. PCT/JP01/00473 on Jan. 25, 2001, now Pat. No. 6,809,092.

(30) Foreign Application Priority Data

Jan. 26, 2000 (JP) ........................................ 2000-017045

(51) Int. Cl.
  *A61K 31/55* (2006.01)
  *A61K 31/553* (2006.01)
  *C07D 223/16* (2006.01)

(52) U.S. Cl. ............................. 514/211.09; 514/213.01; 514/217.01; 514/221; 540/552; 540/569; 540/593; 540/594; 540/595

(58) Field of Classification Search ............ 514/211.09, 514/213.01, 217.01, 221; 540/552, 569, 593, 540/594, 595
See application file for complete search history.

(56) References Cited

U.S. PATENT DOCUMENTS 6,410,556 B1  6/2002 Anderson et al.
6,797,720 B1 *  9/2004 Ohmoto et al. ............. 514/364

FOREIGN PATENT DOCUMENTS

JP       06-192199 A      7/1994

* cited by examiner

*Primary Examiner*—Peter O'Sullivan
(74) *Attorney, Agent, or Firm*—Sughrue Mion, PLLC

(57) ABSTRACT

A benzene-fused heteroring derivative of formula (I)

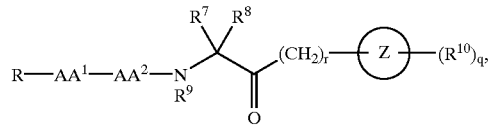

(I)

wherein all symbols are the same as described in the specification, and a non-toxic salt thereof. The compound of formula (I) has an inhibitory activity against cysteine protease and therefore it is useful as an agent for the prophylaxis and/or treatment of immune diseases (autoimmune diseases, infectious diseases, etc.), inflammatory diseases (inflammatory bowel diseases, multiple cerebrosclerosis, arthritis, etc.), nerve degeneration diseases (Alzheimer's disease, muscular dystrophy, etc.), bone resorption diseases (osteoporosis, etc.), respiratory system diseases, diabetes, shock, etc.

18 Claims, No Drawings

BENZENE-FUSED HETERORING DERIVATIVES AND PHARMACEUTICAL AGENTS COMPRISING THE SAME AS ACTIVE INGREDIENT

This is a divisional of application Ser. No. 10/181,713 filed Jul. 22, 2002, now U.S. Pat. No. 6,809,092, which is a 371 of PCT/01/00473 filed Jan. 25, 2001; the disclosures of which is incorporated herein by reference.

TECHNICAL FIELD

The present invention relates to abenzene-fused heteroring derivative.

Particularly, the present invention relates to;
1) a benzene-fused heteroring derivative of formula (I)

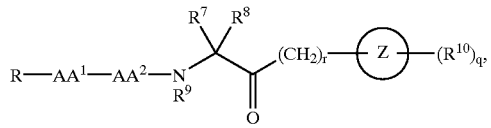

wherein all symbols have the same meanings as hereinafter, and a non-toxic salt thereof,
2) a method for the preparation thereof and
3) a pharmaceutical agent comprising the benzene-fused heteroring derivative and non-toxic salt thereof as active ingredient.

BACKGROUND OF THE INVENTION

Cysteine protease is a generic name of proteases which have a cysteine residue in the activity center and catalyze protein degradation thereat. In animal cells, a large number of cysteine proteases are known; for example, cathepsin family, calpain family, caspase-1, etc. Cysteine protease exists in various kinds of cells extensively and plays a basic and essential role in the homeostasis, such as conversion (processing) of precursor protein into its active form and degradation of proteins which have become out of use, etc. Until now, its physiological effects are being vigorously studied, and as the studies progress and characteristics of the enzymes are revealed, cysteine protease came to be taken as a cause of really various kinds of diseases.

It is revealed that cathepsin S (See J. Immunol., >H, 2731 (1998)) and cathepsin L (See J. Exp. Med., 183, 1331 (1996)) play a role in processing of major histocompatibility antigen class-II in antigen presenting cells which play an important role in the early stage of immune responses. In an experimental inflammatory response model induced by antigens, a specific inhibitor of cathepsin S showed an inhibitory effect (see J. Clin. Invest., 101, 2351 (1998)). It is also reported that in a leishmania-infected immune response model cathepsin B inhibitor inhibited an immune response and by means of this effect it inhibited the proliferation of protozoans (See J. Immunol., 161, 2120 (1998)). In vitro, a result is given that a calpain inhibitor and a cysteine protease inhibitor E-64 inhibited apoptosis which is induced by stimuli on T cell receptors (see J. Exp. Med., 178, 1693 (1993)). Therefore, it is conceivable that cysteine protease is much concerned with the progress of immune responses.

It is speculated that caspase-1 or a cysteine protease similar thereto occupies an important position in the mechanism of cell death including apoptosis. Therefore it is expected for a cysteine protease inhibitor to be used as an agent for the prophylaxis and/or treatment of those diseases concerning apoptosis, such as infectious diseases, deterioration or sthenia of immune function and brain function, tumors, etc. Diseases concerning apoptosis are, acquired immune deficiency syndrome (AIDS), AIDS-related complex (ARC), adult T cell leukemia, hairy cell leukemia, spondylopathy, respiratory apparatus disorder, arthritis, HIV or HTLV-1 related diseases such as uveitis, virus-related diseases such as hepatitis C, cancer, collagenosis (systemic lupus erythematosus, rheumatoid arthritis, etc.), autoimmune diseases (ulcerative colitis, Sjögren's syndrome, primary biliary cirrhosis, spontaneous thrombocytopenic purpura, autoimmune hemolytic anemia, myasthenia gravis, insulin dependent (type I) diabetes, etc.), diseases accompanied by thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type C, A, B, F, etc.) or hepatitis medicamentosus and cirrhosis, dementia (Alzheimer's diseases, Alzheimer's senile dementia, etc.), cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.

Moreover, caspase-1 is concerned with various inflammatory diseases and those diseases caused by immune disorders, by means of interleukin-1β (IL-1β) production. A lot of diseases are shown to be involved with caspase-1 including inflammatory diseases and autoimmune diseases listed below; inflammatory bowel diseases such as ulcerative colitis, insulin-dependent (type-I) diabetes, autoimmune thyroid diseases, infectious diseases, rejection of an organ transplantation, graft versus host diseases, psoriasis, periodontitis (above, see N. Eng. J. Med., 328, 106 (1993)), pancreatitis (see J. Interferon Cytokine Res., 17, 113 (1997)), hepatitis (see J. Leuko. Biol., 58, 90 (1995)), glomerulonephritis (see Kidney Int., 47, 1303 (1995)), endocarditis (see Infect. Immun., 64, 1638 (1996)), myocarditis (see Br. Heart J., 72, 561 (1995)), systemic lupus erythematosus (see Br. J. Rheumatol., 34, 107 (1995)), Hashimoto's diseases (see Autoimmunity, 16, 141 (1993)), etc.), etc. Experimentally, it is reported that in liver injury model induced by lipopolysaccharide and D-galactosamine, a caspase-1 inhibitor depressed the symptoms, and it is expected that a caspase inhibitor shows an effect in sepsis, ischemic reperfusion and hepatitis gravis (see Am. J. Respir. Crit. Care Med., 159, 1308 (1999)).

It is also shown that cysteine protease is concerned with rheumatoid arthritis. IL-1β is shown to be concerned with this disease (see Arthritis Rheum., 39, 1092 (1996)), and in addition, as autoantibody toward calpastatin (endogenous calpain inhibitor) was found in the serum of the patients, it is considered that increase of calpain activity leads to the cause of diseases.

It is also known that cysteine protease causes a disease symptom by decomposing various proteins which compose the organism.

It is reported that cathepsin B plays a role in decomposing muscular protein in the chronic phase of sepsis (see J. Clin. Invest., 97, 1610 (1996)), and in decomposing muscular protein in myodystrophy model (see Biochem. J., 288, 643 (1992)). And it is also reported that calpain decomposes the myocyte cells protein of myodystrophy patients (see J. Biol. Chem., 270, 10909 (1995)).

In the ischemic reperfusion model, a result is given that calpain causes degeneration of brain tissues by means of degradation of protein kinase C-β (see J. Neurochem., 72, 2556 (1999)) and that a cathepsin B inhibitor inhibits nerve injury (see Eur. J. Neurosci., 10, 1723 (1998)).

In the brain ischemic model, it is known that the degradation of spectrin by calpain causes a damage and function disorder in the neurocyte (see Brain Res., 790, 1 (1998)) and it is reported that an IL-1β receptor antagonist relieved the symptoms (see Brain Res. Bull., 29, 243 (1992)).

In myocardial ischemic model it is confirmed that cathepsin B activity increases in the lesion (see Biochem. Med. Metab. Biol., 45, 6 (1991)).

In the experiment utilizing ischemic liver injury model, it proved that necrosis and apoptosis of hepacyte were induced by means of protein-decomposing activity of calpain (see Gastroenterology, 11%, 168 (1999)).

Besides, it is known that calpain causes cornea turbid in cataract by means of degradation of crystalline (see Biol. Chem., 268, 137 (1993)) and that in the lesion of contracted gut mucosa model it was confirmed that the activity of cathepsin B, H and L increased (see JPEN. J. Parenter. Enteral. Nutr., 19, 187 (1995)) and it is shown that cysteine protease is a cause of the diseases resulting from such protein degradation.

It has been revealed that cysteine protease is concerned with systemic disorders of organs and tissues by shock.

It is shown that IL-1β is concerned with septic shock and systemic inflammatory response syndrome (see Igakuno Ayumi, 169, 850 (1994)) and besides, it is reported that in endotoxin shock model induced by lipopolysaccharide, a calpain inhibitor prevented circulatory system disorder, disorders of liver and pancreas and acidosis by means of inhibitory effect of activation of nuclear factor κB (see Br. J. Pharmacol., 121, 695 (1997)).

Since it is reported that calpain is concerned with platelet coagulation process and a calpain inhibitor prevented the coagulation of platelets (see Am. J. Physiol., 259, C862 (1990)), it is conceivable that a cysteine protease inhibitor is useful for the disorder by blood coagulation. From the fact that calpain activity increased in the serum of the patients of purpura (thrombocytopenia) resulting from marrow transplantation, it is conceivable that calpain is concerned with the actual disease symptoms (see Bone Marrow Transplant., 24, 641 (1999)). Caspase-1 inhibitor inhibited the apoptosis of blood vessel endothelial cells, which is seen in the early phase of purpura (thrombocytopenia) and is thought to be important for the progression of the pathology afterwards (see Am. J. Hematol., 59, 279 (1998)), so it is expected that a cysteine protease inhibitor makes effect on purpura and hemolytic uremic syndrome.

The effect of cysteine protease and its inhibitor is being investigated in the field of cancer and metastasis of cancer.

Since the proliferations of pancreas cancer cells (see Cancer Res., 59, 4551 (1999)) and acute myeloid leukemia cells (see Clin. Lab. Haematol., 21, 173 (1999)) were inhibited by an inhibitor or receptor antagonist of caspase-1, it is expected that caspase-1 activity is essential for the process of proliferation of tumor cells, and that an inhibitor thereof is effective for these cancers. Cathepsin B activity increased in colon cancer metastasis model (see Clin. Exp. Metastasis, 16, 159 (1998)). Cathepsin K protein expression was recognized in human breast cancer cells and the relationship of cathepsin K and bone metastasis is shown (Cancer Res., 57, 5386 (1997)). Also, a calpain inhibitor inhibited migaration of the cells and it implied the possibility that calpain inhibition may inhibit metastasis of cancer (J. Biochem., 272, 32719 (1997)). From these, a cysteine protease inhibitor is presumed to show an inhibitory effect on the metastasis of various malignant tumors.

As to AIDS (see AIDS, 10, 1349 (1996)) and AIDS-related complex (ARC) (see Arch. Immunol. Ther. Exp. (Warsz), 41, 147 (1993)), it is shown that IL-1 is concerned with the progress of symptoms, so it is conceivable that cysteine protease inhibition leads to an effective therapy of AIDS and its complication.

Some parasites have cysteine protease activity in their body. Cysteine protease in the phagosome of malaria protozoan is an essential enzyme for supplying nutrition of the parasites. A result is given that the inhibitor of cysteine protease shows an inhibitory effect of the proliferation of the protozoan (see Blood, 87, 4448 (1996)). Thus, it is possible to apply the inhibitor of cysteine protease to malaria.

In Alzheimer-type dementia, it is said that adhesion of non-physiological protein called amyloid to brain is deeply involved with nervous function disorders. Cysteine protease has an activity of generating amyloid by decomposing its precursor protein. Clinically, it is shown that cathepsin B is an enzyme that possesses a processing activity of amyloid proteins in the brains of Alzheimer-type dementia patients (see Biochem. Biophys. Res. Commun., 177, 377 (1991)). Also, expressions of cathepsin B protein (see Virchows Arch. A. Pathol. Anat. Histpathol., 423, 185 (1993)), cathepsin S protein (see Am. J. Pathol., 146, 848 (1995)) and calpain protein (see Proc. Natl. Acad. Sci. USA, 90, 2628 (1993)) and increase of caspase-1 activity (see J. Neuropathol. Exp. Neurol., 58, 582 (1999)) were confirmed in the brain lesions. Besides, by the fact that calpain is concerned with the formation of paired helical filaments which accumulate in Alzheimer dementia patients and production of protein kinase C which stabilizes the protein by phosphorylation (see J. Neurochem., 66, 1539 (1996)) and by the knowledge that caspase is concerned with neurocyte death by β amyloid protein adhesion (see Exp. Cell Res., 234, 507 (1997)), it is implied that cysteine protease is concerned with the disease symptoms.

As to Huntington's chorea, cathepsin H activity increased in the patient's brain (see J. Neurol. Sci., 131, 65 (1995)), and the ratio of activated form of calpain increased (see J. Neurosci., 48, 181 (1997)). In Parkinson's diseases, the increase of expression of m-calpain was recognized in the mesencephalon of the patients (see Neuroscience, 73, 979 (1996)) and IL-1β protein was expressed in brain (see Neurosci. Let., 202, 17 (1995)). Therefore, it is speculated that cysteine protease is concerned with the genesis and progress of these diseases.

Besides, in the central nervous system, spectrin degradation by calpain is found in the process of injury on neurocyte observed in the traumatic brain injury model (see J. Neuropathol. Exp. Neurol., 58, 365 (1999)).

In spinal cord injured model it was recognized that in glia cells calpain messenger RNA increased and its activity increased in the lesion and the possibility was shown that calpain had much to do with the degeneration of myelin and actin after injury (see Brain Res., 816, 375 (1999)). And IL-β was shown to be concerned with the genesis of multiple sclerosis (see Immunol. Today, 14, 260 (1993)). Therefore, it is conceivable that a cysteine protease inhibitor is promising as an agent for the treatment of these nerve-injuring diseases.

Normally, cathepsin S and cathepsin K do not exist in human arterial walls but it was confirmed that they expressed in arterial sclerosis lesion and they had an decomposing activity of alveolus elastica (see J. Clin. Invest., 102, 576 (1998)) and a calpain inhibitor and antisense of m-calpain inhibited the proliferation of human blood vessel smooth muscle cells and it is shown that m-calpain is concerned with the proliferation of smooth muscle (see Arteioscler. Thromb. Vssc. Biol., 18, 493 (1998)), so it is conceivable that a cysteine protease inhibitor is promising for the treatment of blood vessel lesion such as arteriosclerosis, restenosis after percutaneous transluminal coronary angioplasty (PTCA), etc.

It is reported that in liver, cathepsin B is activated in the process of injuring hepatocyte by bile acid (see J. Clin. Invest., 103, 137 (1999)) and so it is expected that a cysteine protease inhibitor is effective for cholestatic cirrhosis.

In lungs and respiratory system, it is shown that cathepsin S is an enzyme that plays a role in elastin degradation by alveolus macrophages (see J. Biol. Chem., 269, 11530 (1994)), so it is probable that cysteine protease is a cause of pulmonary emphysema. And it is also shown that lung injury (see J. Clin. Invest., 97, 963 (1996)), lung fibrosis (see Cytokine, 5, 57 (1993)) and bronchial asthma (see J. Immunol., 149, 3078 (1992)) are caused by production of IL-1β by caspase-1.

It is pointed out that cysteine protease is also concerned with diseases concerning bones and cartilages. Cathepsin K is specifically recognized in osteoclast and it has a decomposing activity against bone matrix (see J. Biol. Chem., 271, 12517 (1996)), so its inhibitor is expected to show an effect against osteoporosis, arthritis, rheumatoid arthritis, osteoarthritis, hypercalcemia and osteometastasis of cancer, where pathologic bone resorption is recognized. And since IL-1β is shown to be concerned with bone resorption and cartilage degradation, and a caspase-1 inhibitor and IL-1β receptor antagonist inhibit the bone resorption and symptoms of arthritis, a caspase-1 inhibitor and IL-1β receptor antagonist are expected to be effective for arthritis (see Cytokine, 8, 377 (1996)) and osteoporosis (J. Clin. Invest., 93, 1959 (1994)). And it is reported that IL-1β is also concerned with osteoarthritis (see Life Sci., 41, 1187 (1987)).

Cysteine protease is involved with production of various hormones. Since increase of messenger RNA of cathepsin S was recognized by stimuli of thytropin on thyroid epitheliocyte strains (see J. Biol. Chem., 267, 26038 (1992)), it is conceivable that a cysteine protease inhibitor is effective for hyperthyrodism.

Since quantity and activity of cathepsin B protein increased in the gingival sulcus liquid of periodontitis patients (see J. Clin. Periodontol., 25, 34 (1998)), it is pointed out that cysteine protease is concerned with periodontitis.

Therefore, it is expected that the compound that possesses the inhibitory activity of cysteine protease is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjögren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosus and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), disease by degradation various proteins which compose the organism (myodystrophy, cataract, periodontitis, hepatocyte disease by bile acid such as cholestatic cirrhosis, etc.), decomposition of alveolus elastica such as pulmonary emphysema, ischemic diseases (brain ischemia, brain disorders (encephalopathy) by ischemic reperfusion, myocardial infarction, ischemic hepatopathy, etc.), shock (septic shock, systemic inflammatory response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as lung fibrosis, bone resorption diseases (osteoporosis, rheumatoid arthritis, arthritis, osteoarthritis, hypercalcemia, osteometastasis of cancer, etc.), endocrinesthenia such as hyperthyroidism.

On the other hand, what is the most important for inhibitors in inhibiting the activity of proteases is, the special reaction site which interacts with the amino acid residue that is the activity center of proteases. The surrounding structure of the reaction sites are represented by ---P3P2P1–P1'P2'P3'---, centering peptide binding (P1–P1') of the reaction site, and at P1 site there exist amino acid residues fitting the substance specificity of proteases which the inhibitors aim. Some reaction sites against cysteine proteases are known, for Example, in the specification of WO99/54317, the followings are described;

P1 position against calpain I, II (norvaline, phenylalanine, etc.),

P1 position against calpain I (arginine, lysine, tyrosine, valine, etc.),

P1 position against papain (homophenylalanine, arginine, etc.),

P1 position against cathepsin B (homophenylalanine, phenylalanine, tyrosine, etc.), P1 position against cathepsin S (valine, norleucine, phenylalanine, etc.), P1 position against cathepsin L (homophenylalanine, lysine, etc.), P1 position against cathepsin K (arginine, homophenylalanine, leucine, etc.),
P1 position against caspase (aspartic acid).

On the other hand, in the specification of JP-A-6-192199, it is disclosed that a ketone derivative of formula (A) is effective as a thiol protease inhibitor,

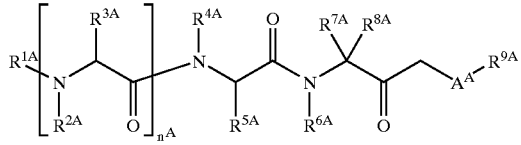

(A)

wherein $R^{1A}$ is hydrogen, $R^{10A}$—CO—, $R^{10A}$—OCO—, $R^{10A}$—SO$_2$— or $R^{10A}$—NHCO—, (1) when $A^A$ is —S—, —SO— or —SO$_2$, $R^{9A}$ is C6–C14 aryl optionally containing substituent (s) or —(CH$_2$)$_m{}^A$—X$^A$, wherein X$^A$ is hydrogen, hydroxy, C1–C5 alkylthio, C2–C6 alkoxycarbonylamino, heterocycle residue optionally containing substituent (s), amino, C1–C5 monoalkylamino, C2–C10 dialkylamino, C2–6 acylamino, halogen, C1–C5 alkoxy, C6–C14 aryl optionally containing substituent(s) or C6–C14 aryloxy optionally containing substituent(s), and $m^A$ is an integer of 0 or 1 to 15, (2) when $A^A$ is —O—, $R^{9A}$ is hydrogen or —(CH$_2$)$_{lA}$—X$^A$, wherein $l^A$ is an integer of 1 to 15, (3) when $A^A$ is —NR$^{11A}$—, $R^{9A}$ is C6–C14 aryl optionally containing substituent(s), —(CH$_2$)$_m{}^A$—X$^A$, $R^{9A}$ and $R^{11A}$ are taken together to form an N-containing heteroring optionally containing substituent (s) (the essential parts are extracted to explain substituents).

And in the specification of JP-A-7-70058, it is disclosed that α-aminoketone derivative of formula (B)

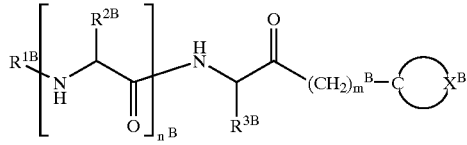

(B)

or its pharmaceutically acceptable salt shows a strong inhibitory activity against thiol protease, wherein $R^{1B}$ is hydrogen, $R^{4B}$—O—C(O)— or $R^{4B}$—C(O)—, wherein $R^{4B}$ is C1–C20 alkyl optionally containing a substituent or more selected from C3–C15 cycloalkyl, C6–C14 aryl optionally containing substituent(s), heterocycle residue optionally containing substituent(s), C3–C15 cycloalkyloxy, C6–C14 aryloxy optionally containing substituent(s), aralkyloxy optionally containing substituent and C6–C1–4 arylthio optionally containing substituent (s); C2–C10 alkenyl optionally substituted with C6–C14 aryl optionally containing substituent(s); C6–C14 aryl optionally containing substituent(s) or heterocycle residue optionally containing substituent), $R^{2B}$ and $R^{3B}$ are each independently, hydrogen or C1–C20 alkyl optionally containing a substituent,

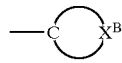

is heterocycle residue optionally containing a substituent, $n^B$ is 0 or 1, $m^B$ is an integer of 1 to 5.

DISCLOSURE OF THE INVENTION

The present inventors have energetically investigated to find out such compounds that have cysteine protease inhibitory activity and found that the benzene-fused heteroring derivative of formula (I) of the present invention accomplishes the purpose.

The benzene-fused heteroring of formula (I) of the present invention is not known at all as a cysteine protease inhibitor at all.

The present invention relates to (1) an oxadiazole derivative of formula (I),

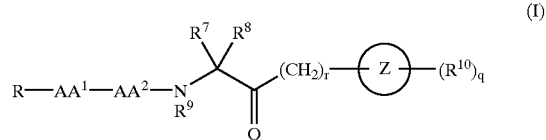

(I)

wherein R is
(i) hydrogen,
(ii) C1–8 alkyl,
(iii) CycA,
(iv) C1–8 alkyl substituted with a group selected from halogen atom, CycA, nitro, CF$_3$ and cyano,

(v)

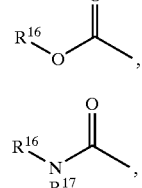

(vi)

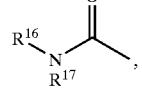

(vii)

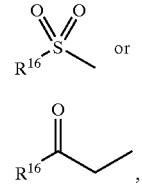

(viii)

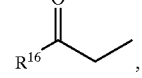

(ix)

CycA is a C3–15 mono-, bi- or tricyclic carboring or a mono-, bi- or tri-cyclic 3–15 membered heteroring comprising 1–4 of nitrogen, 1–2 of oxygen and/or 1 of sulfur;
$R^{16}$ is
(1) C1–8 alkyl,
(2) C2–8 alkenyl,
(3) C2–8 alkynyl,
(4) CycA or
(5) C1–8 alkyl, C2–8 alkenyl or C2–8 alkynyl substituted with a group selected from halogen atom, nitro, CF$_3$, cyano, CycA, NR$^{18}$R$^{19}$ and —NHC(O)-CycA;
$R^{17}$, $R^{18}$ and $R^{19}$ each independently represents hydrogen or C1–4 alkyl, AA¹ is (i) a single bond, or

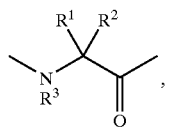  (ii)

wherein R¹ and R² are the same or different to represent
(i) hydrogen,
(ii) C1–8 alkyl,
(iii) CycA or
(iv) C1–8 alkyl substituted with 1–5 of group selected from the following (1) to (8):
(1) —NR²¹R²²,
(2) —OR²³,
(3) —SR²⁴,
(4) —COR²⁵,
(5) —NR²⁶CONR²¹R²²,
(6) guanidino,
(7) CycA,
(8) —NR²⁶SO₂R²¹; or R¹ and R² are taken together to form C2–8 alkylene, wherein one carbon atom may be replaced by oxygen, sulfur or —NR²⁰— and the alkylene may be substituted with —NR²¹R²² or —OR²³, R²⁰ is hydrogen, C1–4 alkyl, —COO—(C1–4 alkyl), phenyl or C1–4 alkyl substituted with phenyl, R²¹, R²², R²³, R²⁴ and R²⁶ are the same or different to represent hydrogen, C1–4 alkyl, phenyl or C1–4 alkyl substituted with phenyl, R²⁵ is C1–4 alkyl, phenyl, —NR²¹R²², wherein all symbols have the same meaning as above, —OR²³, wherein R²³ is the same meaning as above, or C1–4 alkyl substituted with phenyl, R³ is hydrogen, C1–8 alkyl, phenyl or C1–8 alkyl substituted with phenyl or R³ is taken together with R¹ to form C2–6 alkylene, wherein one carbon atom may be replaced by oxygen, sulfur or —NR²⁰— and the alkylene may be substituted with —NR²¹R²² or —OR²³, or when AA¹ is

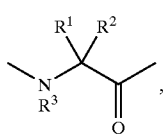

AA¹ and R may be taken together to form

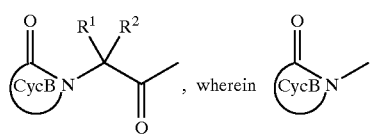, wherein is a 5–12 membered mono- or bi-cyclic heteroring and the other symbols are the same meanings as above, AA² is (i) a single bond,

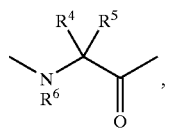  (ii)

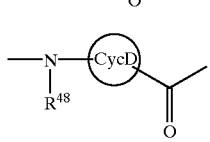  (iii)

or

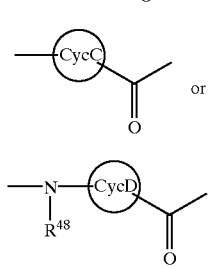  (iv)

wherein R⁴ and R⁵ are the same or different to represent
(1) hydrogen,
(2) C1–8 alkyl,
(3) CycA or
(4) C1–8 alkyl substituted with 1–5 of group selected from the following (a) to (h):
(a) —NR⁴¹R⁴²,
(b) —OR⁴³,
(c) —SR⁴⁴,
(d) —COR⁴⁵,
(e) —NR⁴⁶CONR⁴¹R⁴²,
(f) guanidino,
(g) CycA,
(h) —NR⁴⁶SO₂R⁴¹; or R⁴ and R⁵ are taken together to form C2–8 alkylene, wherein one carbon atom may be replaced by oxygen, sulfur or —NR⁴⁰— and the alkylene may be substituted with —NR⁴¹R⁴² or —OR⁴³, R⁴⁰ is hydrogen, C1–4 alkyl, —COO—(C1–4 alkyl), phenyl or C1–4 alkyl substituted with phenyl, R⁴¹, R⁴², R⁴³, R⁴⁴ and R⁴⁶ are the same or different to represent hydrogen, C1–4 alkyl, phenyl or C1–4 alkyl substituted with phenyl, R⁴⁵ is C1–4 alkyl, phenyl, —NR⁴¹R⁴², wherein all symbols are the same meaning as above, —OR⁴³, wherein R⁴³ is the same meaning as above, or C1–4 alkyl substituted with phenyl, R⁶ is hydrogen, C1–8 alkyl, phenyl or C1–8 alkyl substituted with phenyl or R⁶ is taken together with R⁴ to form C2–6 alkylene, wherein one carbon atom may be replaced by oxygen, sulfur or —NR⁴⁰—and the alkylene may be substituted with —NR⁴¹R⁴² or —OR⁴³, R⁴⁸ is hydrogen, C1–4 alkyl, phenyl or C1–4 alkyl substituted with phenyl or when AA¹ is a single bond, R⁴⁸ and R may be taken together to form C2–6 alkylene, wherein one carbon atom may be replaced by oxygen, sulfur or —NR⁴⁷, wherein R⁴⁷ is hydrogen or C1–4 alkyl, CycC is a 3–17 membered mono- or bi-cyclic heteroring,
CycD is a C3–14 mono- or bi-cyclic carboring or a 3–14 membered mono- or bi-cyclic heteroring, or AA² and AA¹ are taken together to form

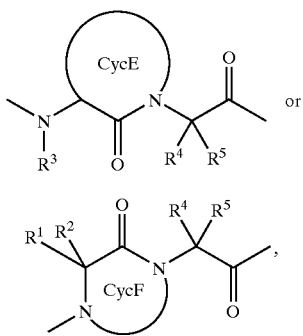

(i)

(ii)

wherein CycE is a 4–18 membered mono- or bi-cyclic heterring, CycF is a 5–8 membered monocyclic heterring, and the other symbols have the same meanings as above, R⁷ and R⁸ are the same or different to represent
(i) hydrogen,
(ii) C1–8 alkyl,
(iii) CycA or
(iv) C1–8 alkyl substituted with 1–5 of group selected from the following (1) to (8);
(1) —NR⁶¹R⁶²,
(2) —OR⁶³,
(3) —SR⁶⁴,
(4) —COR⁶⁵,
(5) —NR⁶⁶CONR⁶¹R⁶²,
(6) guanidino,
(7) CycA,
(8) —NR⁶⁶SO₂R⁶¹, or R⁷ and R⁸ are taken together to form C2–8 alkylene, wherein one carbon atom may be replaced by oxygen, sulfur or —NR⁶⁰— and the alkylene may be substituted with —NR⁶¹R⁶² or —OR⁶³, R⁶⁰ is hydrogen, C1–4 alkyl, —COO—(C1–4 alkyl), phenyl or C1–4 alkyl substituted with phenyl, R⁶¹, R⁶², R⁶³, R⁶⁴ and R⁶⁶ are the same or different to represent hydrogen, C1–4 alkyl, phenyl or C1–4 alkyl substituted with phenyl, R⁶⁵ is C1–4 alkyl, phenyl, —NR⁶¹R⁶², wherein all symbols are the same meanings as above, —OR⁶³, wherein R⁶³ is the same meaning as above, or C1–4 alkyl substituted with phenyl, R⁹ is hydrogen, C1–8 alkyl, phenyl or C1–8 alkyl substituted with phenyl or R⁹ is taken together with R⁷ to form C2–6 alkylene, wherein one carbon atom may be replaced by oxygen, sulfur or —NR⁶⁰— and the alkylene may be substituted with —NR⁶¹R⁶² or —OR⁶³, r is an integer of 1 to 4,

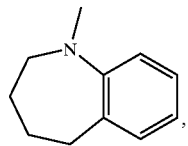

is (i)

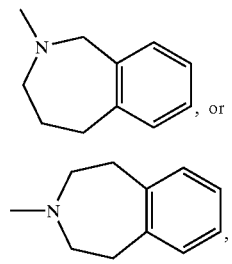

(ii)

, or (iii)

in the ring of (i), (ii) and (iii), one saturated carbon atom or two may be replaced by
(1) oxygen,
(2) —S(O)$_s$— or
(3) —NR⁸³—,
wherein s is 0 or an integer of 1 to 2,
R⁸³ is
(a) hydrogen,
(b) C1–8 alkyl,
(c) CycA or
(d) C1–8 alkyl substituted with 1–5 of group selected from CycA, guanidino, —COR⁶⁸—, —NR⁶⁹R⁷⁰, —OR⁶⁹, cyano and —P(O)(OR⁷⁵)₂,
R⁶⁸ is C1–4 alkyl, phenyl or C1–4 alkyl substituted with phenyl, R⁶⁹ and R⁷⁰ are the same or different to represent hydrogen, C1–4 alkyl, phenyl or C1–4 alkyl substituted with phenyl,
R⁷⁵ is hydrogen, C1–8 alkyl, phenyl or C1–4 alkyl substituted with 1–5 of phenyl, cyano or halogen atom and the ring of (i), (ii) and (iii) may be condensed with a C5–C8 carbon ring or a 5–8 membered heterring containing one nitrogen atom or two, one oxygen atom and/or a sulfur atom,
q is an integer of 0 or 1 to 5,
R¹⁰ is
(i) C1–8 alkyl,
(ii) C2–8 alkenyl,
(iii) C2–8 alkynyl,
(iv) halogen atom,
(v) CycA,
(vi) —COR⁷¹,
(vii) —NR⁷²R⁷³,
(viii) —OR⁷⁴ or
(ix) C1–8 alkyl substituted with 1 to 5 of groups selected from the following <1> to <7>:
<1> CycA,
<2> guanidino,
<3> —COR⁷¹,
<4> —NR⁷²R⁷³,
<5> —OR⁷⁴,
<6> cyano or
<7> —P(O)(OR⁷⁸)₂,
wherein R⁸² is hydrogen, C1–8 alkyl, phenyl or C1–4 alkyl substituted with 1 to 5 of phenyl, cyano or halogen atom,
R⁷¹ is
(1) C1–8 alkyl,
(2) CycA,
(3) —NR⁷²R⁷³,
(4) —OR⁷⁴, or
(5) C1–8 alkyl substituted with CycA;
R⁷² and R⁷³ are the same or different to represent
(1) hydrogen,
(2) C1–8 alkyl,
(3) CycA or (4) C1–8 alkyl substituted with 1 to 5 of groups selected from the following (a) to (f):
(a) CycA,
(b) guanidino,
(c) —NR$^{77}$R$^{78}$, wherein R$^{77}$ and R$^{78}$ have the same or different to represent hydrogen, C1–4 alkyl, phenyl or C1–4 alkyl substituted with phenyl,
(d) —OR$^{77}$, wherein R$^{77}$ has the same meaning as above,
(e) —COR$^{76}$, wherein R$^{76}$ has C1–4 alkyl, phenyl, —NR$^{77}$R$^{78}$, wherein all symbols have the same meanings as above, —OR$^{77}$, wherein R$^{77}$ has the same meaning as above, or C1–4 alkyl substituted with phenyl, and
(f) cyano;
R$^7$ is
(1) hydrogen,
(2) C1–8 alkyl,
(3) CycA, or
(4) C1–8 alkyl substituted with 1 to 5 of groups selected from the following (a) to (h), wherein one carbon atom may be replaced by oxygen, sulfur atom or —NR$^{84}$:
(a) CycA,
(b) guanidino,
(c) —SiR$^{79}$R$^{80}$R$^{81}$, wherein R$^{79}$, R$^{80}$ and R$^{81}$ are the same or different to represent C1–8 alkyl, phenyl or C1–8 alkyl substituted with phenyl,
(d) —NR$^{77}$R$^{78}$, wherein all symbols have the same meanings as above,
(e) —OR$^{77}$, wherein R$^{77}$ has the same meaning as above,
(f) —COR$^{76}$, wherein R$^{76}$ has the same meaning as above,
(g) cyano,
(h) —P(O)(OR$^{82}$)$_2$, wherein all symbols have the same meaning as above;
CycA included in R, R$^1$, R$^2$, R$^4$, R$^5$, R$^7$, R$^8$, R$^{10}$, R$^{16}$, R$^{71}$, R$^{72}$, R$^{73}$, R$^{74}$ and R$^{83}$ are the same or different and CycA, CycB, CycC, CycD, CycE and CycF, independently, may be substituted with 1 to 5 of R$^{27}$;
R$^{27}$ is
(1) C1–8 alkyl,
(2) halogen atom,
(3) —NR$^{11}$R$^{12}$,
(4) —OR$^{13}$,
(5) a C5–10 mono-or bi-cyclic carboring,
(6) nitro,
(7) CF$_3$,
(8) cyano,
(9) a 5–10 membered mono- or bi-cyclic heteroring
(10) —SR$^{14}$,
(11) —COR$^{15}$,
(12) oxo,
(13) —SO$_2$R$^{15}$,
(14) —OCF$_3$ or
(15) C1–8 alkyl substituted with 1–5 of group selected from the following (a) to (m):
(a) halogen atom,
(b) —NR$^{11}$R$^{12}$,
(c) —OR$^{13}$,
(d) a C5–10 mono- or bi-cyclic carboring,
(e) nitro,
(f) CF$_3$,
(g) cyano,
(h) a 5–10 membered mono- or bi-cyclic heteroring,
(j) —SR$^{14}$,
(k) —COR$^{15}$,
(l) —SO$_2$R$^{15}$,
(m) —OCF$_3$,
wherein R$^{11}$ and R$^{12}$ are the same or different to represent hydrogen, C1–4 alkyl, —COO—(C1–4 alkyl), phenyl or C1–4 alkyl substituted with phenyl, R$^{13}$ and R$^{14}$ are the same or different to represent hydrogen, C1–4 alkyl, phenyl or C1–4 alkyl substituted with phenyl,
R$^{15}$ is C1–4 alkyl, phenyl, —NR$^{11}$R$^{12}$, wherein all symbols have the same meanings as above, —OR$^{13}$, wherein R$^{13}$ is the same meaning as above, or C1–4 alkyl substituted with phenyl, or a non-toxic salt thereof,
(2) a method for the preparation thereof and
(3) a pharmaceutical agent comprising the benzene-fused heteroring derivative and non-toxic salt thereof as active ingredient.

DETAILED DESCRIPTION OF THE PRESENT INVENTION

In the compound of formula (I), in

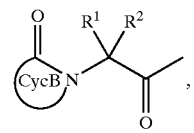

which AA$^1$ and R together form,

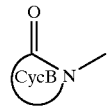

is a 5–12 membered heteroring containing 1–3 of nitrogen, 1 of oxygen, and/or 1 of sulfur (this heteroring may be substituted with 1–5 of R$^2$1).

And to describe

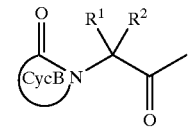

concretely, it is

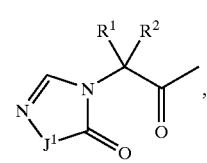

(i)

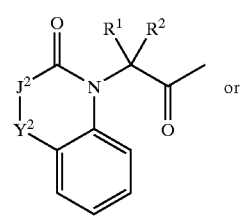

(ii) or

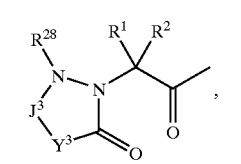

(iii)

wherein J$^1$ is oxygen, sulfur, —NR$^{29}$—, wherein R$^{29}$ is hydrogen, C1–4 alkyl, CycA or C1–4 alkyl substituted with CycA, C1–3 alkylene or C2–3 alkenylene, $J^2$ is a single bond or C1–2 alkylene,
$Y^2$ is —N=CH—, —CH=N— or C1–2 alkylene,
$J^3$ is carbonyl or C1–3 alkylene,
$Y^3$ is C1–3 alkylene, oxygen or —NR$^{29}$—, wherein R$^{29}$ is the same meaning as above,
$R^{28}$ is hydrogen, C1–4 alkyl, CycA or C1–4 alkyl substituted with CycA, or
$R^{28}$ is taken together with $R^1$ to form C2–4 alkylene, and the other symbols have the same meaning as above and each ring may be substituted with 1–5 of R$^{27}$.

In the compound of formula (I), in

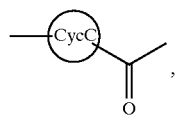   (iii)

which AA$^2$ represents, CycC is a 3–17 membered heteroring which contains 1–2 of nitrogen, 1 of oxygen and/or 1 of sulfur (this ring may be substituted with 1–5 of R$^{27}$).

And to describe

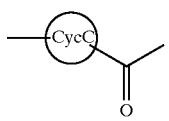

concretely,

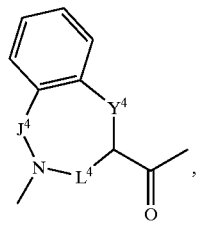   (iii-1)

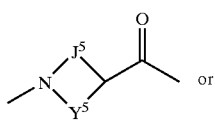   (iii-2)

or

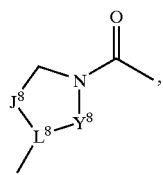   (iii-3)

wherein $J^4$, $Y^4$ and $L^4$ are the same or different to represent a single bond or C1–3 alkylene, wherein $J^4$, $Y^4$ and $L^4$ do not represent a single bond at the same time,
$J^5$ is C1–6 alkylene,
$Y^5$ is a single bond, C1–3 alkylene or —NR$^{67}$—, wherein R$^{67}$ is hydrogen, C1–4 alkyl, phenyl or C1–4 alkyl substituted with phenyl,
$J^8$ is C1–5 alkylene, wherein one carbon atom may be replaced by oxygen,
$Y^8$ is a single bond or C1–4 alkylene,
$L^8$ is —N— or —CH—,
and the other symbols have the same meaning as above and each ring may be substituted with 1–5 of R$^{27}$.

And in

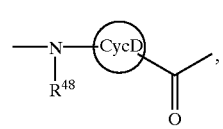   (iv)

which AA$^2$ represents, CycD is a C3–14 mono- or bi-cyclic carboring or 3–14 membered heteroring which contains 1–2 of nitrogen, 1 of oxygen and/or 1 of sulfur (this carboring and heteroring may be substituted with 1–5 of R$^{27}$).

And to describe

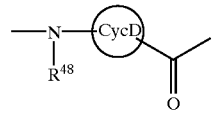

concretely, it is

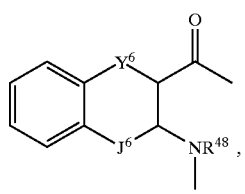   (iv-1)

(iv-2)

(iv-3)

or (iv-4)

wherein $J^6$ and $Y^6$ are the same or different to represent a single bond or C1–3 alkylene, wherein $J^6$ and $Y^6$ do not represent a single bond at the same time,
$J^7$ is C1–6 alkylene, wherein one carbon atom may be replaced by oxygen, sulfur or —NR$^{67}$—, wherein R$^{67}$ has the same meaning as above,
$J^9$ is C1–3 alkylene, oxygen, sulfur or —NR$^{67}$—, wherein R$^{67}$ is the same meaning as above,
and the other symbols have the same meanings as above and each ring may be replaced by 1–5 of R$^{27}$.

In the compounds of the formula (I), in

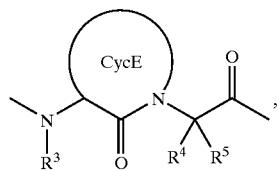
(i)

which AA$^1$ and AA$^2$ together form,

CycE is a 4–18 membered heteroring which contains 1–2 of nitrogen, 1 of oxygen and/or 1 of —S(O)$_p$— (this heteroring may be substituted with 1–5 of R$^{27}$).
And to describe

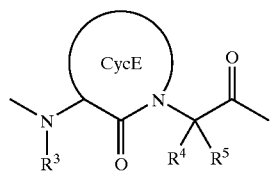

concretely, it is

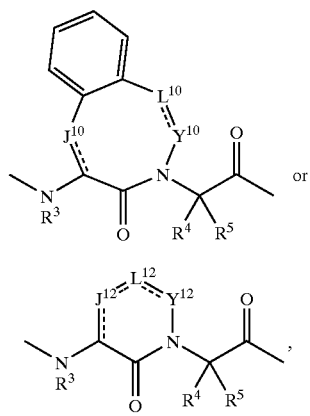
(i-1)

(i-2)

wherein ≡ is a single bond or a double-bond,

J$^{10}$ and Y$^{10}$ are the same or different to represent a single bond or C1–3 alkylene,
L$^{10}$ is a single bond, C1–3 alkylene, —NR$^{57}$—, wherein R$^{57}$ is hydrogen, C1–4 alkyl, phenyl or C1–4 alkyl substituted with phenyl, —N=, oxygen or —S(O)$_p$—, wherein p is 0 or an integer of 1 to 2,
J$^{12}$ and Y$^{12}$ are the same or different to represent a single bond or C1–3 alkylene,
L$^{12}$ is C1–3 alkylene, —NR$^{57}$—, wherein R$^{57}$ is the same meaning as above), —N=, =N—, oxygen or —S(O)$_p$—, wherein p has the same meaning as above, and the other symbols have the same meanings as above and each ring may be substituted with 1–5 of R$^{27}$.

And in

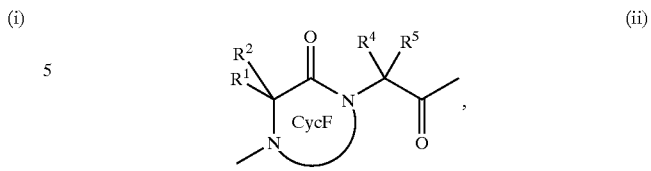
(ii)

which AA$^1$ and AA$^2$ together form,
CycF is a 5–8 membered heteroring containing 2 of nitrogen.
And to describe

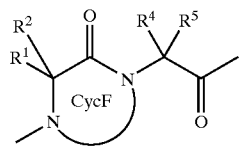

concretely, it is

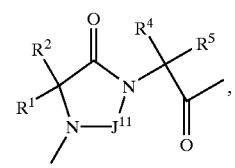

wherein J$^{11}$ is carbonyl or C2–4 alkylene and the other symbols have the same meaning as above and the ring therein may be substituted with 1–5 of R$^{27}$.

In the present specification, C1–4 alkyl is methyl, ethyl, propyl, butyl and isomers thereof.

In the present specification, C1–8 alkyl is methyl, ethyl, propyl, butyl, pentyl, hexyl, heptyl, octyl and isomers thereof.

In the present specification, C2–8 alkenyl is, ethyl, propyl, butyl, pentyl, hexyl, heptyl, octyl containing 1–3 of double bond and isomers thereof. For example, vinyl, propenyl, butenyl, hexenyl, hexadienyl, octadienyl, etc. are included.

In the present specification, C2–8 alkynyl is ethyl, propyl, butyl, pentyl, hexyl, heptyl, octyl containing 1–3 of triple bond and isomers thereof. For example, ethynyl, propynyl, butynyl, pentynyl, hexynyl, heptynyl, octynyl, etc. are included.

In the present specification, C1–4 alkyl substituted with phenyl is phenylmethyl, phenylethyl, phenylpropyl, phenylbutyl and isomers thereof.

In the present specification, C1–8 alkyl substituted with phenyl is phenylmethyl, phenylethyl, phenylpropyl, phenylbutyl, phenylpentyl, phenylhexyl, phenylheptyl, phenyloctyl and isomers thereof.

In the present specification, C1–2 alkylene is, methylene, ethylene and isomers thereof.

In the present specification, C1–3 alkylene is, methylene, ethylene, trimethylene and isomers thereof.

In the present specification, C1–4 alkylene is methylene, ethylene, trimethylene, tetramethylene and isomers thereof.

In the present specification, C1–5 alkylene is methylene, ethylene, trimethylene, tetramethylene, pentamethylene and isomers thereof.

In the present specification, C1–6 alkylene is methylene, ethylene, trimethylene, tetramethylene, pentamethylene, hexamethylene and isomers thereof.

In the present specification, C2–4 alkylene is ethylene, trimethylene, tetramethylene and isomers thereof.

In the present specification, C2–6 alkylene is ethylene, trimethylene, tetramethylene, pentamethylene, hexamethylene and isomers thereof.

In the present specification, C2–8 alkylene is ethylene, trimethylene, tetramethylene, pentamethylene, hexamethylene, heptamethylene, octamethylene and isomers thereof.

In the present specification, C2–6 alkylene whose one carbon atom may be replaced by oxygen, sulfur, —NR$^{20}$—, —NR$^{40}$— or —NR$^{60}$— is ethylene, trimethylene, tetramethylene, pentamethylene, hexamethylene and isomers thereof, wherein one carbon atom thereof may be replaced by oxygen, sulfur, —NR$^{20}$—, —NR$^{40}$—, or —NR$^{10}$—, for example, such groups are —CH$_2$—O—CH$_2$—, —CH$_2$—CH$_2$—O—CH$_2$—, —CH$_2$—CH$_2$—S—CH$_2$—, —CH$_2$—CH$_2$—NH—CH$_2$—, —CH$_2$—CH$_2$—O—CH$_2$—CH$_2$—, —CH$_2$—CH$_2$—S—CH$_2$—CH$_2$—, —CH$_2$—CH$_2$—NH—CH$_2$—CH$_2$—, —CH$_2$—CH$_2$—N(CH$_3$)—CH$_2$—CH$_2$—, etc.

In the present specification, C2–8 alkylene whose one carbon atom may be replaced by oxygen, sulfur, —NR$^{20}$—, —NR$^{40}$— or —NR$^{60}$— is ethylene, trimethylene, tetramethylene, pentamethylene, hexamethylene, heptamethylene, octamethylene and isomers thereof, wherein one carbon atom may be replaced by oxygen, sulfur, —NR$^{20}$—, —NR$^{40}$— or —NR$^{60}$—, for example, such groups are —CH$_2$—O—CH$_2$—, —CH$_2$—CH$_2$—O—CH$_2$—, —CH$_2$—CH$_2$—S—CH$_2$—, —CH$_2$—CH$_2$—NH—CH$_2$—, —CH$_2$—CH$_2$—O—CH$_2$—CH$_2$—, —CH$_2$—CH$_2$—S—CH$_2$—CH$_2$—, —CH$_2$—CH$_2$—NH—CH$_2$—CH$_2$—, —CH$_2$—CH$_2$—N(CH$_3$)—CH$_2$—CH$_2$—, etc.

In the present specification, C2–3 alkenylene means vinylene and allylene and isomers thereof.

In the present specification, C1–4 alkoxy is methoxy, ethoxy, propoxy, butoxy and isomers thereof.

In the present specification, C3–6 alkylene is trimethylene, tetramethylene, pentamethylene, hexamethylene and isomers thereof.

In the present specification, halogen atom means chlorine, fluorine, bromine and iodine atom.

In the present specification, mono- or bi-cyclic C5–10 carboring is mono- or bi-cyclic C5–10 carboaryl or partially or completely saturated one thereof. For example, cyclopentane, cyclohexane, cycloheptane, cyclopentene, cyclohexene, cyclopentadiene, cyclohexadiene, benzene, pentalene, indene, naphthalene, azulene, perhydropentalene, perhydroindene, perhydronaphthalene, perhydroazulene, adamantyl ring, etc. are included.

In the present specification, mono-, bi- or tri-cyclic C3–15 carboring is mono-, bi- or tri-cyclic carboaryl or partially or completely saturated one thereof. For example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantyl ring etc. are included.

In the present specification, mono- or bi-cyclic 5–10 membered heteroring containing 1–4 of nitrogen, 1 of oxygen and/or sulfur is mono- or bi-cyclic 5–10 membered heteroaryl containing 1–4 of nitrogen, 1 of oxygen and/or sulfur or partially or completely saturated one thereof.

Above 5–10 membered mono- or bi-cyclic heteroaryl containing 1–4 of nitrogen, 1 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, thiophene, thiaine (thiopyrane), thiepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, etc.

Above partially or completely saturated mono- or bi-cyclic 5–10 membered heteroaryl containing 1–4 of nitrogen, 1 of oxygen and/or 1 of sulfur is, for example, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetrahydropyrane, dihydrothiophene, tetrahydrothiophene, dihydrothiaine (dihydrothiopyrane), tetrahydrothiaine (tetrahydrothiopyrane), oxazoline (dihydrooxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, etc.

In the present specification, a 3–15 membered mono-, bi- or tri-cyclic heteroring containing 1–4 of nitrogen, 1–2 of oxygen and/or 1 of sulfur is 3–15 membered mono-, bi- or tri-cyclic heteroaryl containing 1–4 of nitrogen, 1–2 of oxygen and/or 1 of sulfur or partially or completely saturated one thereof.

Above 3–15 membered mono-, bi- or tri-cyclic heteroring containing 1–4 of nitrogen, 1–2 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, oxazepine, thiophene, thiaine (thiopyrane), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzoxadiazole, benzothiazole, benzoimidazole, carbazole, acridine ring, etc.

Above partially or completely saturated mono-, bi- or tri-cyclic 3–15 membered heteroring containing 1–4 of nitrogen, 1–2 of oxygen and/or 1 of sulfur is, aziridine, oxirane, azetidine, oxetane, thiirane, thietane, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetrahydropyrane, dihydrothiophene, tetrahydrothiophene, dihydrothiaine (dihydrothiopyrane), tetrahydrothiaine (tetrahydrothiopyrane), oxazoline (dihydroxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, benzoxazepine, benzoxadiazepine, benzothiazepine, benzothiadiazepine, benzazepine, benzodiazepine, indoloxazepine, indolotetrahydroxazepine, indoloxadiazepine, indolotetrahydroxadiazepine, indolothiazepine, indolotetrahydrothiazepine, indolothiadiazepine, indolotetrahydrothiadiazepine, indolazepine, indolotetrahydroazepine, indolodiazepine, indolotetrahydrodiazepine, benzofurazane, benzothiadiazole, benzotriazole, camphor, imidazothiazole, dihydrocarbazole, tetrahydrocarbazole, perhydrocarbazole, dihydroacridine, tetrahydroacridine, perhydroacridine, dioxolane, dioxane, dioxazine ring etc.

In the present specification, C5–8 carboring is C5–8 mono-cyclic carboaryl or partially or completely saturated one thereof. For example, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, cycloheptatriene, cyclooctatriene, etc. are included.

In the present specification, 5–8 membered heteroring containing 1 or 2 of nitrogen, 1 of oxygen and/or 1 of sulfur is, mono-cyclic 5–8 membered heteroaryl containing 1 or 2 of nitrogen, 1 of oxygen and/or 1 of sulfur, or partially or completely saturated one thereof. For example, pyridine, piperidine, pyrrole, pyrrolidine, azepine, hexahydroazepine, diazepine, furan, dioxane, dioxole, pyran, oxepine, oxocine, thiophene, thiane, thiepine, oxathiolane, oxazolidine, pyrazole, oxazole, pyrazine, pyrimidine, pyridazine, etc. are included.

In the present specification, a 5–12 membered heteroring containing 1–3 of nitrogen, 1 of oxygen and/or 1 of sulfur atom, i.e.

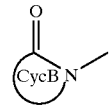

is, for example, a ring represented by

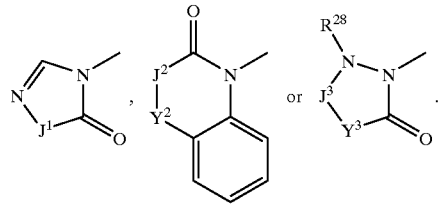

Specifically, 2-oxo-1,3,4-triazoline, 5-oxo-1,2,4-oxadiazoline, 5-oxo-1,2,4-thiadiazoline, 4-oxoimidazoline, 3,4-dihydro-4-oxopyrimidine, 3,4,5,6-tetrahydro-4-oxopyrimidine, 2-oxoindoline, 2-oxo-tetrahydroquinoline, 1,2-dihydro-2-oxoquinazoline, 1,2-dihydro-2-oxoquinoxaline, 3-oxopyrazolidine, perhydro-3-oxopyridazine, 2-oxo-1,3,4-oxadiazolidine, perhydro-2-oxo-1,3,4-oxadiazine, etc. are included.

In the specification, 3–17 membered heteroring containing 1–2 of nitrogen, 1 of oxygen and/or 1 of sulfur represented by CycC is, for example, a ring represented by

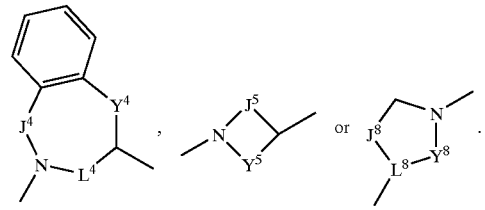

Specifically, pyrrolidine, imidazolidine, pyrazolidine, piperidine, piperazine, perhydropyrimidine, perhydropyridazine, thiazolidine, indoline, isoindoline, tetrahydroquinoline, tetrahydroisoquinoline, etc. are included.

In the specification, a C3–14 mono- or bi-cyclic carboring or 3–14 membered heteroring containing 1–2 of nitrogen, 1 of oxygen, and/or 1 of sulfur represented by CycD is, for example, a ring represented by

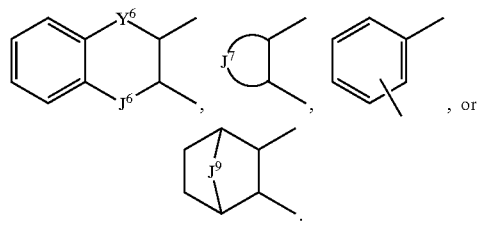

Specifically, cyclopentane, cyclohexane, cycloheptane, benzene, indan, tetrahydronaphthalene, oxorane, oxane, thiorane, thian, pyrrolidine, piperidine, bicyclo[2.2.1]heptane, bicyclo[2.2.2]octane, 7-azabicyclo[2.2.1]heptane, 7-oxobicyclo[2.2.1]heptane, 7-thiabicyclo[2.2.1]heptane, etc. are included.

In the specification, 4–18 membered heteroring containing 1–2 of nitrogen, 1 of oxygen and/or 1 of —S(O)$_p$—, i.e. CycE is, for example, a ring represented by

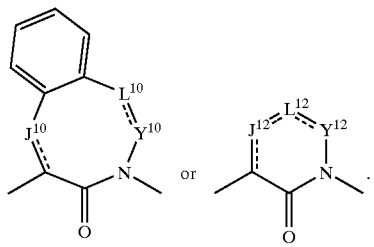

Specifically, 2-oxopyrrolidine, 2-oxopiperidine, 2-oxoperhydroazepine, 2-oxopiperazine, 3-oxomorpholine, 1,1,-dioxo-3-isothiazolidine, 1,1-dioxo-3-isothiazine, 4-oxodiazepine, 2-oxoindoline, 2-oxo-tetrahydroquinoline, 1,1-dioxo-3-benzisothiazolidine, 1,1-dioxo-3-benzisothiazine, etc. are included.

In the present invention, 5–8 membered heteroring which contains 2 of nitrogen. i.e. CycF is, for example, a ring represented by

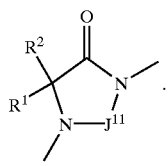

Specifically, 2,4-dioxoimidazolidine, 2-oxopiperazine, 2-oxoperhydrodiazepine substituted by $R^1$ and $R^2$ are included.

In the present invention, as may be easily understood by those skilled in the art, the symbol:

▼ indicates that the substituent attached thereto is in front of the sheet (β-position) unless specified,

⁗ indicates that the substituent attached thereto is behind the sheet (α-position) unless specified, and

＼ indicates that the substituent attached thereto is in β-position or α-position or a mixture thereof.

In the formula (I), all groups represented by R are preferable, but preferably, R is
(i) hydrogen,
(ii) C1–8 alkyl,
(iii) CycA,
(iv) C1–8 alkyl substituted with a group selected from CycA and nitro,

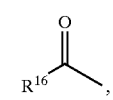
(v)

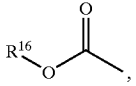
(vi)

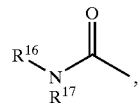
(vii)

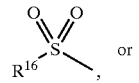
(viii)

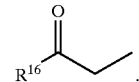
(ix)

more preferably, C1–8 alkyl or C1–8 alkyl substituted with CycA or nitro, or

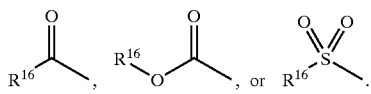

Any group represented by $R^{16}$ is preferable, but more preferably, $R^{16}$ is
[I] (1) C1–8 alkyl,
(2) C2–8 alkenyl,
(3) C2–8 alkynyl,
(4) CycA, or
(5) C1–8 alkyl substituted with a group selected from CycA or —NHC(O)-CycA,
(6) C2–8 alkenyl substituted with CycA or
(7) C2–8 alkynyl substituted with CycA,
wherein CycA may be substituted with 1–5 of $R^{27a}$, and $R^{27a}$ is (1) C1–8 alkyl,
(2) halogen,
(3) —NR$^{11}$R$^{12}$,
(4) —OR$^{13}$,
(5) phenyl,
(6) nitro,
(7) CF$_3$,
(8) cyano,
(9) tetrazole,
(10) —SR$^{14}$,
(11) —COR$^{15}$,
(12) oxo or
(13) C1–8 alkyl substituted with 1–5 of group selected from the following (a) to (k):
(a) halogen, (b) —NR$^{11}$R$^{12}$, (c) —OR$^{13}$, (d) phenyl, (e) nitro, (f) CF$_3$, (g) cyano, (h) tetrazole, (j) —SR$^{14}$, (k) —COR$^{15}$, or
[II] (a) C1–8 alkyl, C2–8 alkenyl or C2–8 alkynyl substituted with a group selected from halogen, CF$_3$, nitro, cyano or NR$^{18}$R$^{19}$ or
(b) (1) CycA containing 1–5 of substituent R$^{27}$ or
(2) C1–8 alkyl, C2–8 alkenyl or C2–8 alkynyl substituted with CycA, which contains 1–5 of substituent R$^{27}$,
wherein at least one of R$^{27}$ described in (1) and (2) is selected from
(i) a C5–10 mono- or bi-cyclic carboring,
(ii) a 5–10 membered mono- or bi-cyclic heteroring,
(iii) —SO$_2$R$^{15}$, (iv) —OCF$_3$ or
(v) C1–8 alkyl substituted with 1–5 of the group selected from (a) halogen, (b) —NR$^{11}$R$^{12}$, (c) —OR$^{13}$, (d) a C5–1 mono-or bi-cyclic carboring, (e) nitro, (f) CF$_3$, (g) cyano, (h) a 5–10 membered mono- or bi-cyclic heteroring, (j) —SR$^{14}$, (k) —COR$^{15}$, (l) —SO$_2$R$^{15}$ and (m) —OCF$_3$ (at least one is a C5–10 mono- or bi-cyclic carboring, a 5–10 mono- or bi-cyclic heteroring, —SO$_2$R$^{15}$ or —OCF$_3$)).
Particularly preferably,

[I] (1) C1–8 alkyl, (2) C2–8 alkenyl, (3) C2–8 alkynyl, (4) CycA or (5) C1–8 alkyl substituted with a group selected from CycA or —NHC(O)-CycA, (6) C2–8 alkenyl substituted with CycA or (7) C2–8 alkynyl substituted with CycA, wherein CycA is a mono- or bi-cyclic C5–10 carboaryl which may be substituted with 1–5 of R$^{27}$ or partially or completely saturated one thereof, or mono- or bi-cyclic 5–10 membered heteroaryl containing 1–2 of nitrogen, 1–2 of oxygen and/or 1 of sulfur atom, or partially or completely saturated one thereof or

[II] (a) C1–8 alkyl, C2–8 alkenyl or C2–8 alkynyl substituted with a group selected from halogen atom, CF$_3$, nitro, cyano and NR$^{18}$R$^{19}$, or (b) CycA containing 1–5 of substituent R$^{27}$ or (2) C1–8 alkyl, C2–8 alkenyl or C2–8 alkynyl substituted with CycA, which contains 1–5 of substituent R$^{27}$, wherein at least one of R$^{27}$ described in (1) and (2) is selected from (i) a C5–10 mono- or bi-cyclic carboring, (ii) a 5–10 membered mono- or bi-cyclic heteroring, (iii) —SO$_2$R$^{15}$, (iv) —OCF$_3$ or (v) C1–8 alkyl substituted with 1–5 of group selected from (a) halogen, (b) —NR$^{11}$R$^{12}$, (c) —OR$^{13}$, (d) a C5–10 mono- or bi-cyclic carboring, (e) nitro, (f) CF$_3$, (g) cyano, (h) a 5–10 membered mono- or bi-cyclic heteroring, (j) —SR$^{14}$, (k) —COR$^{15}$, (l) —SO$_2$R$^{15}$ and (m) OCF$_3$, wherein at least one group is selected from a C5–10 mono- or bi-cyclic carboring or a 5–10 membered mono- or bi-cyclic heteroring, —SO$_2$R$^{15}$ or OCF$_3$, above CycA is C5–10 mono- or bi-cyclic carboaryl or partially or completely saturated one, or 5–10 membered mono- or bi-cyclic heteroaryl containing 1–2 of nitrogen, 1–2 of oxygen and/or 1 of sulfur, or partially or completely saturated one thereof.

Particularly preferably, [I] (1) C1–4 alkyl, (2) C2–4 alkenyl, (3) C2–4 alkynyl, (4) CycA or (5) C1–4 alkyl, C2–4 alkenyl or C2–4 alkynyl substituted with CycA which is preferably cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxazole, tetrahydroquinoline, tetrahydroquinazoline, tetrahydroquinoxaline, optionally substituted with 1–5 of R$^{27a}$ or

[II] (a) C1–8 alkyl, C2–8 alkenyl or C2–8 alkynyl substituted with a group selected from halogen, CF$_3$, nitro, cyano or NR$^{18}$R$^{19}$ or (b) (1) CycA which contains 1–5 of substituent R$^{27}$, or (2) C1–8 alkyl, C2–8 alkenyl or C2–8 alkynyl substituted with CycA which contains 1–5 of substituent R$^{27}$, wherein at least one of R$^{27}$ described in (1) and (2) is selected from (i) a C5–10 mono- or bi-cyclic carboring, (ii) a 5–10 membered mono- or bi-cyclic heteroring, (iii) —SO$_2$R$^{15}$, (iv) —OCF$_3$, or (v) C1–8 alkyl substituted with 1–5 of group selected from (a) halogen atom, (b) —NR$^{11}$R$^{12}$, (c) —OR$^{13}$, (d) a C5–10 mono-or bi-cyclic carboring, (e) nitro, (f) CF$_3$, (g) cyano, (h) a 5–10 membered mono- or bi-cyclic heteroring, (j) —SR$^{14}$, (k) —COR$^{15}$, (l) —SO$_2$R$^{15}$ or (m) —OCF$_3$, wherein at least one group is selected from a C5–10 mono- or bi-cyclic carboring, a 5–10 membered mono- or bi-cyclic heteroring, —SO$_2$R$^{15}$ or —OCF$_3$, and CycA is preferably cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxadiazole, tetrahydroquinoline, tetrahydroquinazoline, or tetrahydroquinoxaline.

In the formula (I), AA$^1$ is preferably a single bond,

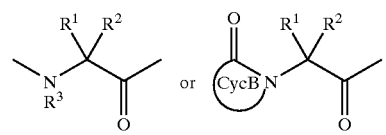

which is formed with R, but more preferably, AA$^1$ is a single bond or

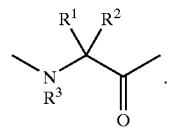

Any group represented by R$^1$ is preferable, but more preferably, R$^1$ is hydrogen, C1–8 alkyl, phenyl or C1–8 alkyl substituted with NH$_2$, C1–4 alkoxy, SH, SCH$_3$, phenyl, hydroxyphenyl, COOH, CONH$_2$, guanidino, imidazole or indole. Particularly preferably, R$^1$ is hydrogen, C1–8 alkyl, phenyl or C1–8 alkyl substituted with C1–4 alkoxy or phenyl. Then, any group represented by R$^2$ is preferable, but hydrogen is particularly preferable.

And C3–6 alkylene which R$^1$ and R$^2$ together form is also preferable.

Any group represented by R$^3$ is preferable, but more preferably R$^3$ is hydrogen or C1–4 alkyl.

And C2–4 alkylene which R$^3$ and R$^1$ together form is also preferable.

In the formula (I), any group represented by AA$^2$ is all preferable, but more preferably, AA$^2$ is a single bond,

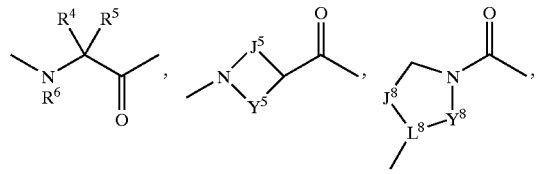

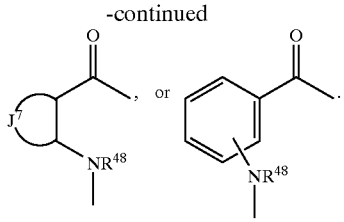

Particularly preferably, AA² is single bond,

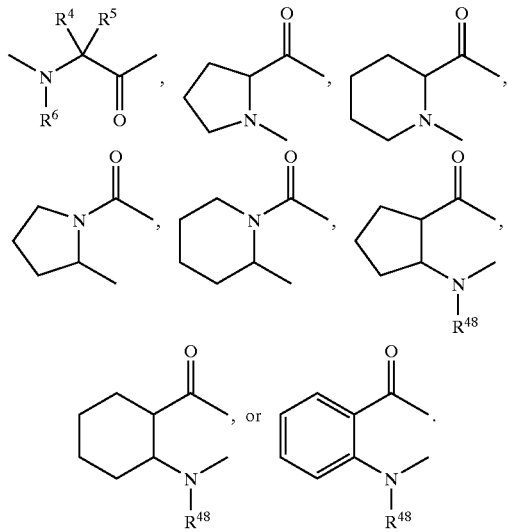

Any group represented by R⁴ is preferable, but more preferably, R⁴ is hydrogen, C1–8 alkyl, phenyl or C1–8 alkyl substituted with $NH_2$, C1–4 alkoxy, SH, $SCH_3$, phenyl, hydroxyphenyl, COOH, $CONH_2$, guanidino, imidazole or indole. Particularly preferably, R⁴ is hydrogen, C1–8 alkyl, phenyl or C1–8 alkyl substituted with C1–4 alkoxy or phenyl. Then, any group represented by R⁵ is preferable, and hydrogen is particularly preferable.

And C3–6 alkylene which R⁴ and R⁵ together form is also preferable.

Any group represented by R⁶ is preferable, but more preferably R⁶ is hydrogen or C1–4 alkyl.

And C2–4 alkylene which R⁶ and R⁴ together form is also preferable.

Any group represented by $R^{48}$ is preferable, but more preferably, $R^{48}$ is

[I] hydrogen, C1–4 alkyl, phenyl or C1–4 alkyl substituted with phenyl, or

[II] C2–6 alkylene, wherein one carbon atom may be replaced by oxygen, sulfur or —$NR^{47}$—, wherein $R^{47}$ is hydrogen or C1–4 alkyl to be formed together with R⁴, when AA¹ is a single bond. Particularly preferably, $R^{48}$ is [I] hydrogen atom or C1–4 alkyl, or

[II] when AA¹ is a single bond, taken together with R to form tetramethylene, pentamethylene, —$CH_2$—$CH_2$—O—$CH_2$—$CH_2$—, —$CH_2$—$CH_2$—NH—$CH_2$—$CH_2$— or —$CH_2$—$CH_2$—N($CH_3$)—$CH_2$—$CH_2$—.

In the formula (I), any group which AA¹ and AA² together form is preferable, but preferably, it is

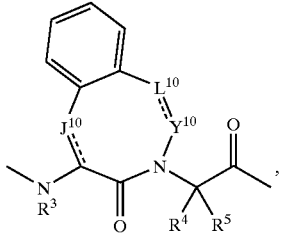

(i)

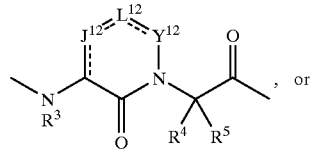

(ii) , or

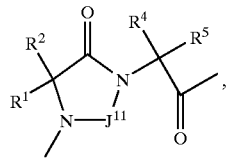

(iii)

particularly preferably, it is

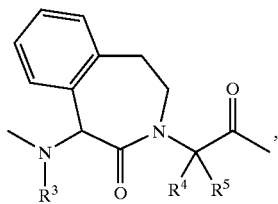

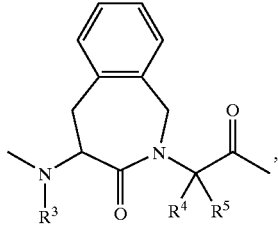

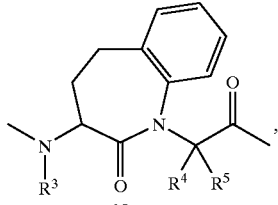

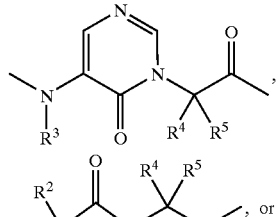

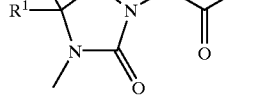 , or

-continued

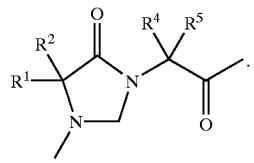

Any group represented by $R^7$ is preferable. More preferably, $R^7$ is hydrogen atom, C1–8 alkyl, phenyl, or C1–8 alkyl substituted with $NH_2$, C1–4 alkoxy, SH, $SCH_3$, phenyl, hydroxyphenyl, COOH, $CONH_2$' guanidino, imidazole or indole.

Particularly preferably, $R^7$ is hydrogen, C1–8 alkyl, phenyl, or C1–8 alkyl substituted with C1–4 alkoxy or phenyl. Then, any group represented by $R^8$ is preferable, but hydrogen is most preferable.

And C3–6 alkylene which $R^7$ and $R^8$ together form is also preferable.

Any group represented by $R^9$ is preferable, but more preferably $R^9$ is hydrogen or C1–4 alkyl.

And C2–4 alkylene which $R^9$ and $R^7$ together form is also preferable.

Any group represented by $R^{10}$ is preferable, but more preferably $R^{10}$ is C1–6 alkyl, C2–4 alkenyl, CycA or C1–6 alkyl or C2–4 alkenyl substituted with $COR^{71}$, $NR^{72}R^{73}$, hydroxy, $OR^{74}$ or CycA, particularly preferably C1–4 alkyl, or C1–4 alkyl substituted with phenyl, $NR^{72}R^{73}$ or C3–6 cycloalkyl.

Any group represented by $R^{10}$ is preferable, but more preferably $R^{10}$ is C1–6 alkyl, CycA or C1–6 alkyl substituted with $COR^{71}$, $NR^{72}R^{73}$, hydroxy, $OR^{74}$ or CycA, more preferably C1–4 alkyl, C2–4 alkenyl, or C1–4 alkyl or C2–4 alkenyl substituted with phenyl, $NR^{72}R^{73}$, C3–6 cycloalkyl, piperidine or pyrrolidine.

is preferably,

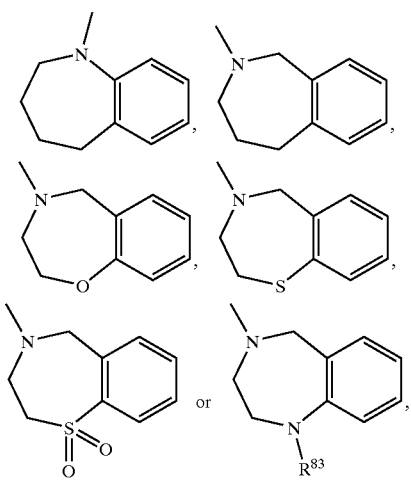

and more preferably,

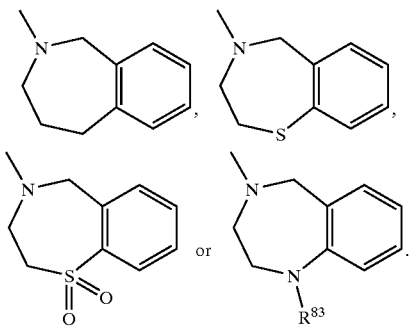

In the ring represented by

the C5–8 carbocycle which is a condensed ring of the rings represented by

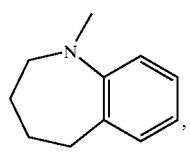

(i)

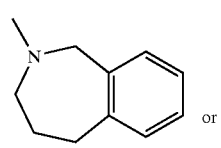

(ii)

or

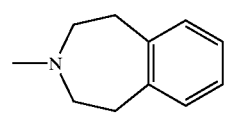

(iii)

or 5–8 membered heteroring which contains 1 or 2 of nitrogen, 1 of oxygen and/or 1 of sulfur atom, are all preferable, but more preferably, C5–6 carboring or 5–6 membered heteroring containing 1 or 2 of nitrogen, 1 of oxygen and/or 1 of sulfur atom, concretely, cyclopentane, cyclohexane, cyclopentene, cyclohexene, cyclopentadiene, cyclohexadiene, benzene, pyridine, piperidine, pyrrole, pyrrolidine, furan, dioxane, dioxole, pyran, thiophene, thian, thiepine, oxathiolane, oxazolidine, pyrazole, oxazole, pyrazine, pyrimidine, pyridazine.

$R^{83}$ is preferably hydrogen atom, C1–4 alkyl, or C1–4 alkyl substituted with Cyc, cyano, —$OR^{69}$ or —$COR^{68}$, and more preferably C1–4 alkyl or C1–4 alkyl substituted with Cyc.

$R^{10}$ is preferably —$OR^{74}$, more preferably hydroxy, C1–4 alkoxy, or C1–4 alkoxy substituted with phenyl.

In the compounds of formula (I), the following compounds are preferred;

the compound of (I-1A)

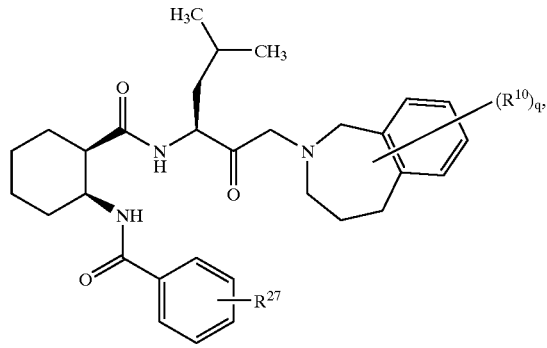

wherein all symbols have the same meanings as above, the compound of formula (I-2A)

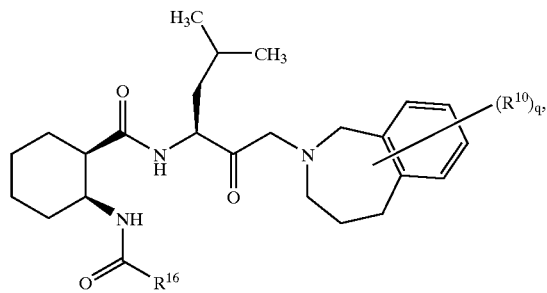

wherein all symbols have the same meanings as above, the compound of formula (I-3A)

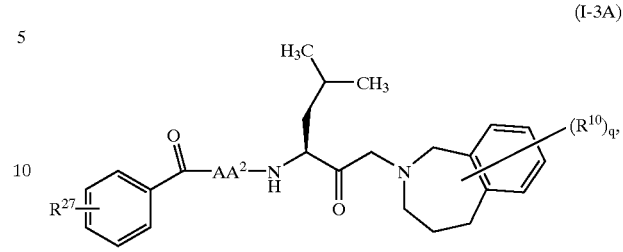

wherein all symbols have the same meanings as above, the compound of formula (I-4A)

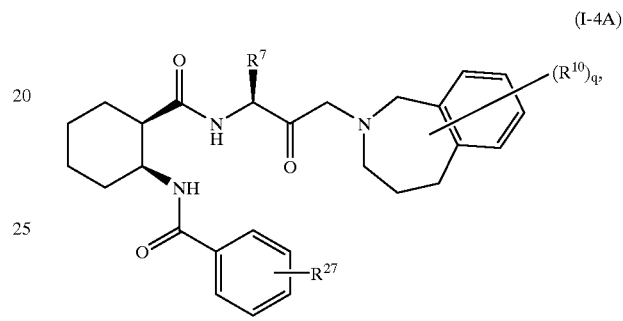

wherein all symbols have the same meanings as above, the compound of formula (I-5A)

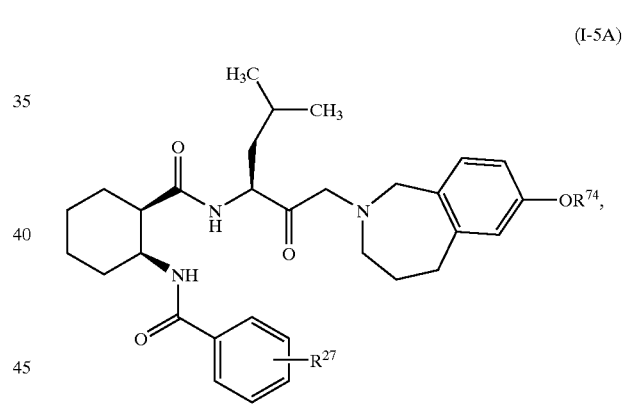

wherein all symbols have the same meanings as above, the compound of formula (I-6A)

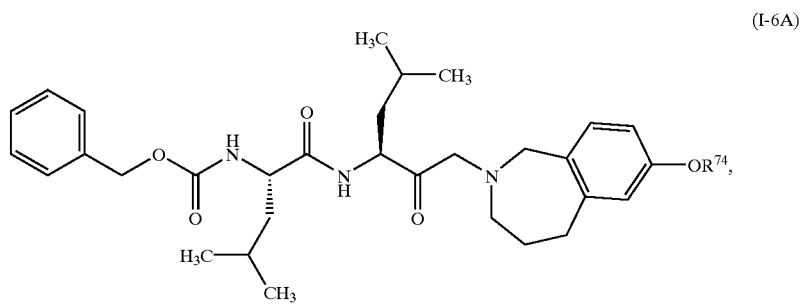

wherein all symbols have the same meanings as above, the compound of formula (I-7A)

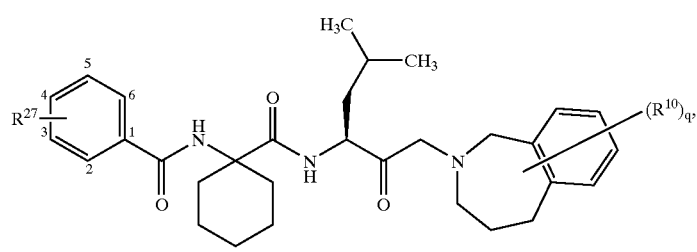
(I-7A)

wherein all symbols have the same meanings as above, the compound of formula (I-8A)

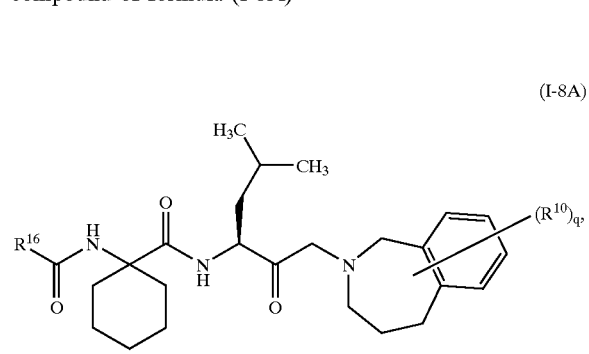
(I-8A)

wherein all symbols have the same meanings as above, the compound of formula (I-9A)

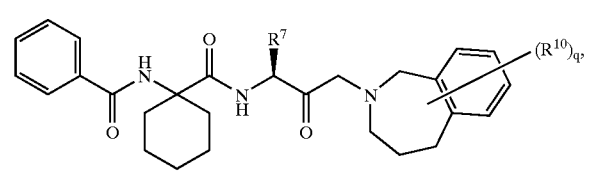
(I-9A)

wherein all symbols have the same meanings as above, the compound of formula (I-10A)

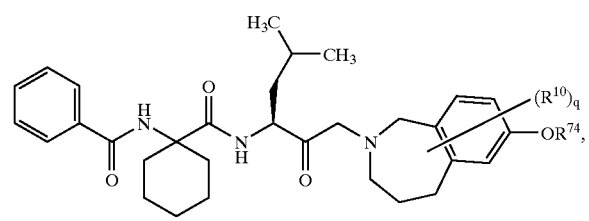
(I-10A)

wherein all symbols have the same meanings as above, the compound of formula (I-1B)

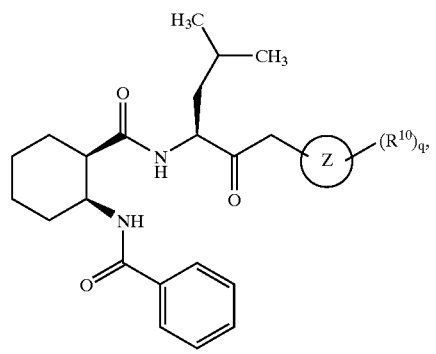
(I-1B)

wherein all symbols have the same meanings as above, the compound of formula (I-2B)

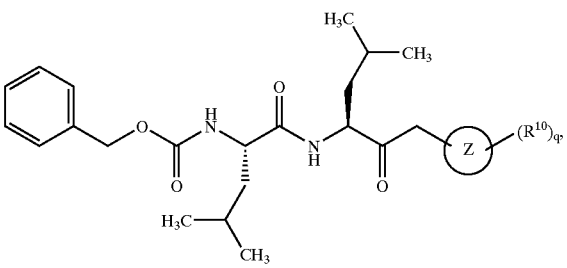
(I-2B)

wherein all symbols have the same meanings as above, the compound of formula (I-3B)

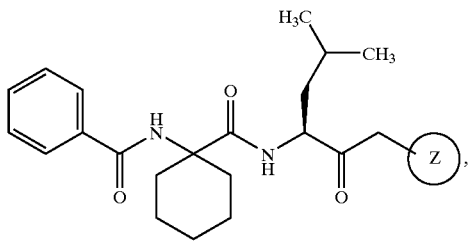
(I-3B)

wherein all symbols have the same meanings as above, the compound of formula (I-1C)

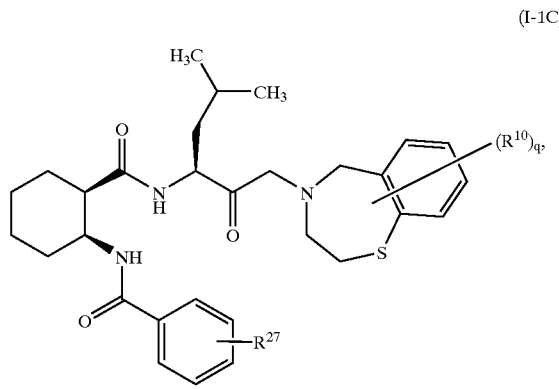
(I-1C)

wherein all symbols have the same meanings as above, the compound of formula (I-2C)

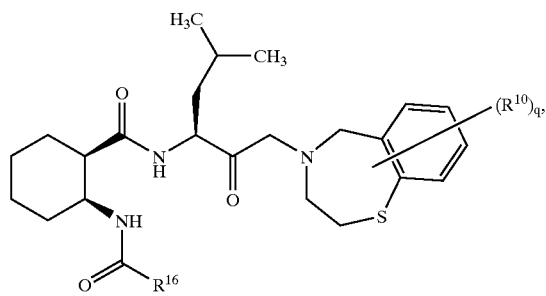
(I-2C)

wherein all symbols have the same meanings as above, the compound of formula (I-3C)

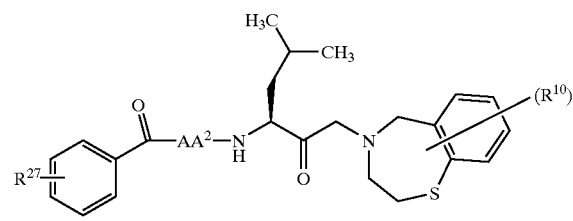
(I-3C)

wherein all symbols have the same meanings as above, the compound of formula (I-4C)

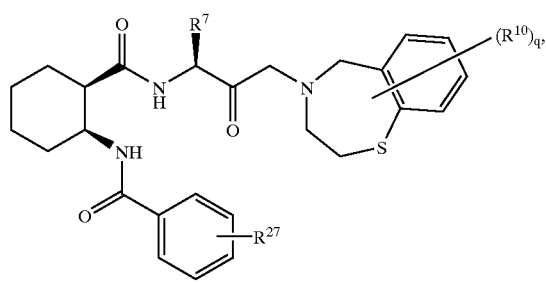
(I-4C)

wherein all symbols have the same meanings as above, the compound of formula (I-5C)

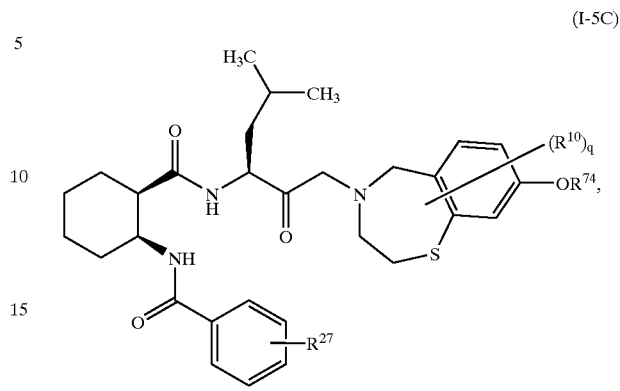
(I-5C)

wherein all symbols have the same meanings as above, the compound of formula (I-6C)

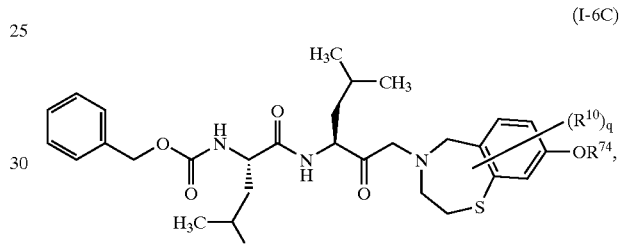
(I-6C)

wherein all symbols have the same meanings as above, the compound of formula (I-7C)

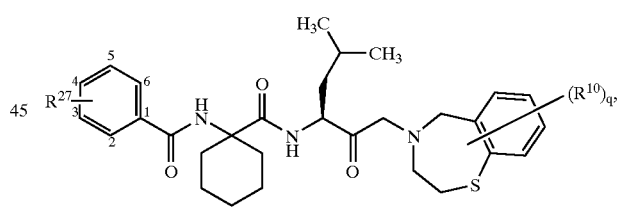
(I-7C)

wherein all symbols have the same meanings as above, the compound of formula (I-8C)

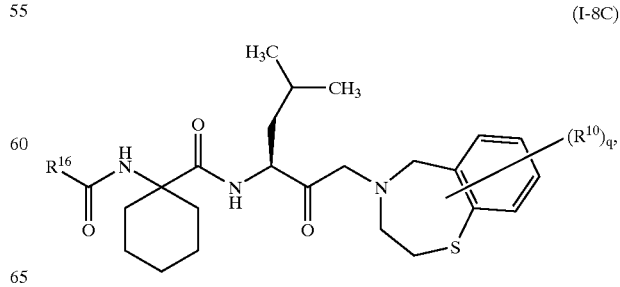
(I-8C)

wherein all symbols have the same meanings as above, the compound of formula (I-9C)

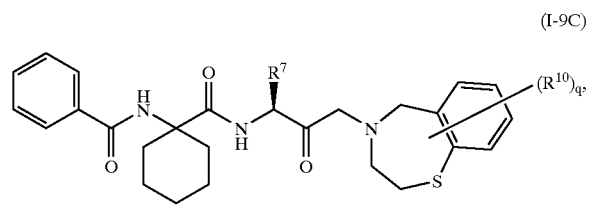
(I-9C)

wherein all symbols have the same meanings as above, the compound of formula (I-10C)

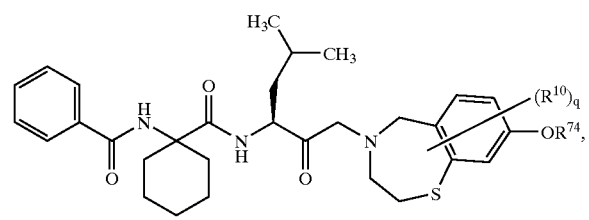
(I-10C)

wherein all symbols have the same meanings as above, the compound of formula (I-1D)

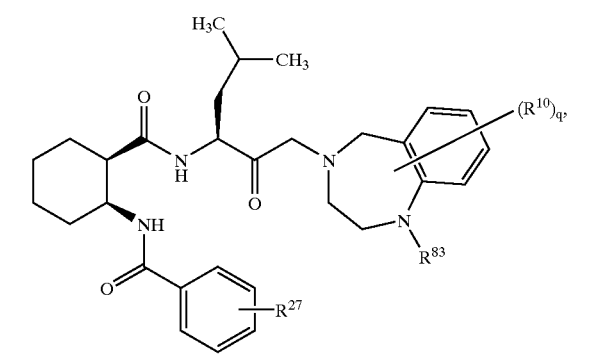
(I-1D)

wherein all symbols have the same meanings as above, and the compound of formula (I-2D)

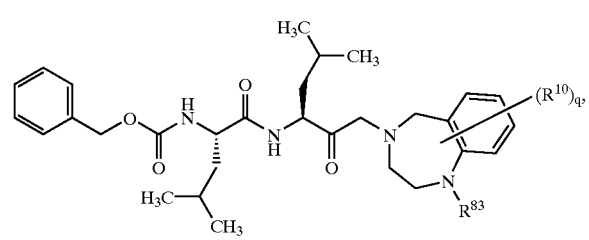
(I-2D)

wherein all symbols have the same meanings as above.

Particularly, the compounds described in the following tables 1 to 30 and the compounds described in the examples or non-toxic salts thereof are preferable. In the following tables, all symbols have the same meanings as above.

TABLE 1

(I-1A-1)

| No. | $R^{27}$ |
|---|---|
| 1 | 3-F |
| 2 | 2-CN |
| 3 | 3-CN |
| 4 | 3-NO$_2$ |
| 5 | 4-NO$_2$ |
| 6 | 3-CH$_3$ |
| 7 | 2-CH$_2$—Cl |
| 8 | 4-CH$_2$—Cl |
| 9 | 4-CH$_2$CH$_3$ |
| 10 | 4-(CH$_2$)$_3$CH$_3$ |
| 11 | 4-N(CH$_3$)$_2$ |
| 12 | 4-OCH$_2$CH$_3$ |
| 13 | 2,3-di-CH$_3$ |
| 14 | 3,5-di-F |
| 15 | 3,4-di-F |
| 16 | 2-OCF$_3$ |
| 17 | 3-OCF$_3$ |
| 18 | 4-CONH$_2$ |
| 19 | 3-CONH$_2$ |
| 20 | 4-COOH |
| 21 | 4-OCH$_2$COOH |
| 22 | 4-O(CH$_2$)$_5$CH$_3$ |
| 23 | 4-CH$_2$CH(CH$_3$)$_2$ |
| 24 | 3-COOH |
| 25 | 3-OCH$_2$COOH |
| 26 | 3-O(CH$_2$)$_5$CH$_3$ |
| 27 | 3-CH$_2$CH(CH$_3$)$_2$ |
| 28 | 2-OCH$_2$COOH |
| 29 | 2-O(CH$_2$)$_5$CH$_3$ |
| 30 | 2-CH$_2$CH(CH$_3$)$_2$ |

TABLE 2

(I-2A-1)

| No. | $R^{16}$ |
|---|---|
| 1 | 3-pyridyl |

TABLE 2-continued (I-2A-1)

| No. | R¹⁶ |
|---|---|
| 2 | 2-furyl |
| 3 | 5-methyl-2,1,3-benzoxadiazol-... |
| 4 | 2-chloro-4-methylpyridin-... |
| 5 | 3-nitro-3-methylhexyl |
| 6 | 2-methyl-2-phenylethenyl |
| 7 | 2-phenylethenyl |
| 8 | but-3-enyl |
| 9 | pentyl |
| 10 | cyclopropyl |
| 11 | 3-chloro-2,2-dimethylpropyl |
| 12 | benzo[1,3]dioxol-5-yl |
| 13 | cyclohexyl |
| 14 | 4-methylpiperidin-4-yl |
| 15 | 4-methyltetrahydropyran-4-yl |
| 16 | 4-(aminoiminomethyl)phenyl |
| 17 | 4-(dimethylamino)but-2-ynyl |
| 18 | 4-(dimethylamino)but-2-enyl |
| 19 | 4-(dimethylamino)butyl |

TABLE 3

(I-3A-1)

| No. | AA2 |
|---|---|
| 1 | 2-(methylamino)cyclohexyl-1-carbonyl |

TABLE 3-continued
(I-3A-1)
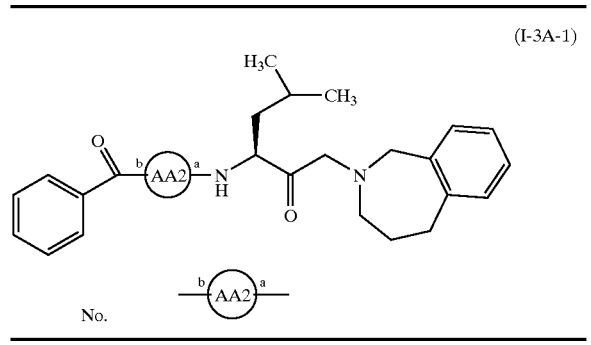
| No. | |
|---|---|
| 2 | 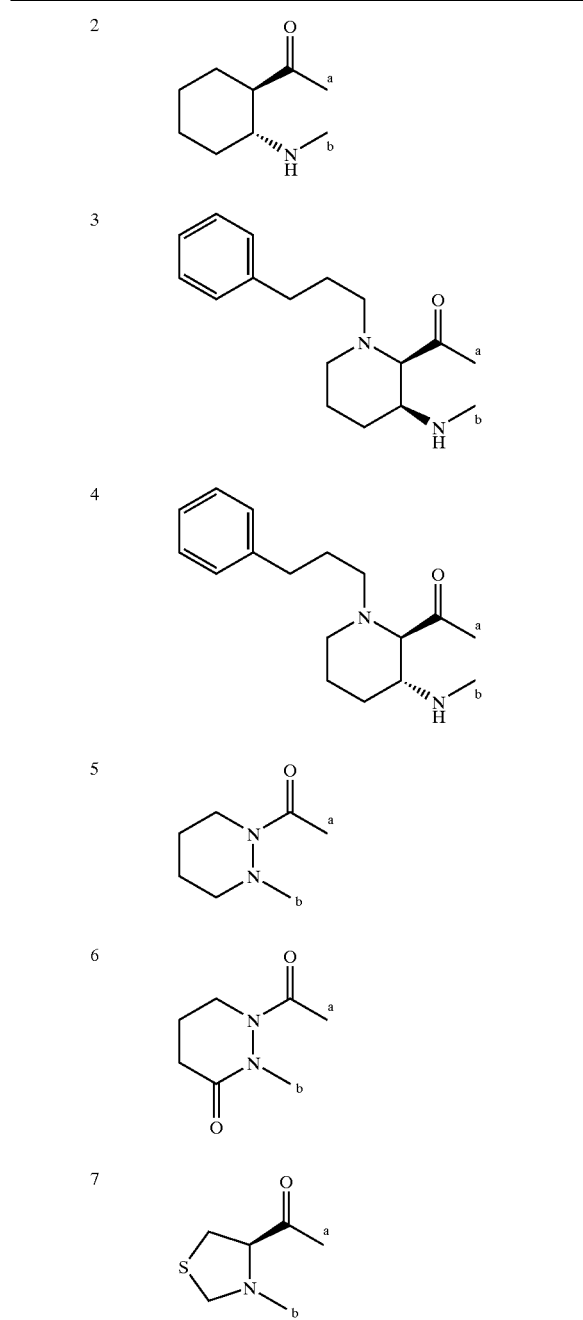 |
TABLE 3-continued
(I-3A-1)
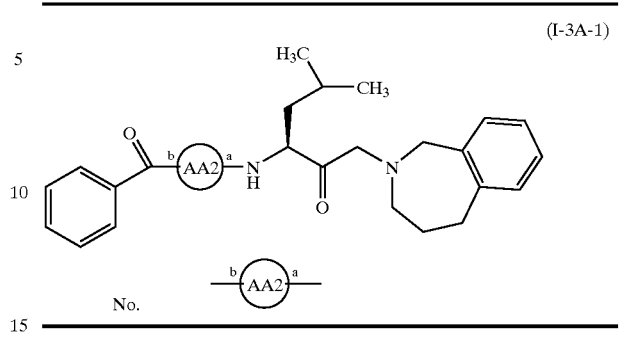
| No. | |
|---|---|
| 8 | 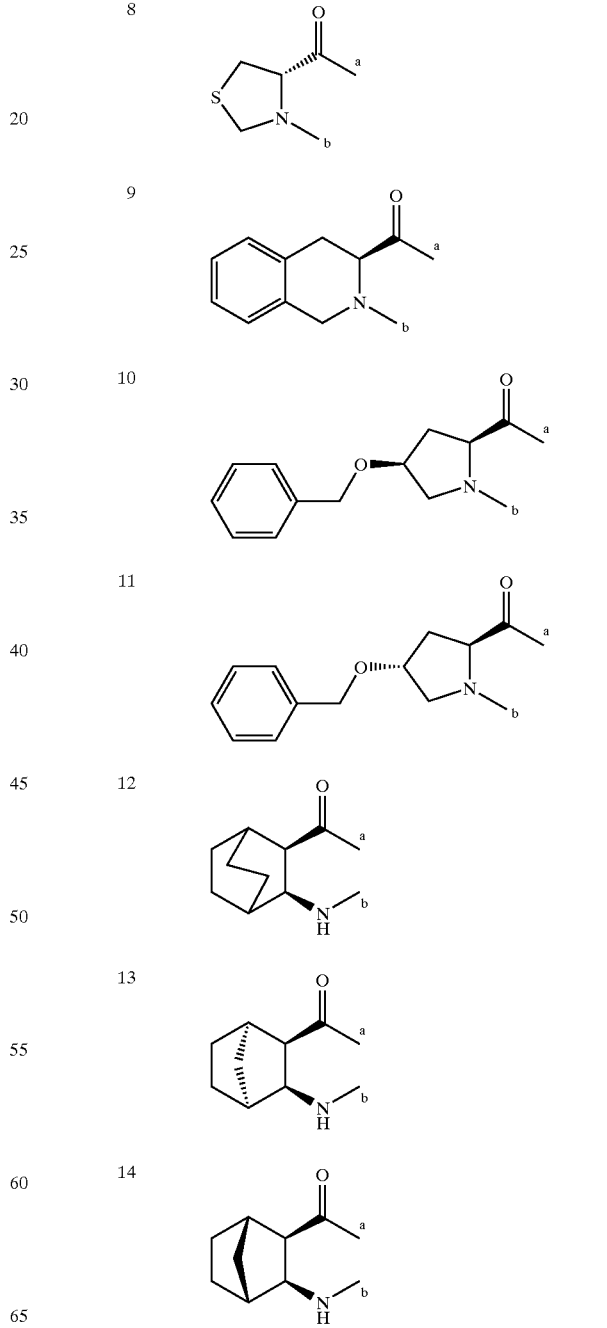 |

TABLE 3-continued
(I-3A-1)
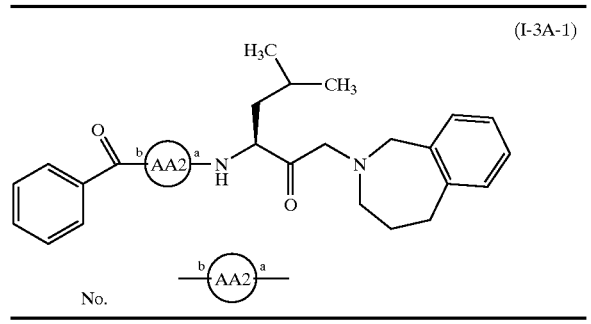
| No. | 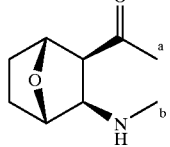 |
|-----|------|
| 15  | 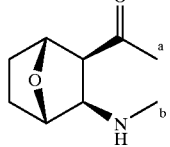 |
| 16  | 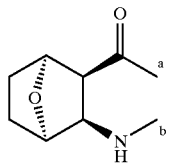 |
| 17  | 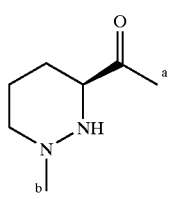 |
| 18  | 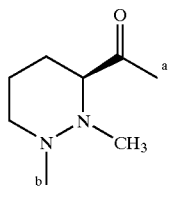 |
TABLE 4
(I-4A-1)
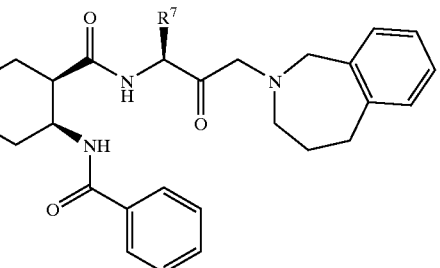
| No. | R[7] |
|-----|------|
| 1   |  |
TABLE 4-continued
(I-4A-1)
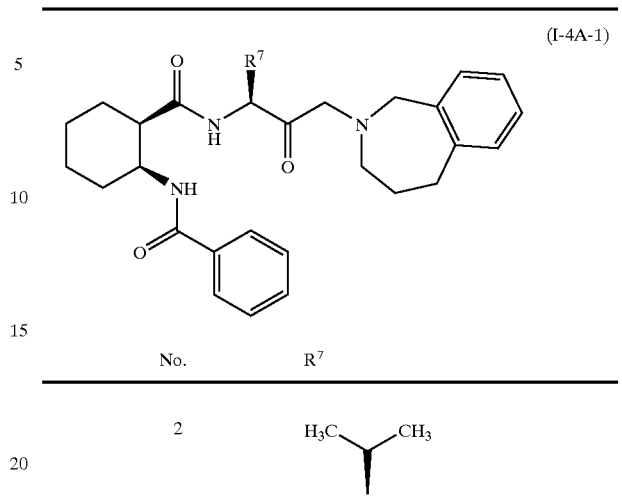
| No. | R[7] |
|-----|------|
| 2   |  |
| 3   |  |
| 4   |  |
| 5   |  |
| 6   |  |
| 7   |  |
| 8   |  |
| 9   |  |
| 10  |  |
| 11  |  |

TABLE 4-continued
(I-4A-1)
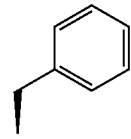
| No. | R⁷ |
|---|---|
| 12 | 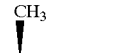 |
| 13 | 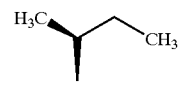 |
| 14 |  |
| 15 | 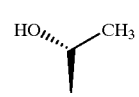 |
| 16 | 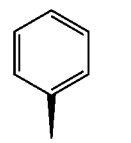 |
| 17 | 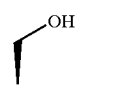 |
| 18 | 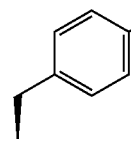 |
| 19 | 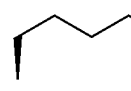 |
| 20 | 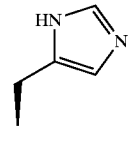 |
| 21 | 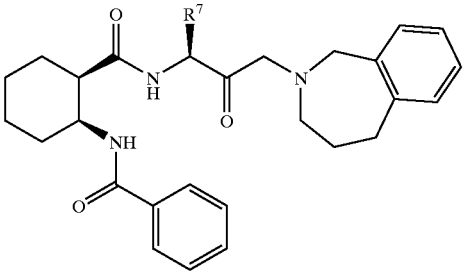 |
TABLE 4-continued
(I-4A-1)
| No. | R⁷ |
|---|---|
| 22 |  |
TABLE 5
(I-5A-1)
| No. | R⁷⁴ |
|---|---|
| 1 | 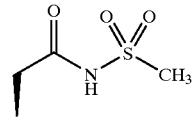 |
| 2 |  |
| 3 | 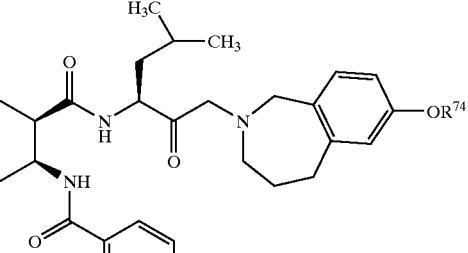 |
| 4 |  |
| 5 |  |

TABLE 5-continued (I-5A-1)

| No. | R⁷⁴ |
|---|---|
| 6 | 2-ethylthiazole |
| 7 | 2-ethyloxazole |
| 8 | 4-ethyltetrahydropyran |
| 9 | propyl-N,N-dimethylamine |
| 10 | propyloxybenzene |
| 11 | butylguanidine |
| 12 | propyl-CN |
| 13 | propanamide (CH₂CH₂C(O)NH₂) |
| 14 | methyl propanoate |
| 15 | ethyl propanoate |
| 16 | butanol |
| 17 | 2-propyl-4,5-dihydroimidazole |
| 18 | butylmorpholine |
| 19 | ethylphosphonic acid |
| 20 | propylaminomethylenebisphosphonic acid |
| 21 | butylpyrrolidine |
| 22 | butyl-N,N-dimethylamine |
| 23 | ethylcyclopropane |

TABLE 6

(I-6A-1)

[Structure of compound I-6A-1: benzyl carbamate-Leu-NH-Leu-CH2-(benzazepine)-OR74]

| No. | R74 |
|-----|-----|
| 1 | –CH2CH2CH2OCH3 |
| 2 | –CH2CH2C(=O)OH |
| 3 | –CH2CH2-(1H-tetrazol-5-yl) |
| 4 | –CH2CH2-(1H-imidazol-2-yl) |
| 5 | –CH2CH2-(1-methylpiperidin-4-yl) |
| 6 | –CH2CH2-(thiazol-2-yl) |
| 7 | –CH2CH2-(oxazol-2-yl) |
| 8 | –CH2CH2-(tetrahydropyran-4-yl) |
| 9 | –CH2CH2CH2N(CH3)2 |
| 10 | –CH2CH2CH2OC6H5 |
| 11 | –CH2CH2CH2CH2NHC(=NH)NH2 |
| 12 | –CH2CH2CH2CN |

TABLE 6-continued
(I-6A-1)
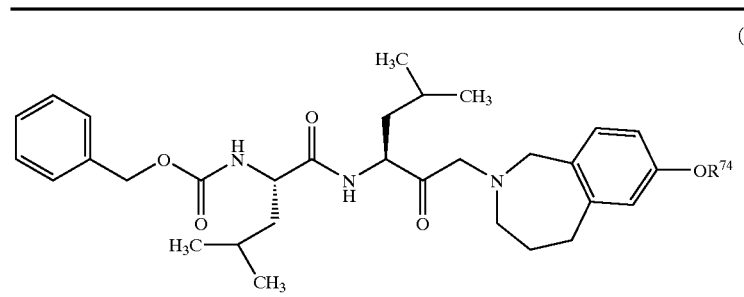
| No. | R⁷⁴ |
|---|---|
| 13 | 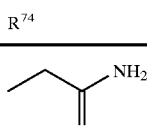 |
| 14 | 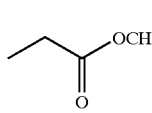 |
| 15 | 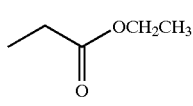 |
| 16 |  |
| 17 | 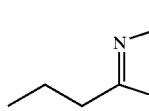 |
| 18 | 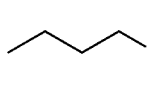 |
| 19 | 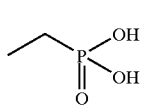 |
| 20 | 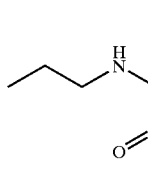 |
| 21 | 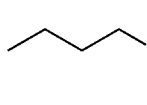 |
| 22 | 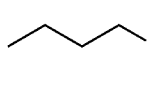 |
| 23 |  |

TABLE 7
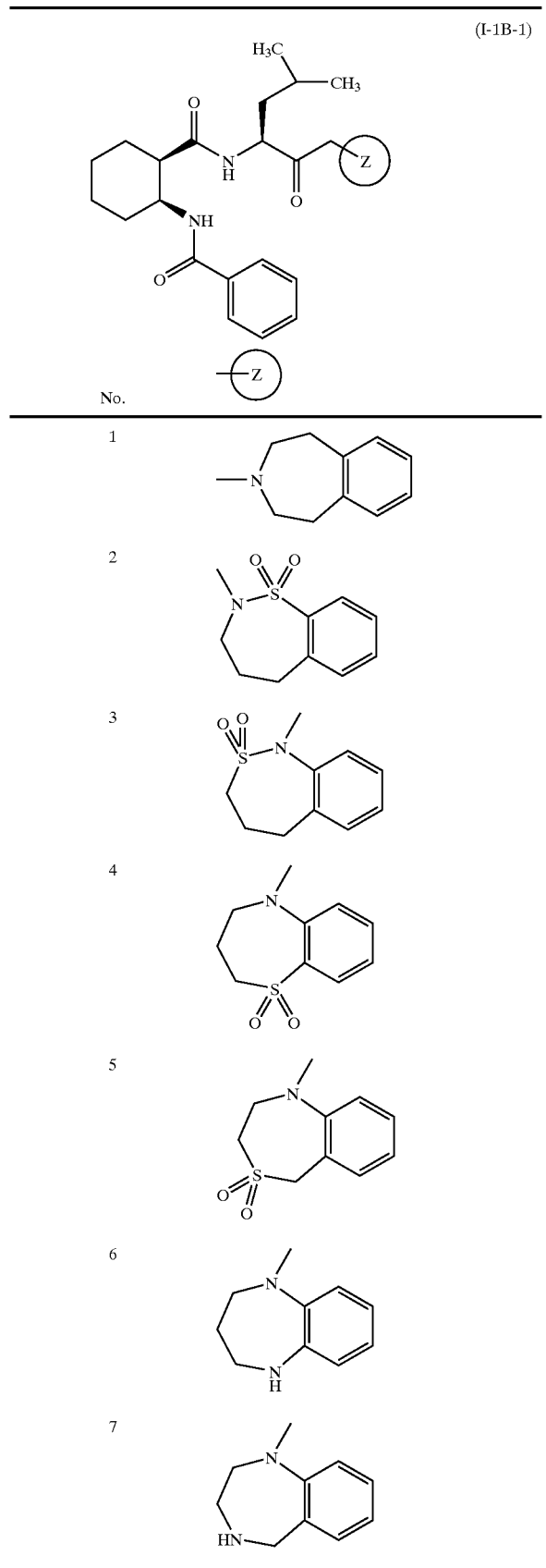
TABLE 7-continued
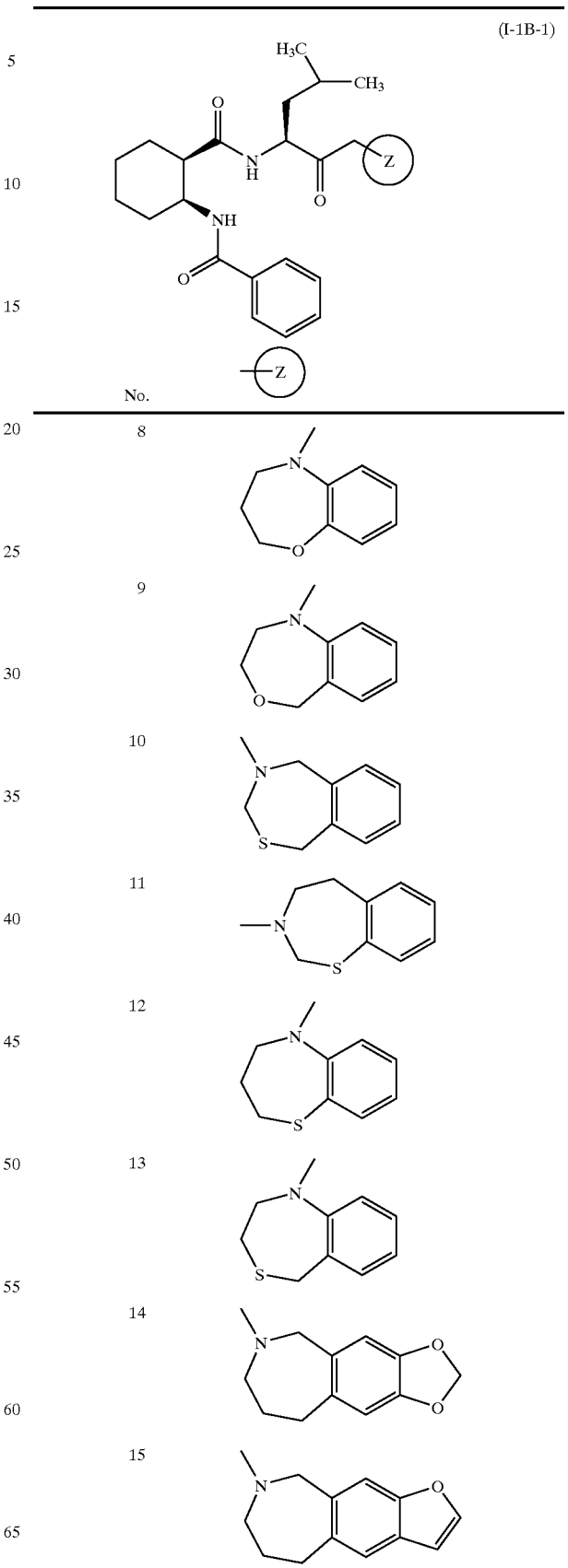

TABLE 7-continued
(I-1B-1)
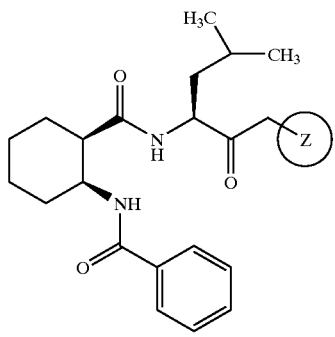
| No. | —Z |
|---|---|
| 16 | 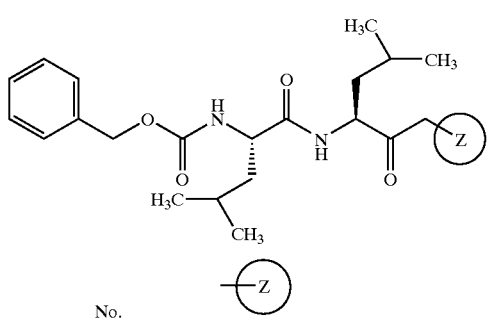 |
| 17 | 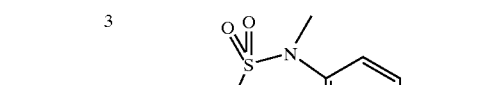 |
| 18 |  |
TABLE 8
(I-2B-1)
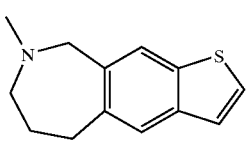
| No. | —Z |
|---|---|
| 1 | 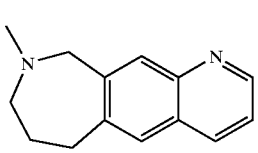 |
| 2 | 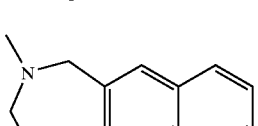 |
TABLE 8-continued
(I-2B-1)
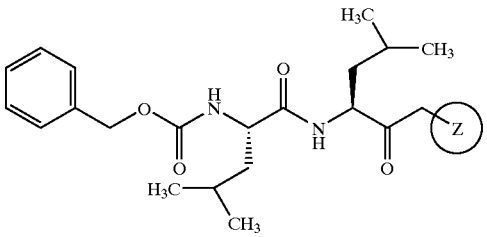
| No. | —Z |
|---|---|
| 3 | 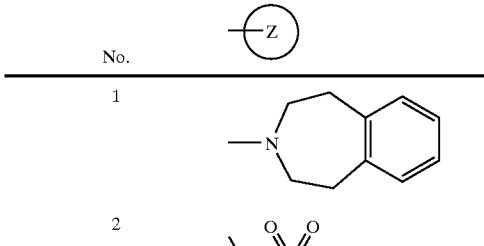 |
| 4 | 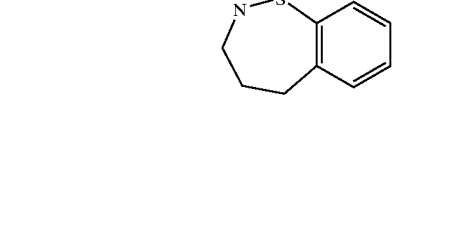 |
| 5 |  |
| 6 | 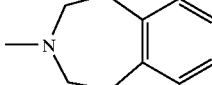 |
| 7 | 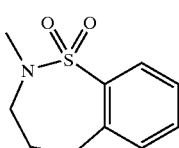 |
| 8 | 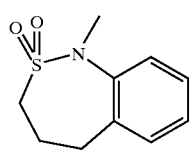 |
| 9 | 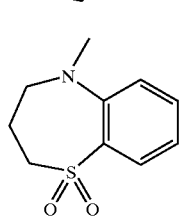 |

TABLE 8-continued
(I-2B-1)
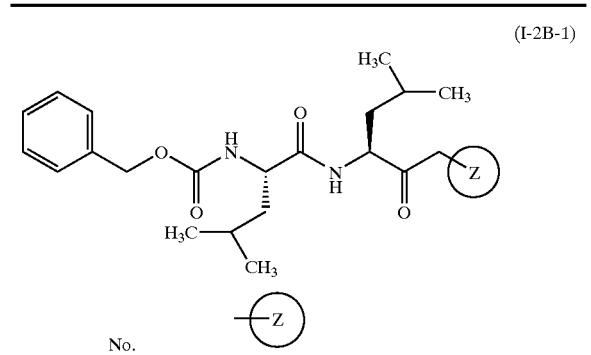
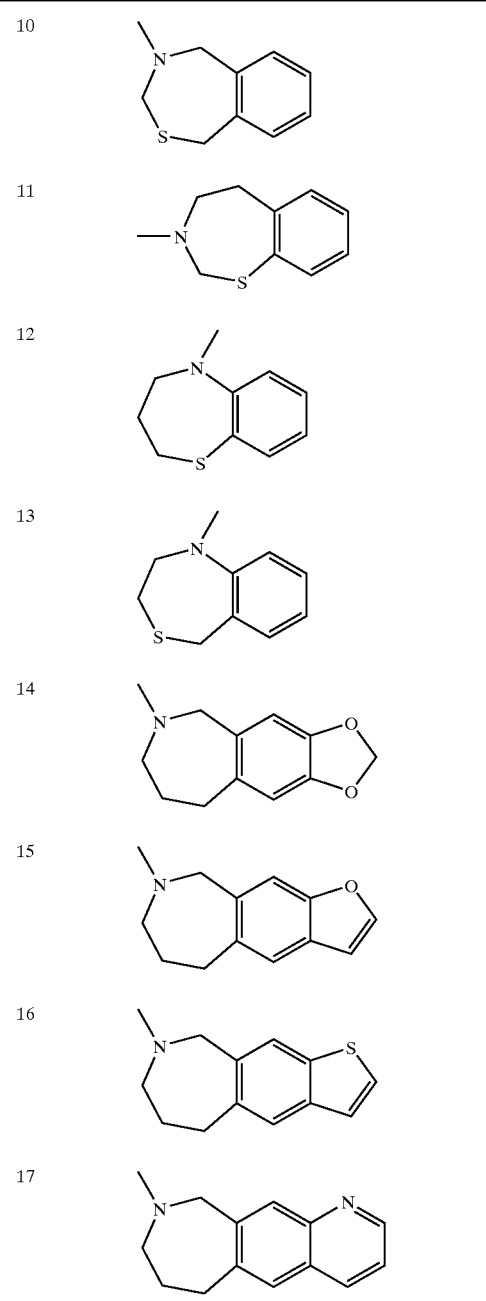
TABLE 8-continued
(I-2B-1)
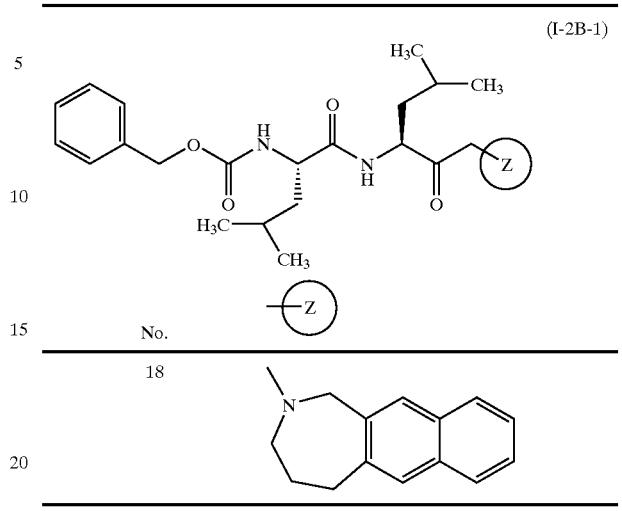
| No. | |
|---|---|
| 18 | (structure) |
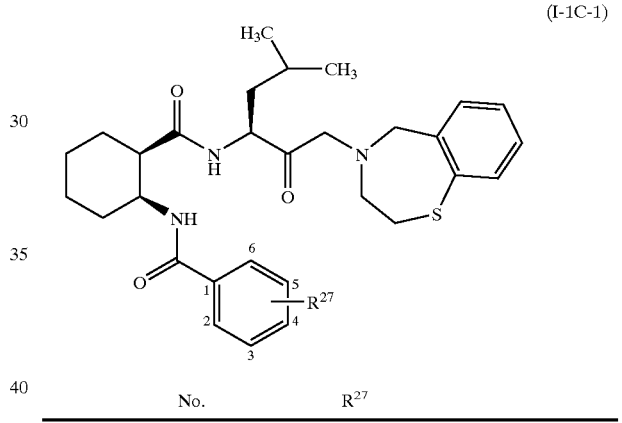
TABLE 9
(I-1C-1)
| No. | R²⁷ |
|---|---|
| 1 | 3-F |
| 2 | 2-CN |
| 3 | 3-CN |
| 4 | 3-NO₂ |
| 5 | 4-NO₂ |
| 6 | 3-CH₃ |
| 7 | 2-CH₂—Cl |
| 8 | 4-CH₂—Cl |
| 9 | 4-CH₂CH₃ |
| 10 | 4-(CH₂)₃CH₃ |
| 11 | 4-N(CH₃)₂ |
| 12 | 4-OCH₂CH₃ |
| 13 | 2,3-di-CH₃ |
| 14 | 3,5-di-F |
| 15 | 3,4-di-F |
| 16 | 2-OCF₃ |
| 17 | 3-OCF₃ |
| 18 | 4-CONH₂ |
| 19 | 3-CONH₂ |
| 20 | 4-COOH |
| 21 | 4-OCH₂COOH |
| 22 | 4-O(CH₂)₅CH₃ |
| 23 | 4-CH₂CH(CH₃)₂ |
| 24 | 3-COOH |
| 25 | 3-OCH₂COOH |
| 26 | 3-O(CH₂)₅CH₃ |
| 27 | 3-CH₂CH(CH₃)₂ |
| 28 | 2-OCH₂COOH |
| 29 | 2-O(CH₂)₅CH₃ |
| 30 | 2-CH₂CH(CH₃)₂ |

TABLE 10
(I-2C-1)
| No. | R[16] |
|---|---|
| 1 | 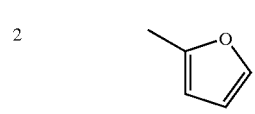 |
| 2 | 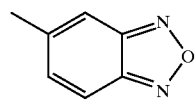 |
| 3 | 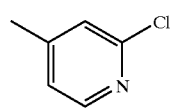 |
| 4 | 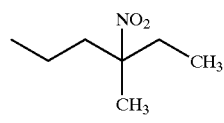 |
| 5 | 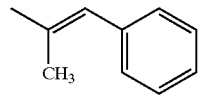 |
| 6 | 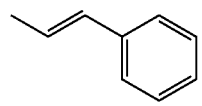 |
| 7 | 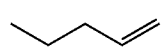 |
| 8 | |
TABLE 10-continued
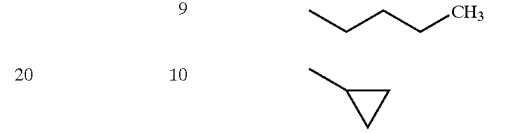
(I-2C-1)
| No. | R[16] |
|---|---|
| 9 |  |
| 10 | 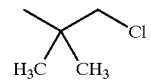 |
| 11 | 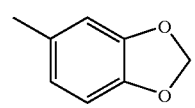 |
| 12 | 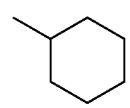 |
| 13 | 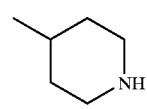 |
| 14 | 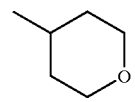 |
| 15 | |
| 16 | 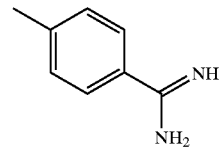 |
| 17 | 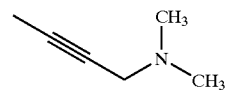 |
| 18 | 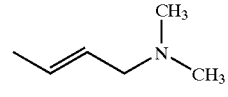 |
| 19 | 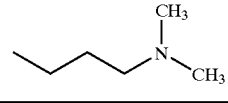 |

TABLE 11
(I-3C-1)
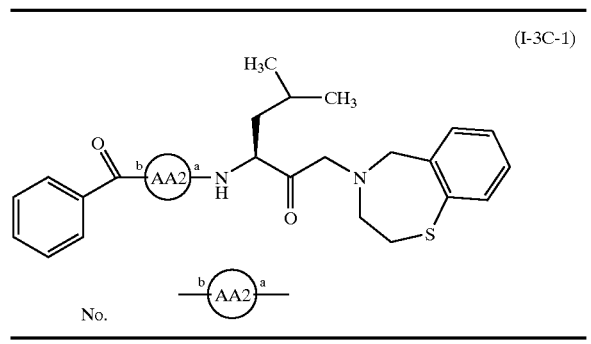
| No. | AA2 |
|---|---|
| 1 | 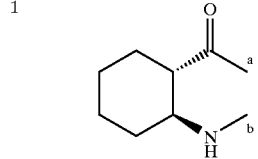 |
| 2 | 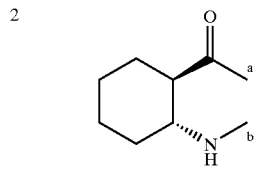 |
| 3 | 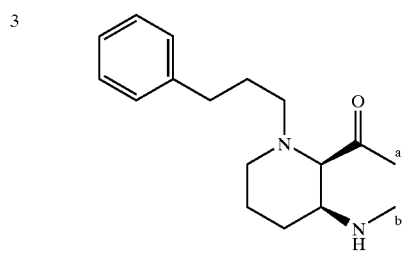 |
| 4 | 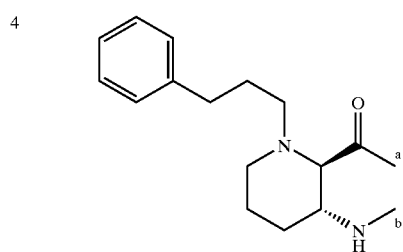 |
| 5 | 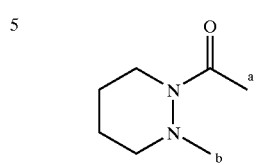 |
| 6 | 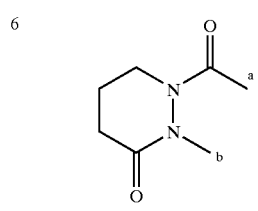 |
TABLE 11-continued
(I-3C-1)
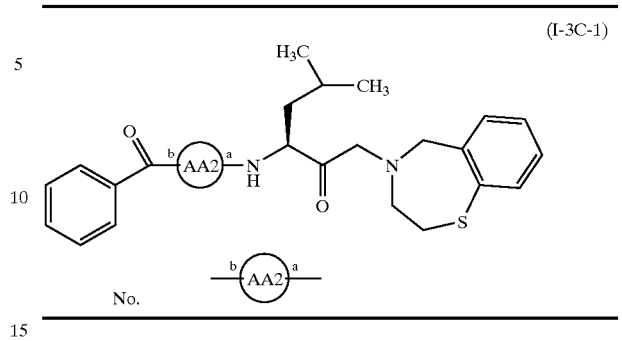
| No. | AA2 |
|---|---|
| 7 | 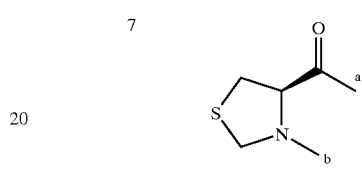 |
| 8 | 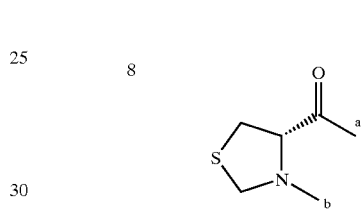 |
| 9 | 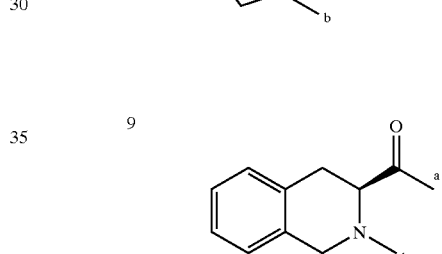 |
| 10 | 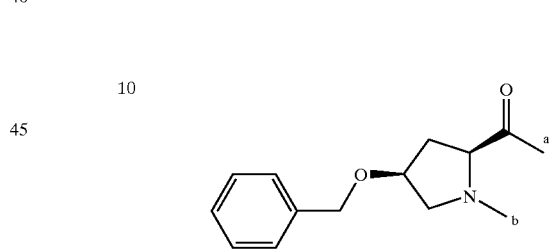 |
| 11 | 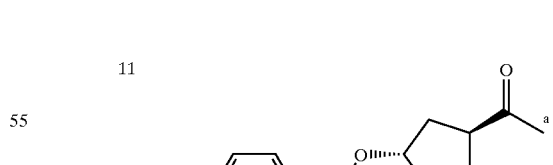 |
| 12 | 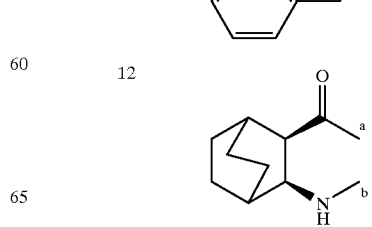 |

TABLE 11-continued (I-3C-1)

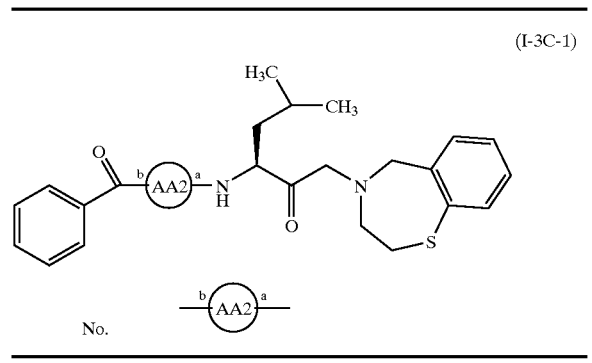

| No. | AA2 |
|---|---|
| 13 | (norbornane with ketone-a and NH-b) |
| 14 | (norbornane with ketone-a and NH-b) |
| 15 | (oxanorbornane with ketone-a and NH-b) |
| 16 | (oxanorbornane with ketone-a and NH-b) |
| 17 | (hexahydropyridazine with ketone-a, NH, N-b) |
| 18 | (hexahydropyridazine with ketone-a, N-CH3, N-b) |

TABLE 12

(I-4C-1)

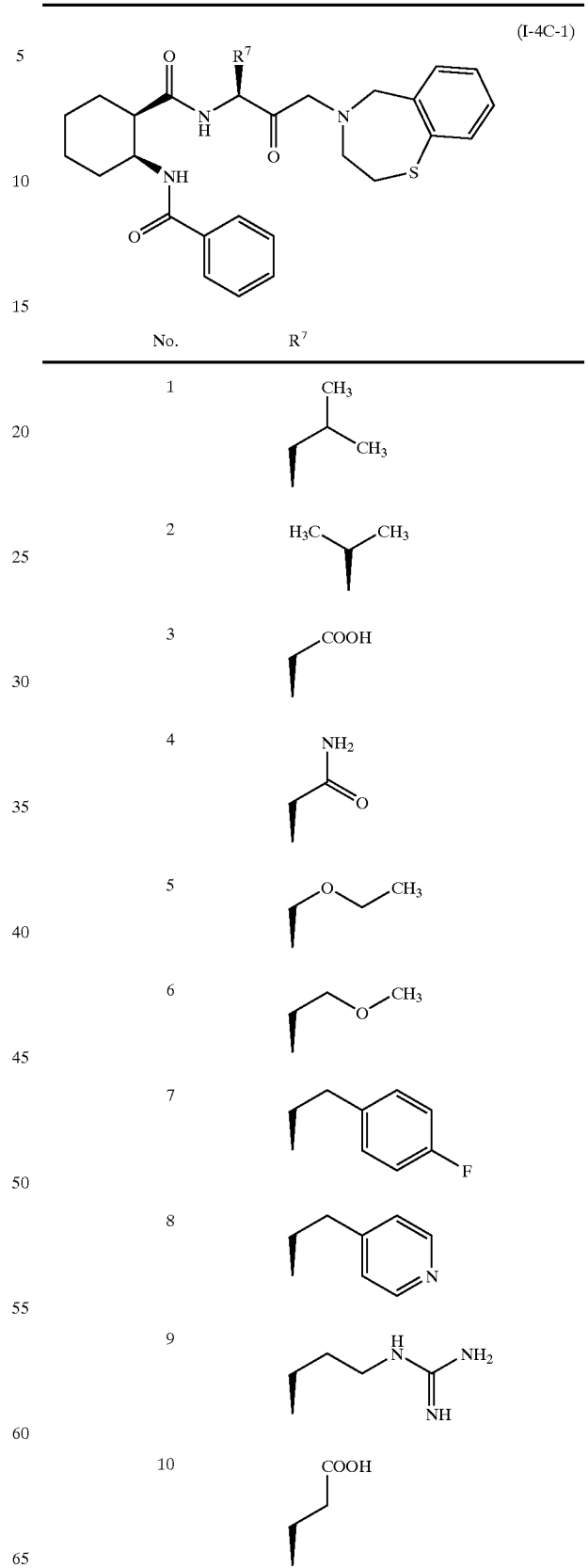

| No. | R⁷ |
|---|---|
| 1 | isobutyl (CH(CH₃)-CH₂CH₃... actually -CH₂-CH(CH₃)-CH₃ sec-butyl type) |
| 2 | isobutyl H₃C-CH(CH₃)- |
| 3 | -CH₂-COOH |
| 4 | -CH₂-C(O)NH₂ |
| 5 | -CH₂-O-CH₂CH₃ |
| 6 | -CH₂CH₂-O-CH₃ |
| 7 | -CH₂-(4-fluorophenyl) |
| 8 | -CH₂CH₂-(4-pyridyl) |
| 9 | -CH₂CH₂CH₂-NH-C(=NH)-NH₂ |
| 10 | -CH₂CH₂CH₂-COOH |

TABLE 12-continued (I-4C-1)

| No. | R⁷ |
|---|---|
| 11 | H₂N-C(=O)-CH₂-CH₂-CH< |
| 12 | benzyl |
| 13 | CH₃- |
| 14 | sec-butyl (H₃C-CH(CH₃)-CH₂-) |
| 15 | H |
| 16 | HO-CH(CH₃)- |
| 17 | phenyl |
| 18 | HO-CH₂- |
| 19 | 4-hydroxybenzyl |
| 20 | H₂N-(CH₂)₄- |
| 21 | (1H-imidazol-5-yl)methyl |
| 22 | -CH₂-C(=O)-NH-S(=O)₂-CH₃ |

TABLE 13

(I-5C-1)

| No. | R⁷⁴ |
|---|---|
| 1 | -CH₂-CH₂-OCH₃ |
| 2 | -CH₂-C(=O)OH |
| 3 | 1H-tetrazol-5-yl-methyl |
| 4 | (1H-imidazol-2-yl)methyl |
| 5 | (1-methylpiperidin-4-yl)methyl |

TABLE 13-continued
(I-5C-1)
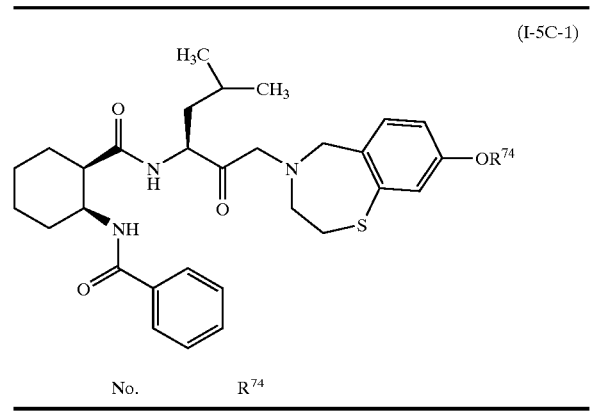
| No. | R74 |
|---|---|
| 6 | 2-ethyl-thiazole |
| 7 | 2-ethyl-oxazole |
| 8 | 4-ethyl-tetrahydropyran |
| 9 | CH2CH2CH2N(CH3)2 |
| 10 | CH2CH2CH2-O-phenyl |
| 11 | CH2CH2CH2CH2-NH-C(=NH)NH2 |
| 12 | CH2CH2CH2CN |
| 13 | CH2CH2C(=O)NH2 |
| 14 | CH2CH2C(=O)OCH3 |
| 15 | CH2CH2C(=O)OCH2CH3 |
| 16 | CH2CH2CH2CH2OH |
| 17 | 2-propyl-4,5-dihydro-imidazole |
| 18 | CH2CH2CH2CH2-morpholine |
| 19 | CH2CH2-P(=O)(OH)2 |
| 20 | CH2CH2CH2-NH-CH(P(=O)(OH)2)2 |
| 21 | CH2CH2CH2CH2-pyrrolidine |
| 22 | CH2CH2CH2CH2N(CH3)2 |
| 23 | CH2CH2-cyclopropyl |
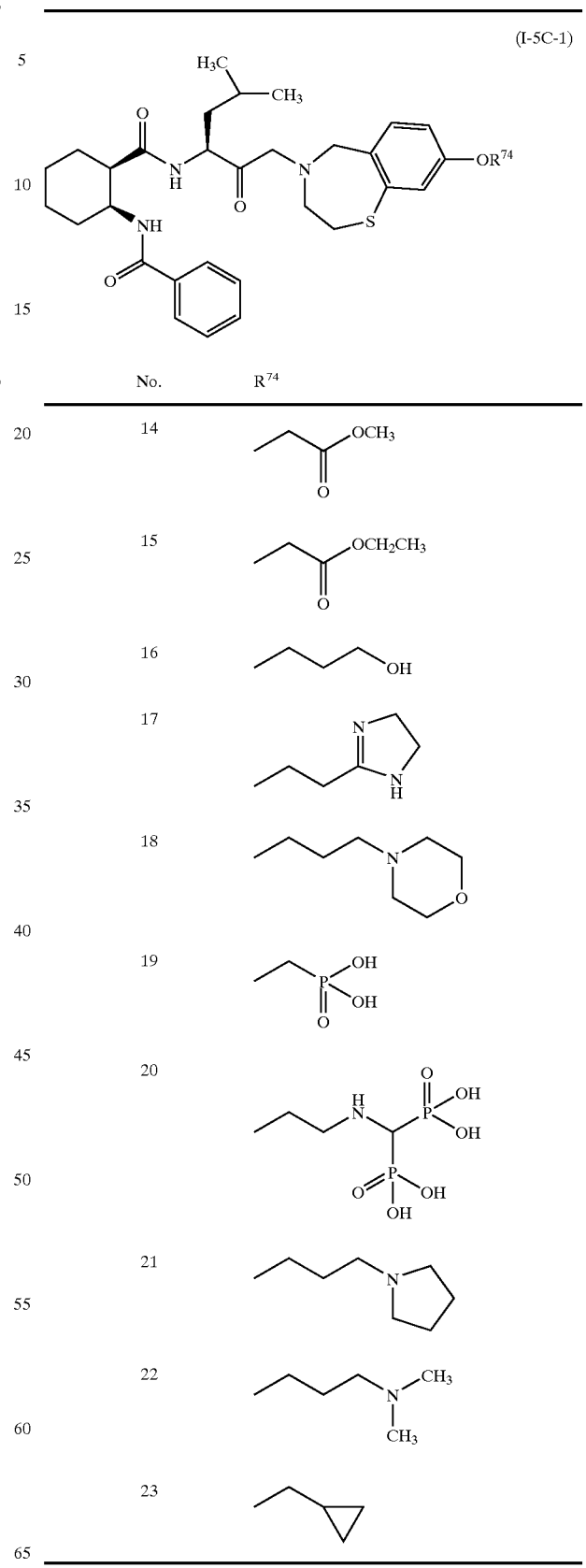

TABLE 14

(I-6C-1)

| No. | R⁷⁴ |
|---|---|
| 1 | ~~~OCH₃ (propyl-OCH₃) |
| 2 | ethyl-C(=O)OH |
| 3 | ethyl-(1H-tetrazol-5-yl) |
| 4 | ethyl-(1H-imidazol-2-yl) |
| 5 | ethyl-(1-methylpiperidin-4-yl) |
| 6 | ethyl-(thiazol-2-yl) |
| 7 | ethyl-(oxazol-2-yl) |
| 8 | ethyl-(tetrahydropyran-4-yl) |
| 9 | propyl-N(CH₃)₂ |
| 10 | propyl-O-phenyl |
| 11 | butyl-NH-C(=NH)NH₂ |
| 12 | propyl-CN |

TABLE 14-continued
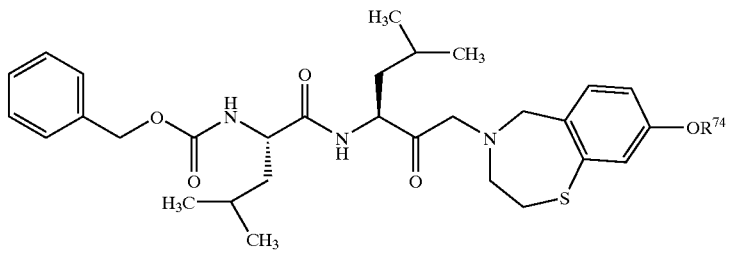
(I-6C-1)
| No. | R[74] |
|---|---|
| 13 | -CH2-C(=O)-NH2 |
| 14 | -CH2-C(=O)-OCH3 |
| 15 | -CH2-C(=O)-OCH2CH3 |
| 16 | -(CH2)3-OH |
| 17 | -CH2-(2-imidazolinyl) |
| 18 | -(CH2)3-morpholino |
| 19 | -CH2-P(=O)(OH)2 |
| 20 | -(CH2)2-NH-CH[P(=O)(OH)2]2 |
| 21 | -(CH2)3-pyrrolidinyl |
| 22 | -(CH2)3-N(CH3)2 |
| 23 | -CH2-cyclopropyl |

TABLE 15

(I-1D-1)

| No. | R83 |
|---|---|
| 1 | propyl-OCH₃ |
| 2 | propanoic acid |
| 3 | ethyl-tetrazole |
| 4 | ethyl-imidazole |
| 5 | ethyl-(N-methylpiperidine) |
| 6 | ethyl-thiazole |
| 7 | ethyl-oxazole |
| 8 | ethyl-tetrahydropyran |
| 9 | propyl-N(CH₃)₂ |
| 10 | propyl-O-phenyl |
| 11 | butyl-NH-C(=NH)-NH₂ |

TABLE 15-continued (I-1D-1)

| No. | R83 |
|---|---|
| 12 | propyl-CN |
| 13 | propanamide |
| 14 | methyl propanoate |
| 15 | ethyl propanoate |
| 16 | butyl-OH |
| 17 | propyl-imidazoline |
| 18 | butyl-morpholine |
| 19 | ethyl-P(=O)(OH)₂ |
| 20 | ethylidene-bis(phosphonic acid) |
| 21 | butyl-pyrrolidine |
| 22 | butyl-N(CH₃)₂ |

TABLE 15-continued (I-1D-1)

| No. | R<sup>83</sup> |
|---|---|
| 23 | ethylcyclopropyl |

TABLE 16

(1-2D-1)

| No. | R<sup>83</sup> |
|---|---|
| 1 | propyl-OCH₃ |
| 2 | propanoic acid |
| 3 | ethyl-tetrazole |
| 4 | ethyl-imidazole |
| 5 | ethyl-(N-methylpiperidine) |
| 6 | ethyl-thiazole |
| 7 | ethyl-oxazole |

TABLE 16-continued (1-2D-1)

| No. | R<sup>83</sup> |
|---|---|
| 8 | ethyl-tetrahydropyran |
| 9 | propyl-N(CH₃)₂ |
| 10 | propyl-O-phenyl |
| 11 | butyl-NH-C(=NH)NH₂ |
| 12 | butyl-CN |
| 13 | propanamide |
| 14 | methyl propanoate |
| 15 | ethyl propanoate |
| 16 | butyl-OH |
| 17 | propyl-imidazoline |
| 18 | butyl-morpholine |
| 19 | ethyl-P(=O)(OH)₂ |

TABLE 16-continued (1-2D-1)

| No. | R$^{83}$ |
|---|---|
| 20 | (ethylidenebisphosphonic acid structure) |
| 21 | (butylpyrrolidine structure) |
| 22 | (N,N-dimethylbutylamine structure) |
| 23 | (ethylcyclopropane structure) |

TABLE 17

(I-7A-1)

| No. | R$^{27}$ |
|---|---|
| 1 | 3-F |
| 2 | 2-CN |
| 3 | 3-CN |
| 4 | 3-NO$_2$ |
| 5 | 4-NO$_2$ |
| 6 | 3-CH$_3$ |
| 7 | 2-CH$_2$—Cl |
| 8 | 4-CH$_2$—Cl |
| 9 | 4-CH$_2$CH$_3$ |
| 10 | 4-(CH$_2$)$_3$CH$_3$ |
| 11 | 4-N(CH$_3$)$_2$ |
| 12 | 4-OCH$_2$CH$_3$ |
| 13 | 2,3-di-CH$_3$ |
| 14 | 3,5-di-F |
| 15 | 3,4-di-F |
| 16 | 2-OCF$_3$ |
| 17 | 3-OCF$_3$ |
| 18 | 4-CONH$_2$ |
| 19 | 3-CONH$_2$ |
| 20 | 4-COOH |
| 21 | 4-OCH$_2$COOH |
| 22 | 4-O(CH$_2$)$_5$CH$_3$ |

TABLE 17-continued (I-7A-1)

| No. | R$^{27}$ |
|---|---|
| 23 | 4-CH$_2$CH(CH$_3$)$_2$ |
| 24 | 3-COOH |
| 25 | 3-OCH$_2$COOH |
| 26 | 3-O(CH$_2$)$_5$CH$_3$ |
| 27 | 3-CH$_2$CH(CH$_3$)$_2$ |
| 28 | 2-OCH$_2$COOH |
| 29 | 2-O(CH$_2$)$_5$CH$_3$ |
| 30 | 2-CH$_2$CH(CH$_3$)$_2$ |

TABLE 18

(I-8A-1)

| No. | R$^{16}$ |
|---|---|
| 1 | (3-methylpyridine structure) |
| 2 | (2-methylfuran structure) |
| 3 | (methylbenzofurazan structure) |
| 4 | (4-methyl-2-chloropyridine structure) |
| 5 | (2-ethyl-2-nitropentane structure with CH$_3$ groups) |
| 6 | (β-methylstyrene structure) |

TABLE 18-continued (I-8A-1)

[Structure: R16-C(=O)-NH-C(cyclohexyl)-C(=O)-NH-CH(CH2CH(CH3)2)-C(=O)-CH2-N(benzazepine)]

| No. | R16 |
|---|---|
| 7 | cinnamyl (CH=CH-phenyl) |
| 8 | CH2-CH2-CH=CH2 (but-3-enyl) |
| 9 | n-pentyl |
| 10 | cyclopropyl-CH2 |
| 11 | CH2-C(CH3)2-CH2Cl |
| 12 | methylenedioxyphenyl-CH2 |
| 13 | cyclohexyl-CH2 |
| 14 | 4-piperidinyl-CH2 |
| 15 | 4-tetrahydropyranyl-CH2 |
| 16 | 4-amidinophenyl-CH2 |
| 17 | CH2-C≡C-CH2-N(CH3)2 |
| 18 | CH2-CH=CH-CH2-N(CH3)2 |

TABLE 18-continued (I-8A-1)

[Same structure as above]

| No. | R16 |
|---|---|
| 19 | CH2CH2CH2CH2-N(CH3)2 |

TABLE 19

(I-9A-1)

[Structure: Ph-C(=O)-NH-C(cyclohexyl)-C(=O)-NH-CH(R7)-C(=O)-CH2-N(benzazepine)]

| No. | R7 |
|---|---|
| 1 | CH2-CH(CH3)-CH3 (isobutyl) |
| 2 | CH(CH3)2 methyl branch (isopropyl-CH2) |
| 3 | CH2-COOH |
| 4 | CH2-C(=O)-NH2 |
| 5 | CH2-O-CH2CH3 |
| 6 | CH2-CH2-O-CH3 |
| 7 | CH2-(4-fluorophenyl) |
| 8 | CH2-(4-pyridyl) |

TABLE 19-continued
(I-9A-1)
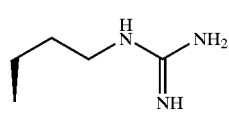
| No. | R⁷ |
|---|---|
| 9 | 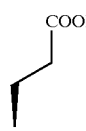 |
| 10 | 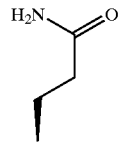 |
| 11 | 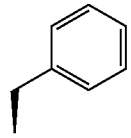 |
| 12 |  |
| 13 | 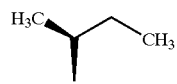 |
| 14 |  |
| 15 | 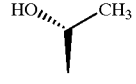 |
| 16 |  |
| 17 |  |
| 18 | 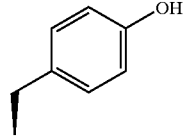 |
| 19 | 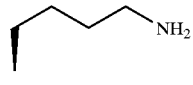 |
| 20 | 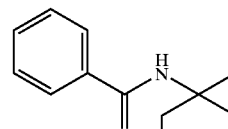 |
TABLE 19-continued
(I-9A-1)
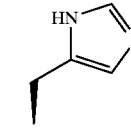
| No. | R⁷ |
|---|---|
| 21 | 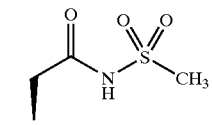 |
| 22 | 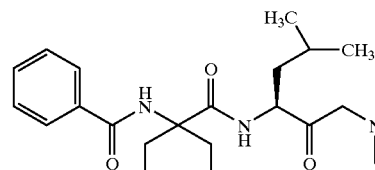 |
TABLE 20
(I-10A-1)
| No. | R⁷⁴ |
|---|---|
| 1 | 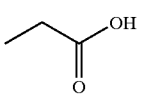 |
| 2 | 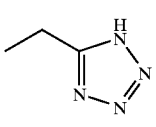 |
| 3 | 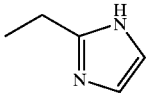 |
| 4 | 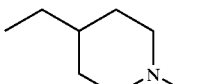 |
| 5 | 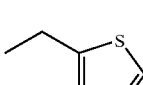 |
| 6 | 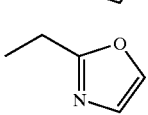 |
| 7 | |

TABLE 20-continued
(I-10A-1)
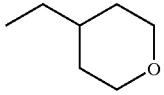
| No. | R74 |
|---|---|
| 8 | 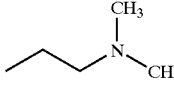 |
| 9 | 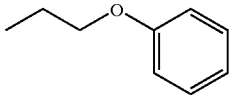 |
| 10 | 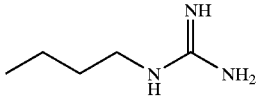 |
| 11 | 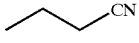 |
| 12 | 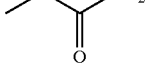 |
| 13 |  |
| 14 | 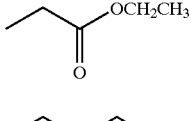 |
| 15 |  |
| 16 | 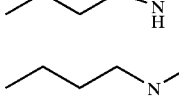 |
| 17 | 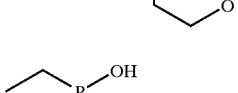 |
| 18 | 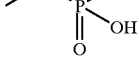 |
| 19 | 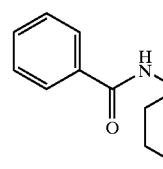 |
TABLE 20-continued
(I-10A-1)
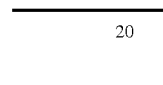
| No. | R74 |
|---|---|
| 20 |  |
| 21 |  |
| 22 | 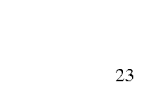 |
| 23 | 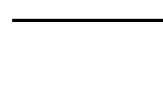 |
TABLE 21
(I-3B-1)
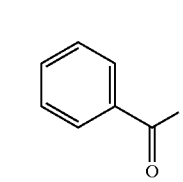
| No. | —Z |
|---|---|
| 1 | 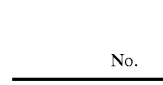 |
| 2 | 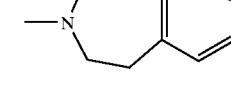 |
| 3 | 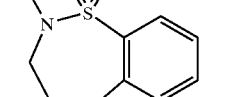 |

TABLE 21-continued
(I-3B-1)
| No. | |
|---|---|
| 4 | 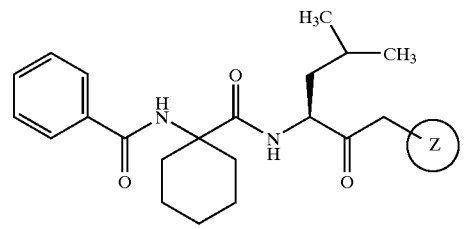 |
| 5 | 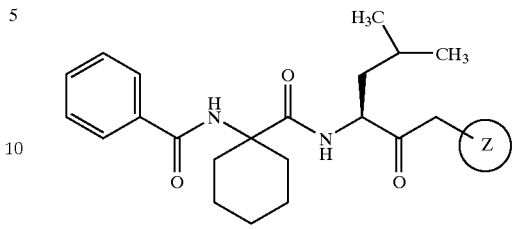 |
| 6 | 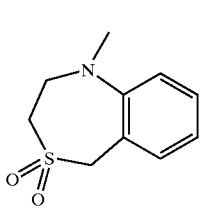 |
| 7 | 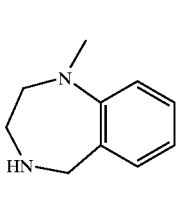 |
| 8 | 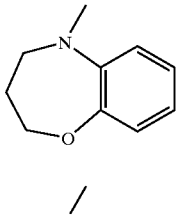 |
| 9 | 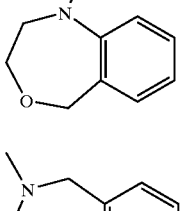 |
| 10 | 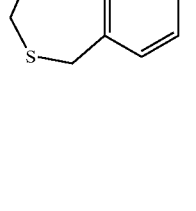 |
TABLE 21-continued
(I-3B-1)
| No. | |
|---|---|
| 11 | 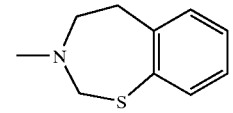 |
| 12 | 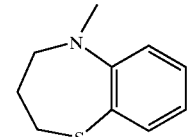 |
| 13 | 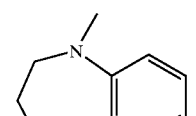 |
| 14 | 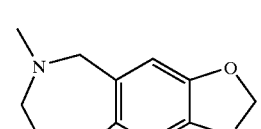 |
| 15 | 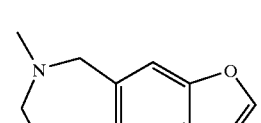 |
| 16 | 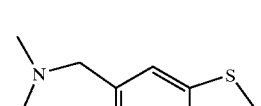 |
| 17 | 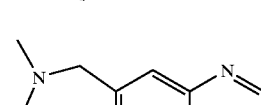 |
| 18 | 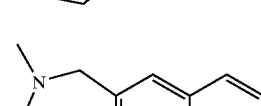 |

TABLE 22

(I-7C-1)

| No. | R²⁷ |
|---|---|
| 1 | 3-F |
| 2 | 2-CN |
| 3 | 3-CN |
| 4 | 3-NO₂ |
| 5 | 4-NO₂ |
| 6 | 3-CH₃ |
| 7 | 2-CH₂—Cl |
| 8 | 4-CH₂—Cl |
| 9 | 4-CH₂CH₃ |
| 10 | 4-(CH₂)₃CH₃ |
| 11 | 4-N(CH₃)₂ |
| 12 | 4-OCH₂CH₃ |
| 13 | 2,3-di-CH₃ |
| 14 | 3,5-di-F |
| 15 | 3,4-di-F |
| 16 | 2-OCF₃ |
| 17 | 3-OCF₃ |
| 18 | 4-CONH₂ |
| 19 | 3-CONH₂ |
| 20 | 4-COOH |
| 21 | 4-OCH₂COOH |
| 22 | 4-O(CH₂)₅CH₃ |
| 23 | 4-CH₂CH(CH₃)₂ |
| 24 | 3-COOH |
| 25 | 3-OCH₂COOH |
| 26 | 3-O(CH₂)₅CH₃ |
| 27 | 3-CH₂CH(CH₃)₂ |
| 28 | 2-OCH₂COOH |
| 29 | 2-O(CH₂)₅CH₃ |
| 30 | 2-CH₂CH(CH₃)₂ |

TABLE 23

(I-8C-1)

| No. | R¹⁶ |
|---|---|
| 1 | 3-pyridyl |
| 2 | 2-furyl |
| 3 | benzofurazanyl |
| 4 | 2-chloro-4-methylpyridinyl |
| 5 | 3-nitro-3-methylhexyl |
| 6 | 2-methyl-2-phenylethenyl |
| 7 | 2-phenylethenyl |
| 8 | pent-4-enyl |
| 9 | pentyl |
| 10 | cyclopropyl |
| 11 | 3-chloro-2,2-dimethylpropyl |
| 12 | 1,3-benzodioxolyl |
| 13 | cyclohexyl |
| 14 | 4-piperidinyl |
| 15 | tetrahydropyranyl |

TABLE 23-continued (I-8C-1)

[Structure: R¹⁶-C(=O)-NH-C(cyclohexyl)(C(=O)-NH-CH(CH₂CH(CH₃)₂)-C(=O)-CH₂-N(benzothiazepine))]

| No. | R¹⁶ |
|---|---|
| 16 | 4-(H₂N-C(=NH)-)-C₆H₄- |
| 17 | (CH₃)₂N-CH₂-C≡C- |
| 18 | (CH₃)₂N-CH₂-CH=CH- |
| 19 | (CH₃)₂N-CH₂-CH₂-CH₂- |

TABLE 24

(I-9C-1)

[Structure: Ph-C(=O)-NH-C(cyclohexyl)(C(=O)-NH-CH(R⁷)-C(=O)-CH₂-N(benzothiazepine))]

| No. | R⁷ |
|---|---|
| 1 | -CH₂-CH(CH₃)₂ (isobutyl) |
| 2 | -CH(CH₃)₂ |
| 3 | -CH₂-COOH |
| 4 | -CH₂-C(=O)-NH₂ |
| 5 | -CH₂-O-CH₂CH₃ |
| 6 | -CH₂-CH₂-O-CH₃ |
| 7 | -CH₂-(4-F-C₆H₄) |
| 8 | -CH₂-(4-pyridyl) |
| 9 | -CH₂-CH₂-CH₂-NH-C(=NH)-NH₂ |
| 10 | -CH₂-CH₂-COOH |
| 11 | -CH₂-CH₂-C(=O)-NH₂ |
| 12 | -CH₂-C₆H₅ |
| 13 | -CH₃ |
| 14 | -CH(CH₃)-CH₂-CH₃ |
| 15 | -H |
| 16 | -CH(OH)-CH₃ |

TABLE 24-continued
(I-9C-1)
| No. | R⁷ |
|---|---|
| 17 |  |
| 18 | 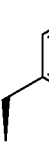 |
| 19 |  |
| 20 | 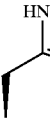 |
| 21 | 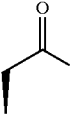 |
| 22 |  |
TABLE 25
(I-10C-1)
| No. | R⁷⁴ |
|---|---|
| 1 |  |
| 2 |  |
| 3 |  |
TABLE 25-continued
(I-10C-1)
| No. | R⁷⁴ |
|---|---|
| 4 |  |
| 5 |  |
| 6 |  |
| 7 |  |
| 8 |  |
| 9 |  |
| 10 |  |
| 11 |  |
| 12 |  |
| 13 |  |
| 14 |  |
| 15 | |
| 16 | |

TABLE 25-continued (I-10C-1)

| No. | R[74] |
|---|---|
| 17 | 2-imidazoline-CH2CH2- |
| 18 | morpholine-N-(CH2)3- |
| 19 | HO-P(=O)(OH)-CH2CH2- |
| 20 | [HO-P(=O)(OH)]2CH-CH(CH3)- (bisphosphonate) |
| 21 | pyrrolidine-N-(CH2)3- |
| 22 | (CH3)2N-(CH2)3- |
| 23 | cyclopropyl-CH2- |

TABLE 26

(I-3D-1)

| No. | R[83] |
|---|---|
| 1 | CH3O-(CH2)2- |
| 2 | HOOC-CH2- |
| 3 | 5-ethyl-tetrazole |
| 4 | 2-ethyl-1H-imidazole |
| 5 | 1-methyl-4-ethyl-piperidine |
| 6 | 2-ethyl-thiazole |
| 7 | 2-ethyl-oxazole |
| 8 | 4-ethyl-tetrahydropyran |
| 9 | (CH3)2N-(CH2)3- |
| 10 | PhO-(CH2)3- |
| 11 | H2N-C(=NH)-NH-(CH2)4- |
| 12 | NC-(CH2)3- |
| 13 | H2N-C(=O)-CH2CH2- |

TABLE 26-continued (I-3D-1)

| No. | R<sup>83</sup> |
|---|---|
| 14 | -CH₂CH₂C(O)OCH₃ |
| 15 | -CH₂CH₂C(O)OCH₂CH₃ |
| 16 | -CH₂CH₂CH₂CH₂OH |
| 17 | -CH₂CH₂-(2-imidazolinyl) |
| 18 | -CH₂CH₂CH₂-(4-morpholinyl) |
| 19 | -CH₂CH₂P(O)(OH)₂ |
| 20 | -CH₂CH(P(O)(OH)₂)(P(O)(OH)₂) |
| 21 | -CH₂CH₂CH₂CH₂-(1-pyrrolidinyl) |
| 22 | -CH₂CH₂CH₂CH₂N(CH₃)₂ |
| 23 | -CH₂-cyclopropyl |

TABLE 27

(I-7A-2)

| No. | R²⁷ |
|---|---|
| 1 | 2-CH₂N(CH₃)₂ |
| 2 | 3-CH₂N(CH₃)₂ |
| 3 | 4-CH₂N(CH₃)₂ |
| 4 | 2-CH₂-(1-pyrrolidinyl) |
| 5 | 3-CH₂-(1-pyrrolidinyl) |
| 6 | 4-CH₂-(1-pyrrolidinyl) |
| 7 | 2-CH₂-(4-morpholinyl) |
| 8 | 3-CH₂-(4-morpholinyl) |
| 9 | 4-CH₂-(4-morpholinyl) |

TABLE 28

(I-7C-2)

| No. | R²⁷ |
|---|---|
| 1 | 2-CH₂N(CH₃)₂ |
| 2 | 3-CH₂N(CH₃)₂ |
| 3 | 4-CH₂N(CH₃)₂ |
| 4 | 2-CH₂-(1-pyrrolidinyl) |

TABLE 28-continued
(I-7C-2)
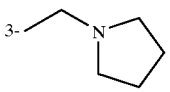
| No. | R²⁷ |
|---|---|
| 5 | 3-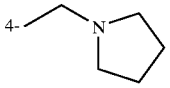 |
| 6 | 4-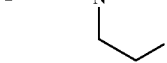 |
| 7 | 2-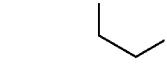 |
| 8 | 3-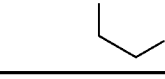 |
| 9 | 4-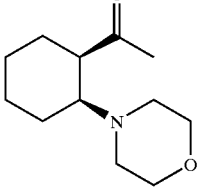 |
TABLE 29
(I-11A-1)
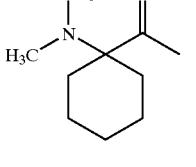
| No. | R-AA1-AA2 |
|---|---|
| 1 | 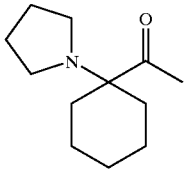 |
| 2 | 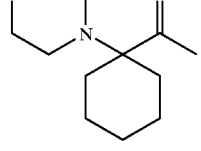 |
| 3 | 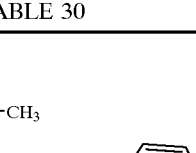 |
| 4 | 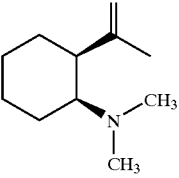 |
| 5 | 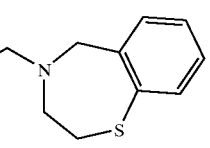 |
| 6 | 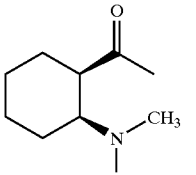 |
TABLE 30
(I-11C-1)
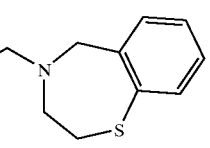
| No. | R-AA1-AA2 |
|---|---|
| 1 | 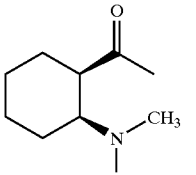 |

TABLE 30-continued

| No. | R-AA1-AA2 |
|---|---|
| (I-11C-1) | (structure shown) |
| 2 | (structure: cyclohexane with ketone and pyrrolidine) |
| 3 | (structure: cyclohexane with ketone and morpholine) |
| 4 | (structure: cyclohexane with N(CH3)2 and ketone) |
| 5 | (structure: cyclohexane with pyrrolidine and ketone) |
| 6 | (structure: cyclohexane with morpholine and ketone) |

The Methods for the Preparation of the Compound of the Present Invention (1) Among the compounds of formula (I), the compound wherein AA and AA² represent a single bond at the same time, none of R, $R^7$, $R^8$, $R^{10}$ or

Contains carboxy, hydroxy, amino, thiol, guanidino, amidino or phosphono, and R does not represent hydrogen, i.e. the compound of formula (IA)

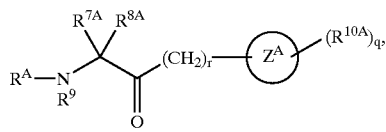

(IA)

wherein $R^A$, $R^{7A}$, $R^{8A}$ and $R^{10A}$ and

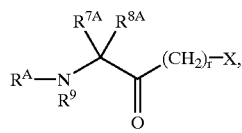

have the same meanings as R, $R^7$, $R^8$, $R^{10}$ and (Z)

respectively, with proviso that none of them contains carboxy, hydroxy, amino, thiol, guanidino, amidino or phosphono and $R^A$ does not represent hydrogen, may be prepared by subjecting to a reaction a compound of formula (IIA)

(IIA)

$$R^A-N(R^9)-C(R^{7A})(R^{8A})-C(O)-(CH_2)_r-X,$$

wherein X is halogen atom or a leaving group such as mesyl and tosyl and the other symbols have the same meanings as above, and a compound of formula (IIB)

(IIB)

$$H-Z^A-(R^{10A})_q,$$

wherein all symbols have the same meanings as above. The reaction of the compound of formula (IIA) and the compound of formula (IIB) is, for example, carried out in an organic solvent (dimethylformamide, acetonitrile, etc.) in the presence or absence of a tertiary amine (triethylamine, N-methylmorpholine, diisopropylethylamine, etc.), a base (sodium hydride etc.), an alkali (potassium carbonate, sodium carbonate, etc.) or fluoride (sodium fluoride, potassium fluoride, cesium fluoride, etc.) at a temperature of 20 to 40° C.

[2] Among the compounds of formula (I), wherein $AA^1$ and $AA^2$ are a single bond at the same time, R is hydrogen and none of $R^7$, $R^8$, $R^{10}$ and (Z)

contains carboxy, hydroxy, amino, thiol, guanidino, amidino, phosphono, i.e. the compound of formula (IB)

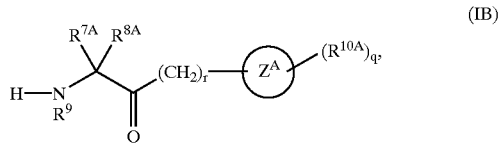

(IB)

wherein all symbols have the same meanings as above, may be prepared by subjecting to a deprotection reaction the compound, among the compounds of formula (IA), wherein $R^A$ is a protective group of amino, i.e. the compound of formula (IA-1)

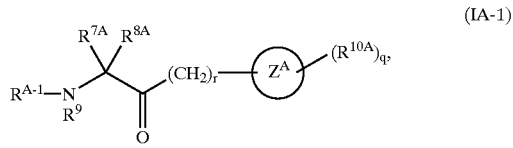

(IA-1)

wherein $R^{A-1}$ is a protective group of amino and the other symbols have the same meanings as above.

As protective groups for amino group, for example, benzyloxycarbonyl, t-butoxycarbonyl, trifluoroacetyl, 9-fluorenylmethoxycarbonyl may be included, but other groups that can be easily and selectively eliminated may also be used instead. For example, the groups described in T. W. Greene, Protective Groups in Organic Synthesis, Wiley, New York, 1991 may be used.

Deprotection reaction for protective groups of amino group is known, for example,
1) deprotection reaction under alkaline conditions,
2) deprotection reaction under acidic conditions,
3) deprotection reaction by hydration, etc. may be included.
To explain these methods concretely,
1) deprotection reaction under alkaline conditions is carried out, for example, in an organic solvent (methanol, tetrahydrofuran, dioxane, dimethylformamide, etc.) using a hydroxide of alkali metals (sodium hydroxide, potassium hydroxide, lithium hydroxide, etc.), hydroxide of alkaline earth metals (barium hydroxide, calcium hydroxide, etc.), organic amine (triethylamine, N-methylmorpholine, diisopropylethylamine, piperidine, etc.) or a quaternary ammonium salt (tetrabutyl ammonium fluoride etc.) or a solution thereof or a mixture thereof at a temperature of 0 to 40° C.;
2) deprotection reaction under acidic conditions is carried out, for example, in an organic solvent (methylene chloride, chloroform, dioxane, ethyl acetate, anisole, etc.), using organic acid (acetic acid, trifluoroacetic acid, methanesulfonic acid, etc.) or inorganic acid (hydrochloric acid, sulfuric acid, etc.) or a mixture thereof (hydrobromic acid/acetic acid, etc.) at a temperature of 0 to 100° C.;
3) deprotection reaction by hydration is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitriles such as acetonitrile, amides such as dimethylformamide, water, ethyl acetate, acetic acid or a mixture of more than two from above, etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature of 0 to 200° C.

As easily understood by those skilled in the art, the compounds of the present invention may be easily prepared by selecting these reactions.

[3] Among the compounds of formula (I), wherein $AA^1$ and $AA^2$ are a single bond at the same time, and at least one of R, $R^7$, $R^8$, $R^{10}$ or

contains carboxy, hydroxy, amino, thiol, guanidino, amidino, phosphono or R is hydrogen, i.e. the compound of formula (IC)

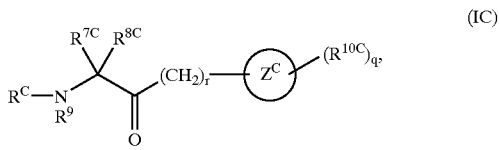

(IC)

wherein $R^C$, $R^{7C}$, $R^{8C}$, $R^{10C}$ and

have the same meanings as R, $R^7$, $R^8$, $R^{10}$ and

respectively, with proviso that at least one contains carboxy, hydroxy, amino, thiol, guanidino, amidino, phosphono or R is hydrogen, may be prepared by subjecting to deprotection reaction of protective groups of carboxy, hydroxy, amino, thiol, guanidino, amidino or phosphono, the compound among the compounds of formula (IA) prepared by a previous method, wherein at least one of $R^A$, $R^{7A}$, $R^{8A}$, $R^{10A}$ or

contains a protected form of carboxy, hydroxy, amino, thiol, guanidino, amidino or phosphono, i.e. the compound of formula (IA-2)

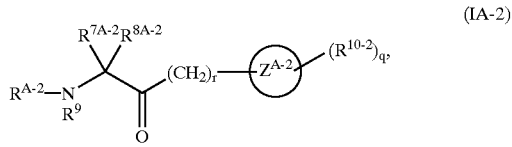

(IA-2)

wherein $R^{A-2}$, $R^{7A-2}$, $R^{8A-2}$, $R^{10A-2}$ and

have the same meanings as $R^A$, $R^{7A}$, $R^{8A}$, $R^{10A}$ and

respectively, with proviso that at least one of $R^{A-2}$, $R^{7A-2}$, $R^{8A-2}$, $R^{10A-2}$ and

is a protected form of carboxy, hydroxy, amidno, thiol, guanidino, amidino or phosphono, or $R^{A-2}$ is a protective group of amino, and the other symbols have the same meanings as above, or the compound among the compounds of formula (IB) prepared by a method above described, wherein at least one group is a protected form of carboxy, hydroxy, amino, thiol, guanidino, amidino or phosphono, i.e. the compound of formula (IB-1)

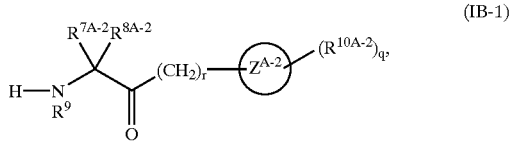

(IB-1)

wherein all symbols have the same meanings as above.

Protective groups for carboxy include, for example, methyl, ethyl, t-butyl and benzyl.

Protective groups for hydroxy include, for example, methoxymethyl, 2-tetrahydropyranyl, t-butyldimethylsilyl, t-butyldiphenylsilyl, acetyl and benzyl.

Protective groups for amino include the ones shown above.

Protective groups for thiol include, for example, benzyl, methoxybenzyl, methoxymethyl, 2-tetrahydropyranyl, diphenylmethyl and acetyl.

Protective groups for guanidino and amidino include, for example, benzyloxycarbonyl, t-butoxycarbonyl and 9-fluorenylmethoxycarbonyl.

Protective groups for phosphono include, for example, C1–2 alkyl, phenyl, benzyl, 2,2,2-trichloroethyl and cyanoethyl.

As to protective groups for carboxy, hydroxy, amino, thiol, guanidino, amidino or phosphono group, other groups than above listed may also be used instead, if easily and selectively eliminated. For example, the groups described in T. W. Greene, Protective Groups in Organic Synthesis, Wiley, New York, 1991 may be used.

Deprotection reactions of the protective groups of carboxy, hydroxy, amino, thiol, guanidino or amidino are well known, for example,
1) a deprotection reaction under alkaline conditions,
2) a deprotection reaction under acidic conditions,
3) a deprotection reaction by hydration,
4) a deprotection reaction of silyl-containing groups, etc. may be included.
The methods of 1), 2) and 3) are carried out by the methods described above.
4) A deprotection reaction of silyl-containing group is carried out, for example, in a water-miscible organic solvent (tetrahydrofuran, acetonitrile, etc.) using tetrabutylammonium fluoride at a temperature of 0 to 40° C.

Deprotection reaction of protective groups of phosphono is known, for example, (a) Elimination of C1–2 alkyl is carried out in an organic solvent such as chloroform using halogenated trimethylsilyl (chlorotrimethylsilyl, bromotrimethylsilyl, iodotrimethylsilyl, etc.) as a reagent, in the presence or absence of alkali metal iodide (sodium iodide, potassium iodide, etc.) at a temperature of 0 to 40° C.

(b) Elimination of phenyl is carried out under atmosphere of hydrogen in an organic solvent (methanol, ethanol, tetrahydrofuran, etc.) or without a solvent in the presence or absence of a catalyst such as platinum oxide and an organic acid such as acetic acid or an inorganic acid such as hydrochloric acid at a temperature of 0 to 50° C. for 24 hours to 3 days.

(c) Elimination of benzyl is carried out under atmosphere of hydrogen in an organic solvent (methanol, ethanol, tetrahydrofuran, pyridine, acetic acid, etc.) in the presence of a catalyst (palladium-carbon, palladium black, palladium hydroxide, etc.) at a temperature of 0 to 50° C.

(d) Elimination of 2,2,2-trichloroethyl is carried out in an organic solvent (methanol, ethanol, tetrahydrofuran, etc.) or without a solvent using a micropowder of zinc and others and an organic acid such as acetic acid or an inorganic acid such as hydrochloric acid at a temperature of 0 to 50° C.

(e) Elimination of cyanoethyl is carried out in a solvent (water, methanol, ethanol, tetrahydrofuran, pyridine, etc.) or without a solvent, in the presence of a base (triethylamine, dimethylamine, t-butylamine, etc.) at a temperature of 0 to 100° C.

As easily understood by those skilled in the art, the target compounds of the present invention may be easily prepared by selecting these reactions.

[4] Among the compounds of formula (I), wherein $AA^1$ and $AA^2$ do not represent a single bond at the same time, and none of R, $AA^1$, $AA^2$, $R^7$, $R^8$, $R^{10}$ and

contains carboxy, hydroxy, amino, thiol, guanidino, amidino, phosphono, i.e. the compound of formula (ID)

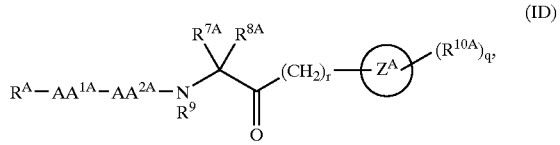

(ID)

wherein $AA^{1A}$ and $AA^{2A}$ have the same meanings as $AA^1$ and $AA^2$, with proviso that no group contains carboxy, hydroxy, amino, thiol, guanidino, amidino, phosphono, and $AA^{1A}$ and $AA^{2A}$ do not represent a single bond at the same time, and the other symbols have the same meanings as above, may be prepared according to the following method of (A) or (B).

(A) The compound of formula (ID) may be prepared by subjecting to amidation reaction the compound of formula (IIC)

$R^A$—$AA^{1A}$—$AA^{2A}$—OH (IIC), wherein all symbols have the same meanings as above, and the compound of formula (IB) above described.

Amidation reaction is known, for example,
1) a method using acid halide,
2) a method using mixed anhydride,
3) a method using a condensing agent (EDC, DCC, etc.), etc.

To explain these methods concretely, 1) the method using acid halide is carried out, for example, by subjecting to a reaction carboxylic acid and acid-halogenating agent (oxalyl chloride, thionyl chloride, etc.) in an organic solvent (chloroform, methylene chloride, diethyl ether, tetrahydrofuran, etc.) or without a solvent, at a temperature between −20° C. and refluxing temperature, and then subjecting to a reaction thus obtained acid halide in the presence of tertiary amine (pyridine, triethylamine, dimethylaniline, dimethylaminopyridine, etc.) in an inert organic solvent (chloroform, methylene chloride, diethyl ether, tetrahydrofuran, etc.) at a temperature between 0 to 40° C.

And it may be carried out by subjecting to a reaction with acid halide in an organic solvent (dioxane, tetrahydrofuran, etc.) using an aqueous alkali solution (an aqueous solution of sodium bicarbonate or sodium hydroxide, etc.) at a temperature between 0 to 40° C.

2) The method using mixed anhydride is carried out, for example, by subjecting to a reaction in an organic solvent (chloroform, methylene chloride, diethyl ether, tetrahydrofuran, etc.) or without a solvent, in the presence of tertiary amine (pyridine, triethylamine, dimethylaniline, dimethylaminopyridine, etc.), carboxylic acid with acid halide (pivaloyl chloride, tosyl chloride, mesylchloride, etc.) or acid derivative (chloroethyl formate, chloroisobutyl formate, etc.) at a temperature between 0 to 40° C., and then subjecting to a reaction thus obtained mixed anhydride with amine in an organic solvent (chloroform, methylene chloride, diethyl ether, tetrahydrofuran, etc.) at a temperature between 0 to 40° C.

3) The method using a condensing agent is carried out, for example, in an organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, etc.), using a condensing agent (1,3-dicychlorohexylcarbodiimide (DCC), 1-ethyl-3-[3-(dimethylamino)propyl]carbodiimide (EDC), 1,1′-carbonyldiimidazole (CDI), 2-chloro-1-methylpyridinium iodide, etc.) in the presence or absence of 1-hydroxybenzotriazole (1-HOBt), by subjecting to a reaction carboxylic acid and amine at a temperature between 0 and 40° C.

The reactions 1), 2) and 3) are desirably carried out under atmosphere of inert gas (argon, nitrogen, etc.) and anhydrous conditions.

(B) The compound of formula (ID) may be prepared by subjecting to a reaction the compound of formula (IID)

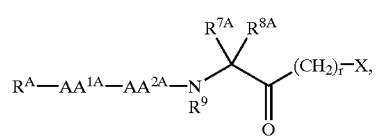
(IID)

wherein all symbols have the same meanings as above, and the compound of formula (IIB) above described. The reaction of the compound of formula (IID) and the compound of formula (IIB) is carried out according to the same method of the reaction of the compound of formula (IIA) and the compound of formula (IIB) above described.

[5] Among the compounds of formula (I), wherein $AA^1$ and $AA^2$ do not represent a single bond at the same time, and at least one of R, $AA^1$, $AA^2$, $R^7$, $R^8$, $R^{10}$ and

represents a group which contains carboxy, hydroxy, amino, thiol, guanidino, amidino or phosphono, i.e. the compound of formula (IE)

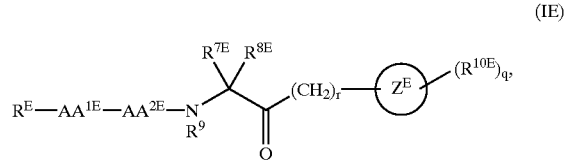
(IE)

wherein $R^E$, $AA^{1E}$, $AA^{2E}$, $R^{7E}$, $R^{8E}$, $R^{10E}$ and

have the same meanings as R, $AA^1$, $AA^2$, $R^7$, $R^8$, $R^{10}$ and

respectively, with proviso that at least one of them contains carboxy, hydroxy, amino, thiol, guanidino, amidino or phosphono, or $R^E$ is hydrogen, and the other symbols have the same meanings as above, may be prepared by subjecting to a deprotection reaction of protective group of carboxy, hydroxy, amino, thiol, guanidino, amidino or phosphono, the compound among the compounds of formula (ID), which contains at least one protected form of carboxy, hydroxy, amino, thiol, guanidino, amidino or phosphono, i.e. the compound of formula (ID-1)

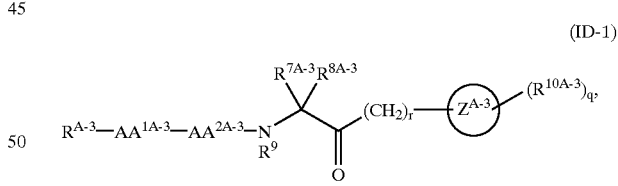
(ID-1)

wherein $R^{A-3}$, $AA^{1A-3}$, $AA^{2A-3}$, $R^{7A-3}$, $R^{8A-3}$, $R^{10A-3}$ and

have the same meanings as $R^A$, $AA^{1A}$, $AA^{2A}$, $R^{7A}$, $R^{8A}$, $R^{10A}$ and

respectively, with proviso that at least one of $R^{A-3}$, $AA^{1A-3}$, $AA^{2A-3}$, $R^{7A-3}$, $R^{8A-3}$, $R^{10A-3}$ and

contains at least one protected form of carboxy, hydroxy, amino, thiol, guanidino, amidino or phosphono or $R^{A-3}$ is a protected form of amino, and the other symbols have the same meanings as above.

Deprotection reaction of the protective groups of carboxy, hydroxy, amino, thiol, guanidino, amidino or phosphono is carried out according to the method described above.

The compound of formula (IA) above described may also be prepared by subjecting the compound of formula (IB) to a reaction of (A) amidation, (B) sulfonamideation, (C) forming an urea, (D) forming an urethane, (E) N-alkylation.

(A) Amidation reaction is carried out by subjecting to a reaction the compound of formula (IB) and the compound of formula (IIE-A)

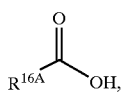
(IIE-A)

wherein $R^{16A}$ has the same meaning as $R^{16}$, but $R^{16A}$ represents a group which does not contain carboxy, hydroxy, amino, thiol, guanidino or amidino. Amidation reaction is carried out according to the method described above.

(B) Sulfonamidation reaction is carried out by subjecting to a reaction the compound of formula (IB) and the compound of formula (IIE-B)

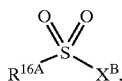
(IIE-B)

wherein $X^B$ is halogen and the other symbols are the same meanings as above.

Sulfonamidation reaction is known, for example, it is carried out by subjecting sulfonic acid to a reaction with acid halide (oxalyl chloride, thionyl chloride, etc.) at a temperature of −20° C. to refluxing temperature in an inert organic solvent (chloroform, methylene chloride, diethyl ether, tetrahydrofuran, etc.) or without a solvent, followed by subjecting thus obtained sulfonyl halide to a reaction with amine in the presence of tertiary amine (pyridine, triethylamine, dimethylaniline, dimethylaminopyridine, etc.) in an inert organic solvent (chloroform, methylene chloride, diethyl ether, tetrahydrofuran, etc.) at a temperature of 0 to 40° C.

(C) A reaction to form urea is carried out according to the following method of (1) or (2).

(1) A Method of Subjecting to a Reaction The Compound of Formula (IB) and the Compound of Formula (IIE-C-1)

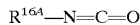 (IIE-C-1)

The reaction is carried out, for example, in an organic solvent (tetrahydrofuran, methylene chloride, diethyl ether, etc.) at a temperature of 0 to 100° C.

(2) A Method of Subjecting to a Reaction the Compound of Formula (IB) and the Compound of Formula (IIE-C-2)

(IIE-C-2)

in the presence of phosgene or 1,1-carbonyldiimidazole

This reaction is carried out, for example, in an organic solvent (tetrahydrofuran, methylene chloride, diethyl ether, dimethylformamide, etc.) at a temperature of 0 to 120° C.

(D) A reaction to form urethane is carried out according to the following method of (1) or (2).

(1) A method of subjecting to a reaction the compound of formula (IB) and the compound of formula (IIE-D-1)

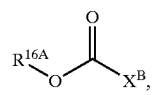
(IIE-D-1)

wherein all symbols have the same meanings as above.

This reaction is carried out, for example, in an organic solvent (tetrahydrofuran, methylene chloride, diethyl ether, etc.) at a temperature of −78 to 40° C.

(2) A method of subjecting to a reaction the compound of formula (IB) and the compound of formula (IIE-D-2)

 (IIE-D-2)

in the presence of N,N'-disuccinylcarbonate (DSC).

This reaction is carried out, for example, in an organic solvent (tetrahydrofuran, methylene chloride, diethyl ether, dimethylformamide, etc.) at a temperature of −78 to 120° C.

(E) N-alkylation reaction is carried out by subjecting to a reaction the compound of formula (IB) and the compound of (IIE-E)

 (IIE-E), wherein $R^X$ is C1–8 alkyl, Cyc, C1–8 alkyl substituted with Cyc or nitro, or

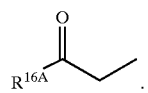

N-alkylation is known, for example, it is carried out in an inert organic solvent (dimethylformamide, dimethylsulfoxide, chloroform, methylene chloride, diethyl ether, tetrahydrofuran, acetonitrile, etc.) in the presence or absence of a base (triethylamine, pyridine, etc.) at a temperature of 0 to 100° C.

Furthermore, the compound of formula (ID) may also be prepared according to the method of 1) or 2).

1) The compound of formula (ID) may be prepared by subjecting to amidation reaction the compound among the compounds of formula (IE), wherein $R^E$ is hydrogen atom, $AA^{1A}$ is a single bond, and none of $AA^{2E}$, $R^{7E}$, $R^{8E}$,

or $R^{10E}$ contains carboxy, hydroxy, amino, thiol, guanidino, amidino or phosphono, i.e. the compound of formula (IE-1)

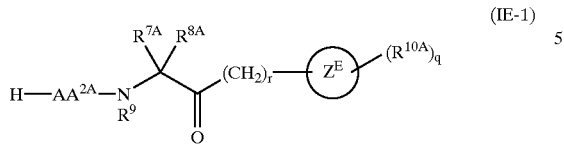

(IE-1)

and the compound of formula (IIF)

$R^A$—$AA^{1A}$—OH    (IIF), wherein all symbols have the same meanings as above.

2) The compound of formula (ID) may also be prepared by the reactions of the compound among the compounds of formula (IE), wherein $R^E$ is hydrogen, and none of $AA^{1E}$, $AA^{2E}$, $R^{7E}$, $R^{8E}$,

and $R^{10E}$ contains carboxy, hydroxy, amino, thiol, guanidino, amidino or phosphono, i.e. the compound of formula (IE-2)

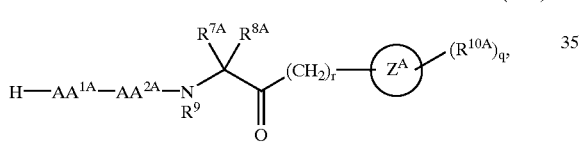

(IE-2)

wherein all symbols have the same meanings as above, and the compound of formula (IIE-A), (IIE-B), (IIE-C-1), (IIE-C-2), (IIE-D-1), (IIE-D-2) or (IIE-E).

That is, the compound of formula (ID) may also be prepared by subjecting to

2-A) an amidation reaction the compound of formula (IE-2) and the compound of formula (IIE-A),
2-B) a sulfonamidation reaction the compound of formula (IE-2) and the compound of formula (IIE-B),
2-C) a reaction to form urea the compound of formula (IE-2) and the compound of formula (IIE-C-1) or (IIE-C-2),
2-D) a reaction to form urethane the compound of formula (IE-2) and the compound of formula (IIE-D-1) or (IIE-D-2), or
2-E) an N-alkylation reaction the compound of formula (IE-2) and the compound of formula (IIE-E).

Amidation, sulfonamidation, reactions to form urea and urethane, and N-alkylation may be carried out according to the methods described above.

The compounds of formula (IIA), (IIB), (IIC), (IID), (IIE-A), (IIE-B), (IIE-C), (IIE-D), (IIE-E) and (IIF) are known per se or may be prepared according to known methods.

For example, among the compound of formula (IIB), the compound of formula (IIB-1)

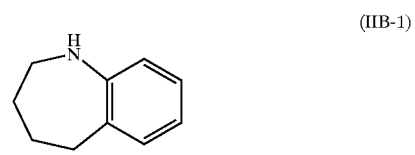

(IIB-1)

is known as CAS No. 4424-20-8 and the compound of formula (IIB-2)

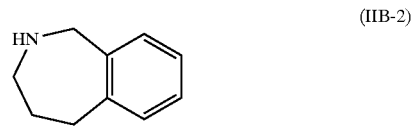

(IIB-2)

may be prepared according to the following reaction scheme (1).

Reaction Scheme 1

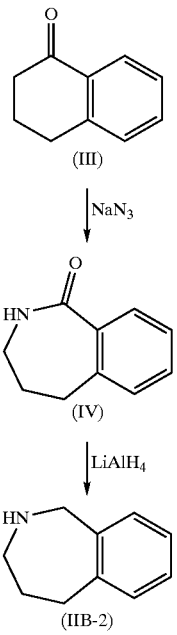

The compounds of formula (IIA) and (IID) may be prepared according to known methods, for example, the methods described in J. Med. Chem., 37, 563 (1994), EP 0623592-A, etc.

In each reaction of the present specification, reaction products may be purified by conventional techniques. For example, purification may be carried out by distillation under atmospheric or reduced pressure, by high performance liquid chromatography using silica gel or magnesium silicate, by washing or by recrystallization, etc. Purification may be carried out after each reaction, or after a series of reactions. Other starting materials and agents used in the present invention are known per se or may be prepared by conventional methods.

Pharmacological Activity of the Compounds of the Present Invention

The compound of formula (I) of the present invention has an inhibitory activity against cysteine proteases, and therefore it is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjoegren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosa and cirrhosis, dementia such as Alzheimer's diseases and Alzheimer's senile dementia, cerebrovascular injury, nerve degeneration diseases; adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), desease by decomposing various proteins which compose the organism (myodystrophy, cataract, periodontitis, hepatocyte desease by bile acid such as cholestatic cirrhosis, etc.), decomposition of alveolus elastica such as pulmonary emphysema, ischemic diseases (brain ischemia, brain disorders by ischemic reperfusion, myocardial infarction, ischemic hepatopathy, etc.), shock (septic shock, systemic inflammation response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as fibroid lungs, bone resorption diseases (osteoporosis, rheumatoid arthritis, arthritis, osteoarthritis, hypercalcemia, osteometastasis of cancer etc.), endocrinesthenia such as hyperthyroidism.

It was confirmed by the following experiments that the compounds of the present invention of formula (I) have an inhibitory activity against cysteine protease.

(i) Measurement of Cathepsin K Inhibitory Activity

65 µL of Cathepsin K enzyme reaction buffer (50 mmol/L of 2-(N-morpholino)ethanesulfonate, 2 mmol/L of ethylenediamine tetraacetate (EDTA) and 4 mmol/L of dithiothreitol (DTT) were mixed to adjust to pH 5.5), 5 µL of cysteine protease inhibitor solution of several concentrations, 20 µL of synthesized substrate (t-butyloxycarbonyl-L-alanyl-glycyl-L-prolyl-L-arginine-4-methyl-chromanyl-7-amide) solution of several concentrations and 10 µL of cathepsin K enzyme solution were mixed and the increase of fluorescence intensity when reacted at 37° C. was measured (λ ex (excitation wavelength)=355 nm, λ em (fluorescence wavelength)=460 nm). As to the substrate and the compound of the present invention, enzyme reactions were carried out in combination of several appropriate concentrations and Dixon plotting was prepared, to define the absolute value of X-coordinate of the intersection point of the graph as Ki value.

It was confirmed that the compound of the present invention of formula (I) had an inhibitory activity more than 50% at 10 µM. For example, the Ki values of inhibitory activity of the compounds of example 3, example 3(14) and example 31 were 0.17 µM, 0.10 µM and 0.081 µM respectively.

(ii) Measurement of Cathepsin B Inhibitory Activity

10 µL of synthesized substrate (carbobenzoxy-L-arginyl-L-arginine-4-methyl-chromanyl-7-amide or carbobenzoxy-L-phenylalanyl-L-arginine-4-methyl-chromanyl-7-amide) solution of several concentrations, 10 µL of cysteine protease inhibitor solution of several concentrations, 70 µL of cathepsin B enzyme reaction buffer (mixture of 400 mmol/L in acetic acid, 4 mmol/L EDTA, 8 mmol/L DDT to adjust to pH 5.5) and 10 µL of cathepsin B enzyme solution were mixed and the increase of fluorescence intensity was measured (λ ex (excitation wavelength)=355 nm, λ em (fluorescence wavelength)=460 nm) when reacted at 37° C.

It was confirmed that the compound of the present invention of formula (I) had an inhibitory activity more than 50% at 10 µM. For example, the inhibitory activity of the compound of example 10 was 95% at 1 µM.

(iii) Measurement of Cathepsin S Inhibitory Activity

10 µL of synthesized substrate (carbobenzoxy-L-leucyl-L-leucyl-L-arguinine-4-methyl-chromanyl-7-amide) solution and 5 µL of cysteine protease inhibitor solution of several concentrations, 75 µL of cathepsin S enzyme reaction buffer (100 mmol/L of sodium phosphate, 2 mmol/L of EDTA, 2 mmol/L of DTT were mixed to adjust to pH 6.5) and 10 µL of cathepsin S enzyme solution were mixed and the increase of fluorescence intensity was measured (λ ex(excitation wavelength)=355 nm, λ em (fluorescence wavelength)=460 nm) when reacted at 37° C.

It was confirmed that the compound of the present invention of formula (I) has an inhibitory effect more than 50% at 10 µM. For example, the inhibitory activity of the compound of example 18 was 98% at 1 µM.

(iv) Measurement of Cathepsin L Inhibitory Activity

5 µL of synthesized substrate (carbobenzoxy-L-phenylalanyl-L-arguine-4-methyl-chromanyl-7-amide or L-prolyl-L-phenylalanyl-L-arguinine-4-methyl-chromanyl-7-amide) solution and 5 µL of cysteine protease inhibitor solution of several concentrations, 80 µL of cathepsin L enzyme reaction buffer (400 mmol/L acetic acid, 4 mmol/L EDTA, 8 mmol/L DTT were mixed to adjust to pH 5.5) and 10 µL of cathepsin L enzyme solution were mixed and the increase of fluorescence intensity was measured (λ ex (excitation wavelength)=355 nm, λ em (fluorescence wavelength)=460 nm) when reacted at 37° C.

It was confirmed that the compound of the present invention of formula (I) had an inhibitory activity of more than 50% at 10 µM. For example, the inhibitory activity of the compound of example 22(4) was 97% at 1 µM.

(v) Measurement of Calpain Inhibitory Activity

The activity was measured according to the method described in Calcium-depending protease, Seibutsukagaku- Jikkenhou (Biochemistry Experimental Method) Tanpa-kubunkaikouso (Protease) I, 57 (1993).

(vi) Measurement of Caspase-1 Inhibitory Activity

50 μL of caspase-1 enzyme reaction solution (20 mmol/L of 4-(2-hydroxyethyl)-1-piperazinethanesulfonate-sodium hydroxide buffer pH 7.4, 10 mmol/L of potassium chloride, 1.5 mmol/L of magnesium chloride, 0.1 mmol/L EDTA, 10% glycerol) and 50 μL of cysteine protease inhibitor solution of several concentrations, 50 μL of caspase-1 enzyme solution and 100 μL of synthesized substrate (acetyl-L-tyrosinyl-L-valinyl-L-alanyl-L-aspartic acid-4-methyl-chromanyl-7-amide) solution of several concentrations were reacted at 37° C. and the fluorescence intensity was measured (λ ex (excitation wavelength)=355 nm, λ em (fluorescence wavelength)=460 nm).

(vii) Investigation in Bone Resorption Inhibitory Activity Using Mouse Calvaria Cultivation System Mouse neonatal calvaria was cultured in D-minimal essential medium containing cysteine protease inhibitor (mixture of Penicillin G potassium (final concentration 100 U/ml), streptomycin sulfate (final concentration 0.1 mg/ml), bovine serum albumin (final concentration 0.1%), glutamine (final concentration 0.3 mg/ml) in D-minimal essential medium) at 37° C. and the calcium concentration in the culture medium was measured.

(viii) Bone Resorption Pit Formation Test Using Rabbit Osteoclast Cells

Osteoclast cells collected from rabbit bones were sowed over slices of bovine cortical bone, ivory or teeth of toothed whale and were cultured at 37° C. in α-minimal essential medium containing final concentration 5% of fetal bovine serum and various concentrations of cysteine protease inhibitor. The pits formed on the slices by the osteoclast cells were observed and at the same time type-I collagen C-terminal telopeptide (CTx) concentration in culture medium was measured.

(ix) Investigation of Immune Reaction Inhibitory Effect Using Antigen-Sensitized Mouse Spleen Cells Spleen cells were collected from mice sensitized by ovalbumin (OVA) several times. Inhibitory effect of cysteine protease inhibitors against immune response induced by OVA stimulus was investigated, using cytokine concentration and immunoglobulin concentration in culture solution as indicators.

(x) Investigation in Inhibitory Effect Against Bone Resorption Using the Rat PTH Hypercalcemia Model The effect of cysteine protease inhibitor (compulsory oral administration, intraperitoneal administration) on bone resorption which was promoted by intravenous administration of parathyroid hormone (PTH) solution (30 μg/ml) was investigated in rats, using calcium concentration in blood as an indicator.

(xi) Studies on Bone Resorption Inhibitory Effect Using TPTx Rat PTHrP-Induced Hypercalcemia Model The effect of cysteine protease inhibitor (compulsory oral administration, intraperitoneal administration) on bone resorption, promoted by subcutaneous administration of parathyroid hormone related peptide (PTHrP) to a fasting rat (thyroparathyroidectomized; TPTx) was investigated, using calcium concentration in blood as an indicator.

Toxicity

The toxicity of the compounds of the present invention is very low and therefore it was confirmed that the compounds are safe for pharmaceutical use.

INDUSTRIAL APPLICABILITY

Application to Pharmaceuticals

The compound of formula (I) of the present invention has an inhibitory activity against cysteine proteases, and therefore it is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjoegren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosa and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), desease by decomposing various proteins which compose the organism (myodystrophy, cataract, periodontitis, hepatocyte desease by bile acid such as cholestatic cirrhosis, etc.), decomposition of alveolus elastica such as pulmonary emphysema, ischemic diseases (brain ischemia, brain disorders by ischemic reperfusion, myocardial infarction, ischemic hepatopathy, etc.), shock (septic shock, systemic inflammation response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as fibroid lungs, bone resorption diseases (osteoporosis, rheumatoid arthritis, arthritis, osteoarthritis, hypercalcemia, osteometastasis of cancer etc.), endocrinesthenia such as hyperthyroidism.

For the purpose described above, the compounds of formula (I), of the present invention, non-toxic salts thereof, acid addition salts thereof or hydrates thereof may normally be administered systemically or locally, usually by oral or parenteral administration.

The doses to be administered are determined depending upon, for example, age, body weight, symptom, the desired therapeutic effect, the route of administration, and the duration of the treatment. In the human adult, the doses per person at a time are generally from 1 mg to 1000 mg, by oral administration, up to several times per day, and from 1 mg to 100 mg, by parenteral administration (preferably intravenous administration), up to several times per day, or continuous administration for from 1 to 24 hours per day from vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules.

Capsules include hard capsules and soft capsules.

In such solid compositions, one or more of the active compound(s) may be used as a dosage form, as is normal practice, to admix with excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or asparatic acid) and the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, one or more of the active compound(s) are dissolved, suspended or emulsified in diluent commonly used (e.g. purified water, ethanol or mixture thereof). Furthermore, such liquid compositions may also comprise wetting agents or suspending agents, emulsifying agents, sweetening agents, flavouring agents, perfuming agents, preserving agents buffer agent etc.

Injections for parenteral administration include solutions, suspensions, emulsions and solids which are dissolved or suspended to use at a time to use. One or more of the active compound(s) in injections are dissolved, suspended and emulsified in a solvent. The solvents are, for example, distilled water for injection, physiological salt solution, vegetable oil, propylene glycol, polyethylene glycol, alcohol such as ethanol or mixture thereof. Moreover the injections may also include stabilizing agents, agents to assist dissolution (e.g. glutamic acid, aspartic acid or POLYSORBATE80 (registered trade mark)), suspending agents, emulsifying agents, soothing agents, buffer agents, preserving agents, etc. They are sterilized in the last process or manufactured and prepared by sterile procedure. They may also be manufactured in the form of sterile solid compositions such as freeze-dried one and they may be sterilized or dissolved to use in sterile distilled water for injection or some other solvents immediately before use.

Other compositions for parenteral administration include liquids for external use, and ointment, endermic liniments, inhale, spray, suppositories for rectal administration and pessaries for vaginal administration which comprise one or more of the active compound(s) and are prescribed by methods known per se.

Spray compositions may comprise additional substances other than diluents: e.g. stabilizing agents (e.g. sodium sulfite hydride), isotonic buffers (e.g. sodium chloride, sodium citrate or citric acid). For preparation of such spray compositions, for example, the method described in the U.S. Pat. No. 2,868,691 or No. 3,095,355 may be used.

BEST MODE FOR CARRYING OUT THE INVENTION

The following reference examples and examples illustrate the present invention, but do not limit the present invention.

The solvents in the parentheses show the eluting or developing solvents and the ratios of the solvents used are by volume in chromatographic separations or TLC.

The solvents in the parentheses in NMR show the solvents used in measurement.

REFERENCE EXAMPLE 1

(3S)-1-bromo-3-(t-butoxycarbonylamino)-5-methyl-2-hexanone

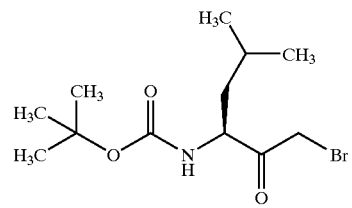

Under atmosphere of argon, to a solution of (2S)-2-(t-butoxycarbonylamino)-4-methylpentanoic acid (t-butoxycarbonyl-L-leucine) (37.4 g) in tetrahydrofuran (800 ml) was added N-methylmorpholine (33 ml) at −25° C. and the mixture was stirred for 10 minutes. To the mixture was added chloroethylformate (15.8 ml) and the mixture was stirred for 20 minutes. Thereto was added a solution of diazomethane in diethyl ether and the mixture was stirred for another 2 hours. Thereto was added a mixture of 47% hydrobromic acid-acetic acid (1:1) at 0° C. and the mixture was stirred for 15 minutes. To the reaction mixture was added water and was extracted with a mixture of ethyl acetate-hexane. The organic layer was washed with a saturated aqueous solution of sodium bicarbonate and a saturated aqueous solution of sodium chloride successively, dried over anhydrous sodium sulfate and was concentrated. The residue was washed with cooled hexane to give the title compound (27.4 g) having the following physical data.

TLC: Rf 0.56 (n-hexane:ethyl acetate=3:1);

NMR (CDCl$_3$): δ 4.89 (m, 1H), 4.53 (m, 1H), 4.08 (m, 2H), 1.80–1.31 (m, 12H), 0.97 (m, 6H).

EXAMPLE 1

(3S)-3-(t-butoxycarbonylamino)-5-methyl-1-(1,3,4,5-tetrahydro-2H-2-benzazepin-2-yl)-2-hexanone

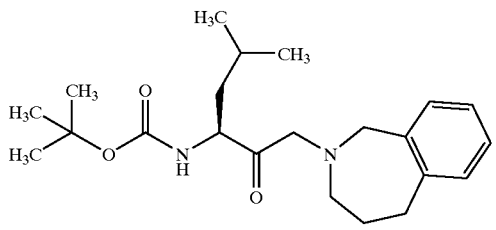

To a solution of 1,3,4,5-tetrahydro-2H-2-benzazepin (2.2 g) in dimethylformamide (30 ml) was added the compound prepared in reference example 1 (4.1 g) and the mixture was stirred for 1.5 hours. To the reaction mixture was added diisopropylethylamine (2.3 ml) and the mixture was stirred for another 3.5 hours. To the reaction mixture was added ice-water and was extracted with ethyl acetate. The organic layer was washed with a saturated aqueous solution of sodium bicarbonate, water and a saturated aqueous solution of sodium chloride successively, dried over anhydrous sodium sulfate and was concentrated. The residue was purified by column chromatography on silica gel (n-hexane:ethyl acetate=5:1–3:1–1:1) to give the compound of the present invention (4.7 g) having the following physical data.

TLC: Rf 0.48 (n-hexane:ethyl acetate=6:4);

NMR (CDCl$_3$): δ 7.20–7.00 (m, 4H), 4.97 (d, J=8.4 Hz, 1H), 4.40–4.30 (m, 1H), 3.98 (s, 2H), 3.33 (d, J=18.2 Hz, 1H), 3.30 (d, J=18.2 Hz, 1H), 3.17 (t, J=5.3 Hz, 2H), 2.95–2.85 (m, 2H), 1.80–1.70 (m, 2H), 1.42 (s, 9H), 1.50–1.20 (m, 3H), 0.892 (d, J=6.6 Hz, 3H), 0.887 (d, J=6.3 Hz, 3H).

EXAMPLE 2

(3S)-3-amino-5-methyl-1-(1,3,4,5-tetrahydro-2H-2-benzazepin-2-yl)-2-hexanone dihydrochloride

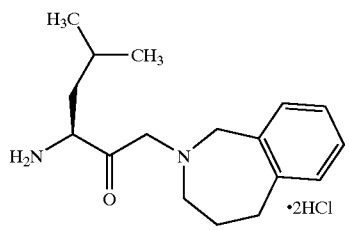

To a solution of the compound prepared in example 1 (187 mg) in methanol (1 ml) was added 4N hydrochloric acid in ethyl acetate (4 ml) at 0° C. and the mixture was stirred for 1 hour. The reaction mixture was concentrated to give a crude product of the present invention having the following physical data. The crude product was used in the next reaction without further purification.

TLC: Rf 0.71 (chloroform:methanol: 28% ammonia water=8:2:0.4);

NMR (CD$_3$OD): δ 7.50–7.05 (m, 4H), 5.02–4.90 (m, 3H), 4.60–4.30 (m, 2H), 3.75–3.60 (m, 2H), 3.20–3.00 (m, 2H), 2.20–2.00 (m, 2H), 1.90–1.60 (m, 3H), 1.12–0.90 (m, 6H).

EXAMPLE 3

N-[(3S)-5-methyl-2-oxo-1-(1,3,4,5-tetrahydro-2H-2-benzazepin-2-yl)-3-hexyl]-1-[(1R,2S)-2-benzamidecyclohexyl]carboxamide

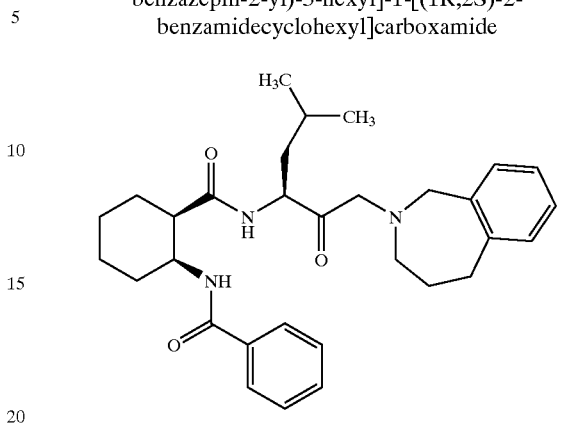

To a solution of (−)-2-benzamidocyclohexanecarboxylic acid ((1R,2S)-2-benzamidocyclohexanecarboxylic acid) (148 mg) and 1-hydroxybenzotriazole (107 mg) in dimethylformamide (2 ml) was added 1-ethyl-3-[3-(dimethylamino)propyl]carbodiimide hydrochloride (134 mg) and the mixture was stirred for 30 minutes, and thereto was added the compound prepared in example 2 and triethylamine (140 ml) and was stirred for another 2 hours. To the reaction mixture was added ice-water and was extracted with ethyl acetate. The organic layer was washed with a saturated aqueous solution of sodium bicarbonate, water and a saturated aqueous solution of sodium chloride successively, dried over anhydrous sodium sulfate and was concentrated. The residue was purified by column chromatography on silica gel (chloroform methanol=1:0–100:1) to give the compound of the present invention as a free compound (225 mg). It was converted into its hydrochloride by a known method to give the hydrochloride having the following physical data.

[Free Compound]

TLC: Rf 0.48 (chloroform:methanol=9:1);

NMR (CDCl$_3$): δ 7.85–7.70 (m, 2H), 7.60–6.95 (m, 8H), 6.12 (d, J=8.7 Hz, 1H), 4.75–4.60 (m, 1H), 4.35–4.25 (m, 1H), 3.98 and 3.94 (each s, totally 2H), 3.35–3.25 (m, 2H), 3.20–3.05 (m, 2H), 2.95–2.85 (m, 2H), 2.80–2.70 (m, 1H), 2.20–1.20 (m, 13H), 0.90–0.65 (m, 6H).

[Hydrochloride]

TLC: Rf 0.64 (chloroform:methanol=9:1);

NMR (CDCl$_3$): δ 8.19 and 7.60 (each br, total 1H), 7.86–7.66 (m, 2H), 7.53–7.01 (m, 8H), 4.60–4.22 (m, 5H), 3.77–3.45 (m, 3H), 3.04–2.78 (m, 3H), 2.19–1.26 (m, 13H), 0.98–0.62 (m, 6H).

EXAMPLE 3(1)–EXAMPLE 3(24)

By the same procedure as described in example 3 using a carboxylic acid corresponding to (1R,2S)-2-benzamidocyclohexanecarboxylic acid and the compound prepared in example 2 or a corresponding amine, the compound of the present invention having the following physical data was obtained.

EXAMPLE 3(1)

N-[(3S)-5-methyl-2-oxo-1-(1,3,4,5-tetrahydro-2H-2-benzazepin-2-yl)-3-hexyl]-1-cyclohexylcarboxamide

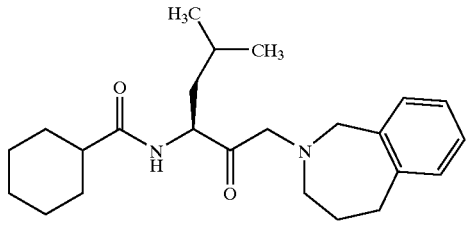

TLC: Rf 0.55 (chloroform:methanol=9:1);

NMR (CDCl$_3$): δ 7.20–7.00 (m, 4H), 5.90 (d, J=8.0 Hz, 1H), 4.80–4.65 (m, 1H), 3.98 (s, 2H), 3.33 (s, 2H), 3.25–3.10 (m, 2H), 2.95–2.80 (m, 2H), 2.20–2.00 (m, 1H), 2.00–1.10 (m, 15H), 0.88 (d, J=6.4 Hz, 3H), 0.88 (d, J=6.2 Hz, 3H).

EXAMPLE 3(2)

N-[(3S)-5-methyl-2-oxo-1-(1,3,4,5-tetrahydro-2H-2-benzazepin-2-yl)-3-hexyl]-1-[(1S,2R)-2-benzoylaminocyclohexyl]carboxamide

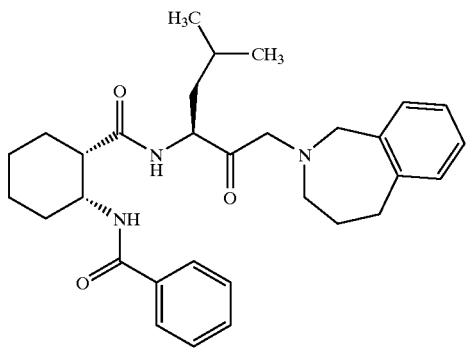

TLC: Rf 0.48 (chloroform:methanol=9:1);

NMR (CDCl$_3$): δ 7.90–7.70 (m, 2H), 7.57 (d, J=8.4 Hz, 1H), 7.50–7.35 (m, 3H), 7.20–6.95 (m, 4H), 6.08 (d, J=7.8 Hz, 1H), 4.80–4.65 (m, 1H), 4.35–4.20 (m, 1H), 3.97 and 3.93 (each s, totally 2H), 3.35–3.20 (m, 2H), 3.20–3.05 (m, 2H), 2.95–2.85 (m, 2H), 2.80–2.70 (m, 1H), 2.10–1.20 (m, 13H), 0.87, 0.75 and 0.74 (each d, J=6.3 Hz, totally 6H).

EXAMPLE 3(3)

N-[(3S)-5-methyl-2-oxo-1-(1,3,4,5-tetrahydro-2H-2-benzazepin-2-yl)-3-hexyl]benzamide

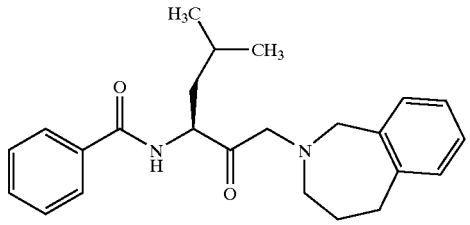

TLC: Rf 0.57 (chloroform:methanol=9:1);

NMR (CDCl$_3$): δ 7.85–7.75 (m, 2H), 7.55–7.40 (m, 3H), 7.20–7.00 (m, 4H), 6.72 (d, J=8.1 Hz, 1H), 5.05–4.95 (m, 1H), 3.99 (each s, totally 2H), 3.39 (d, J=17.7 Hz, 1H), 3.36 (d, J=17.7 Hz, 1H), 3.25–3.10 (m, 2H), 2.95–2.85 (m, 2H), 1.80–1.40 (m, 5H), 0.95 (d, J=6.3 Hz, 3H), 0.92 (d, J=6.3 Hz, 3H).

EXAMPLE 3(4)

4-benzyloxy-N-[(3S)-5-methyl-2-oxo-1-(1,3,4,5-tetrahydro-2H-2-benzazepin-2-yl)-3-hexyl]benzamide

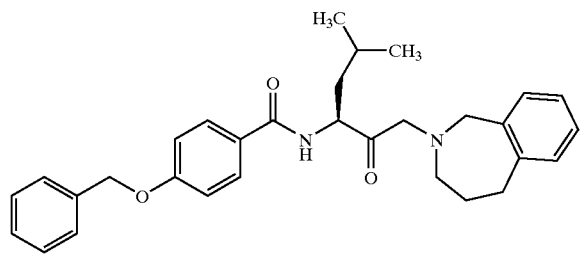

TLC: Rf 0.28 (n-hexane ethyl acetate=1:1);

NMR (CDCl$_3$): δ 7.75 (d, J=8.8 Hz, 2H), 7.50–7.30 (m, 5H), 7.20–6.90 (m, 6H), 6.65 (d, J=8.8 Hz, 1H), 5.12 (s, 2H), 4.96 (dt, J=8.8, 3.8 Hz, 1H), 3.99 (s, 2H), 3.40 (d, J=17.6 Hz, 1H), 3.36 (d, J=17.6 Hz, 1H), 3.25–3.10 (m, 2H), 2.95–2.85 (m, 2H), 1.90–1.20 (m, 5H), 0.93 (d, J=6.0 Hz, 3H), 0.91 (d, J=6.2 Hz, 3H).

EXAMPLE 3(5)

3-benzyloxy-N-[(3S)-5-methyl-2-oxo-1-(1,3,4,5-tetrahydro-2H-2-benzazepin-2-yl)-3-hexyl]benzamide

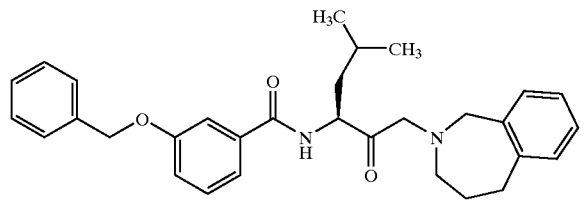

TLC: Rf 0.36 (n-hexane:ethyl acetate=1:1);

NMR (CDCl$_3$): δ 7.50–7.30 (m, 8H), 7.20–7.00 (m, 5H), 6.70 (d, J=8.4 Hz, 1H), 5.11 (s, 2H), 4.96 (dt, J=8.4, 4.0 Hz, 1H), 3.99 (s, 2H), 3.37 (s, 2H), 3.25–3.10 (m, 2H), 2.95–2.85 (m, 2H), 1.80–1.20 (m, 5H), 0.94 (d, J=6.4 Hz, 3H), 0.92 (d, J=6.2 Hz, 3H).

EXAMPLE 3(6)

2-benzyloxy-N-[(3S)-5-methyl-2-oxo-1-(1,3,4,5-tetrahydro-2H-2-benzazepin-2-yl)-3-hexyl]benzamide

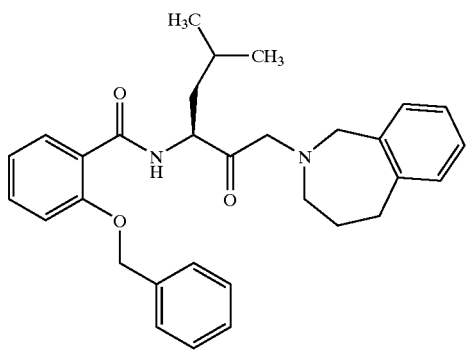

TLC: Rf 0.31 (n-hexane:ethyl acetate 1:1);

NMR (CDCl₃): δ 8.30–8.10 (m, 2H), 7.55–7.35 (m, 6H), 7.20–6.95 (m, 6H), 5.18 (d, J=10.6 Hz, 1H), 5.14 (d, J=10.6 Hz, 1H), 4.80–4.70 (m, 1H), 3.95 (s, 2H), 3.37 (d, J=17.8 Hz, 1H), 3.31 (d, J=17.8 Hz, 1H), 3.20–3.10 (m, 2H), 2.95–2.80 (m, 2H), 1.80–1.00 (m, 5H), 0.75 (d, J=6.0 Hz, 3H), 0.66 (d, J=6.2 Hz, 3H).

EXAMPLE 3(7)

N-[(3S)-5-methyl-2-oxo-1-(1,3,4,5-tetrahydro-2H-2-benzazepin-2-yl)-3-hexyl]cinnamide

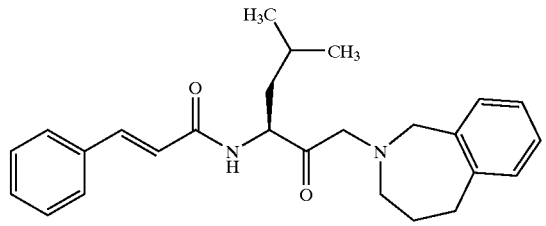

TLC: Rf 0.27 (n-hexane:ethyl acetate=1:1);

NMR (CDCl₃): δ 7.62 (d, J=15.6 Hz, 1H), 7.55–7.45 (m, 2H), 7.40–7.30 (m, 3H), 7.20–7.00 (m, 4H), 6.41 (d, J=15.6 Hz, 1H), 6.19 (d, J=8.6 Hz, 1H), 4.94 (dt, J=8.6, 4.4 Hz, 1H), 3.99 (s, 2H), 3.56 (s, 2H), 3.25–3.10 (m, 2H), 2.95–2.85 (m, 2H), 1.80–1.20 (m, 5H), 0.93 (d, J=6.0 Hz, 3H), 0.91 (d, J=6.2 Hz, 3H).

EXAMPLE 3(8)

N-[(3S)-5-methyl-2-oxo-1-(1,3,4,5-tetrahydro-2H-2-benzazepin-2-yl)-3-hexyl]-3-cyclopentylpropanamide

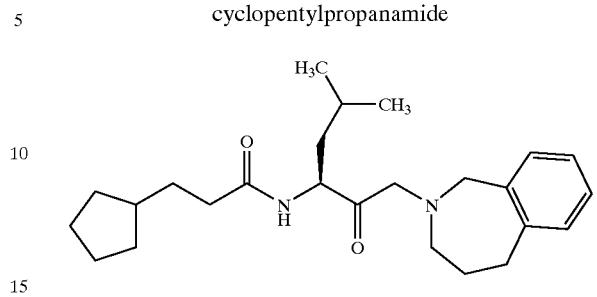

TLC: Rf 0.30 (n-hexane:ethyl acetate=1:1);

NMR (CDCl₃): δ 7.20–7.03 (m, 4H), 6.08 (d, J=8.1 Hz, 1H), 4.71 (m, 1H), 4.04 (s, 2H), 3.46 (d, J=18.0 Hz, 1H), 3.35 (d, J=18.0 Hz, 1H), 3.23 (m, 2H), 2.92 (m, 2H), 2.21 (t, J=7.5 Hz, 2H), 1.80–1.20 and 1.18–1.00 (totally 16H), 0.89 (d, J=6.6 Hz, 3H), 0.88 (d, J=6.6 Hz, 3H).

EXAMPLE 3(9)

N-[(3S)-5-methyl-2-oxo-1-(1,3,4,5-tetrahydro-2H-2-benzazepin-2-yl)-3-hexyl]-2-(5-phenylimidazolidin-2,4-dion-3-yl)acetamide

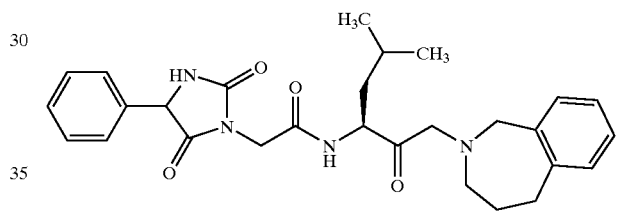

TLC: Rf 0.41 (chloroform:methanol=9:1);

NMR (CDCl₃): δ 7.50–7.29 (m, 5H), 7.22–6.98 (m, 4H), 6.74–6.51 (m, 1H), 6.31, 6.19, 6.14 and 6.11 (each brs, totally 1H), 5.15 (s, 1H), 4.78–4.64 (m, 1H), 4.28–4.11 (m, 2H), 3.95 and 3.94 (each s, totally 2H), 3.43–3.19 (m, 2H), 3.19–3.05 (m, 2H), 2.94–2.83 (m, 2H), 1.80–1.20 (m, 5H), 1.00–0.77 (m, 6H)

EXAMPLE 3(10)

N-[(3S)-5-methyl-2-oxo-1-(1,3,4,5-tetrahydro-2H-2-benzazepin-2-yl)-3-hexyl]-2-(2-phenyl-1,6-dihydropyrimidin-6-on-1-yl)acetamide

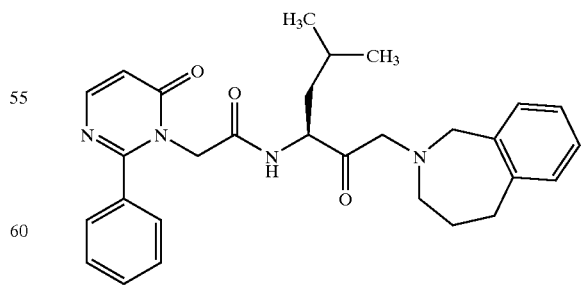

TLC: Rf 0.47 (chloroform:methanol=9:1);

NMR (CDCl₃): δ 8.00 (d, J=6.5 Hz, 1H), 7.65–7.40 (m, 5H), 7.23–7.00 (m, 4H), 6.51 (d, J=8.0 Hz, 1H), 6.50 (d, J=6.5 Hz, 1H), 4.74 (ddd, J=12.0, 8.0 and 4.2 Hz, 1H), 4.57

(d, J=15.3 Hz, 1H), 4.46 (d, J=15.3 Hz, 1H), 3.97 (s, 2H), 3.38 (d, J=17.4 Hz, 1H), 3.28 (d, J=17.4 Hz, 1H), 3.22–3.09 (m, 2H), 2.97–2.84 (m, 2H), 1.83–1.20 (m, 5H), 0.87 (d, J=6.3 Hz, 6H).

EXAMPLE 3(11)

2-benzoylamino-N-[(3S)-5-methyl-2-oxo-1-(1,3,4,5-tetrahydro-2H-2-benzazepin-2-yl)-3-hexyl]benzamide

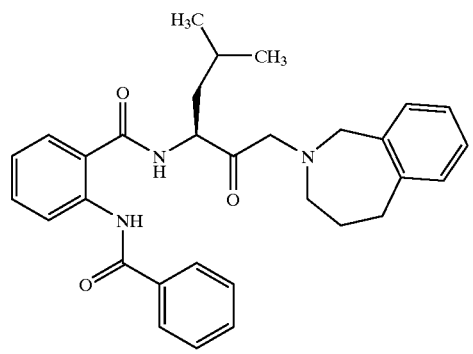

TLC: Rf 0.32 (hexane:ethyl acetate=6:4);

NMR (CDCl$_3$): δ 12.07 (s, 1H), 8.85 (d, J=8.4 Hz, 1H), 8.02 (dd, J=7.6, 2.2 Hz, 2H), 7.65–7.40 (m, 5H), 7.20–7.00 (m, 5H), 6.97 (d, J=8.8 Hz, 1H), 5.01 (dt, J=3.6, 8.8 Hz, 1H), 4.00 (s, 2H), 3.42 (d, J=17.4 Hz, 1H), 3.36 (d, J=17.4 Hz, 1H), 3.25–3.10 (m, 2H), 3.00–2.85 (m, 2H), 2.00–1.60 (m, 5H), 0.95 (d, J=5.8 Hz, 3H), 0.93 (d, J=5.8 Hz, 3H).

EXAMPLE 3(12)

(3S)-5-methyl-3-(2-methylpropoxycarbonylamino)-1-(1,3,4,5-tetrahydro-2H-2-benzazepin-2-yl)hexan-2-one

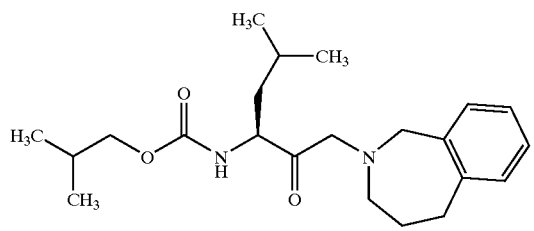

TLC: Rf 0.45 (hexane:ethyl acetate=6:4);

NMR (CDCl$_3$): δ 7.20–7.00 (m, 4H), 5.16 (d, J=8.4 Hz, 1H), 4.55–4.35 (m, 1H), 3.97 (s, 2H), 3.83 (d, J=6.6 Hz, 2H), 3.31 (s, 2H), 3.25–3.10 (m, 2H), 2.95–2.85 (m, 2H), 2.00–1.20 (m, 6H), 1.00–0.80 (m, 12H).

EXAMPLE 3(13)

(2S)-N-[5-methyl-2-oxo-1-(1,3,4,5-tetrahydro-2H-2-benzazepin-2-yl)-3-hexyl]-1-[1-phenethylpiperidin-2-yl]carboxamide

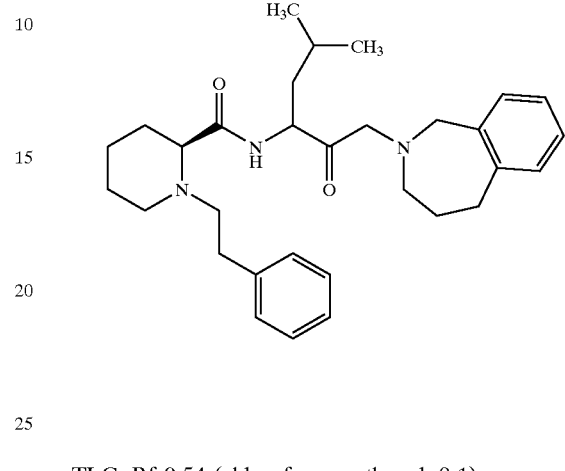

TLC: Rf 0.54 (chloroform:methanol=9:1);

NMR (CDCl$_3$): δ 7.35–7.00 (m, 9H), 6.94 and 6.70 (each d, J=8.4 and 7.6 Hz, totally 1H), 4.65–4.45 (m, 1H), 3.97 (s, 2H), 3.40–3.10 (m, 5H), 3.10–2.65 (m, 6H), 2.60–1.00 (m, 13H), 1.00–0.70 (m, 6H).

EXAMPLE 3(14)

(2S)-N-[(3S)-5-methyl-2-oxo-1-(1,3,4,5-tetrahydro-2H-2-benzazepin-2-yl)-3-hexyl]-4-methyl-2-benzyloxycarbonylaminopentanamide

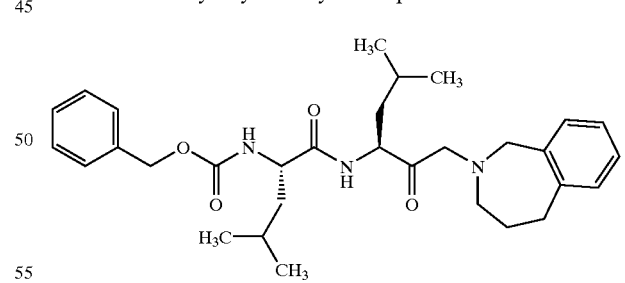

TLC: Rf 0.45 (n-hexane:ethyl acetate=1:1);

NMR (CDCl$_3$): δ 7.40–7.00 (m, 9H), 6.35 (d, J=7.5 Hz, 1H), 5.13 (d, J=9.3 Hz, 1H), 5.10 (s, 2H), 4.70 (m, 1H), 4.15 (m, 1H), 3.97 (s, 2H), 3.30 (s, 2H), 3.16 (m, 2H), 2.90 (m, 2H), 1.80–1.20 (m, 8H), 0.93 (m, 6H), 0.86 (m, 6H).

EXAMPLE 3(15)

(2S)-N-[5-methyl-2-oxo-1-(1,3,4,5-tetrahydro-2H-2-benzazepin-2-yl)-3-hexyl]-4-methyl-2-benzyloxycarbonylaminopentanamide

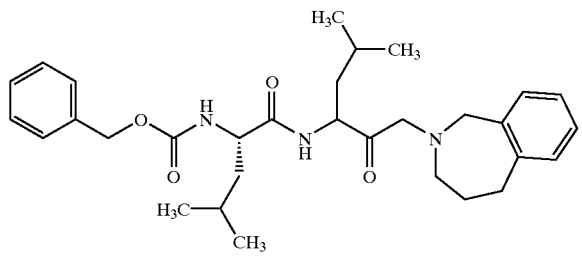

TLC: Rf 0.45 (methanol:ethyl acetate=19:1);

NMR (CDCl$_3$): δ 7.40–7.00 (m, 9H), 6.57 and 6.38 (each brd, J=7.8 Hz, totally 1H), 5.20–5.12 (m, 3H), 4.69 (m, 1H), 4.20 (m, 1H), 3.99 and 3.97 (each s, totally 2H), 3.30 (m, 2H), 3.17 (m, 2H), 2.91 (m, 2H), 1.80–1.30 (m, 8H), 1.00–0.80 (m, 12H).

EXAMPLE 3(16)

(2S)-N-[(3R)-5-methyl-2-oxo-1-(1,3,4,5-tetrahydro-2H-2-benzazepin-2-yl)-3-hexyl]-4-methyl-2-benzyloxycarbonylaminopentanamide

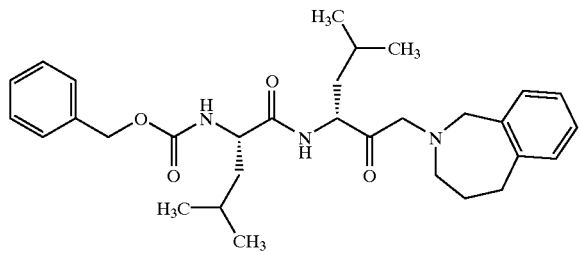

TLC: Rf 0.42 (hexane:ethyl acetate=1:1);

NMR (CDCl$_3$): δ 7.49–6.95 (m, 9H), 6.70 and 6.50 (each d, J=7.2 and 6.0 Hz, totally 1H), 5.30–4.96 (m, 3H), 4.74–4.58 (m, 1H), 4.30–4.06 (m, 1H), 4.01 (s, 2H), 3.50–3.03 (m, 4H), 3.03–2.80 (m, 2H), 2.11–1.20 (m, 8H), 1.07–0.74 (m, 12H).

EXAMPLE 3(17)

(2R)-N-[(3R)-5-methyl-2-oxo-1-(1,3,4,5-tetrahydro-2H-2-benzazepin-2-yl)-3-hexyl]-4-methyl-2-benzyloxycarbonylaminopentanamide

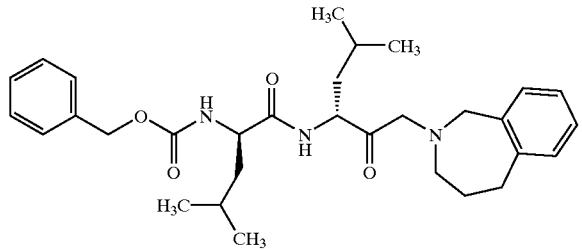

TLC: Rf 0.42 (hexane:ethyl acetate=1:1);

NMR (CDCl$_3$): δ 7.51–6.96 (m, 9H), 6.60 and 6.46 (each d, J=8.4 Hz, totally 1H), 5.30–4.92 (m, 3H), 4.77–4.60 (m, 1H), 4.30–4.06 (m, 1H), 3.99 (s, 2H), 3.46–3.04 (m, 4H), 3.04–2.77 (m, 2H), 2.05–1.20 (m, 2H), 1.07–0.74 (m, 12H).

EXAMPLE 3(18)

1-cyclohexyl-N-[(3R)-5-methyl-2-oxo-1-(1,3,4,5-tetrahydro-2H-2-benzazepin-2-yl)-3-hexyl] carboxamide

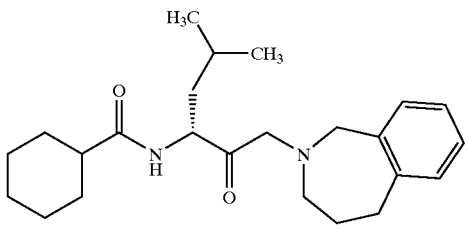

TLC: Rf 0.31 (hexane:ethyl acetate=1:1);

NMR (CDCl$_3$): δ 7.24–7.00 (m, 4H), 5.95 (d, J=8.1 Hz, 1H), 4.70 (ddd, J=9.8, 8.1, 3.9 Hz, 1H), 4.01 (s, 2H), 3.40 (d, J=18.0 Hz, 1H), 3.32 (d, J=18.0 Hz, 1H), 3.25–3.14 (m, 2H), 2.97–2.86 (m, 2H), 2.19–2.00 (m, 1), 1.95–1.06 (m, 15H), 0.89 (d, J=6.5 Hz, 3H), 0.88 (d, J=6.5 Hz, 3H).

EXAMPLE 3(19)

N-[(3R)-5-methyl-2-oxo-1-(1,3,4,5-tetrahydro-2H-2-benzazepin-2-yl)-3-hexyl]-3-cyclopentylpropanamide

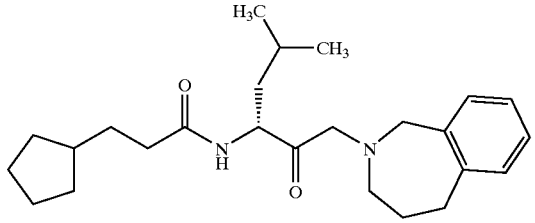

TLC: Rf 0.32 (hexane:ethyl acetate=1:1);

NMR (CDCl$_3$): δ 7.23–7.00 (m, 4H), 5.95 (d, J=8.4 Hz, 1H), 4.74 (ddd, J=9.8, 8.4, 4.2 Hz, 1H), 4.00 (s, 2H), 3.39 (d, J=18.0 Hz, 1H), 3.31 (d, J=18.0 Hz, 1H), 3.23–3.14 (m, 2H), 2.95–2.86 (m, 2H), 2.29–2.14 (m, 2H), 1.96–1.20 and 1.20–0.96 (each m, totally 13H), 0.89 (d, J=6.6 Hz, 3H), 0.88 (d, J=6.6 Hz, 3H).

EXAMPLE 3(20)

N-[(3R)-5-methyl-2-oxo-1-(1,3,4,5-tetrahydro-2H-2-benzazepin-2-yl)-3-hexyl]-1-[(1R,2S)-2-benzoylaminocyclohexyl]carboxamide

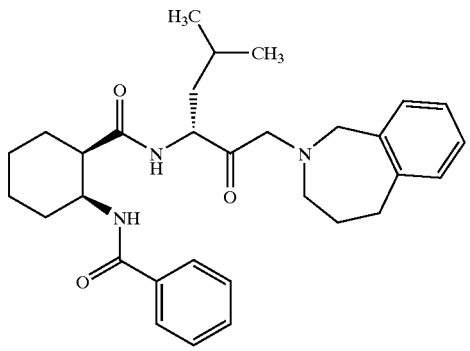

TLC: Rf 0.52 (chloroform:methanol=9:1);

NMR (CDCl$_3$): δ 7.90–7.70 (m, 2H), 7.60–7.33 (m, 4H), 7.22–6.95 (m, 4H), 6.24 and 6.17 (each d, J=8.1 Hz, totally 1H), 4.76–4.57 (m, 1H), 4.40–4.19 (m, 1H), 3.98 and 3.97 (each s, totally 2H), 3.44–3.22 (m, 2H), 3.22–3.02 (m, 2H), 2.96–2.80 (m, 2H), 2.80–2.66 (m, 1H), 2.16–1.15 (m, 13H), 0.86, 0.75 and 0.74 (each d, J=6.5 Hz, totally 6H).

EXAMPLE 3(21)

N-[(3R)-5-methyl-2-oxo-1-(1,3,4,5-tetrahydro-2H-2-benzazepin-2-yl)-3-hexyl]-1-[(1S,2R)-2-benzoylaminocyclohexyl]carboxamide

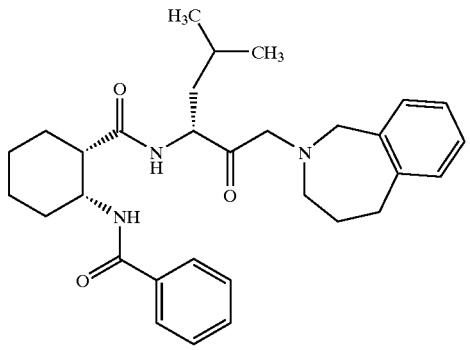

TLC: Rf 0.52 (chloroform:methanol=9:1);

NMR (CDCl$_3$): δ 7.90–7.70 (m, 2H), 7.57–7.31 (m, 4H), 7.21–6.96 (m, 4H), 6.34 and 6.20 (each d, J=8.7 Hz, totally 1H), 4.78–4.60 (m, 1H), 4.41–4.16 (m, 1H), 4.00 (s, 2H), 3.48–3.24 (m, 2H), 3.24–3.07 (m, 2H), 2.98–2.81 (m, 2H), 2.81–2.68 (m, 1H), 2.20–1.20 (m, 13H), 0.87, 0.75 and 0.74 (each d, J=6.6 Hz, totally 6H).

EXAMPLE 3(22)

(2S)-N-[1-(2-(1,3,4,5-tetrahydro-2H-2-benzazepin-2-yl)acetyl)cyclohexan-1-yl]-4-methyl-2-benzyloxycarbonylaminopentanamide

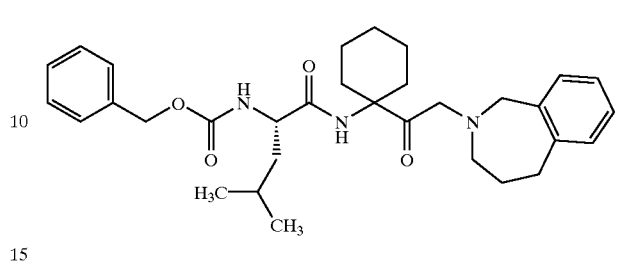

TLC: Rf 0.39 (chloroform:methanol=9:1);

NMR (CDCl$_3$): δ 7.34 (s, 5H), 7.17–7.00 (m, 4H), 6.39 (brs, 1H), 5.12 (d, J=12.3 Hz, 1H), 5.06 (d, J=12.3 Hz, 1H), 5.00 (m, 1H), 4.08 (m, 1H), 3.96 (s, 2H), 3.40 (s, 2H), 3.13 (t, J=5.4 Hz, 2H), 2.87 (m, 2H), 1.90 (m, 2H), 1.80–1.10 (m, 13H), 1.00–0.84 (m, 6H).

EXAMPLE 3(23)

(2S)-N-[1-(2-(1,3,4,5-tetrahydro-2H-2-benzazepin-2-yl)acetyl)cyclohexan-1-yl]-1-[(1R,2S)-2-benzoylaminocyclohexyl]carboxamide

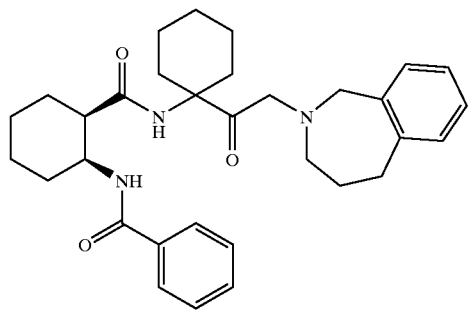

TLC: Rf 0.41 (ethyl acetate);

NMR (CDCl$_3$): δ 7.81 (m, 2H), 7.60–6.93 (m, 8H), 5.83 (brs, 1H), 4.30 (m, 1H), 3.93 (d, J=14.7 Hz, 1H), 3.88 (d, J=14.7 Hz, 1H), 3.40 (m, 2H), 3.20–2.78 (m, 5H), 2.10–1.10 (m, 20H).

EXAMPLE 3(24)

N-[(3S)-5-methyl-2-oxo-1-(1,3,4,5-tetrahydro-2H-2-benzazepin-2-yl)-3-hexyl]-2-(1,3-diazaspiro[4,5]decane-2,4-dion-3-yl)acetamide

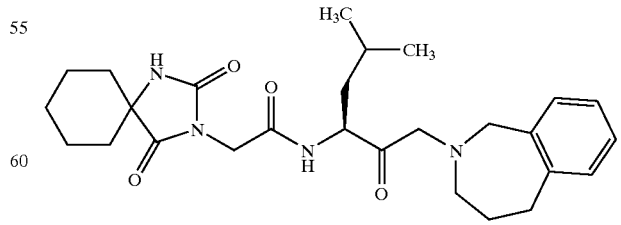

TLC: Rf 0.32 (chloroform:methanol=9:1);

NMR (CDCl$_3$): δ 7.25–7.00 (m, 4H), 6.76 and 6.66 (each d, J=8.0 Hz, totally 1H), 6.40 and 6.26 (each brs, totally 1H), 4.80–4.64 (m, 1H), 4.25–4.04 (m, 2H), 3.98 (s, 2H), 3.38 (d, J=17.7 Hz, 1H), 3.29 (d, J=17.7 Hz, 1H), 3.24–3.10 (m, 2H), 2.97–2.83 (m, 2H), 2.03–1.20 (m, 15H), 0.88 (d, J=6.3 Hz, 3H), 0.87 (d, J=6.3 Hz, 3H).

REFERENCE EXAMPLE 2

(1R,2S)-2-(t-butoxycarbonylamino)cyclohexylmethylalcohol

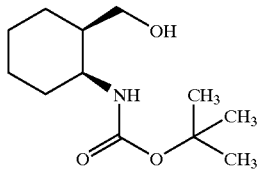

To a solution of (1R,2S)-2-aminocyclohexylmethylalcohol (500 mg) in tetrahydrofuran (25 ml) was added di-t-butyl-dicarbonate (0.98 ml) and the mixture was stirred for 1 hour at room temperature. The reaction mixture was concentrated and the residue was dried under reduced pressure to give the title compound (1.18 g) having the following physical data.

TLC: Rf 0.32 (n-hexane:ethyl acetate=3:1);

NMR (CD$_3$OD): δ 3.92–3.80 (br, 1H), 3.48–3.26 (m, 2H), 1.80–1.10 (m, 9H), 1.44 (s, 9H).

REFERENCE EXAMPLE 3

(1R,2S)-2-(t-butoxycarbonylamino)cyclohexanecarbaldehyde

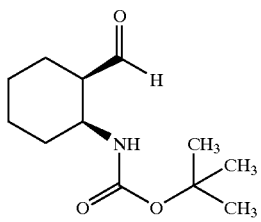

Under atmosphere of argon, to a solution of the compound prepared in reference example 2 (1.18 g) in dimethylsulfoxide (12 ml) were added triethylamine (1.62 ml) and sulfur trioxide-pyridine complex (1.85 g) under cooling with ice and the mixture was stirred for 1 hour at room temperature. The reaction mixture was poured into ice-water and was extracted with ethyl acetate. The organic layer was washed with 10% aqueous solution of citric acid, water and a saturated aqueous solution of sodium chloride successively, dried over anhydrous magnesium sulfate, and was concentrated and the residue was dried under reduced pressure to give the title compound (810 mg) having the following physical data.

TLC: Rf 0.51 (n-hexane:ethyl acetate=3:1);

NMR (CDCl$_3$): δ 9.70 (d, J=1.5 Hz, 1H), 5.45–4.98 (br, 1H), 4.07–3.86 (m, 1H), 2.82–2.58 (m, 1H), 2.06–1.85 (m, 1H), 1.82–1.19 (m, 7H), 1.43 (s, 9H).

REFERENCE EXAMPLE 4

(1R,2S)-2-(t-butoxycarbonylamino)cyclohexanecarboxylic acid

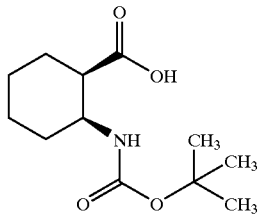

To a solution of the compound prepared in reference example 3 (810 mg) in t-butanol (6.2 ml)-water (6.2 ml) were added 2-methyl-2-butene (1.85 ml), sodium dihydrogenphosphate dihydrate (723 mg) and sodium chlorite (80%, 1.53 g) under cooling with ice and the mixture was stirred for 2 hours at room temperature. To the reaction mixture was added 10% aqueous solution of citric acid and was extracted with ethyl acetate. The organic layer was washed with 10% aqueous solution of citric acid, water and a saturated aqueous solution of sodium chloride successively, dried over anhydrous magnesium sulfate and was concentrated. The residue was purified by column chromatography on silica gel (n-hexane:ethyl acetate=3:1) to give the title compound (734 mg) having the following physical data.

TLC: Rf 0.21 (n-hexane:ethyl acetate=3:1);

NMR (CD$_3$OD): δ 3.96–3.78 (m, 1H), 2.77–2.59 (m, 1H), 2.05–1.17 (m, 8H), 1.43 (s, 9H).

EXAMPLE 4

N-[(3S)-5-methyl-2-oxo-1-(1,3,4,5-tetrahydro-2H-2-benzazepin-2-yl)-3-hexyl]-1-[(1R,2S)-2-(t-butoxycarbonylamino)cyclohexyl]carboxamide

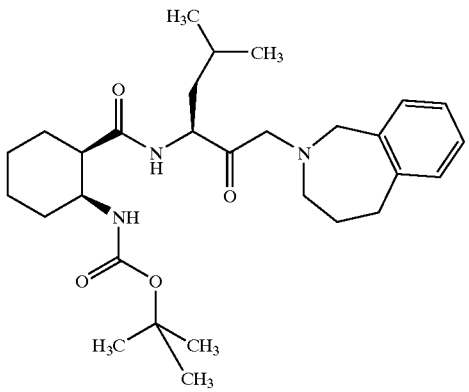

To a solution of the compound prepared in reference example 4 (374 mg) in dimethylformamide (5 ml) was added the compound prepared in example 2 (243 mg) and 1-hydroxybenzotriazole (199 mg) and 1-ethyl-3-[3-(dimethylamino)propyl]carbodiimide hydrochloride (211 mg) and triethylamine (0.28 ml) and the mixture was stirred for 4 hours at room temperature. To the reaction mixture was added ethyl acetate and the mixture was washed with a saturated aqueous solution of sodium bicarbonate, water and a saturated aqueous solution of sodium chloride successively, dried over anhydrous magnesium sulfate and was concentrated. The residue was purified by column chromatography on silica gel (n-hexane:ethyl acetate 2:1) to give the compound of the present invention (352 mg) having the following physical data.

TLC: Rf 0.24 (hexane:ethyl acetate=1:1);

NMR (CDCl$_3$): δ 7.25–6.97 (m, 4H), 6.22 and 6.07 (each d, J=8.1 Hz, totally 1H), 5.49 and 5.23 (each d, J=7.8 Hz, totally 1H), 4.75–4.60 (m, 1H), 3.98 (s, 2H), 3.87–3.66 (m, 1H), 3.45–3.34 (m, 2H), 3.32–3.08 (m, 2H), 3.00–2.80 (m, 2H), 2.67–2.53 (m, 1H), 2.08–1.15 (m, 13H), 1.43 and 1.41 (each s, totally 9H), 0.99–0.78 (m, 6H).

EXAMPLE 5

N-[(3S)-5-methyl-2-oxo-1-(1,3,4,5-tetrahydro-2H-2-benzazepin-2-yl)-3-hexyl]-1-[(1R,2S)-2-aminocyclohexyl]carboxamide dihydrochloride

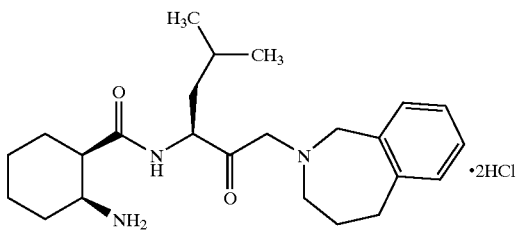

By the same procedure as described in example 2 using the compound prepared in example 4 in place of the compound prepared in example 1, the compound of the present invention having the following physical data was obtained.

TLC: Rf 0.83 (chloroform:methanol: 28% ammonia water=8:2:0.4);

NMR (CD$_3$OD): δ 7.46–7.09 (m, 4H), 4.62–4.15 (m, 5H), 3.75–3.54 (m, 2H), 3.54–3.42 (m, 1H), 3.20–2.95 (m, 2H), 2.95–2.79 (m, 1H), 2.19–1.38 (m, 13H), 0.98 (d, J=6.3 Hz, 3H), 0.93 (d, J=6.3 Hz, 3H).

EXAMPLE 6

N-[(3S)-5-methyl-2-oxo-1-(1,3,4,5-tetrahydro-2H-2-benzazepin-2-yl)-3-hexyl]-1-[(1R,2S)-2-(4-chlorophenyl carbonylamino)cyclohexyl]carboxamide

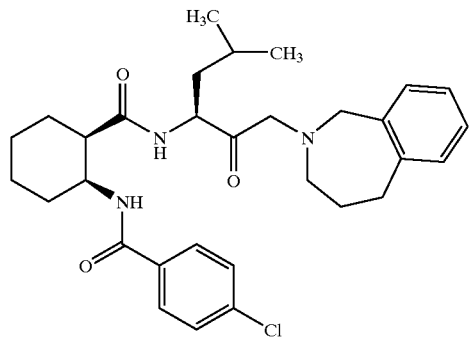

To a suspension of the compound prepared in example 5 in dichloroethane (4 ml) was added triethylamine (0.33 ml) and the mixture was stirred for 15 minutes at room temperature. Thereto was added 4-chlorobenzoyl chloride (148 mg) and the mixture was stirred for another 4 hours. To the reaction mixture was added ethyl acetate and was washed with a saturated aqueous solution of sodium bicarbonate, water and a saturated aqueous solution of sodium chloride successively. The organic layer was dried over anhydrous magnesium sulfate and was concentrated. The residue was purified by column chromatography on silica gel (ethyl acetate:n-hexane=2:1) to give the compound of the present invention (284 mg) having the following physical data.

TLC: Rf 0.51 (ethyl acetate);

NMR (CDCl$_3$): δ 7.79 and 7.71 (each d, J=9.0 Hz, totally 2H), 7.61 (d, J=9.0 Hz, 0.3H), 7.44–7.33 (m, 2.7H), 7.21–6.97 (m, 4H), 6.14 and 6.07 (each d, J=8.4 Hz, totally 1H), 4.78–4.62 (m, 1H), 4.34–4.16 (m, 1H), 4.04–3.86 (m, 2H), 3.38–3.20 (m, 2H), 3.20–3.07 (m, 2H), 3.02–2.83 (m, 2H), 2.79–2.68 (m, 1H), 2.19–1.15 (m, 13H), 0.88, 0.87, 0.77 and 0.75 (each d, J=6.6 Hz, totally 6H).

EXAMPLE 6(1)–EXAMPLE 6(27)

By the same procedure as described in example 6 using a halogenated compound corresponding to 4-chlorobenzoylchloride, the compound of the present invention having the following physical data was obtained.

EXAMPLE 6(1)

N-[(3S)-5-methyl-2-oxo-1-(1,3,4,5-tetrahydro-2H-2-benzazepin-2-yl)-3-hexyl]-1-[(1R,2S)-2-phenylacetylaminocyclohexyl]carboxamide

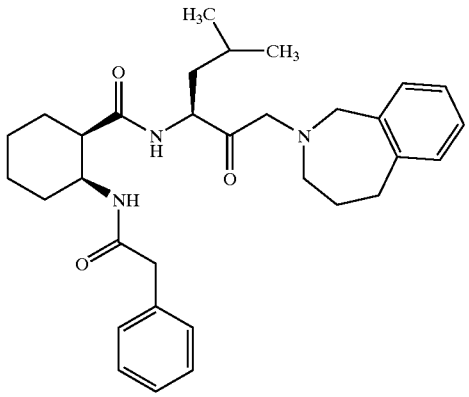

TLC: Rf 0.66 (chloroform:methanol=9:1);

NMR (CDCl$_3$): δ 7.35–7.00 (m, 9H), 6.63 and 6.44 (each d, J=8.4 and 8.1 Hz, totally 1H), 6.08 (d, J=84 Hz, 1H), 4.70–4.50 (m, 1H), 4.20–4.00 (m, 1H), 3.99 and 3.98 (each s, totally 2H), 3.65–3.45 (m, 2H), 3.35–3.20 (m, 2H), 3.20–3.10 (m, 2H), 2.95–2.85 (m, 2H), 2.56 (q, J=5.2 Hz, 1H), 1.90–1.15 (m, 13H), 0.90–0.75 (m, 6H).

EXAMPLE 6(2)

N-[(3S)-5-methyl-2-oxo-1-(1,3,4,5-tetrahydro-2H-2-benzazepin-2-yl)-3-hexyl]-1-[(1R,2S)-2-hydrocinnamoylaminocyclohexyl]carboxamide

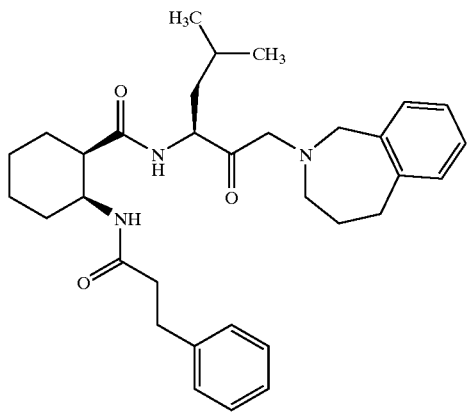

TLC: Rf 0.68 (chloroform:methanol 9:1);

NMR (CDCl$_3$): δ 7.35–6.95 (m, 9H), 6.61 and 6.39 (each d, J=8.8 and 8.0 Hz, totally 1H), 6.07 and 5.92 (each d, J=8.6 and 7.6 Hz, totally 1H), 4.75–4.55 (m, 1H), 4.20–3.90 (m, 1H), 3.98 (s, 2H), 3.32 (s, 2H), 3.25–3.10 (m, 2H), 3.05–2.75 (m, 4H), 2.60–2.35 (m, 3H), 2.00–1.10 (m, 13H), 1.00–0.70 (m, 6H).

EXAMPLE 6(3)

N-[5-methyl-2-oxo-1-(1,3,4,5-tetrahydro-2H-2-benzazepin-2-yl)-3-hexyl]-1-[(1R,2S)-2-acetylaminocyclohexyl]carboxamide

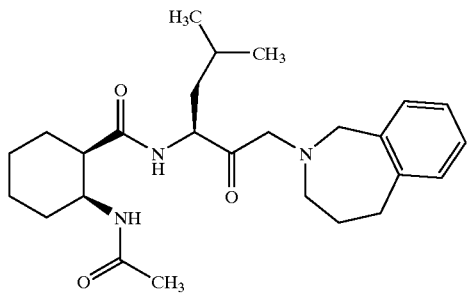

TLC: Rf 0.62 (chloroform:methanol=9:1);

NMR (CDCl$_3$): δ 7.40–7.00 (m, 4H), 6.65 and 6.43 (each d, J=8.8 and 8.2 Hz, totally 1H), 6.15 (d, J=7.8 Hz, 1H), 4.75–4.55 (m, 1H), 4.20–3.95 (m, 1H), 3.99 (s, 2H), 3.34 and 3.32 (each s, totally 2H), 3.25–3.10 (m, 2H), 3.00–2.80 (m, 2H), 2.75–2.55 (m, 1H), 2.25–1.20 (m, 13H), 2.01 and 1.93 (each s, totally 3H), 1.05–0.75 (m, 6H).

EXAMPLE 6(4)

N-[5-methyl-2-oxo-1-(1,3,4,5-tetrahydro-2H-2-benzazepin-2-yl)-3-hexyl]-1-[(1R,2S)-2-(6-aminonicotinoyl)aminocyclohexyl]carboxamide

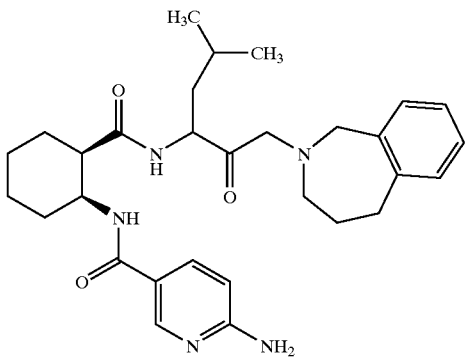

TLC: Rf 0.40 (chloroform:methanol=9:1);

NMR (CDCl$_3$): δ 8.57 and 8.49 (each d, J=2.0 Hz, totally 1H), 7.92 and 7.83 (each dd, J=8.8 and 2.0 Hz, totally 1H), 7.60–7.30 (m, 1H), 7.25–6.95 (m, 4H), 6.47 and 6.44 (each d, J=8.8 Hz, totally 1H), 6.24–6.00 (m, 1H), 4.89 (brs, 2H), 4.85–4.54 (m, 1H), 4.40–4.13 (m, 1H), 3.98 and 3.95 (each s, totally 2H), 3.32 (s, 2H), 3.25–3.04 (m, 2H), 3.00–2.83 (m, 2H), 2.83–2.62 (m, 1H), 2.19–1.08 (m, 13H), 0.87, 0.86, 0.78, and 0.76 (each d, J=6.4 Hz, totally 6H).

EXAMPLE 6(5)

N-[(3S)-5-methyl-2-oxo-1-(1,3,4,5-tetrahydro-2H-2-benzazepin-2-yl)-3-hexyl]-1-[(1R,2S)-2-(4-(t-butoxycarbonyl)piperazin-1-ylcarbonylamino)cyclohexyl]carboxamide

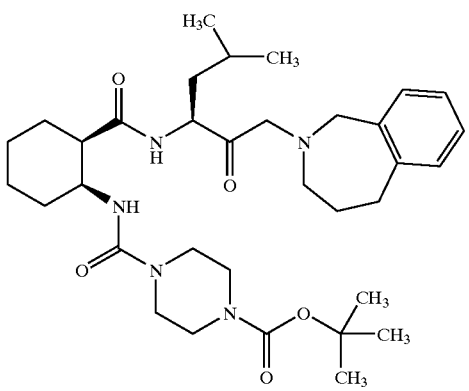

TLC: Rf 0.38 (ethyl acetate);

NMR (CDCl$_3$): δ 7.23–6.98 (m, 4H), 6.16 (d, J=8.7 Hz, 1H), 5.76 (d, J=7.7 Hz, 1H), 4.75–4.63 (m, 1H), 4.02–3.86 (m, 1H), 3.97 (brs, 2H), 3.48–3.36 (m, 4H), 3.36–3.25 (m, 4H), 3.32 (s, 2H), 3.22–3.12 (m, 2H), 2.96–2.86 (m, 2H), 2.70–2.57 (m, 1H), 2.03–1.24 (m, 13H), 1.46 (s, 9H), 0.87 (d, J=6.6 Hz, 3H), 0.85 (d, J=6.6 Hz, 3H).

EXAMPLE 6(6)

N-[(3S)-5-methyl-2-oxo-1-(1,3,4,5-tetrahydro-2H-2-benzazepin-2-yl)-3-hexyl]-1-[(1R,2S)-2-(quinoxalin-2-ylcarbonylamino)cyclohexyl]carboxamide

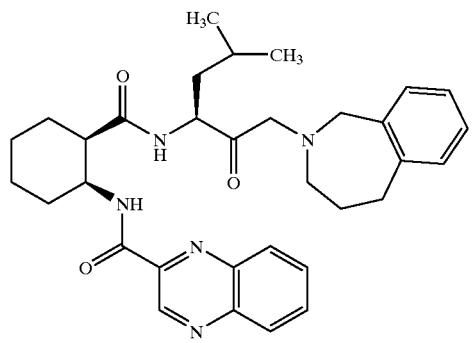

TLC: Rf 0.44 (ethyl acetate);

NMR (CDCl$_3$): δ 9.65 and 9.64 (each s, totally 1H), 8.77 and 8.63 (each d, J=8.4 Hz, totally 1H), 8.24–8.10 (m, 2H), 7.94–7.76 (m, 2H), 7.25–6.87 (m, 4H), 6.25 and 6.12 (each d, J=8.4 Hz, totally 1H), 4.78–4.63 (m, 1H), 4.51–4.32 (m, 1H), 3.96 and 3.83 (each s, totally 2H), 3.34–3.18 (m, 2H), 3.18–3.10 and 3.04–2.85 (each m, totally 4H), 2.85–2.73 (m, 1H), 2.34–1.10 (m, 13H), 0.86, 0.85, 0.62 and 0.58 (each d, J=6.3 Hz, totally 6H).

EXAMPLE 6(7)

N-[(3S)-5-methyl-2-oxo-1-(1,3,4,5-tetrahydro-2H-2-benzazepin-2-yl)-3-hexyl]-1-[(1R,2S)-2-naphthoylaminocyclohexyl]carboxamide

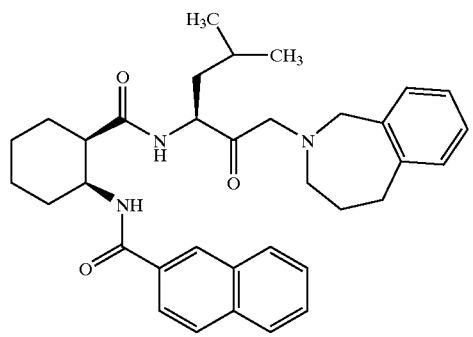

TLC: Rf 0.47 (ethyl acetate);

NMR (CDCl$_3$): δ 8.39 and 8.29 (each s, totally 1H), 7.99–7.79 (m, 4H), 7.70 and 7.43 (each d, J=7.5 Hz, totally 1H), 7.61–7.48 (m, 2H), 7.22–6.89 (m, 4H), 6.17 and 6.11 (each d, J=8.4 Hz, totally 1H), 4.79–4.61 (m, 1H), 4.44–4.26 (m, 1H), 4.03–3.88 (m, 2H), 3.37–3.22 (m, 2H), 3.21–3.05 (m, 2H), 3.01–2.87 (m, 2H), 2.87–2.76 (m, 1H), 2.20–1.10 (m, 13H), 0.86, 0.85, 0.72 and 0.71 (each d, J=6.6 Hz, totally 6H).

EXAMPLE 6(8)

N-[(3S)-5-methyl-2-oxo-1-(1,3,4,5-tetrahydro-2H-2-benzazepin-2-yl)-3-hexyl]-1-[(1R,2S)-2-(1-benzothiophen-2-ylcarbonylamino)cyclohexyl]carboxamide

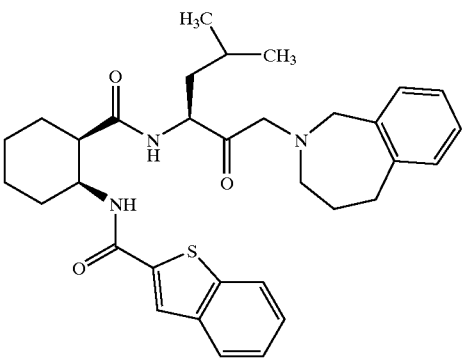

TLC: Rf 0.56 (ethyl acetate);

NMR (CDCl$_3$): δ 7.90–7.75 (m, 2H), 7.72 (s, 1H), 7.45–7.31 (m, 3H), 7.23–6.94 (m, 4H), 6.14 and 6.08 (each d, J=8.1 Hz, totally 1H), 4.79–4.62 (m, 1H), 4.36–4.16 (m, 1H), 4.02–3.88 (m, 2H), 3.33 (s, 2H), 3.22–3.06 (m, 2H), 3.02–2.81 (m, 2H), 2.81–2.72 (m, 1H), 2.20–1.12 (m, 13H), 0.87, 0.86, 0.76 and 0.75 (each d, J=6.3 Hz, totally 6H).

EXAMPLE 6(9)

N-[(3S)-5-methyl-2-oxo-1-(1,3,4,5-tetrahydro-2H-2-benzazepin-2-yl)-3-hexyl]-1-[(1R,2S)-2-(4-methoxybenzoylamino)cyclohexyl]carboxamide

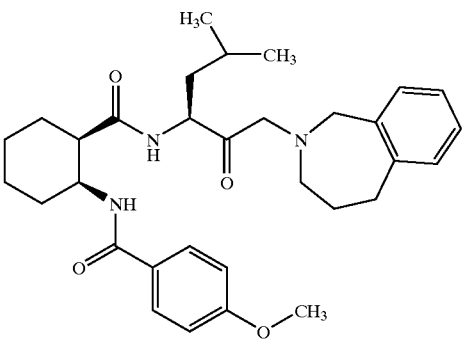

TLC: Rf 0.43 (ethyl acetate);

NMR (CDCl$_3$): δ 7.81 and 7.73 (each d, J=9.0 Hz, totally 2H), 7.44 (d, J=8.4 Hz, 0.3H), 7.23–6.95 (m, 4.7H), 6.90 (d, J=9.0 Hz, 2H), 6.14 and 6.10 (each d, J=8.4 Hz, totally 1H), 4.76–4.60 (m, 1H), 4.34–4.18 (m, 1H), 3.97 and 3.93 (each brs, totally 2H), 3.84 and 3.83 (each s, totally 3H), 3.37–3.21 (m, 2H), 3.21–3.06 (m, 2H), 3.01–2.82 (m, 2H), 2.80–2.69 (m, 1H), 2.18–1.12 (m, 13H), 0.87, 0.75 and 0.74 (each d, J=6.3 Hz, totally 6H).

EXAMPLE 6(10)

N-[(3S)-5-methyl-2-oxo-1-(1,3,4,5-tetrahydro-2H-2-benzazepin-2-yl)-3-hexyl]-1-[(1R,2S)-2-(4-nitrobenzoylamino)cyclohexyl]carboxamide

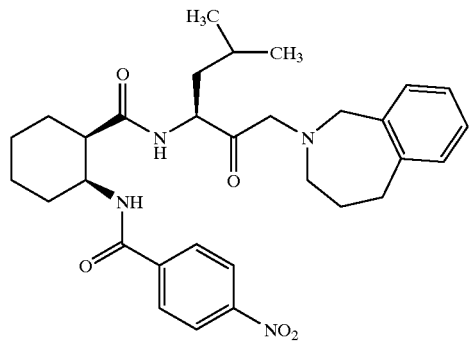

TLC: Rf 0.51 (ethyl acetate);

NMR (CDCl₃): δ 8.31–8.21 (m, 2H), 8.01 and 7.94 (each d, J=9.0 Hz, totally 2H), 7.85 and 7.76 (each d, J=7.5 Hz, totally 1H), 7.23–6.96 (m, 4H), 6.17 and 6.08 (each d, J=8.4 Hz, totally 1H), 4.80–4.66 (m, 1H), 4.36–4.18 (m, 1H), 4.06–3.88 (m, 2H), 3.40–3.24 (m, 2H), 3.24–3.07 (m, 2H), 3.02–2.84 (m, 2H), 2.80–2.70 (m, H), 2.20–1.20 (m, 13H), 0.89, 0.88, 0.80 and 0.78 (each d, J=6.6 Hz, totally 6H).

EXAMPLE 6(11)

N-[(3S)-5-methyl-2-oxo-1-(1,3,4,5-tetrahydro-2H-2-benzazepin-2-yl)-3-hexyl]-1-[(1R,2S)-2-(4-phenylbenzoylamino)cyclohexyl]carboxamide

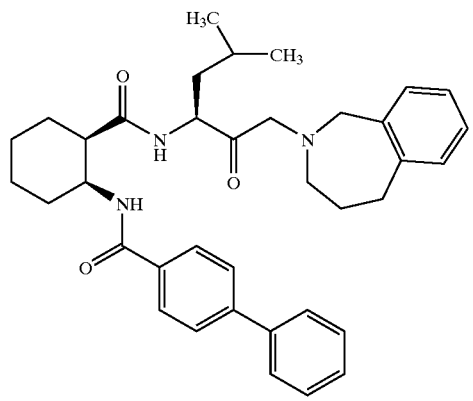

TLC: Rf 0.33 (ethyl acetate);

NMR (CDCl₃): δ 7.92 and 7.84 (each d, J=9.0 Hz, totally 2H), 7.70–7.55 (m, 4H), 7.51–7.30 (m, 4H), 7.23–6.97 (m, 4H), 6.20–6.09 (m, 1H), 4.79–4.63 (m, 1H), 4.42–4.20 (m, 1H), 3.98 and 3.95 (each s, totally 2H), 3.40–3.21 (m, 2H), 3.21–3.03 (m, 2H), 3.03–2.81 (m, 2H), 2.81–2.69 (m, 1H), 2.20–1.12 (m, 13H), 0.87 and 0.76 (each d, J=6.6 Hz, totally 6H).

EXAMPLE 6(12)

N-[(3S)-5-methyl-2-oxo-1-(1,3,4,5-tetrahydro-2H-2-benzazepin-2-yl)-3-hexyl]-1-[(1R,2S)-2-(4-fluorobenzoylamino)cyclohexyl]carboxamide

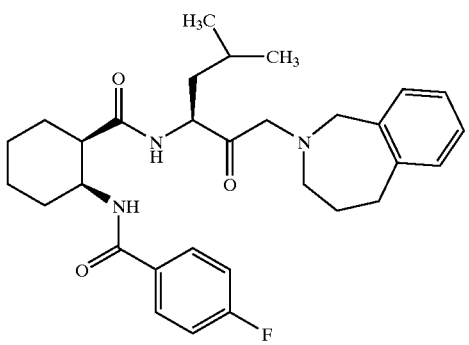

TLC: Rf 0.36 (ethyl acetate);

NMR (CDCl₃): δ 7.89–7.73 (m, 2H), 7.57 and 7.33 (each d, J=8.1 Hz, totally 1H), 7.22–6.97 (m, 6H), 6.13 and 6.08 (each d, J=8.1 Hz, totally 1H), 4.77–4.62 (m, 1H), 4.34–4.16 (m, 1H), 3.98 and 3.95 (each s, totally 2H), 3.32 (s, 2H), 3.23–3.08 (m, 2H), 3.03–2.84 (m, 2H), 2.79–2.67 (m, 1H), 2.15–1.16 (m, 13H), 0.88, 0.87, 0.77 and 0.75 (each d, J=6.6 Hz, totally 6H).

EXAMPLE 6(13)

N-[(3S)-5-methyl-2-oxo-1-(1,3,4,5-tetrahydro-2H-2-benzazepin-2-yl)-3-hexyl]-1-[(1R,2S)-2-(2-pyridylcarbonylamino)cyclohexyl]carboxamide

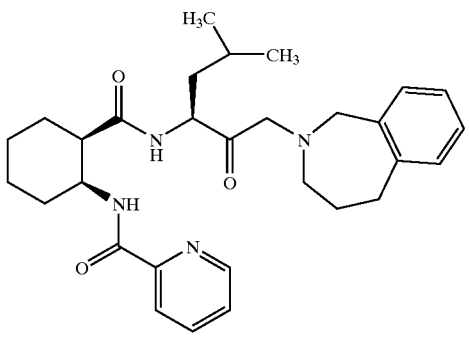

TLC: Rf 0.28 (ethyl acetate);

NMR (CDCl₃): δ 8.60 (d. J=8.4 Hz, 1H), 8.55 (ddd, J=5.0, 2.0 and 1.2 Hz, 1H), 8.14 (dt, J=7.8 and 1.2 Hz, 1H), 7.82 (dt, J=2.0 and 7.8 Hz, 1H), 7.40 (ddd, J=7.8, 5.0 and 1.2 Hz, 1H), 7.23–6.96 (m, 4H), 6.17 (d, J=8.4 Hz, 1H), 4.72–4.59 (m, 1H), 4.44–4.30 (m, 1H), 3.96 (s, 2H), 3.34 (d, J=18.3 Hz, 1H), 3.27 (d, J=18.3 Hz, 1H), 3.20–3.08 (m, 2H), 2.96–2.83 (m, 2H), 2.79–2.68 (m, 1H), 2.20–1.10 (m, 13H), 0.65 and 0.63 (each d, J=6.0 Hz, totally 6H).

EXAMPLE 6(14)

N-[(3S)-5-methyl-2-oxo-1-(1,3,4,5-tetrahydro-2H-2-benzazepin-2-yl)-3-hexyl]-1-[(1R,2S)-2-(4-t-butylbenzoylamino)cyclohexyl]carboxamide

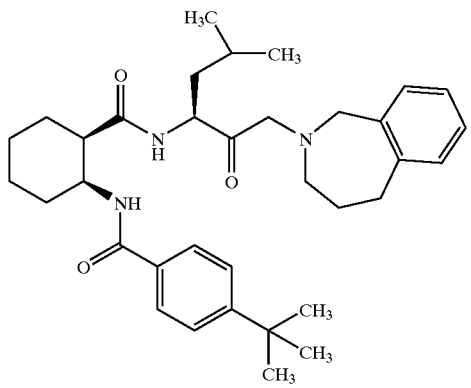

TLC: Rf 0.39 (ethyl acetate);

NMR (CDCl$_3$): δ 7.77 and 7.70 (each d, J=9.0 Hz, totally 2H), 7.49 (d, J=8.0 Hz, 0.3H), 7.42 (d, J=9.0 Hz, 2H), 7.25–6.94 (m, 4.7H), 6.14 (d, J=8.4 Hz, 1H), 4.74–4.60 (m, 1H), 4.36–4.20 (m, 1H), 3.98 and 3.95 (each s, totally 2H), 3.33 and 3.30 (each s, totally 2H), 3.22–3.07 (m, 2H), 3.00–2.84 (m, 2H), 2.79–2.69 (m, 1H), 2.15–1.18 (m, 13H), 1.32 and 1.31 (each s, totally 9H), 0.86 and 0.74 (each d, J=6.3 Hz, totally 6H).

EXAMPLE 6(15)

N-[(3S)-5-methyl-2-oxo-1-(1,3,4,5-tetrahydro-2H-2-benzazepin-2-yl)-3-hexyl]-1-[(1R,2S)-2-(2-methylthionicotinoylamino)cyclohexyl]carboxamide

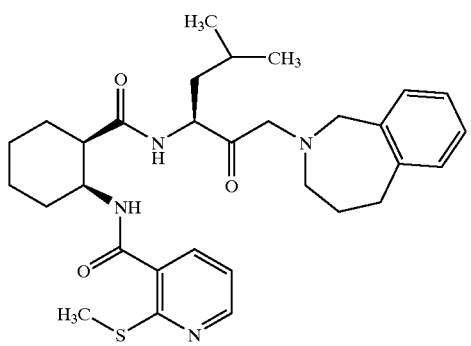

TLC: Rf 0.32 (ethyl acetate);

NMR (CDCl$_3$): δ 8.53–8.44 (m, 1H), 7.78 and 7.73 (each dd, J=7.7 and 1.7 Hz, totally 1H), 7.45 (d, J=9.6 Hz, 0.3H), 7.25–6.92° (m, 5.7H), 6.19 and 6.12 (each d, J=8.4 Hz, totally 1H), 4.74–4.58 (m, 1H), 4.40–4.24 (m, 1H), 4.01–3.82 (m, 2H), 3.31 and 3.27 (each s, totally 2H), 3.21–3.06 (m, 2H), 3.01–2.84 (m, 2H), 2.81–2.70 (m, 1H), 2.54 (s, 3H), 2.20–1.20 (m, 13H), 0.88, 0.85, 0.80 and 0.77 (each d, J=6.6 Hz, totally 6H).

EXAMPLE 6(16)

N-[(3S)-5-methyl-2-oxo-1-(1,3,4,5-tetrahydro-2H-2-benzazepin-2-yl)-3-hexyl]-1-[(1R,2S)-2-(1-naphthylacetylamino)cyclohexyl]carboxamide

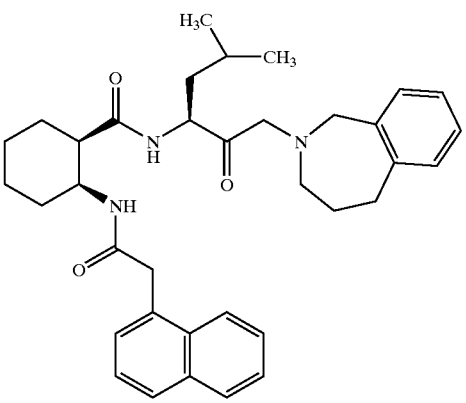

TLC: Rf 0.29 (ethyl acetate);

NMR (CDCl$_3$): δ 8.07–7.92 (m, 1H), 7.89–7.74 (m, 2H), 7.55–7.30 (m, 4H), 7.22–6.97 (m, 4H), 6.58 and 6.41 (each d, J=8.7 Hz, totally 1H), 6.05 (br, 0.3H), 6.00 (d, J=7.8 Hz, 0.7H), 4.60–4.45 (m, 1H), 4.21–3.76 (m, 5H), 3.27 (s, 2H), 3.20–3.08 (m, 2H), 3.01–2.85 (m, 2H), 2.54–2.39 (m, 1H), 1.90–1.05 (m, 13H), 0.89, 0.86, 0.85 and 0.81 (each d, J=6.3 Hz, totally 6H).

EXAMPLE 6(17)

N-[(3S)-5-methyl-2-oxo-1-(1,3,4,5-tetrahydro-2H-2-benzazepin-2-yl)-3-hexyl]-1-[(1R,2S)-2-(2-fluorobenzoylamino)cyclohexyl]carboxamide

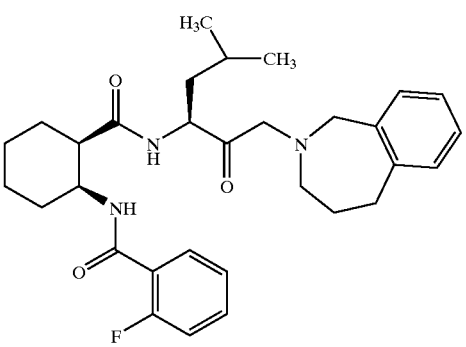

TLC: Rf 0.42 (ethyl acetate);

NMR (CDCl$_3$): δ 8.07–7.98 (m, 1H), 7.83–7.65 and 7.65–7.34 (each m, totally 2H), 7.30–6.94 (m, 6H), 6.21 and 6.11 (each d, J=8.4 Hz, totally 1H), 4.77–4.63 (m, 1H), 4.46–4.28 (m, 1H), 3.96 and 3.91 (each s, totally 2H), 3.40–3.21 (m, 2H), 3.21–3.04 (m, 2H), 2.96–2.82 (m, 2H), 2.80–2.68 (m, 1H), 2.20–1.16 (m, 13H), 0.88, 0.87 and 0.72 (each d, J=6.3 Hz, totally 6H).

EXAMPLE 6(18)

N-[(3S)-1-(1,3,4,5-tetrahydro-2H-benzazepin-2-yl)-5-methyl-2-oxo-3-hexyl]-1-[(1R,2S)-2-(6-chloronicotinoylamino)cyclohexyl]carboxamide

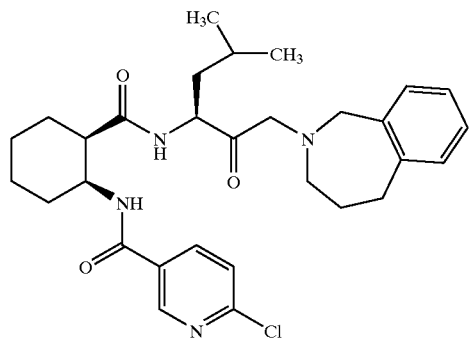

TLC: Rf 0.32 (ethyl acetate);

NMR (CDCl$_3$): δ 8.85 and 8.77 (each d, J=2.7 Hz, totally 1H), 8.12 and 8.04 (each dd, J=8.4 and 2.7 Hz, totally 1H), 7.80 and 7.71 (each d, J=7.5 Hz, totally 1H), 7.38 and 7.37 (each d, J=8.4 Hz, totally 1H), 7.23–6.95 (m, 4H), 6.14 and 6.03 (each d, J=8.4 Hz, totally 1H), 4.81–4.64 (m, 1H), 4.34–4.15 (m, 1H), 4.06–3.85 (m, 2H), 3.32 and 3.31 (each s, totally 2H), 3.24–3.07 (m, 2H), 3.02–2.84 (m, 2H), 2.79–2.66 (m, 1H), 2.15–1.17 (m, 13H), 0.89, 0.87, 0.81 and 0.79 (each d, J=6.3 Hz, totally 6H)

EXAMPLE 6(19)

N-[(3S)-5-methyl-2-oxo-1-(1,3,4,5-tetrahydro-2H-2-benzazepin-2-yl)-3-hexyl]-1-[(1R,2S)-2-(4-trifluoromethylbenzoylamino)cyclohexyl]carboxamide

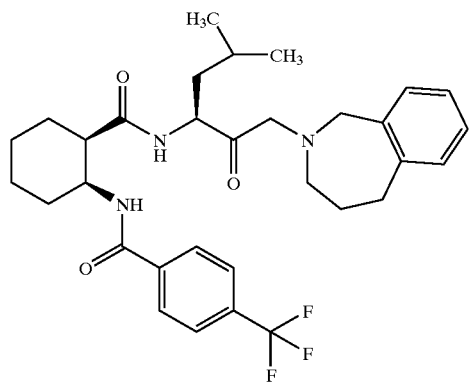

TLC: Rf 0.41 (ethyl acetate);

NMR (CDCl$_3$): δ 7.96 and 7.88 (each d, J=8.1 Hz, totally 2H), 7.68 (d, J=8.1 Hz, 2H), 7.57 (d, J=7.5 Hz, 1H), 7.24–6.96 (m, 4H), 6.15 (d, J=7.8 Hz, 1H), 4.78–4.65 (m, 1H), 4.35–4.18 (m, 1H), 4.06–3.90 (m, 2H), 3.33 (s, 2H), 3.25–3.04 (m, 2H), 3.04–2.84 (m, 2H), 2.80–2.67 (m, 1H), 2.18–1.20 (m, 13H), 0.88, 0.87, 0.78 and 0.76 (each d, J=6.6 Hz, totally 6H).

EXAMPLE 6(20)

N-[(3S)-5-methyl-2-oxo-1-(1,3,4,5-tetrahydro-2H-2-benzazepin-2-yl)-3-hexyl]-1-[(1R,2S)-2-(4-cyanobenzoylamino)cyclohexyl]carboxamide

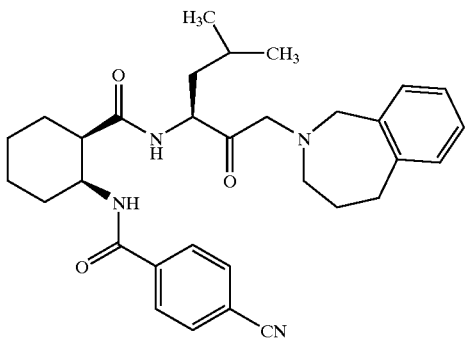

TLC: Rf 0.36 (ethyl acetate);

NMR (CDCl$_3$): δ 7.95 and 7.88 (each d, J=9.0 Hz, totally 2H), 7.77–7.64 (m, 3H), 7.24–6.96 (m, 4H), 6.16 and 6.09 (each d, J=8.4 Hz, totally 1H), 4.79–4.65 (m, 1H), 4.32–4.17 (m, 1H), 4.05–3.90 (m, 2H), 3.32 and 3.31 (each s, totally 2H), 3.25–3.04 (m, 2H), 3.04–2.82 (m, 2H), 2.77–2.65 (m, 1H), 2.18–1.18 (m, 13H), 0.89, 0.88, 0.79 and 0.77 (each d, J=6.3 Hz, totally 6H).

EXAMPLE 6(21)

N-[(3S)-5-methyl-2-oxo-1-(1,3,4,5-tetrahydro-2H-2-benzazepin-2-yl)-3-hexyl]-1-[(1R,2S)-2-(4-methylbenzoylamino)cyclohexyl]carboxamide

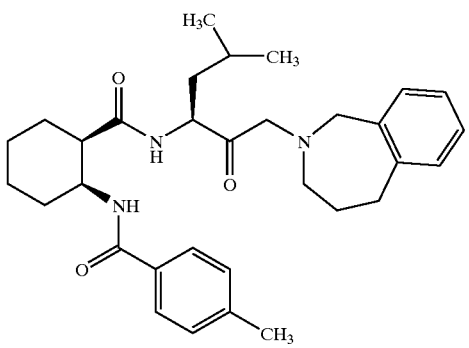

TLC: Rf 0.32 (ethyl acetate);

NMR (CDCl$_3$): δ 7.73 and 7.65 (each d, J=8.1 Hz, totally 2H), 7.49 (d, J=7.8 Hz, 0.2H), 7.24–6.96 (m, 6.8H), 6.15 (d, J=8.4 Hz, 1H), 4.76–4.61 (m, 1H), 4.34–4.19 (m, 1H), 3.98 and 3.94 (each s, totally 2H), 3.43–3.21 (m, 2H), 3.21–3.05 (m, 2H), 3.03–2.81 (m, 2H), 2.81–2.67 (m, 1H), 2.38 (s, 3H), 2.22–1.15 (m, 13H), 0.86, 0.75 and 0.74 (each d, J=6.6 Hz, totally 6H)

EXAMPLE 6(22)

N-[(3S)-5-methyl-2-oxo-1-(1,3,4,5-tetrahydro-2H-2-benzazepin-2-yl)-3-hexyl]-1-[(1R,2S)-2-(4-trifluoromethyloxybenzoylamino)cyclohexyl]carboxamide

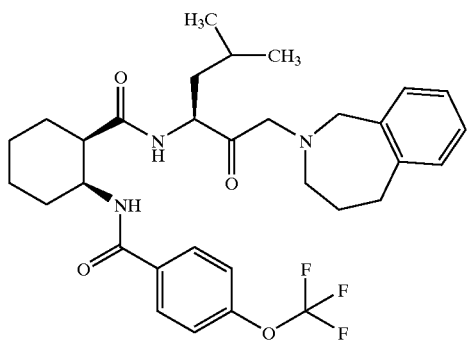

TLC: Rf 0.41 (ethyl acetate);

NMR (CDCl$_3$): δ 7.90 and 7.82 (each d, J=8.7 Hz, total 2H), 7.65 and 7.44 (each d, J=7.8 Hz, total 1H), 7.34–6.93 (m, 6H), 6.15 (d, J=8.1 Hz, 1H), 4.78–4.62 (m, 1H), 4.34–4.17 (m, 1H), 4.06–3.90 (m, 2H), 3.33 (s, 2H), 3.25–3.06 (m, 2H), 3.03–2.82 (m, 2H), 2.82–2.65 (m, 1H), 2.20–1.15 (m, 13H), 0.87, 0.77 and 0.75 (each d, J=6.3 Hz, total 6H).

EXAMPLE 6(23)

N-[(3S)-5-methyl-2-oxo-1-(1,3,4,5-tetrahydro-2H-2-benzazepin-2-yl)-3-hexyl]-1-[(1R,2S)-2-(3-t-butyl-1-methyl pyrazol-5-ylcarbonylamino)cyclohexyl]carboxamide

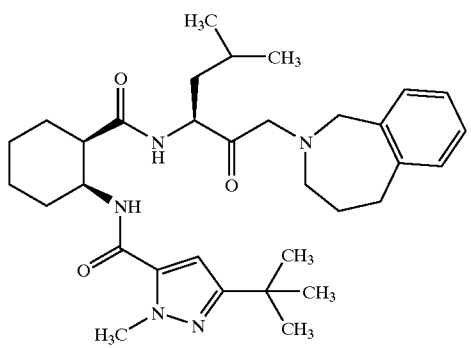

TLC: Rf 0.42 (ethyl acetate);

NMR (CDCl$_3$): δ 7.37 (d, J=9.0 Hz, 0.2H), 7.22–6.98 (m, 4.8H), 6.49 and 6.31 (each s, total 1H), 6.12 and 6.05 (each d, J=8.1 Hz, total 1H), 4.80–4.64 (m, 1H), 4.28–4.05 (m, 1H), 4.12 and 4.09 (each s, total 3H), 4.05–3.90 (m, 2H), 3.33 (s, 2H), 3.24–3.08 (m, 2H), 3.03–2.84 (m, 2H), 2.80–2.65 (m, 1H), 2.15–1.13 (m, 13H), 1.29 and 1.28 (each s, total 9H), 0.88, 0.87, 0.80 and 0.79 (each d, J=6.3 Hz, total 6H).

EXAMPLE 6(24)

N-[(3S)-5-methyl-2-oxo-1-(1,3,4,5-tetrahydro-2H-2-benzazepin-2-yl)-3-hexyl]-1-[(1R,2S)-2-(N,N-di-n-propyl-4-sulfamoyl)benzoylamino)cyclohexyl]carboxamide

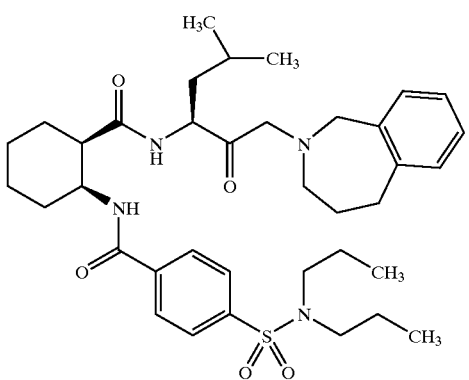

TLC: Rf 0.42 (ethyl acetate);

NMR (CDCl$_3$): δ 7.89 (d, J=8.7 Hz, 2H), 7.84 (d, J=8.7 Hz, 2H), 7.60 (d, J=7.8 Hz, 1H), 7.25–6.96 (m, 4H), 6.19 (d, J=8.4 Hz, 1H), 4.80–4.66 (m, 1H), 4.36–4.18 (m, 1H), 3.99 (s, 2H), 3.34 (s, 2H), 3.25–3.13 (m, 2H), 3.13–3.00 (m, 4H), 2.97–2.84 (m, 2H), 2.80–2.68 (m, 1H), 2.13–1.20 (m, 17H), 0.87 (t, J=7.5 Hz, 6H), 0.79 and 0.76 (each d, J=6.3 Hz, total 6H).

EXAMPLE 6(25)

N-[(3S)-5-methyl-2-oxo-1-(1,3,4,5-tetrahydro-2H-2-benzazepin-2-yl)-3-hexyl]-1-[(1R,2S)-2-mesylaminocyclohexyl]carboxamide

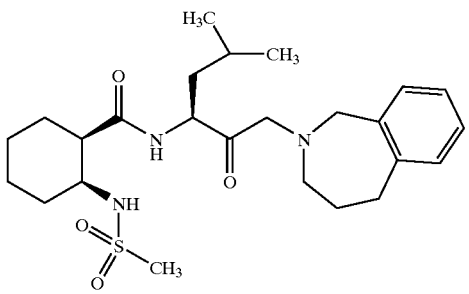

TLC: Rf 0.39 (ethyl acetate);

NMR (CDCl$_3$): δ 7.24–6.99 (m, 4H)$_1$, 6.30 and 5.64 (each d, J=7.5 Hz, total 1H), 6.08 (d, J=8.1 Hz, 1H), 4.77–4.62 (m, 1H), 3.97 (s, 2H), 3.74–3.56 (m, 1H), 3.34 and 3.32 (each s, total 2H), 3.22–3.12 (m, 2H), 3.00–2.85 (m, 2H), 2.98 and 2.92 (each s, total 3H), 2.76–2.59 (m, 1H), 2.17–1.20 (m, 13H), 0.96–0.80 (m, 6H).

EXAMPLE 6(26)

N-[(3S)-5-methyl-2-oxo-1-(1,3,4,5-tetrahydro-2H-2-benzazepin-2-yl)-3-hexyl]-1-[(1R,2S)-2-phenylsulfonylaminocyclohexyl]carboxamide

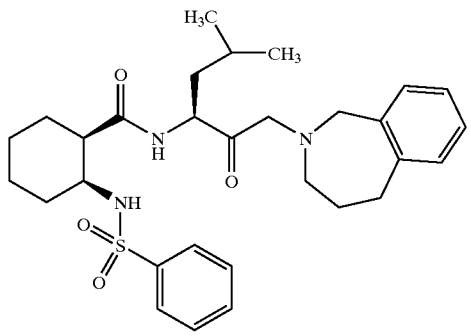

TLC: Rf 0.58 (ethyl acetate);

NMR (CDCl$_3$): δ 7.92–7.82 (m, 2H), 7.60–7.40 (m, 3H), 7.23–6.98 (m, 4H), 6.14 (d, J=6.6 Hz, 1H), 6.11–5.96 (br, 1H), 4.71–4.56 (m, 1H), 4.00 (s, 2H), 3.52–3.24 (brs, 3H), 3.24–3.11 (m, 2H), 3.02–2.83 (m, 2H), 2.52–2.40 (m, 1H), 2.02–1.17 (m, 13H), 0.88 and 0.86 (each d, J=6.3 Hz, total 6H).

EXAMPLE 6(27)

N-[(3S)-5-methyl-2-oxo-1-(1,3,4,5-tetrahydro-2H-2-benzazepin-2-yl)-3-hexyl]-1-[(1R,2S)-2-(4-dimethylaminobenzoylamino)cyclohexyl]carboxamide

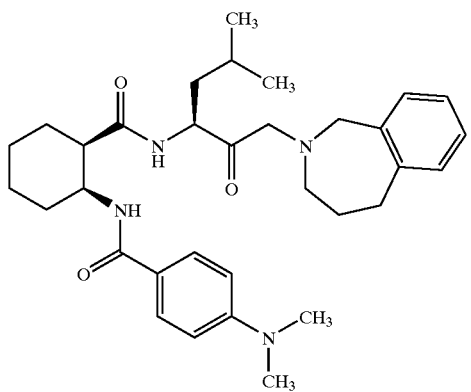

TLC: Rf 0.19 (ethyl acetate);

NMR (CDCl$_3$): δ 7.75 and 7.66 (each d, J=9.2 Hz, total 2H), 7.32–7.24 and 7.22–6.87 (each m, total 5H), 6.65 (d, J=9.2 Hz, 2H), 6.23–6.04 (m, 1H), 4.77–4.54 (m, 1H), 4.40–4.16 (m, 1H), 3.97 and 3.93 (each brs, total 2H), 3.39–3.22 (m, 2H), 3.22–3.04 (m, 2H), 3.00 and 2.99 (each s, total 6H), 2.97–2.81 (m, 2H), 2.81–2.65 (m, 1H), 2.17–1.14 (m, 13H), 0.86 and 0.73 (each d, J=6.0 Hz, total 6H).

EXAMPLE 7

N-[(3S)-5-methyl-2-oxo-1-(1,3,4,5-tetrahydro-2H-2-benzazepin-2-yl)-3-hexyl]-1-[(1R,2S)-2-(piperazin-1-ylcarbonylamino)cyclohexyl]carboxamide dihydrochloride

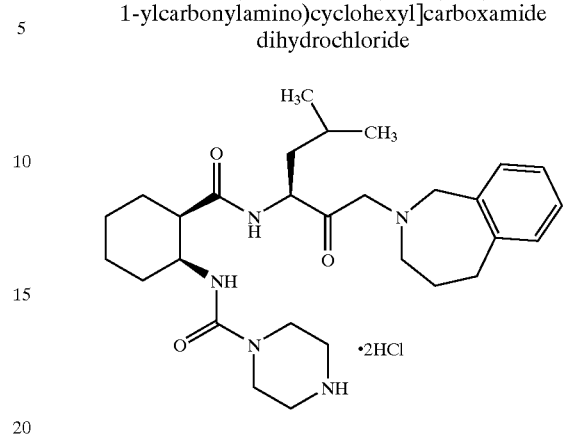

By the same procedure as described in example 2 using the compound prepared in example 6 (5) in place of the compound prepared in example 1, the compound of the present invention having the following physical data was obtained.

TLC: Rf 0.22 (chloroform:methanol: acetic acid=10:2:1);

NMR (CD$_3$OD): δ 7.48–7.20 (m, 4H), 4.47 (brs, 2H), 4.34 (dd, J=10.2 and 4.8 Hz, 1H), 4.31–4.01 (m, 3H), 3.71–3.47 (m, 6H), 3.19 (t, J=5.4 Hz, 4H), 3.12–3.01 (m, 2H), 2.75–2.56 (m, 1H), 2.18–1.16 (m, 13H), 0.96 (d, J=6.3 Hz, 3H), 0.88 (d, J=6.3 Hz, 3H).

EXAMPLE 8

(3S)-3-(t-butoxycarbonylamino)-5-methyl-1-(2,3,4,5-tetrahydro-1H-1-benzazepin-1-yl)hexan-2-one

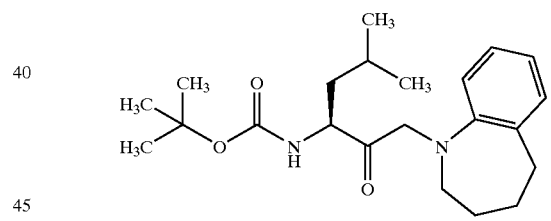

To a solution of the compound prepared in Reference Example 1 (3.08 g) and 2,3,4,5-tetrahydro-1H-1-benzazepine (2.21 g) in acetonitrile (28 ml) was added diisopropylethylamine (2.61 ml) at 0° C. and the mixture was stirred at room temperature for 62 hours. To the reaction mixture was added water and was extracted with ethyl acetate. The organic layer was washed with a saturated aqueous solution of sodium chloride, dried over anhydrous sodium sulfate and was concentrated. The residue was purified by column chromatography on silica gel (n-hexane:ethyl acetate=10:1) to give the compound of the present invention (3.16 g) having the following physical data.

TLC: Rf 0.50 (n-hexane:ethyl acetate=7:3);

NMR (CDCl$_3$): δ 7.11 (d, J=7.2 Hz, 1H), 7.10 (t, J=7.2 Hz, 1H), 6.88 (t, J=7.2 Hz, 1H), 6.75 (d, J=7.2 Hz, 1H), 5.00 (d, J=8.4 Hz, 1H), 4.59 (m, 1H), 4.15 (d, J=15.3 Hz, 1H), 4.10 (d, J=15.3 Hz, 1H), 3.00–2.80 (m, 4H), 1.89–1.30 (m, 4H), 1.43 (s, 9H), 0.96 (d, J=6.3 Hz, 3H), 0.90 (d, J=6.3 Hz, 3H).

EXAMPLE 9

(3S)-3-amino-5-methyl-1-(2,3,4,5-tetrahydro-1H-1-benzazepin-1-yl)hexan-2-one dihydrochloride

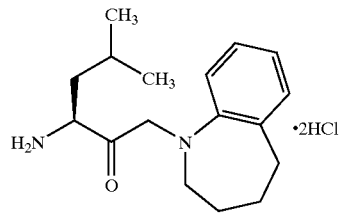

By the same procedure as described in example 2 using the compound prepared in example 8 in place of the compound prepared in example 1, the compound of the present invention having the following physical data was obtained as a crude product. The crude product was used in the next reaction without further purification.

TLC: Rf 0.35 (chloroform:methanol:water=10:1:0.1).

EXAMPLE 10–EXAMPLE 10 (9)

By the same procedure as described in example 3 using the compound prepared in example 9 in place of the compound prepared in example 2 and (−)-2-benzamidocyclohexanecarboxylic acid or a corresponding carboxylic acid thereto, the compound of the present invention having the following physical data was obtained.

EXAMPLE 10

N-[(3S)-5-methyl-2-oxo-1-(2,3,4,5-tetrahydro-1H-1-benzazepin-1-yl)-3-hexyl]-1-[(1R,2S)-2-benzoylaminocyclohexyl]carboxamide

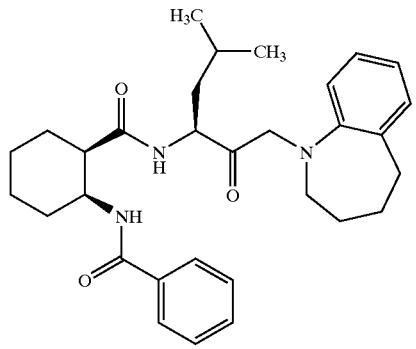

TLC: Rf 0.35 (n-hexane:ethyl acetate=3:1);

NMR (CDCl$_3$): δ 7.78 (dd, J=7.6, 1.8 Hz, 1H), 7.50–7.36 (m, 3H), 7.24 (d, J=9.6 Hz, 1H), 7.14–7.06 (m, 2H), 6.89 (dt, J=1.8, 7.6 Hz, 1H), 6.75 (d, J=7.6 Hz, 1H), 6.13 (d, J=8.4 Hz, 1H), 4.96 (dt, J=3.4, 8.4 Hz, 1H), 4.29 (m, 1H), 4.16 (d, J=17.2 Hz, 1H), 4.08 (d, J=17.2 Hz, 1H), 3.00–2.68 (m, 4H), 2.20–2.00 (m, 1H), 2.00–1.10 (m, 15H), 0.82 (d, J=6.0 Hz, 3H), 0.76 (d, J=6.0 Hz, 3H).

EXAMPLE 10(1)

(2S)-N-[(3S)-5-methyl-2-oxo-1-(2,3,4,5-tetrahydro-1H-1-benzazepin-1-yl)-3-hexyl]-4-methyl-2-benzyloxycarbonylaminopentanamide

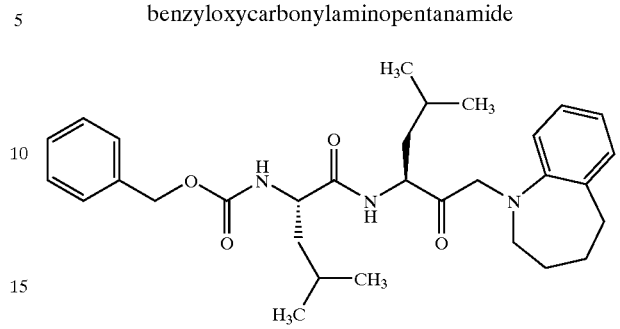

TLC: Rf 0.50 (chloroform:ethyl acetate=9:1);

NMR (CDCl$_3$): δ 7.34 (m, 5H), 7.10 (m, 2H), 6.89 (dt, J=0.9, 7.5 Hz, 1H), 6.74 (d, J=7.5 Hz, 1H), 6.38 (brd, J=8.4 Hz, 1H), 5.10 (m, 3H), 4.96 (ddd, J=9.9, 8.4, 3.9 Hz, 1H), 4.20–4.00 (m, 3H), 3.02–2.78 (m, 2H), 1.92–1.60 (m, 10H), 1.00–0.85 (m, 12H).

EXAMPLE 10(2)

N-[(3S)-5-methyl-2-oxo-1-(2,3,4,5-tetrahydro-1H-1-benzazepin-1-yl)-3-hexyl]-1-cyclohexylcarboxamide

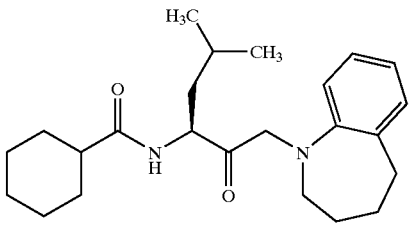

TLC: Rf 0.70 (n-hexane:ethyl acetate=7:3);

NMR (CDCl$_3$): δ 7.11 (d, J=7.2 Hz, 1H), 7.10 (dt, J=1.8, 7.2 Hz, 1H), 6.89 (dt, J=1.8, 7.2 Hz, 1H), 6.75 (d, J=7.2 Hz, 1H), 5.87 (d, J=8.4 Hz, 1H), 4.97 (ddd, J=10.2, 8.4, 3.9 Hz, 1H), 4.14 (d, J=17.4 Hz, 1H), 4.06 (d, J=17.4 Hz, 1H), 3.05–2.77 (m, 4H), 2.09 (tt, J=11.4, 3.3 Hz, 1H), 1.90–1.20 (m, 17H), 0.95 (d, J=6.3 Hz, 3H) and 0.90 (d, J=6.3 Hz, 3H).

EXAMPLE 10(3)

N-[(3S)-5-methyl-2-oxo-1-(2,3,4,5-tetrahydro-1H-1-benzazepin-1-yl)-3-hexyl]-4-benzyloxybenzamide

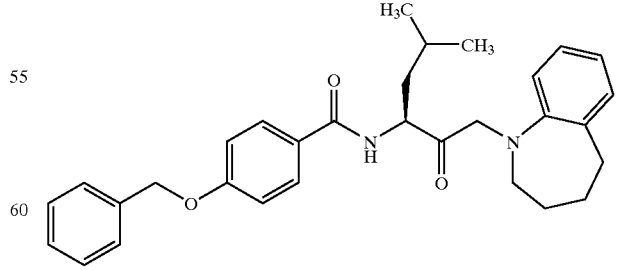

TLC: Rf 0.60 (n-hexane:ethyl acetate=7:3);

NMR (CDCl$_3$): δ 7.73 (d, J=8.7 Hz, 2H), 7.48–7.32 (m, 5H), 7.14–7.08 (m, 2H), 6.99 (d, J=8.7 Hz, 2H), 6.89 (dt, J=1.8, 7.6 Hz, 1H), 6.78 (d, J=7.6 Hz, 1H), 6.54 (d, J=8.7 Hz,

1H), 5.20 (m, 1H), 5.11 (s, 2H), 4.22 (d, J=17.1 Hz, 1H), 4.18 (d, J=17.1 Hz, 1H), 3.18–2.78 (m, 4H), 1.99–1.43 (m, 7H), 1.00 (d, J=6.6 Hz, 3H), 0.92 (d, J=6.6 Hz, 3H).

EXAMPLE 10(4)

N-[(3S)-5-methyl-2-oxo-1-(2,3,4,5-tetrahydro-1H-1-benzazepin-1-yl)-3-hexyl]-3-benzyloxybenzamide

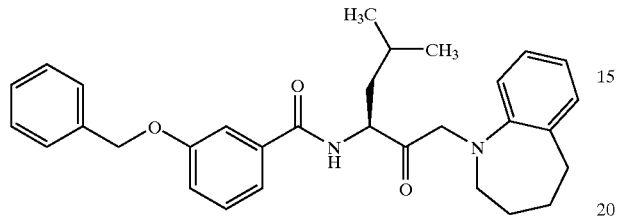

TLC: Rf 0.65 (n-hexane:ethyl acetate=7:3);

NMR (CDCl₃): δ 7.50–7.20 and 7.20–7.05 (each m, totally 11H), 6.90 (dt, J=1.8, 7.6 Hz, 1H), 6.79 (d, J=7.6 Hz, 1H), 6.62 (d, J=8.0 Hz, 1H), 5.30–5.18 (m, 1H), 5.11 (s, 2H), 4.20 (d, J=17.2 Hz, 1H), 4.13 (d, J=17.2 Hz, 1H), 3.10–2.80 (m, 4H), 1.95–1.40 (m, 7H), 1.02 (d, J=6.2 Hz, 3H), 0.93 (d, J=6.2 Hz, 3H).

EXAMPLE 10(5)

N-[(3S)-5-methyl-2-oxo-1-(2,3,4,5-tetrahydro-1H-1-benzazepin-1-yl)-3-hexyl]-2-benzyloxybenzamide

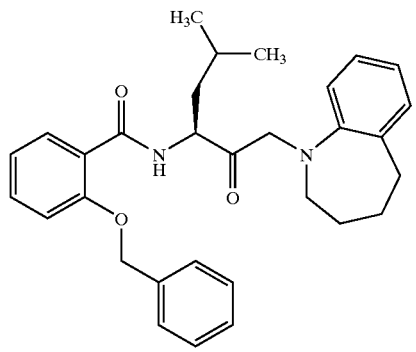

TLC: Rf 0.55 (n-hexane:ethyl acetate=7:3);

NMR (CDCl₃): δ 8.26 (d, J=7.2 Hz, 1H), 8.21 (dd, J=7.8, 1.8 Hz, 1H), 7.52–7.38 (m, 6H), 7.13–7.05 (m, 4H), 6.85 (t, J=7.2 Hz, 1H), 6.73 (d, J=7.2 Hz, 1H), 5.19 (d, J=10.5 Hz, 1H), 5.16 (d, J=10.5 Hz, 1H), 4.96–4.89 (m, 1H), 4.19 (d, J=17.7 Hz, 1H), 4.12 (d, J=17.7 Hz, 1H), 3.09–2.72 (m, 4H), 1.90–1.05 (m, 7H), 0.82 (d, J=6.0 Hz, 3H), 0.67 (d, J=6.0 Hz, 3H).

EXAMPLE 10(6)

N-[(3S)-5-methyl-2-oxo-1-(2,3,4,5-tetrahydro-1H-1-benzazepin-1-yl)-3-hexyl]-1-[(1S,2R)-2-benzoylaminocyclohexyl]carboxamide

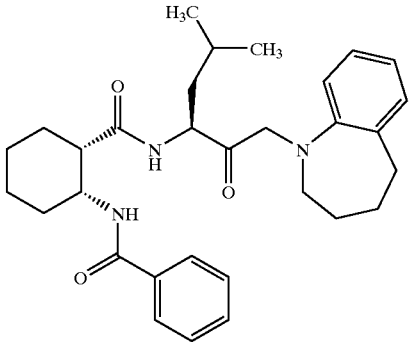

TLC: Rf 0.25 (n-hexane:ethyl acetate=7:3);

NMR (CDCl₃): δ 7.80 (dd, J=8.4, 1.8 Hz, 2H), 7.51–7.36 and 7.13–7.00 (each m, totally 6H), 6.89 (dt, J=1.8, 8.0 Hz, 1H), 6.72 (d, J=8.0 Hz, 1H), 6.07 (d, J=8.4 Hz, 1H), 4.91 (ddd, J=10.4, 8.4, 4.4 Hz, 1H), 4.29 (m, 1H), 4.11 (d, J=17.2 Hz, 1H), 4.05 (d, J=17.2 Hz, 1H), 2.98–2.69 (m, 4H), 2.10–1.25 (m, 16H), 0.94 (d, J=6.2 Hz, 3H), 0.89 (d, J=6.2 Hz, 3H).

EXAMPLE 10(7)

N-[(3S)-5-methyl-2-oxo-1-(2,3,4,5-tetrahydro-1H-1-benzazepin-1-yl)-3-hexyl]benzamide

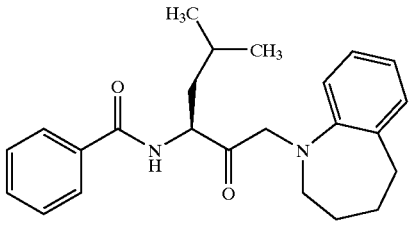

TLC: Rf 0.60 (n-hexane:ethyl acetate=7:3);

NMR (CDCl₃): δ 7.78 (dd, J=8.4, 1.8 Hz, 2H), 7.54–7.38 (m, 3H), 7.15–7.07 (m, 2H), 6.90 (t, J=7.4 Hz, 1H), 6.79 (d, J=7.4 Hz, 1H), 6.64 (d, J=8.0 Hz, 1H), 5.23 (dt, J=4.0, 8.0 Hz, 1H), 4.22 (d, J=16.8 Hz, 1H), 4.14 (d, J=16.8 Hz, 1H), 3.10–2.77 (m, 4H), 1.95–1.43 (m, 7H), 1.02 (d, J=6.0 Hz, 3H), 0.93 (d, J=6.0 Hz, 3H).

EXAMPLE 10(8)

N-[(3S)-5-methyl-2-oxo-1-(2,3,4,5-tetrahydro-1H-1-benzazepin-1-yl)-3-hexyl]-3-cyclopentylpropanamide

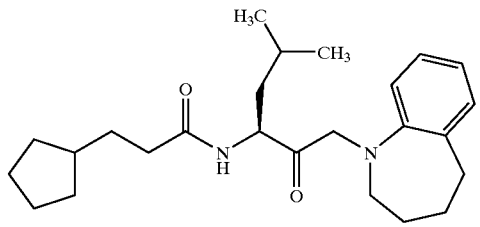

TLC: Rf 0.50 (n-hexane:ethyl acetate=7:3);

NMR (CDCl₃): δ 7.14–7.06 (m, 2H), 6.88 (dt, J=1.8, 8.0 Hz, 1H), 6.75 (d, J=8.0 Hz, 1H), 5.95 (d, J=8.0 Hz, 1H), 5.00 (ddd, J=9.8, 8.0, 4.0 Hz, 1H), 4.15 (d, J=17.2 Hz, 1H), 4.08 (d, J=17.2 Hz, 1H), 3.08–2.80 (m, 4H), 2.20 (dd, J=9.0, 7.6 Hz, 2H), 1.90–1.30 and 1.20–1.00 (each m, totally 18H), 0.95 (d, J=6.4 Hz, 3H), 0.90 (d, J=6.4 Hz, 3H).

EXAMPLE 10(9)

N-[(3S)-5-methyl-2-oxo-1-(2,3,4,5-tetrahydro-1H-1-benzazepin-1-yl)-3-hexyl]cinnamide

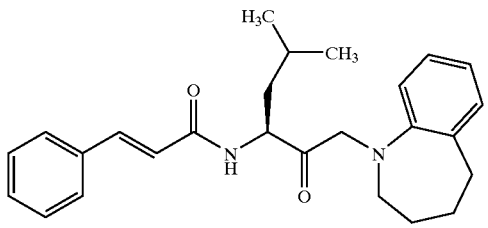

TLC: Rf 0.60 (n-hexane:ethyl acetate=7:3);

NMR (CDCl₃): δ 7.62 (d, J=15.6 Hz, 1H), 7.50–7.47 and 7.39–7.34 (each m, totally 5H), 7.14–7.09 (m, 2H), 6.88 (dt, J=1.8, 8.1 Hz, 1H), 6.79 (d, J=8.1 Hz, 1H), 6.41 (d, J=15.6 Hz, 1H), 6.16 (d, J=8.4 Hz, 1H), 5.18 (ddd, J=10.2, 8.4, 4.2 Hz, 1H), 4.15 (d, J=17.1 Hz, 1H), 4.12 (d, J=17.1 Hz, 1H), 3.08–2.78 (m, 4H), 1.98–1.38 (m, 7H), 1.00 (d, J=6.6 Hz, 3H), 0.91 (d, J=6.6 Hz, 3H).

EXAMPLE 11

N-[(3S)-5-methyl-2-oxo-1-(1,3,4,5-tetrahydro-2H-2-benzazepin-2-yl)-3-hexyl]benzenesulfonamide

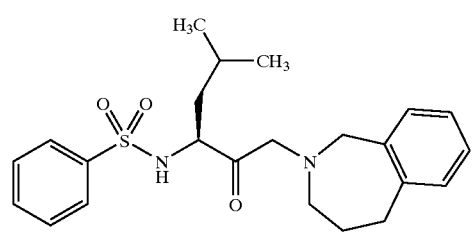

To a solution of the compound prepared in example 2 (137 mg) in dimethylformamide (2 ml) were added benzenesulfonyl chloride (0.07 ml) and triethylamine (0.08 ml) dropwise and the mixture was stirred for 55 hours at room temperature. To the reaction mixture was added 10% aqueous solution of citric acid and was extracted with ethyl acetate. The organic layer was washed with a saturated aqueous solution of sodium bicarbonate, water and a saturated aqueous solution of sodium chloride successively, dried over anhydrous sodium sulfate and was concentrated. The residue was purified by column chromatography on silica gel (n-hexane:ethyl acetate=3:1) to give the compound of the present invention (10.1 mg) having the following physical data.

TLC: Rf 0.30 (n-hexane:ethyl acetate=1:1);

NMR (CDCl₃): δ 7.84 (dd, J=8.7, 1.8 Hz, 2H), 7.60–7.47 (m, 3H), 7.20–7.05 (m, 3H), 6.85 (d, J=6.9 Hz, 1H), 5.90–5.30 (br, 1H), 4.08 (dd, J=9.6, 4.2 Hz, 1H), 3.82 (d, J=15.0 Hz, 1H), 3.65 (d, J=15.0 Hz, 1H), 3.09 (d, J=18.0 Hz, 1H), 3.05 (d, J=18.0 Hz, 1H), 2.91–2.84 (m, 4H), 1.80–1.50 and 1.40–1.20 (each m, totally 5H), 0.84 (d, J=6.6 Hz, 3H), 0.75 (d, J=6.6 Hz, 3H).

EXAMPLE 11(1)

N-[(3S)-5-methyl-2-oxo-1-(2,3,4,5-tetrahydro-1H-1-benzazepin-1-yl)-3-hexyl]benzenesulfonamide

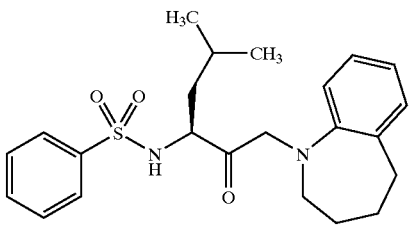

By the same procedure as described in example 11 using the compound prepared in example 9 in place of the compound prepared in example 2, the compound of the present invention having the following physical data was obtained.

TLC: Rf 0.50 (n-hexane:ethyl acetate=7:3);

NMR (CDCl₃): δ 7.78 (dd, J=6.9, 1.8 Hz, 2H), 7.56–7.42 (m, 3H), 7.10 (dd, J=7.2, 1.8 Hz, 1H), 7.05 (dt, J=1.8, 7.2 Hz, 1H), 6.90 (dt, J=1.8, 7.2 Hz, 1H), 6.57 (d, J=7.2 Hz, 1H), 5.47 (d, J=9.3 Hz, 1H), 4.24 (dt, J=3.9, 9.3 Hz, 1H), 3.92 (d, J=17.4 Hz, 1H), 3.81 (d, J=17.4 Hz, 1H), 2.85–2.50 (m, 4H), 1.90–1.20 (m, 7H), 0.84 (d, J=6.6 Hz, 6H).

REFERENCE EXAMPLE 5

7-hydroxy-1,3,4,5-tetrahydro-2H-2-benzazepin-1-one

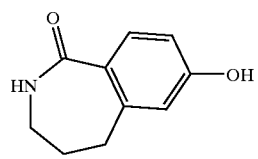

To a solution of 6-hydroxy-1-tetralone (6.5 g) in methanesulfonic acid (140 ml) was added sodium azide (3.4 g) under cooling with ice and the mixture was stirred for 30 minutes at 0° C. and for 15 hours at room temperature. The reaction mixture was poured into ice-water and thereto was added potassium carbonate to alkalify and was extracted with methylene chloride. The organic layer was washed with water, a saturated aqueous solution of sodium bicarbonate and a saturated aqueous solution of sodium chloride successively, dried over anhydrous magnesium sulfate and was concentrated to give the title compound having the following physical data as a crude product. The crude product was used in the next reaction without further purification.

TLC: Rf 0.39 (chloroform:methanol=9:1).

REFERENCE EXAMPLE 6

7-benzyloxy-1,3,4,5-tetrahydro-2H-2-benzazepin-1-one

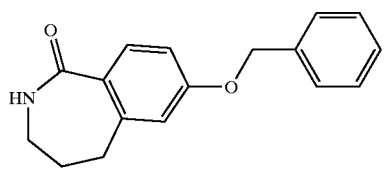

Under atmosphere of argon, to a solution of the compound prepared in reference example 5 (4.79 g) in dimethylformamide (60 ml) were added potassium carbonate (11.2 g) and benzyl bromide (3.57 ml) at 0° C. and the mixture was stirred for 30 minutes at room temperature. To the reaction mixture was added water and was extracted with ethyl acetate. The organic layer was washed with water, a saturated aqueous solution of sodium bicarbonate and a saturated aqueous solution of sodium chloride successively, and was dried over anhydrous magnesium sulfate and was concentrated. The residue was purified by column chromatography on silica gel (ethyl acetate:n-hexane=3:1) to give the title compound (3.8 g) having the following physical data.

TLC: Rf 0.48 (chloroform:methanol=19:1);

NMR (CDCl$_3$): δ 7.67 (d, J=8.4 Hz, 1H), 7.50–7.30 (m, 5H), 6.92 (dd, J=8.4, 2.6 Hz 1H), 6.80 (d, J=2.6 Hz, 1H), 6.20 (m, 1H), 5.10 (s, 2H), 3.14 (m, 2H), 2.84 (t, J=7.0 Hz, 2H), 2.01 (quintet, J=7.0 Hz, 2H).

REFERENCE EXAMPLE 7

7-benzyloxy-1,3,4,5-tetrahydro-2H-2-benzazepin hydrochloride

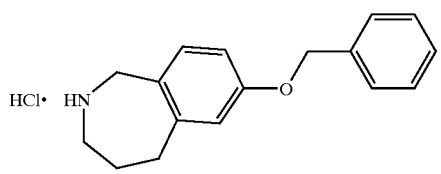

To a solution of the compound prepared in reference example 6 (3.75 g) in tetrahydrofuran (30 ml) was added a suspension of lithium alminum hydride (1.86 g) in tetrahydrofuran (90 ml) at 0° C. and the mixture was stirred for 4 hours at 80° C. To the reaction mixture was added ice-water and 15% aqueous solution of sodium hydroxide and the mixture was filtered. To the filtrate was added water and was extracted with methylene chloride. The organic layer was washed with water and a saturated aqueous solution of sodium chloride successively, dried over anhydrous magnesium sulfate to give the title compound having the following physical data as a free compound (3.5 g). A solution thereof in ethyl acetate (20 ml) was added 4N hydrochloric acid-ethyl acetate (20 ml) at 0° C. and the mixture was stirred for 30 minutes at room temperature. The reaction mixture was concentrated and the residue was washed with diethyl ether to give the title compound having the following physical data.

NMR (DMSO-d$_6$): δ 8.84 (m, 1H), 7.45–7.24 (m, 6H, O), 6.94 (d, J=2.7 Hz, 1H), 6.84 (dd, J=8.4, 2.7 Hz, 1H), 5.11 (s, 2H), 4.23 (s, 2H), 3.30 (m, 2H), 1.82 (m, 2H).

EXAMPLE 12

1-(7-benzyloxy-1,3,4,5-tetrahydro-2H-2-benzazepin-2-yl)-3-(t-butoxycarbonylamino)-5-methyl-2-hexanone

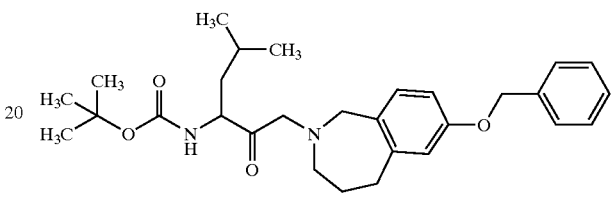

To a solution of the compound prepared in reference example 7 (2.9 g) in a suspension of acetonitrile (30 ml) was added diisopropylethylamine (5.22 ml) and the compound prepared in reference example 1 (3.1 g) successively and the mixture was stirred for 30 minutes at room temperature. To the reaction mixture was added water and was extracted with ethyl acetate. The organic layer was washed with a saturated aqueous solution of sodium bicarbonate and a saturated aqueous solution of sodium chloride successively, dried over anhydrous magnesium sulfate and was concentrated. The residue was purified by column chromatography on silica gel (n-hexane:ethyl acetate=2:1) to give the compound of the present invention (4.4 g) having the following physical data.

TLC: Rf 0.31 (hexane ethyl acetate=3:1);

NMR (CDCl$_3$): δ 7.45–7.30 (m, 5H), 6.97 (d, J=8.1 Hz, 1H), 6.80 (d, J=2.7 Hz, 1H), 6.60 (dd, J=8.1, 2.7 Hz, 1H), 5.05 (s, 2H), 4.98 (brd, J=8.4 Hz, 1H), 4.38 (m, 1H), 3.94 (s, 2H), 3.33 (brs, 2H), 3.16 (t, J=5.1 Hz, 2H), 2.85 (t, J=5.4 Hz, 2H), 1.85–1.60 (m, 5H), 1.43 (s, 9H), 0.94–0.88 (d, J=6.6 Hz, 6H)

EXAMPLE 13

3-amino-1-(7-benzyloxy-1,3,4,5-tetrahydro-2H-2-benzazepin-2-yl)-5-methyl-2-hexanone dihydrochloride

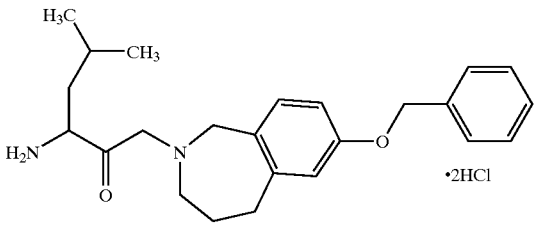

By the same procedure as described in example 2 using the compound prepared in example 12 in place of the compound prepared in example 1, the compound of the present invention having the following physical data was obtained.

TLC: Rf 0.56 (chloroform:methanol:acetic acid=9:1:1).

EXAMPLE 14

(2S)-N-[(3S)-1-(7-benzyloxy-1,3,4,5-tetrahydro-2H-2-benzazepin-2-yl)-5-methyl-2-oxo-3-hexyl]-4-methyl-2-benzyloxycarbonylaminopentanamide

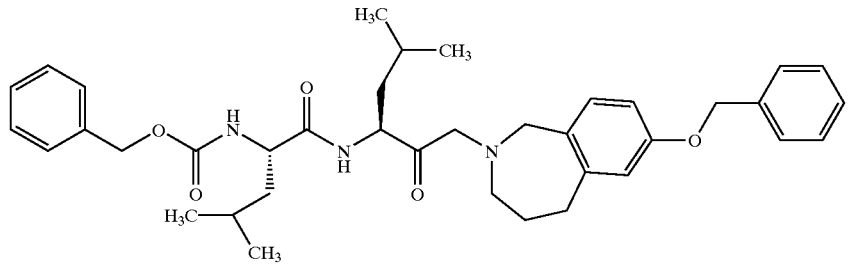

To a suspension of the compound prepared in reference example 7 (145 mg) in acetonitrile (3 ml) was added diisopropylethylamine (0.19 ml) at 0° C. and then was added (2S)-N-[(3S)-1-bromo-5-methyl-2-oxo-3-hexyl]-4-methyl-2-benzyloxycarbonylaminopentanamide (250 mg) and the mixture was stirred for 2 hours at room temperature. To the reaction mixture was added water and was extracted with ethyl acetate. The organic layer was washed with a saturated aqueous solution of sodium bicarbonate and a saturated aqueous solution of sodium chloride successively, dried over anhydrous magnesium sulfate and was concentrated. The residue was purified by column chromatography on silica gel (n-hexane:ethyl acetate=7:3) to give the compound of the present invention (242 mg) having the following physical data.

TLC: Rf 0.31 (n-hexane:ethyl acetate=2:1);

NMR (CDCl$_3$): δ 7.48–7.23 (m, 10H), 6.94 (m, 1H), 6.79 (d, J=2.7 Hz, 1H), 6.68 (dd, J=8.4, 2.7 Hz, 1H), 6.37 (brd, J=8.1 Hz, 1H), 5.20–5.08 (m, 3H), 5.03 (s, 2H), 4.72 (m, 1H), 4.20 (m, 1H), 3.92 (brs, 2H), 3.29 (brs, 2H), 3.12 (m, 2H), 2.85 (m, 2H), 1.80–1.30 (m, 8H), 1.00–0.84 (m, 12H).

EXAMPLE 15

N-[1-(7-benzyloxy-1,3,4,5-tetrahydro-2H-2-benzazepin-2-yl)-5-methyl-2-oxo-3-hexyl]-1-[(1S,2R)-2-benzoylaminocyclohexyl]carboxamide

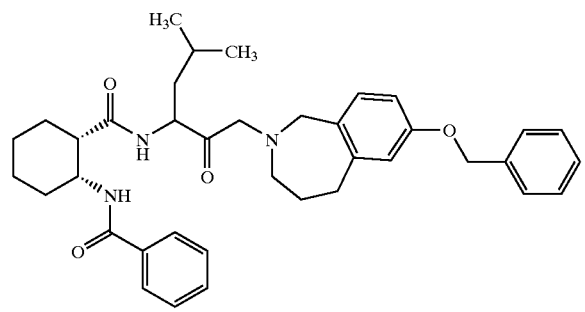

To a solution of the compound prepared in example 13 (398 mg) in dimethylformamide (4 ml) were added (1S,2R)-benzamidecyclohexanecarboxylic acid (239 mg), 1-ethyl-3-[3-(dimethylamino)propyl]carbodiimide hydrochloride (185 mg), 1-hydroxybenzotriazole (148 mg) and N-methylmorpholine (0.46 ml) at 0° C. and the mixture was stirred for 18 hours at room temperature. To the reaction mixture was added water and was extracted with ethyl acetate. The organic layer was washed with water, a saturated aqueous solution of sodium bicarbonate and a saturated aqueous solution of sodium chloride successively, dried over anhydrous sodium sulfate and was concentrated. The residue was purified by column chromatography on silica gel (chloroform:methanol=98:2) to give the compound of the present invention (358 mg) having the following physical data.

TLC: Rf 0.69 (chloroform:methanol=9:1);

NMR (CDCl$_3$): δ 7.82 and 7.76 (each d, J=6.0 Hz, totally 2H), 7.54 (brd, J=8.2 Hz, 1H), 7.50–7.24 (m, 8H), 6.95 and 6.92 (each d, J=8.4 Hz, totally 1H), 6.80 and 6.77 (each d, J=2.4 Hz, totally 1H), 6.67 and 6.63 (each dd, J=8.4, 2.4 Hz, totally 1H), 6.25 and 6.17 (each brd, J=8.1 Hz, totally 1H), 5.01 (s, 2H), 4.69 (m, 1H), 4.31 (m, 1H), 3.92 (m, 2H), 3.34 (m, 2H), 3.12 (m, 2H), 2.84 (m, 2H), 2.76 (m, 1H), 2.20–1.20 (m, 13H), 0.87, 0.86 and 0.75 (each d, J=6.3 Hz, totally 6H).

EXAMPLE 15(1)–EXAMPLE 15(6)

By the same procedures as described in example 15 using a carboxylic acid corresponding to (1S,2R)-benzamidecyclohexanecarboxylic acid, the compounds of the present invention having the following physical data were obtained.

EXAMPLE 15(1)

N-[1-(7-benzyloxy-1,3,4,5-tetrahydro-2H-2-benzazepin-2-yl)-5-methyl-2-oxo-3-hexyl]-1-[(1R,2S)-2-benzoylaminocyclohexyl]carboxamide

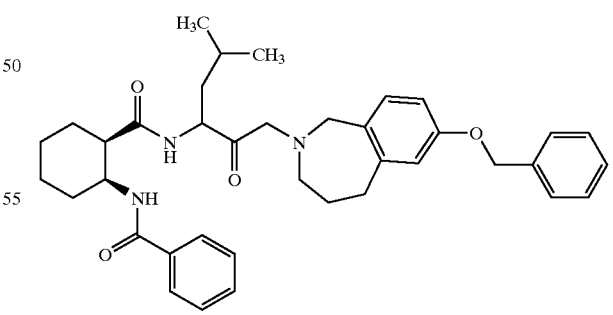

TLC: Rf 0.61 (chloroform:methanol=9:1);

NMR (CDCl$_3$): δ 7.83 and 7.76 (each d, J=7.8 Hz, totally 2H), 7.60–7.25 (m, 9H), 6.95 and 6.92 (each d, J=8.4 Hz, totally 1H), 6.80 and 6.77 (each d, J=2.4 Hz, totally 1H), 6.67 and 6.63 (each dd, J=8.4, 2.4 Hz, totally 1H), 6.30 and 6.20 (each brd, J=8.4 Hz, totally 1H), 5.02 (s, 2H), 4.72 (m, 1H), 4.29 (m, 1H), 3.94 (s, 2H), 3.33 (m, 2H), 3.15 (m, 2H), 2.90–2.70 (m, 3H), 2.20–1.20 (m, 13H), 0.87, 0.86 and 0.75 (each d, J=6.3 Hz, totally 6H).

EXAMPLE 15(2)

N-[1-(7-benzyloxy-1,3,4,5-tetrahydro-2H-2-benzazepin-2-yl)-5-methyl-2-oxo-3-hexyl]-1-cyclohexylcarboxamide

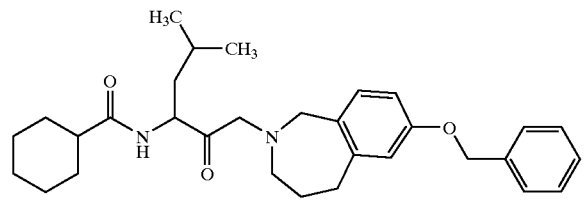

TLC: Rf 0.41 (n-hexane:ethyl acetate=1:1);

NMR (CDCl$_3$): δ 7.44–7.30 (m, 5H), 6;97 (d, J=8.4 Hz, 1H), 6.80 (d, J=2.4 Hz, 1H), 6.66 (dd, J=8.4, 2.4 Hz, 1H) 5.95 (brd, J=8.4 Hz, 1H), 5.04 (s, 2H), 4.73 (m, 1H), 3.93 (s, 2H), 3.37 (d, J=16.8 Hz, 1H), 3.33 (d, J=16.8 Hz, 1H), 3.16 (t, J=5.4 Hz, 2H), 2.86 (t, J=5.4 Hz, 2H), 2.10 (m, 1H), 1.90–1.18 (m, 15H), 0.88 (d, J=6.3 Hz, 6H)

EXAMPLE 15(3)

N-[1-(7-benzyloxy-1,3,4,5-tetrahydro-2H-2-benzazepin-2-yl)-5-methyl-2-oxo-3-hexyl]benzamide

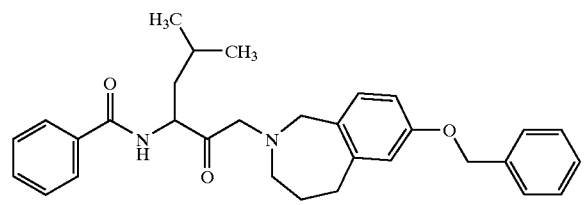

TLC: Rf 0.51 (n-hexane:ethyl acetate 1:1);

NMR (CDCl$_3$): δ 7.81 (d, J=7.8 Hz, 2H), 7.56–7.30 (m, 8H), 6.97 (d, J=8.4 Hz, 1H), 6.80 (m, 3H), 6.66 (dd, J=8.4, 2.4 Hz, 1H), 5.03 (s, 2H), 5.00 (m, 1H), 3.93 (s, 2H), 3.43 (d, J=17.4 Hz, 1H), 3.35 (d, J=17.4 Hz, 1H), 3.18 (t, J=5.4 Hz, 2H), 2.86 (t, J=5.4 Hz, 2H), 1.90–1.40 (m, 5H), 0.95 (d, J=6.0 Hz, 3H), 0.92 (d, J=6.0 Hz, 3H).

EXAMPLE 15(4)

N-[1-(7-benzyloxy-1,3,4,5-tetrahydro-2H-2-benzazepin-2-yl)-5-methyl-2-oxo-3-hexyl]-3-cyclopentylpropanamide

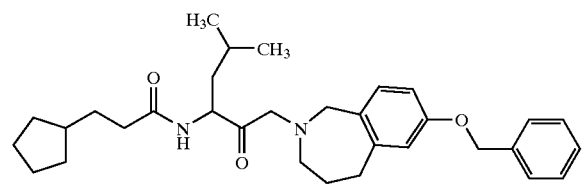

TLC: Rf 0.39 (n-hexane:ethyl acetate=1:1);
NMR (CDCl$_3$): δ 7.48–7.26 (m, 5H), 6.97 (d, J=8.4 Hz, 1H), 6.80 (d, J=2.7 Hz, 1H), 6.68 (dd, J=8.4, 2.7 Hz, 1H), 5.96 (brd, J=7.8 Hz, 1H), 5.04 (s, 2H), 4.75 (m, 1H), 3.93 (s, 2H), 3.39 (d, J=16.8 Hz, 1H), 3.32 (d, J=16.8 Hz, 1H), 3.17 (t, J=5.4 Hz, 2H), 2.86 (t, J=5.4 Hz, 2H), 2.21 (t, J=7.5 Hz, 2H), 1.84–0.93 (m, 16H), 0.89 (d, J=6.3 Hz, 6H)

EXAMPLE 15(5)

N-[1-(7-benzyloxy-1,3,4,5-tetrahydro-2H-2-benzazepin-2-yl)-5-methyl-2-oxo-3-hexyl]-1-(2-benzyloxyphenyl)carboxamide

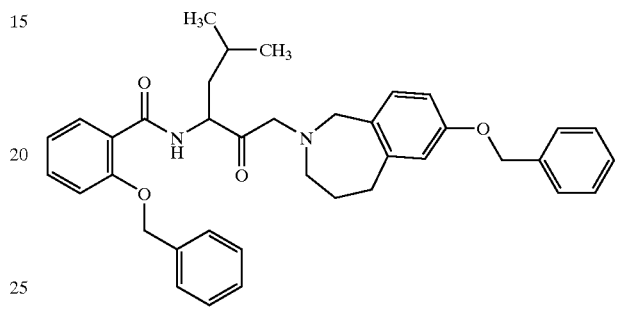

TLC: Rf 0.30 (n-hexane:ethyl acetate=1:1);

NMR (CDCl$_3$): δ 8.21 (brd, J=7.2 Hz, 1H), 8.18 (dd, J=7.5, 1.5 Hz, 1H), 7.53–7.23 (m, 11H), 7.10 (m, 2H), 6.96 (d, J=7.8 Hz, 1H), 6.78 (d, J=3.0 Hz, 1H), 6.64 (dd, J=7.8, 3.0 Hz, 1H), 5.18 (d, J=10.2 Hz, 1H), 5.12 (d, J=10.2 Hz, 1H), 5.01 (s, 2H), 4.70 (m, 1H), 3.99 (brs, 2H), 3.40 (m, 2H), 3.20 (m, 2H), 2.86 (m, 2H), 1.80–1.00 (m, 5H), 0.75 (d, J=6.0 Hz, 3H), 0.66 (d, J=6.0 Hz, 3H).

EXAMPLE 15(6)

N-[1-(7-benzyloxy-1,3,4,5-tetrahydro-2H-2-benzazepin-2-yl)-5-methyl-2-oxo-3-hexyl]cinnamide

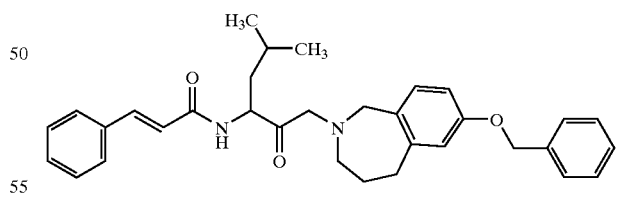

TLC: Rf 0.26 (n-hexane:ethyl acetate=1:1);

NMR (CDCl$_3$): δ 7.63 (d, J=15.6 Hz, 1H), 7.55–7.30 (m, 10H), 7.00 (d, J=8.1 Hz, 1H), 6.81 (d, J=2.7 Hz, 1H), 6.70 (dd, J=8.1, 2.7 Hz, 1H), 6.43 (d, J=15.6 Hz, 1H), 6.34 (brd, J=7.5 Hz, 1H), 5.03 (s, 2H), 4.92 (m, 1H), 3.97 (brs, 2H), 3.43 (d, J=17.4 Hz, 1H), 3.34 (d, J=17.4 Hz, 1H), 3.19 (m, 2H), 2.85 (m, 2H), 1.84–1.40 (m, 5H), 1.00–0.93 (m, 6H).

EXAMPLE 16

1-(7-hydroxy-1,3,4,5-tetrahydro-2H-2-benzazepin-2-yl)-3-(t-butoxycarbonylamino)-5-methyl-2-hexanone

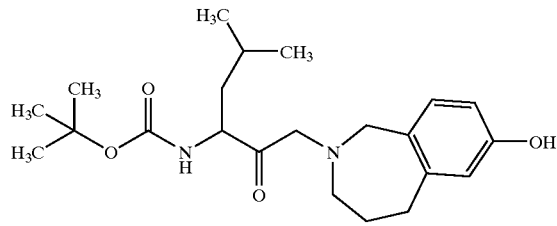

To a solution of the compound prepared in Example 12 (1.41 g) in ethanol (26 ml) was added 10% palladium-carbon (140 mg) and the mixture was stirred for 6 hours under atmosphere of hydrogen. The reaction mixture was filtered and the filtrate was concentrated. The residue was purified by column chromatography on silica gel (chloroform:methanol=97:3) to give the compound of the present invention (275 mg) having the following physical data.

TLC: Rf 0.38 (chloroform:methanol=9:1);

NMR (CDCl$_3$): δ 6.89 (d, J=8.1 Hz, 1H), 6.63 (d, J=2.7 Hz, 1H), 6.53 (dd, J=8.1, 2.7 Hz, 1H), 5.00 (brd, J=7.4 Hz, 1H), 4.40 (m, 1H), 3.90 (s, 2H), 3.31 (s, 2H), 3.14 (m, 2H), 2.83 (m, 2H), 1.70 (m, 2H), 1.60–1.20 (m, 12H), 0.90 (d, J=6.6 Hz, 6H).

EXAMPLE 17

1-(7-hydroxy-1,3,4,5-tetrahydro-2H-2-benzazepin-2-yl)-3-amino-5-methyl-2-hexanone dihydrochloride

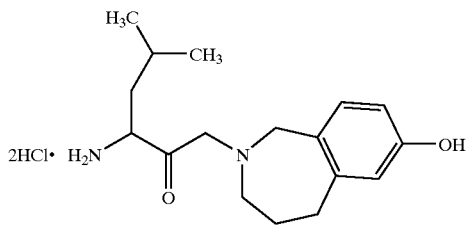

By the same procedure as described in example 2 using the compound prepared in example 16 in place of the compound prepared in example 1, the compound of the present invention having the following physical data was obtained.

NMR (DMSO-d$_6$): δ 9.80 (m, 1H), 8.62 (m, 2H), 7.10 (m, 1H), 6.70 (d, J=2.4 Hz, 1H), 6.63 (brd, J=8.4 Hz, 1H), 4.60–4.10 (m, 5H), 3.40 (m, 2H), 2.90 (m, 2H), 2.00–1.42 (m, 5H), 1.00–0.80 (m, 6H)

EXAMPLE 18

(2S)-N-[1-(7-hydroxy-1,3,4,5-tetrahydro-2H-2-benzazepin-2-yl)-5-methyl-2-oxo-3-hexyl]-4-methyl-2-benzyloxycarbonylaminopentanamide

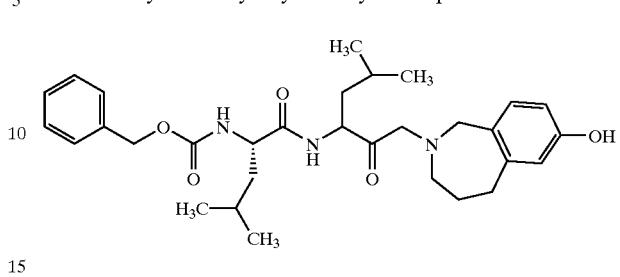

To a solution of the compound prepared in example 17 (120 mg) in dimethylformamide (2 ml) were added (2S)-2-benzyloxycarbonylamino-4-methylpentanoic acid (95 mg), 1-ethyl-3-[3-(dimethylamino)propyl]carbodiimide hydrochloride (69 mg), 1-hydroxybenzotriazole (55 mg) and N-methylmorpholine (0.084 ml) at 0° C. and the mixture was stirred for 18 hours at room temperature. To the reaction mixture was added water and was extracted with ethyl acetate. The organic layer was washed with water, a saturated aqueous solution of sodium bicarbonate and a saturated aqueous solution of sodium chloride successively, dried over anhydrous magnesium sulfate and was concentrated. The residue was purified by column chromatography on silica gel (n-hexane:ethyl acetate=1:1) to give the compound (89 mg) of the present invention having the following physical data.

TLC: Rf 0.65 (ethyl acetate);

NMR (CDCl$_3$): δ 7.34 (m, 5H), 6.88 (m, 1H), 6.63 (m, 1H), 6.51 (m, 1H), 6.58 and 6.40 (each brd, J=7.8 Hz, totally 1H), 5.20–5.08 (m, 3H), 4.72 (m, 1H), 4.20 (m, 1H), 3.86 (s, 2H), 3.28 (m, 2H), 3.11 (m, 2H), 2.82 (m, 2H), 1.90–1.20 (m, 8H), 1.00–0.84 (m, 12H).

EXAMPLE 18(1)

N-[1-(7-hydroxy-1,3,4,5-tetrahydro-2H-2-benzazepin-2-yl)-5-methyl-2-oxo-3-hexyl]-1-[(1R,2S)-2-benzoylaminocyclohexyl]carboxamide

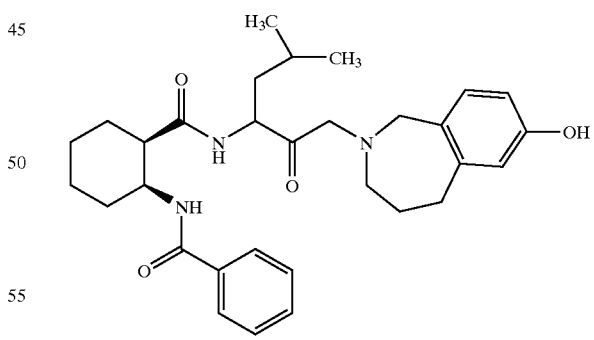

By the same procedure as described in example 18 using (−)-2-benzamidocyclohexanecarboxylic acid ((1R,2S)-2-benzamidecyclohexanecarboxylic acid) in place of (2S)-2-benzyloxycarbonylamino-4-methylpentanoic acid, the compound of the present invention having the following physical data was obtained.

TLC: Rf 0.33 (ethyl acetate);

NMR (CDCl$_3$): δ 7.88–7.70 (m, 2H), 7.62–7.30 (m, 4H), 6.86 and 6.80 (each d, J=8.4 Hz, totally 1H), 6.64 and 6.57

(each d, J=2.7 Hz, totally 1H), 6.51 and 6.47 (each dd, J=8.4, 2.7 Hz, totally 1H), 6.17 and 6.09 (each brd, J=8.4 Hz, totally 1H), 4.68 (m, 1H), 4.28 (m, 1H), 3.91 and 3.86 (each s, totally 2H), 3.32–3.25 (m, 2H), 3.13 (m, 2H), 2.90–2.60 (m, 3H), 2.20–1.20 (m, 13H), 0.88 and 0.75 (each d, J=6.3 Hz, totally 6H).

REFERENCE EXAMPLE 8

4-(t-butoxycarbonyl)-2,3,4,5-tetrahydro-1H-1,4-benzodiazepine

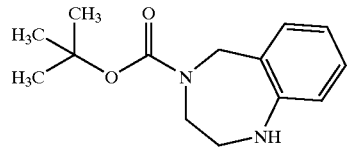

By the same procedure as described in reference example 2 using 2,3,4,5-tetrahydro-1H-1,4-benzodiazepine in place of (1R,2S)-2-aminocyclohexylmethylalcohol, the title compound having the following physical data was obtained.

TLC: Rf 0.70 (n-hexane:ethyl acetate=1:1);

NMR (CDCl$_3$): δ 7.21–7.10 (m, 2H), 7.12 (t, J=6.8 Hz, 1H), 6.79 (d, J=6.8 Hz, 1H), 4.43–4.35 (m, 2H), 3.65 (m, 2H), 3.15 (m, 2H), 1.53 and 1.41 (each s, totally 9H).

REFERENCE EXAMPLE 9

1-benzyl-4-(t-butoxycarbonyl)-2,3,4,5-tetrahydro-1H-1,4-benzodiazepine

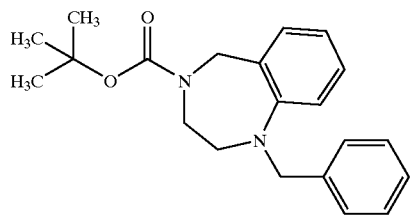

Under atmosphere of argon, to a solution of the compound prepared in reference example 8 (276 mg) in dimethylformamide (3.0 ml) was added potassium carbonate (336 mg) and the mixture was stirred for 30 minutes at room temperature, then thereto was added benzyl bromide (0.30 ml) and the mixture was stirred for another 30 hours. To the reaction mixture was added water and was extracted with ethyl acetate. The organic layer was washed with a saturated aqueous solution of sodium bicarbonate and a saturated aqueous solution of sodium chloride successively, dried over anhydrous magnesium sulfate and was concentrated. The residue was purified by column chromatography on silica gel (n-hexane:ethyl acetate=9:1) to give the title compound (366 mg) having the following physical data.

TLC: Rf 0.60 (n-hexane:ethyl acetate=3:1);

NMR (CDCl$_3$): δ 7.43–7.19 (m, 8H), 7.00 (d, J=8.7 Hz, 1H), 6.93 (t, J=8.7 Hz, 1H), 4.55 (m, 2H), 4.37 (s, 2H), 3.48 (m, 2H), 3.00 (m, 2H), 1.42 (s, 9H, Boc).

REFERENCE EXAMPLE 10

1-benzyl-2,3,4,5-tetrahydro-1H-1,4-benzodiazepine dihydrochloride

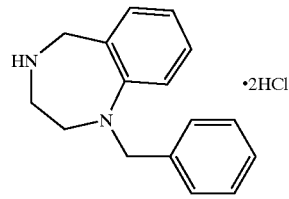

By the same procedure as described in example 2 using the compound prepared in reference example 9 in place of the compound described in example 1, the title compound having the following physical data was obtained.

TLC: Rf 0.23 (chloroform:methanol=9:1);

NMR (DMSO-d$_6$): δ 9.35 (m, 1H), 7.43–7.20 (m, 7H), 7.07 (d, J=8.1 Hz, 1H), 6.95 (t, J=7.5 Hz, 1H), 4.41 (m, 2H), 4.24 (m, 2H), 3.20–3.02 (m, 4H).

EXAMPLE 19

(3S)-3-amino-1-(1-benzyl-2,3,4,5-tetrahydro-1H-1,4-benzodiazepin-4-yl)-5-methyl-2-heptanone trihydrochloride

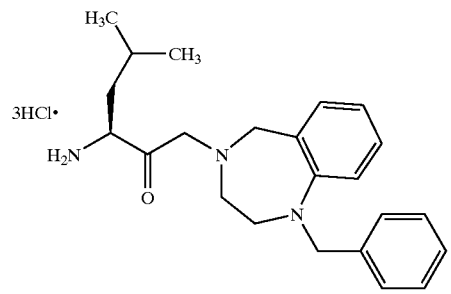

By the same procedure as described in example 1->example 2 using the compound prepared in reference example 10 in place of 1,3,4,5-tetrahydro-2-benzazepine, the compound of the present invention having the following physical data was obtained.

TLC: Rf 0.65 (chloroform:methanol=9:1);

NMR (DMSO-d$_6$): δ 8.70 (m, 2H), 7.50–7.21 (m, 7H), 7.06 (d, J=8.1 Hz, 1H), 6.98 (t, J=7.5 Hz, 1H), 4.80–4.20 (m, 5H), 3.40 (m, 6H), 1.90–1.50 (m, 3H), 1.00–0.90 (m, 6H).

EXAMPLE 20

(2S)-N-[(3S)-5-methyl-2-oxo-1-(1-benzyl-2,3,4,5-tetrahydro-1H-1,4-benzodiazepin-4-yl)-3-hexyl]-4-methyl-2-benzyloxycarbonylaminopentanamide

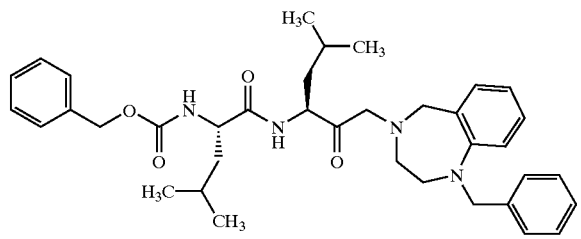

By the same procedure as described in example 14 using the compound prepared in reference example 10 in place of the compound prepared in reference example 7, the compound of the present invention having the following physical data was obtained.

TLC: Rf 0.30 (n-hexane:ethyl acetate=2:1);

NMR (CDCl$_3$): δ 7.43–6.82 (m, 14H), 6.39 (brd, J=8.4 Hz, 1H), 5.20–5.05 (m, 3H), 4.78 (m, 1H), 4.34 (s, 2H), 4.19 (m, 1H), 3.95 (s, 2H), 3.35 (s, 2H), 3.00–2.72 (m, 4H), 1.80–1.21 (m, 6H), 1.00–0.82 (m, 12H).

EXAMPLE 21–EXAMPLE 21(3)

By the same procedure as described in example 3 using the compound prepared in example 19 in place of the compound prepared in example 2, and a carboxylic acid corresponding to (–)-2-benzamidecyclohexanecarboxylic acid ((1R,2S)-2-benzamidecyclohexanecarboxylic acid), the compounds of the present invention having the following physical data were obtained.

EXAMPLE 21

N-[(3S)-1-(1-benzyl-2,3,4,5-tetrahydro-1H-1,4-benzodiazepin-4-yl)-5-methyl-2-oxo-3-hexyl]-1-cyclohexylcarboxamide

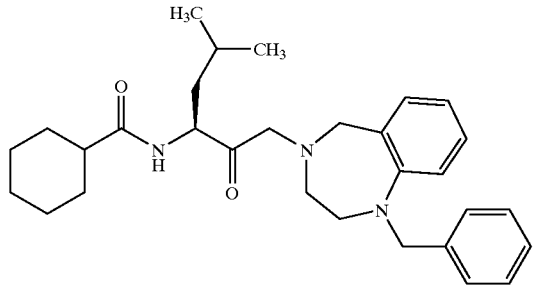

TLC: Rf 0.68 (n-hexane:ethyl acetate=1:1);

NMR (CDCl$_3$): δ 7.43–7.18 (m, 6H), 7.15 (d, J=7.5 Hz, 1H), 7.01 (d, J=7.8 Hz, 1H), 6.91 (t, J=7.5 Hz, 1H), 5.93 (brd, J=8.4 Hz, 1H), 4.79 (m, 1H), 4.34 (s, 2H), 3.97 (s, 2H), 3.43 (d, J=17.2 Hz, 1H), 3.39 (d, J=17.2 Hz, 1H), 3.00–2.80 (m, 4H), 2.12 (m, 1H), 1.90–1.20 (m, 13H), 0.90 (d, J=6.3 Hz, 6H).

EXAMPLE 21(1)

N-[(3S)-1-(1-benzyl-2,3,4,5-tetrahydro-1H-1,4-benzodiazepin-4-yl)-5-methyl-2-oxo-3-hexyl]-3-cyclopentylpropanamide

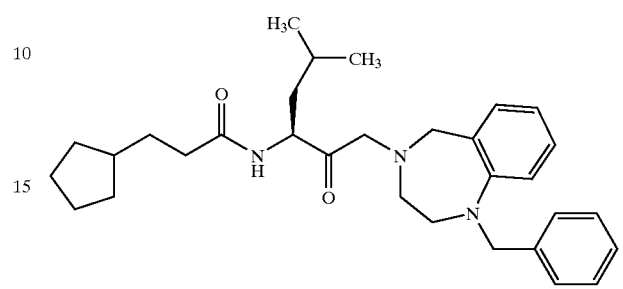

TLC: Rf 0.72 (n-hexane:ethyl acetate=1:1);

NMR (CDCl$_3$): δ 7.42–7.20 (m, 6H), 7.16 (d, J=8.1 Hz, 1H), 7.03 (d, J=7.8 Hz, 1H), 6.93 (t, J=8.1 Hz, 1H), 5.99 (brd, J=8.7 Hz, 1H), 4.80 (m, 1H), 4.34 (s, 2H), 4.00 (s, 2H), 3.48 (d, J=17.4 Hz, 1H), 3.41 (d, J=17.4 Hz, 1H), 3.00–2.80 (m, 4H), 2.21 (t, J=7.5 Hz, 2H), 1.84–0.92 (m, 14H), 0.90 (d, J=6.3 Hz, 6H).

EXAMPLE 21(2)

N-[(3S)-1-(1-benzyl-2,3,4,5-tetrahydro-1H-1,4-benzodiazepin-4-yl)-5-methyl-2-oxo-3-hexyl]-1-[(1R,2S)-2-benzoylaminocyclohexyl]carboxamide

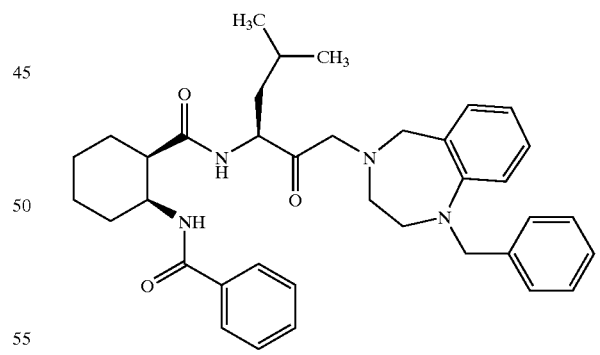

TLC: Rf 0.33 (n-hexane:ethyl acetate=1:1);

NMR (CDCl$_3$): δ 7.80 (m, 2H), 7.75–7.05 (m, 11H), 7.01 (d, J=7.8 Hz, 1H), 6.93 (t, J=8.1 Hz, 1H), 6.20 (brd, J=8.0 Hz, 1H), 4.79 (m, 1H), 4.35 (s, 2H), 4.31 (m, 1H), 3.99 (s, 2H), 3.40 (s, 2H), 3.00–2.65 (m, 5H), 2.20–1.20 (m, 11H), 1.00–0.7.0 (m, 6H).

EXAMPLE 21(3)

N-[(3S)-1-(1-benzyl-2,3,4,5-tetrahydro-1H-1,4-benzodiazepin-4-yl)-5-methyl-2-oxo-3-hexyl]-2-benzyloxybenzamide

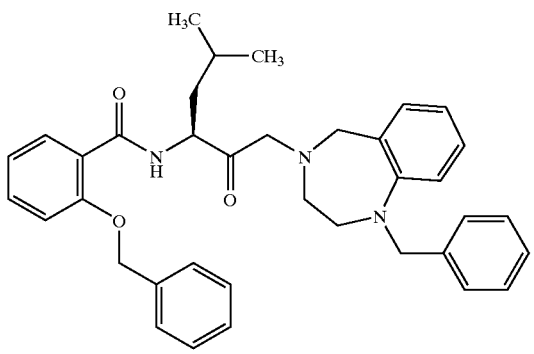

TLC: Rf 0.70 (n-hexane:ethyl acetate 1:1);

NMR (CDCl₃): δ 8.21 (m, 2H), 7.60–7.02 (m, 15H), 6.99 (d, J=8.1 Hz, 1H), 6.88 (t, J=7.5 Hz, 1H), 5.17 (d, J=10.5 Hz, 1H), 5.12 (d, J=10.5 Hz, 1H), 4.79 (m, 1H), 4.33 (s, 2H), 3.92 (s, 2H), 3.43 (d, J=17.7 Hz, 1H), 3.36 (d, J=17.7 Hz, 1H), 2.98–2.73 (m, 4H), 1.40–0.82 (m, 3H), 0.76 (d, J=6.0 Hz, 3H), 0.66 (d, J=6.0 Hz, 3H).

REFERENCE EXAMPLE 11 ethyl 2-(4-(t-butoxycarbonyl)-2,3,4,5-tetrahydro-1H-1,4-benzodiazepin-1-yl)acetate

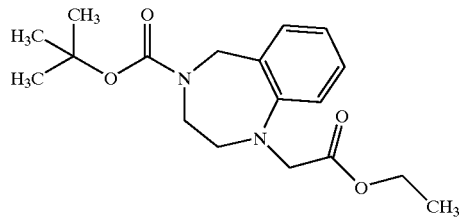

To a solution of the compound prepared in reference example 8 (2.48 g) in dimethylformamide (1 ml) were added a suspension of sodium hydride (0.6 g) in dimethylformamide (1 ml) and bromoethyl acetate (1.66 ml) at 0° C. and the mixture was stirred for 2.5 hours at 80° C. To the reaction mixture was added water and was extracted with ethyl acetate. The organic layer was washed with water and a saturated aqueous solution of sodium chloride successively, dried over anhydrous magnesium sulfate and was concentrated. The residue was purified by column chromatography on silica gel (n-hexane:ethyl acetate=9:1) to give the compound of the present invention (1.38 g) having the following physical data.

TLC: Rf 0.68 (n-hexane:ethyl acetate=2:1);

NMR (CDCl₃): δ 7.18 (m, 2H), 6.91 (dd, J=7.2, 0.9 Hz, 1H), 6.79 (m, 1H), 4.40 (m, 2H), 4.23 (q, J=6.9 Hz, 2H), 4.01 (s, 2H), 3.64 (m, 2H), 3.20 (m, 2H), 1.41 (s, 9H), 1.30 (t, J=6.9 Hz, 3H).

REFERENCE EXAMPLE 12

2-(2,3,4,5-tetrahydro-1H-1,4-benzodiazepin-1-yl)acetic acid ethyl ester dihydrochloride

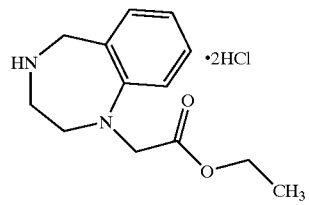

By the same procedure as described in example 2 using the compound prepared in reference example 11 in place of the compound prepared in example 1, the title compound having the following physical data was obtained.

TLC: Rf 0.01 (chloroform:methanol=9:1);

NMR (DMSO-d₆): δ 9.20 (br, 1H), 7.32 (dd, J=7.5, 1.5 Hz, 1H), 7.27 (dt, J=1.5, 7.5 Hz, 1H), 6.93 (dt, J=0.6, 7.2 Hz, 1H), 6.81 (d, J=8.4 Hz, 1H), 4.22–4.03 (m, 6H), 3.42–3.18 (m, 4H), 1.21 (m, 3H).

EXAMPLE 22

(2S)-N-[(3S)-1-(1-ethoxycarbonylmethyl-2,3,4,5-tetrahydro-1H-1,4-benzodiazepin-4-yl)-5-methyl-2-oxo-3-hexyl]-2-benzyloxycarbonylamino-4-methylpentanamide

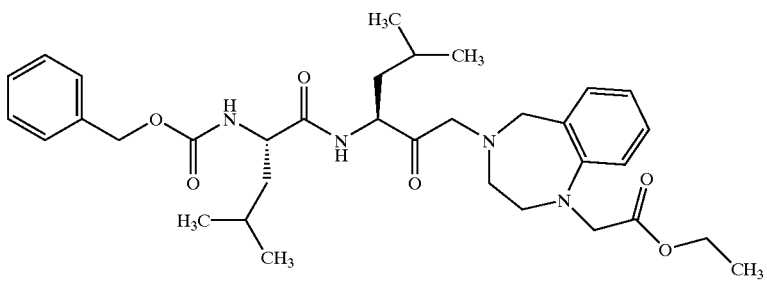

By the same procedure as described in example 14 using the compound prepared in reference example 12 in place of the compound prepared in reference example 7, the compound of the present invention having the following physical data was obtained.

TLC: Rf 0.33 (n-hexane:ethyl acetate=1:1);

NMR (CDCl₃): δ 7.34 (s, 5H), 7.26 (t, J=7.8 Hz, 1H), 7.07 (d, J=7.8 Hz, 1H), 6.88 (t, J=7.8 Hz, 1H), 6.74 (d, J=7.8 Hz, 1H), 6.42 (brd, J=8.4 Hz, 1H), 5.13 (m, 3H), 4.78 (m, 1H), 4.23 (q, J=6.9 Hz, 2H), 4.20 (m, 1H), 3.99 (s, 2H), 3.90 (s, 2H), 3.41 (m, 2H), 3.20 (m, 2H), 3.00 (m, 2H), 1.80–1.30 (m, 6H), 1.28 (t, J=6.9 Hz, 3H), 1.00–0.84 (m, 12H).

EXAMPLE 22(1)–EXAMPLE 22(4)

By the same procedure as described in reference example 11->reference example 12->example 22 using a halogen compound corresponding to bromoacetic acid, the compound of the present invention having the following physical data was obtained.

EXAMPLE 22(1)

(2S)-N-[(3S)-5-methyl-1-(1-methyl-2,3,4,5-tetrahydro-1H-1,4-benzodiazepin-4-yl)-2-oxo-3-hexyl]-2-benzyloxycarbonyl amino-4-methylpentanamide

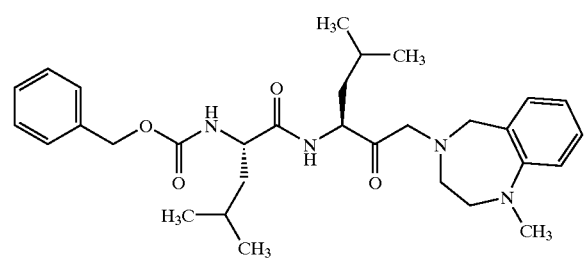

TLC: Rf 0.24 (n-hexane:ethyl acetate=1:1);

NMR (CDCl₃): δ 7.40–6.80 (m, 9H), 6.40 (brd, J=8.2 Hz, 1H), 5.20–5.08 (m, 3H), 4.75 (m, 1H), 4.20 (m, 1H), 3.86 (s, 2H), 3.37 (s, 2H), 2.97 (s, 4H), 2.89 (s, 3H), 1.80–1.21 (m, 6H), 1.00–0.82 (m, 12H).

EXAMPLE 22(2)

(2S)-N-[(3S)-5-methyl-2-oxo-1-(1-(3-phenylpropyl)-2,3,4,5-tetrahydro-1H-1,4-benzodiazepin-4-yl)-3-hexyl]-2-benzyloxycarbonylamino-4-methylpentanamide

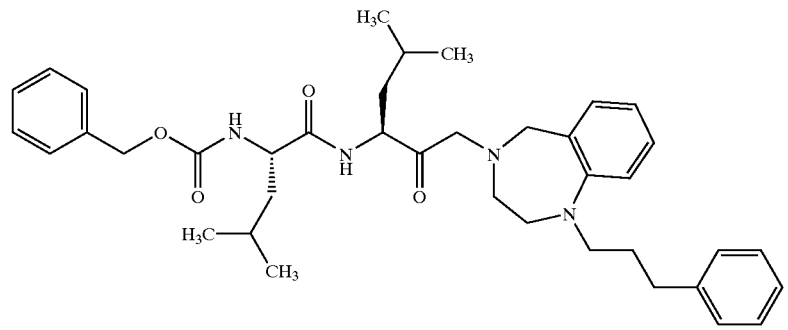

TLC: Rf 0.65 (n-hexane:ethyl acetate=1:1);

NMR (CDCl₃): δ 7.40–7.04 (m, 12H), 6.88 (m, 2H), 6.60 and 6.44 (each brd, J=7.8 Hz, totally 1H), 5.20–5.06 (m, 3H), 4.79 (m, 1H), 4.20 (m, 1H), 3.85 (s, 2H), 3.36 (s, 2H), 3.18 (t, J=6.9 Hz, 2H), 2.95 (m, 4H), 2.70 (t, J=6.9 Hz, 2H), 1.90 (quintet, J=6.9 Hz, 2H), 1.80–1.30 (m, 6H), 1.00–0.82 (m, 12H).

EXAMPLE 22(3)

(2S)-N-[(3S)-5-methyl-2-oxo-1-(1-phenethyl-2,3,4,5-tetrahydro-1H-1,4-benzodiazepin-4-yl)-3-hexyl]-2-benzyloxycarbonylamino-4-methylpentanamide

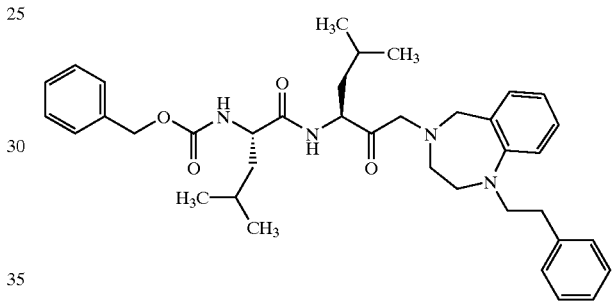

TLC: Rf 0.71 (n-hexane:ethyl acetate=1:1);

NMR (CDCl₃): δ 7.40–6.80 (m, 14H), 7.08 (d, J=7.5 Hz, 1H), 6.98 (d, J=7.5 Hz, 1H), 6.87 (d, J=7.5 Hz, 1H), 6.38 (m, 1H), 5.12 (m, 3H), 4.75 (m, 1H), 4.20 (m, 1H), 3.80 (s, 2H), 3.44 (t, J=6.9 Hz, 2H), 3.35 (s, 2H), 3.04 (m, 2H), 2.88 (m, 4H), 1.75–1.30 (m, 6H), 1.00–0.82 (m, 12H).

EXAMPLE 22(4)

(2S)-N-[(3S)-5-methyl-1-(1-isopropyl-2,3,4,5-tetrahydro-1H-1,4-benzodiazepin-4-yl)-2-oxo-3-hexyl]-2-benzyloxycarbonylamino-4-methylpentanamide

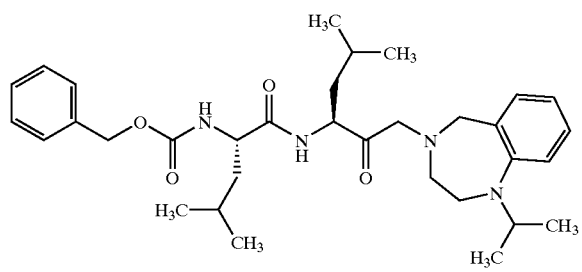

TLC: Rf 0.53 (n-hexane:ethyl acetate=1:1);

NMR (CDCl$_3$): δ 7.34 (s, 5H), 7.20 (t, J=7.5 Hz, 1H), 7.07 (d, J=7.5 Hz, 1H), 6.97 (d, J=7.5 Hz, 1H), 6.82 (t, J=7.5 Hz, 2H), 6.40 (brd, J=8.1 Hz, 1H), 5.20–5.08 (m, 3H), 4.79 (m, 1H), 4.20 (m, 1H), 3.80 (m, 3H), 3.40 (s, 2H), 2.98 (m, 2H), 2.88 (m, 2H), 1.76–1.34 (m, 6H), 1.22 (d, J=6.6 Hz, 6H), 1.00–0.85 (m, 12H).

EXAMPLE 23

(2S)-N-[5-methyl-1-(1-carboxymethyl-2,3,4,5-tetrahydro-1H-1,4-benzodiazepin-4-yl)-2-oxo-3-hexyl]-2-benzyloxycarbonylamino-4-methylpentanamide

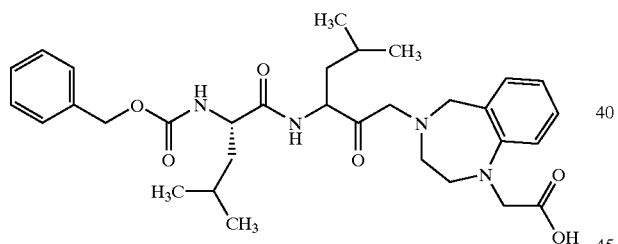

To a solution of the compound prepared in example 22 (550 mg) in tetrahydrofuran (3 ml)-methanol (3 ml) was added 1N aqueous solution of sodium hydroxide (1 ml) and the mixture was stirred for 2 hours at room temperature. The reaction mixture was neutralized by adding 1N hydrochloric acid and was extracted with ethyl acetate. The organic layer was washed with a saturated aqueous solution of sodium chloride, dried over anhydrous magnesium sulfate and was concentrated. The residue was washed with a mixture of hexane-ethyl acetate to give the compound of the present invention (522 mg) having the following physical data.

TLC: Rf 0.50 (chloroform:methanol=4:1);

NMR (DMSO-d$_6$): δ 8.25 and 8.13 (each brd, J=7.5 Hz, totally 1H), 7.40 (brd, J=7.8 Hz, 1H), 7.33 (s, 5H), 7.09 (t, J=7.3 Hz, 1H), 7.02 (d, J=7.3 Hz, 1H), 6.75 (t, J=7.3 Hz, 1H), 6.69 (d, J=7.3 Hz, 1H), 5.00 (s, 2H), 4.45–4.30 (m, 1H), 4.04 (m, 1H), 3.90 (brs, 2H), 3.69 (brs, 2H), 3.40 (m, 2H), 3.10 (m, 2H), 2.80 (m, 2H), 1.70–1.30 (m, 6H), 0.92–0.70 (m, 12H).

EXAMPLE 24

(2S)-N-[(3S)-5-methyl-2-oxo-1-(2,3,4,5-tetrahydro-1H-1,4-benzodiazepin-4-yl)-3-hexyl]-2-benzyloxycarbonylamino-4-methylpentanamide

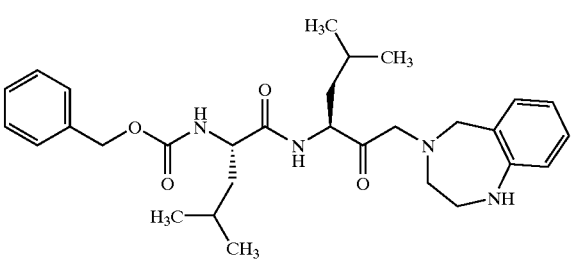

By the same procedure as described in example 14 using 2,3,4,5-tetrahydro-1H-1,4-benzodiazepine in place of the compound prepared in reference example 7, the compound of the present invention having the following physical data.

TLC: Rf 0.43 (chloroform:methanol=9:1);

NMR (CDCl$_3$): δ 7.34 (s, 5H), 7.10 (t, J=7.8 Hz, 1H), 7.05 (d, J=7.8 Hz, 1H), 6.83 (t, J=7.8 Hz, 1H), 6.75 (d, J=7.8 Hz, 1H), 6.42 (brd, J=8.4 Hz, 1H), 5.11 (m, 3H), 4.75 (m, 1H), 4.19 (m, 1H), 3.89 (s, 2H), 3.43 (s, 2H), 3.16–3.00 (m, 4H), 1.78–1.32 (m, 6H), 1.00–0.82 (m, 12H).

REFERENCE EXAMPLE 13

2-(4-(t-butoxycarbonyl)-2,3,4,5-tetrahydro-1H-1,4-benzodiazepin-1-yl)acetic acid

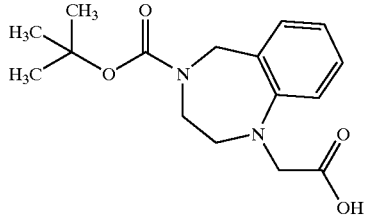

By the same procedure as described in example 23 using the compound prepared in reference example 11 in place of the compound prepared in example 22, the compound of the present invention having the following physical data.

TLC: Rf 0.18 (ethyl acetate);

NMR (DMSO-d$_6$): δ 7.10 (m, 2H), 6.82 (m, 1H), 6.65 (m, 1H), 4.38 (m, 2H), 3.96 (m, 2H), 3.56 (m, 2H), 3.22 (m, 2H), 1.45–1.23 (m, 9H).

REFERENCE EXAMPLE 14

2-(4-(t-butoxycarbonyl)-2,3,4,5-tetrahydro-1H-1,4-benzodiazepin-1-yl)acetamide

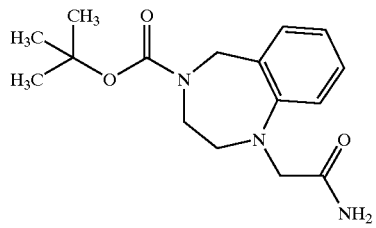

To a solution of the compound prepared in reference example 13 (400 mg) in dimethylformamide (5 ml) were added ammonium carbonate (308 mg) and 2-ethoxy-1-ethoxycarbonyl-1,2-dihydroquinoline (353 mg) and the mixture was stirred for 2 hours at 80° C. To the reaction mixture was added a saturated aqueous solution of sodium bicarbonate and was extracted with ethyl acetate. The organic layer was washed with water, a saturated aqueous solution of sodium bicarbonate and a saturated aqueous solution of sodium chloride successively, dried over anhydrous magnesium sulfate and was concentrated. The residue was purified by column chromatography on silica gel (n-hexane ethyl acetate=1:1) to give the compound of the present invention (285 mg) having the following physical data.

TLC: Rf 0.32 (ethyl acetate);

NMR (CDCl$_3$): δ 7.40–6.85 (m, 4H), 6.62 and 5.43 (each m, totally 2H), 4.51 (m, 2H), 3.89 (s, 2H), 1.43 (m, 9H).

REFERENCE EXAMPLE 15

2-(2,3,4,5-tetrahydro-1H-1,4-benzodiazepin-1-yl)acetamide dihydrochloride

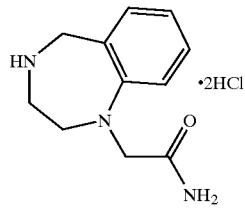

By the same procedure as described in example 2 using the compound prepared in reference example 14 in place of the compound prepared in example 1, a crude product having the following physical data of the title compound was given. The crude product was used in the next reaction without further purification.

TLC: Rf 0.01 (chloroform:methanol: acetic acid=9:1:1).

EXAMPLE 25

(2S)-N-[(3S)-1-(1-aminocarbonylmethyl-2,3,4,5-tetrahydro-1H-1,4-benzodiazepin-4-yl)-5-methyl-2-oxo-3-hexyl]-2-benzyloxycarbonylamino-4-methylpentanamide

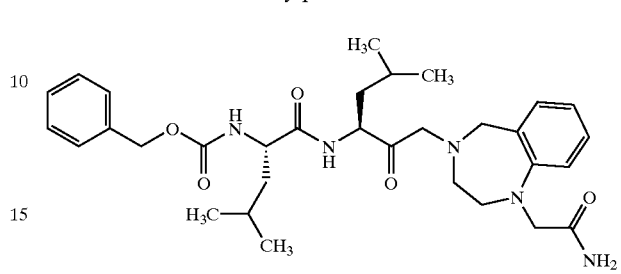

By the same procedure as described in example 14 using the compound prepared in reference example 15 in place of the compound prepared in reference example 7, the compound of the present invention having the following physical data was obtained.

TLC: Rf 0.33 (chloroform:methanol=9:1);

NMR (CDCl$_3$): δ 7.34 (m, 5H), 7.21 (t, J=6.9 Hz, 1H), 7.10 (d, J=6.9 Hz, 1H), 7.04–6.88 (m, 3H), 6.51 (brd, J=7.5 Hz, 1H), 5.68 (brs, 1H), 5.20 (brd, J=7.2 Hz, 1H), 5.10 (s, 2H), 4.70 (m, 1H), 4.21 (m, 1H), 3.93 (brs, 2H), 3.90 (s, 2H), 3.50 (d, J=13.2 Hz, 1H), 3.40 (d, J=13.2 Hz, 1H), 3.20–2.90 (m, 4H), 1.80–1.38 (m, 6H), 1.05–0.87 (m, 12H).

REFERENCE EXAMPLE 16

4-(t-butoxycarbonyl)-1-(2-hydroxyethyl)-2,3,4,5-tetrahydro-1H-1,4-benzodiazepine

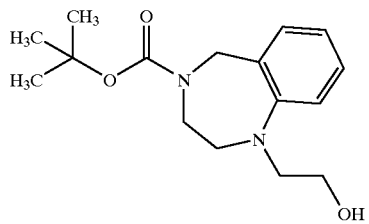

To a solution of the compound prepared in reference example 11 (200 mg) in tetrahydrofuran (3 ml) was added a suspension of lithium aluminum hydride (34 mg) in tetrahydrofuran at 0° C. and the mixture was stirred for 2 hours at room temperature. To the reaction mixture was added ice-water and 15% aqueous solution of sodium hydroxide and the mixture was filtered. The filtrate was concentrated and the residue was dried under reduced pressure to give the title compound having the following physical data as a crude product. The crude product was used in the next reaction without further purification.

TLC: Rf 0.22 (n-hexane:ethyl acetate=2:1);

NMR (CDCl$_3$): δ 7.20 (m, 2H), 6.92 (m, 2H), 4.42 (brs, 2H), 3.80–3.60 (m, 4H), 3.43 (m, 2H), 3.30–3.10 (m, 2H), 1.35 (s, 9H).

REFERENCE EXAMPLE 17

1-(2-hydroxyethyl)-2,3,4,5-tetrahydro-1H-1,4-benzodiazepine dihydrochloride

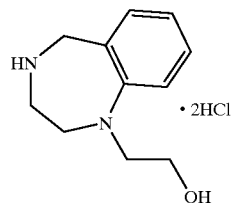

By the same procedure as described in example 2 using the compound prepared in reference example 16 in place of the compound prepared in example 1, a crude product of the title compound was obtained. The crude product was used in the next reaction without further purification.

EXAMPLE 26

(2S)-N-[1-(1-(2-hydroxyethyl)-2,3,4,5-tetrahydro-1H-1,4-benzodiazepin-4-yl)-5-methyl-2-oxo-3-hexyl]-2-benzyloxycarbonylamino-4-methylpentanamide

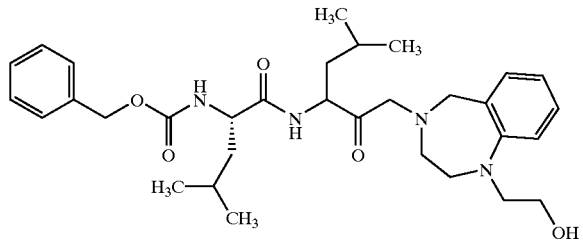

By the same procedure as described in example 14 using the compound prepared in reference example 17 in place of the compound prepared in reference example 7, and (2S)-N-[1-bromo-5-methyl-2-oxo-3-hexyl]-4-methyl-2-benzyloxycarbonylaminopentanamide in place of (2S)-N-[(3S)-1-bromo-5-methyl-2-oxo-3-hexyl]-4-methyl-2-benzyloxycarbonylaminopentanamide, the compound of the present invention having the following physical data was obtained.

TLC: Rf 0.48 (ethyl acetate);

NMR (CDCl$_3$): δ 7.40–6.82 (m, 9H), 6.77 and 6.44 (each brd, J=7.8 Hz, totally 1H), 5.20–5.08 (m, 3H), 4.70 (m, 1H), 4.20 (m, 1H), 3.87 (m, 2H), 3.71 (t, J=5.4 Hz, 2H), 3.41 (m, 4H), 3.05 (m, 2H), 2.97 (m, 2H), 1.90–1.30 (m, 6H), 1.00–0.82 (m, 12H).

REFERENCE EXAMPLE 18

4-(t-butoxycarbonyl)-1-cyanomethyl-2,3,4,5-tetrahydro-1H-1,4-benzodiazepine

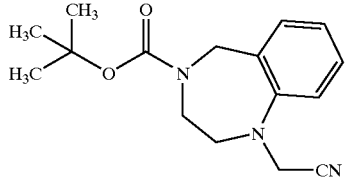

To a solution of the compound prepared in reference example 14 (101 mg) in methylene chloride (2 ml) were added pyridine (60 μl) and tosyl chloride (138 mg) at 0° C. and the mixture was stirred for 2 hours at 80° C. To the reaction mixture was added water and was extracted with ethyl acetate. The organic layer was washed with water, a saturated aqueous solution of sodium bicarbonate and a saturated aqueous solution of sodium chloride successively, and dried over anhydrous magnesium sulfate. The residue was purified by column chromatography on silica gel (hexane:ethyl acetate=7:3) to give the compound (33 mg) having the following physical data.

TLC: Rf 0.88 (chloroform:methanol=9:1);

NMR (CDCl$_3$): δ 7.40–7.20 (m, 2H), 7.11 (d, J=8.1 Hz, 1H), 7.04 (t, J=8.1 Hz, 1H), 4.42–4.30 (m, 2H), 4.11 (s, 2H), 3.63 (br, 2H), 3.15 (m, 2H), 1.42 (s, 9H).

EXAMPLE 27

(2S)-N-[(3S)-1-(1-cyanomethyl-2,3,4,5-tetrahydro-1H-1,4-benzodiazepin-4-yl)-5-methyl-2-oxo-3-hexyl]-2-benzyloxycarbonylamino-4-methylpentanamide

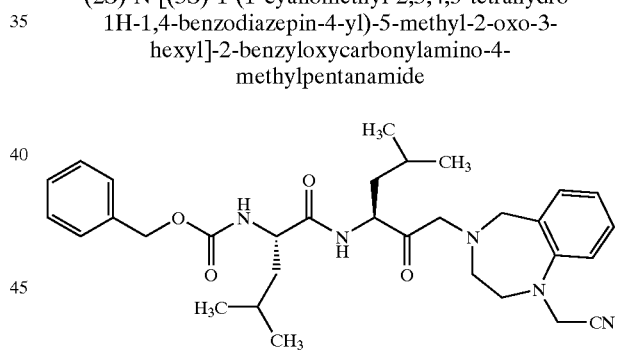

By the same procedure as described in example 2->example 14 using the compound prepared in reference example 18 in place of the compound prepared in example 1, the compound of the present invention having the following physical data was obtained.

TLC: Rf 0.26 (n-hexane:ethyl acetate=1:1);

NMR (CDCl$_3$): δ 7.40–7.25 (m, 6H), 7.13 (d, J=6.6 Hz, 1H), 7.05 (d, J=6.6 Hz, 1H), 7.00 (t, J=6.6 Hz, 1H), 6.35 (brd, J=7.5 Hz, 1H), 5.10 (m, 3H), 4.75 (m, 1H), 4.19 (m, 1H), 4.08 (s, 2H), 3.87 (s, 2H), 3.36 (m, 2H), 3.18–3.00 (m, 4H), 1.80–1.38 (m, 6H), 1.00–0.88 (m, 12H).

REFERENCE EXAMPLE 19-A–REFERENCE EXAMPLE 19-B

To a solution of 4-chromanone (5.00 g) in chloroform (60 ml) were added under cooling with ice conc. sulfic acid (25 ml) and sodium azide (4.42 g) over a period of 30 minutes and the mixture was stirred for 2 hours at room temperature. The reaction mixture was poured into ice-water and the mixture was alkalified with potassium carbonate and was extracted with methylene chloride. The organic layer was washed with water, a saturated aqueous solution of sodium bicarbonate and a saturated aqueous solution of sodium chloride successively, dried over anhydrous magnesium sulfate and was concentrated. The residue was purified by column chromatography on silica gel (toluene:ethyl acetate= 1:1) to give the compound of reference example 19-A (3.1 g) and the compound of reference example 19-B (100 mg) having the following physical data.

REFERENCE EXAMPLE 19-A 2,3,4,5-tetrahydro-1,4-benzoxazepin-5-one

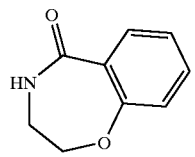

TLC: Rf 0.45 (chloroform:methanol=9:1);

NMR (CDCl$_3$): δ 7.60 (m, 1H), 7.10–6.87 (m, 4H), 4.47 (t, J=6.0 Hz, 2H), 2.86 (t, J=6.0 Hz, 2H).

REFERENCE EXAMPLE 19-B 2,3,4,5-tetrahydro-1,5-benzoxazepin-4-one

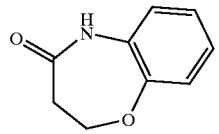

TLC: Rf 0.48 (chloroform:methanol=9:1);

NMR (CDCl$_3$): δ 7.97 (dd, J=11.1, 1.5 Hz, 1H), 7.44 (dt, J=1.5, 8.1 Hz, 1H), 7.37 (m, 1H), 7.14 (dt, J=1.2, 8.1 Hz, 1H), 7.02 (dd, J=1.2, 8.1 Hz, 1H), 4.40 (t, J=4.8 Hz, 0.2H), 3.51 (q, J=4.8 Hz, 2H).

REFERENCE EXAMPLE 20-A 2,3,4,5-tetrahydro-1,4-benzoxazepine hydrochloride

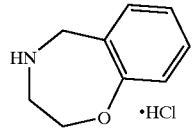

To a solution of the compound prepared in reference example 19-A (3.05 g) in tetrahydrofuran (30 ml) was added a suspension of lithium aluminum hydride (2.5 g) in tetrahydrofuran (80 ml) and the mixture was refluxed for 24 hours. To the reaction mixture were added ice-water and 15% aqueous solution of sodium hydroxide and the mixture was filtered. To the filtrate was added water and the mixture was extracted with methylene chloride. The organic layer was washed with water and a saturated aqueous solution of sodium chloride successively, dried over anhydrous magnesium sulfate and was concentrated. The residue was dissolved in ethyl acetate (20 ml) and thereto was added 4N hydrochloric acid-ethyl acetate (40 ml) under cooling with ice, and the mixture was stirred for 30 minutes at room temperature. The reaction mixture was concentrated. The residue was washed with diethyl ether-ethyl acetate (7:3) to give the title compound (3.30 g) having the following physical data.

TLC: Rf 0.71 (chloroform:methanol:water=6:4:1);

NMR (DMSO-d$_6$): δ 9.72 (m, 2H), 7.47–7.27 (m, 2H), 7.20–7.01 (m, 4H), 3.50 (m, 2H).

REFERENCE EXAMPLE 20-B 2,3,4,5-tetrahydro-1,5-benzoxazepine

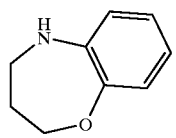

To a solution of the compound prepared in reference example 19-B (95 mg) in tetrahydrofuran (1 ml) was added a suspension of lithium aluminum hydride (77 mg) in tetrahydrofuran (1 ml) at 0° C. and the mixture was refluxed for 2 hours. To the reaction mixture was added ice-water and 15% aqueous solution of sodium hydroxide and was filtered. The filtrated was extracted with methylene chloride. The organic layer was washed with water and a saturated aqueous solution of sodium chloride successively, dried over anhydrous sodium sulfate and was concentrated. The residue was purified by column chromatography on silica gel (toluene:ethyl acetate=1:1) to give the title compound (45 mg) having the following physical data.

TLC: Rf (n-hexane:ethyl acetate=2:1);

NMR (CDCl$_3$): δ 6.96 (dd, J=7.8, 1.5 Hz, 1H), 6.87 (dt, J=1.5, 7.8 Hz, 1H), 6.78 (dt, J=18, 7.8 Hz, 1H), 6.72 (dd, J=7.8, 1.8 Hz, 1H), 6.72 (dd, J=7.8, 1.8 Hz, 1H), 4.40 (t, J=4.8 Hz, 2H), 3.51 (q, J=4.8 Hz, 2H).

EXAMPLE 28

(2S)-N-[(3S)-1-(2,3,4,5-tetrahydro-1,4-benzoxazepin-4-yl)-5-methyl-2-oxo-3-hexyl]-2-benzyloxycarbonylamino-4-methylpentanamide

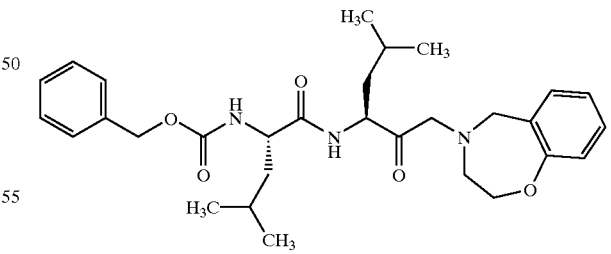

By the same procedure as described in example 14 using the compound prepared in reference example 20-A in place of the compound prepared in reference example 7, the compound of the present invention having the following physical data.

TLC: Rf 0.45 (n-hexane:ethyl acetate=1:1);

NMR (CDCl$_3$): δ 7.40–6.95 (m, 9H), 6.34 (brd, J=7.5 Hz, 1H), 5.10 (brs, 3H), 4.75 (m, 1H), 4.20 (m, 1H), 4.06 (m, 2H), 3.94 (d, J=14.7 Hz, 1H), 3.88 (d, J=14.7 Hz, 1H), 3.44 (s, 2H), 3.14 (m, 2H), 1.80–1.30 (m, 6H), 1.00–0.84 (m, 12H).

EXAMPLE 29

(2S)-N-[(3S)-5-methyl-2-oxo-1-(2,3,4,5-tetrahydro-1,5-benzoxazepin-5-yl)-3-hexyl]-2-benzyloxycarbonylamino-4-methylpentanamide

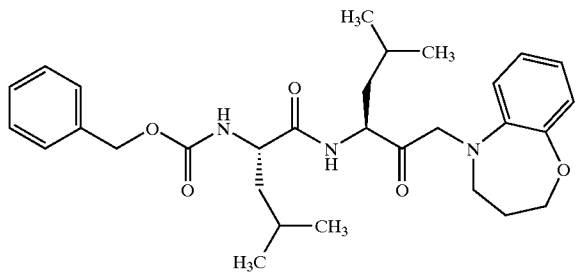

By the same procedure as described in Example 14, using the compound prepared in Reference Example 20-B in place of the compound prepared in reference example 7, the compound of the present invention was obtained.

TLC: Rf 0.53 (n-hexane:ethyl acetate=2:1);

NMR (CDCl₃): δ 7.34 (s, 5H), 6.98–6.58 (m, 4H), 6.42 (brd, J=6.6 Hz, 1H), 5.10 (m, 3H), 4.78 (m, 1H), 4.23–4.05 (m, 5H), 3.38–3.19 (m, 2H), 2.18–1.98 (m, 2H), 1.74–1.40 (m, 6H), 1.00–0.84 (m, 12H).

EXAMPLE 30

N-[(3S)-5-methyl-2-oxo-1-(2,3,4,5-tetrahydro-1,4-benzoxazepin-4-yl)-3-hexyl]-1-[(1R,2S)-2-benzoylaminocyclohexyl]carboxamide

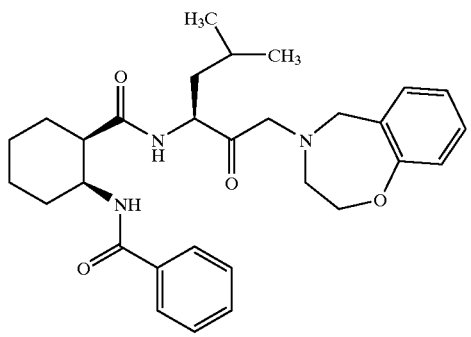

By the same procedure as described in example 1->example 2->example 3 using the compound prepared in reference example 20-A in place of 1,3,4,5-tetrahydro-2-benzazepine, the compound of the present invention having the following physical data was obtained.

TLC: Rf 0.30 (n-hexane:ethyl acetate=1:1);

NMR (CDCl₃): δ 7.77 (dd, J=8.0, 1.8 Hz, 2H), 7.50–7.38 (m, 3H), 7.30–6.95 (m, 5H), 6.15 (brd, J=8.0 Hz, 1H), 4.81–4.70 (m, 1H), 4.40–4.22 (m, 1H), 4.10–4.00 (m, 2H), 3.91 (d, J=14.8 Hz, 1H), 3.88 (d, J=14.8 Hz, 1H), 3.45 (s, 2H), 3.20–3.10 (m, 2H), 2.82–2.71 (m, 1H), 2.20–1.20 (m, 11H), 0.76 (d, J=6.2 Hz, 3H), 0.74 (d, J=6.2 Hz, 3H).

REFERENCE EXAMPLE 21

2,3,4,5-tetrahydro-1,4-benzothiazepin-5-one

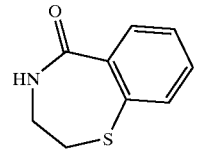

By the same procedure as described in reference example 5 using 3,4-dihydro-2H-1-benzothiin-4-one in place of 6-hydroxy-1-tetralone, the title compound having the following physical data was obtained as a crude product. The crude product was used in the next reaction without further purification.

TLC: Rf 0.44 (chloroform:methanol=9:1).

REFERENCE EXAMPLE 22

2,3,4,5-tetrahydro-1,4-benzothiazepine hydrochloride

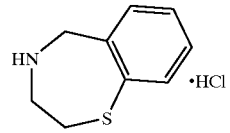

To a solution of the compound prepared in reference example 21 (820 mg) in tetrahydrofuran (10 ml) was added boron hydride (1M tetrahydrofuran solution, 11.5 ml) and the mixture was stirred for 3 hours. To the reaction mixture was added methanol and was concentrated. To the residue was added 6N hydrochloric acid and was refluxed for 3 hours. The reaction mixture was concentrated to give the title compound having the following physical data as a crude product.

TLC: Rf 0.48 (chloroform:methanol:acetic acid=9:1:1);

NMR (DMSO-d₆): δ 9.61 (m, 1H), 7.58 (m, 2H), 7.37 (m, 2H), 4.39 (brs, 2H), 3.42 (m, 2H), 3.05 (m, 2H).

EXAMPLE 31

(2S)-N-[(3S)-5-methyl-2-oxo-1-(2,3,4,5-tetrahydro-1,4-benzothiazepin-4-yl)-3-hexyl]-2-benzyloxycarbonylamino-4-methylpentanamide

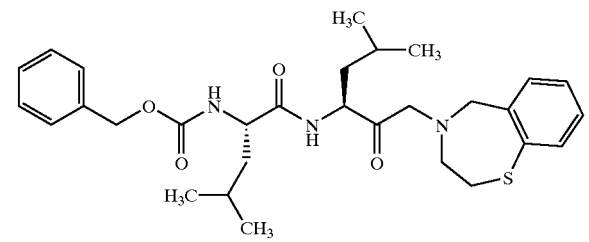

By the same procedure as described in example 14 using the compound prepared in reference example 22 in place of the compound prepared in reference example 7, the compound of the present invention having the following physical data was obtained.

TLC: Rf 0.18 (n-hexane:ethyl acetate=1:1);

NMR (CDCl$_3$): δ 7.55 (m, 1H), 7.35 (s, 5H), 7.15 (m, 3H), 6.38 (brd, J=7.8 Hz, 1H), 5.11 (m, 3H), 4.72 (m, 1H), 4.20 (m, 3H), 3.38 (m, 4H), 2.78 (m, 2H), 1.80–1.35 (m, 6H), 1.05–0.87 (m, 12H).

EXAMPLE 31(1)

N-[(3S)-5-methyl-2-oxo-1-(2,3,4,5-tetrahydro-1,4-benzothiazepin-4-yl)-3-hexyl]-1-[(1R,2S)-2-benzoylaminocyclohexyl]carboxamide

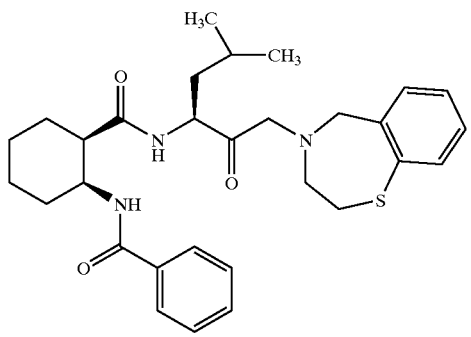

By the same procedure as described in example 1->example 2->example 3 using the compound prepared in reference example 22 in place of 1,3,4,5-tetrahydro-2-benzazepine, the compound of the present invention having the following physical data was obtained.

TLC: Rf 0.54 (n-hexane:ethyl acetate=1:1);

NMR (CDCl$_3$): δ 7.76 (m, 2H), 7.60–7.32 (m, 4H), 7.30–7.10 (m, 4H), 6.10 (brd, J=8.4 Hz, 1H), 4.75 (m, 1H), 4.30 (m, 1H), 4.21 (s, 2H), 3.38 (m, 4H), 2.79 (m, 3H), 2.10–1.21 (m, 11H), 0.80 (d, J=6.2 Hz, 6H).

REFERENCE EXAMPLE 23

4-(t-butoxycarbonyl)-2,3,4,5-tetrahydro-1,4-benzothiazepine

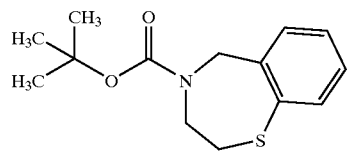

By the same procedure as described in reference example 2 using the compound prepared in reference example 22 in place of (1R,2S)-2-aminocyclohexylmethylalcohol, the title compound having the following physical data was obtained.

TLC: Rf 0.53 (n-hexane:ethyl acetate=3:1);

NMR (CDCl$_3$): δ 7.60–7.12 (m, 4H), 4.58 (m, 2H), 3.92 (m, 2H), 2.81 (m, 2H), 1.45 (m, 9H).

REFERENCE EXAMPLE 24

4-(t-butoxycarbonyl)-2,3,4,5-tetrahydro-1,4-benzothiazepine-1,1-dioxide

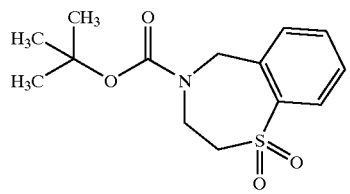

To a solution of the compound prepared in reference example 23 (140 mg) in methylene chloride (4 ml) was added 3-chloroperbenzoic acid (400 mg) and the mixture was stirred for 2 hours at room temperature. The reaction mixture was concentrated, and to the residue was added ethyl acetate, and the organic layer was washed with water, a saturated aqueous solution of sodium bicarbonate and a saturated aqueous solution of sodium chloride successively, and was dried. The residue was purified by column chromatography on silica gel (n-hexane:ethyl acetate=3:1) to give the title compound (190 mg) having the following physical data.

TLC: Rf 0.27 (n-hexane:ethyl acetate=3:1);

NMR (CDCl$_3$): δ 8.09 (m, 1H), 7.61–7.35 (m, 3H), 4.73 (s, 2H), 4.10 (m, 2H), 3.35 (m, 2H), 1.38 (s, 9H).

REFERENCE EXAMPLE 25

2,3,4,5-tetrahydro-1,4-benzothiazepine-1,1-dioxide hydrochloride

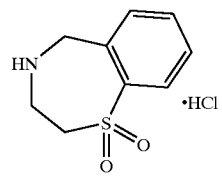

By the same procedure as described in example 2 using the compound prepared in reference example 24 in place of the compound prepared in example 1, the title compound having the following physical data was obtained.

TLC: Rf 0.57 (chloroform:methanol:ethyl acetate=9:1:1);

NMR (DMSO-d$_6$): δ 9.79 (m, 1H), 8.00 (d, J=7.8 Hz, 1H), 7.85–7.67 (m, 3H), 4.58 (s, 2H), 3.83 (m, 2H), 3.70 (m, 2H).

EXAMPLE 32

(2S)-N-[(3S)-5-methyl-2-oxo-1-(1,1-dioxo-2,3,4,5-tetrahydro-1,4-benzothiazepin-4-yl)-3-hexyl]-2-benzyloxycarbonylamino-4-methylpentanamide

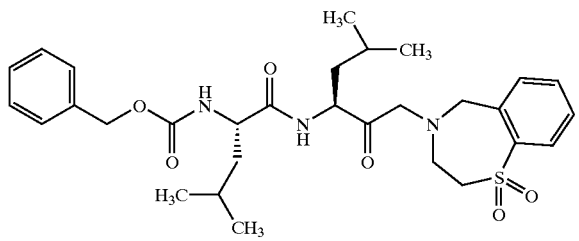

By the same procedure as described in example 14 using the compound prepared in reference example 25 in place of the compound prepared in reference example 7, the compound of the present invention having the following physical data was obtained.

TLC: Rf 0.36 (n-hexane:ethyl acetate=1:1);

NMR (CDCl$_3$): δ 8.08 (dd, J=7.4, 1.8 Hz, 1H), 7.60–7.42 (m, 2H), 7.34 (s, 5H), 7.23 (m, 1H), 6.35 (brd, J=7.8 Hz, 1H), 5.15–5.00 (m, 3H), 4.62 (m, 1H), 4.39 (brs, 2H), 4.19 (m, 1H), 3.60 (m, 2H), 3.38 (m, 4H), 1.80–1.38 (m, 6H), 1.01–0.84 (m, 12H).

EXAMPLE 32(1)

N-[(3S)-5-methyl-2-oxo-1-(1,1-dioxo-2,3,4,5-tetrahydro-1,4-benzothiazepin-4-yl)-3-hexyl]-1-[(1R,2S)-2-benzoylaminocyclohexyl]carboxamide

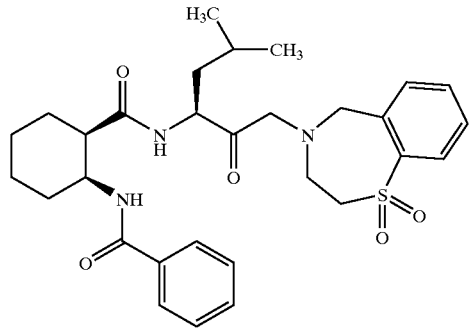

By the same procedure as described in example 1->example 2->example 3 using the compound prepared in reference example 25 in place of 1,3,4,5-tetrahydro-2-benzazepine, the compound of the present invention having the following physical data was obtained.

TLC: Rf 0.39 (chloroform:methanol 9:1);

NMR (CDCl$_3$): δ 8.08 (dd, J=7.2, 2.1 Hz, 1H), 7.75 (m, 2H), 7.55–7.40 (m, 5H), 7.24 (m, 1H), 7.11 (brd, J=8.4 Hz, 1H), 6.05 (brd, J=8.1 Hz, 1H), 4.63 (q, J=8.1 Hz, 1H), 4.50–4.30 (m, 3H), 3.60 (m, 2H), 3.41–3.22 (m, 4H), 2.80 (q, J=5.1 Hz, 1H), 2.10–1.21 (m, 11H), 0.83–0.74 (m, 6H).

REFERENCE EXAMPLE 26

1,2,4,5-tetrahydro-3,2-benzothiazepine-3,3-dioxide

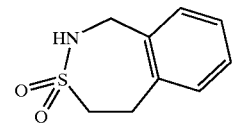

To a solution of 2-phenylethanesulfonamide (3.62 g) in methanesulfonic acid (20 ml)-acetic acid (5 ml) was added a solution of trioxane (582 mg) in trifluoroacetic acid (3 ml) and the mixture was stirred for 3 hours at 35° C. To the reaction mixture was added water and was extracted with chloroform. The organic layer was washed with water and a saturated aqueous solution of sodium bicarbonate, dried over anhydrous sodium sulfate and was concentrated. The residue was purified by column chromatography on silica gel (chloroform:methanol=100:1) to give the title compound (1.78 g) having the following physical data.

TLC: Rf 0.55 (chloroform:methanol=100:1);

NMR (CDCl$_3$): δ 7.40–7.20 (m, 4H), 4.42–4.20 (br, 3H), 3.20–3.05 (br, 4H).

EXAMPLE 33

(2S)-N-[(3S)-5-methyl-2-oxo-1-(3,3-dioxo-1,2,4,5-tetrahydro-3,2-benzothiazepin-2-yl)-3-hexyl]-2-benzyloxycarbonylamino-4-methylpentanamide

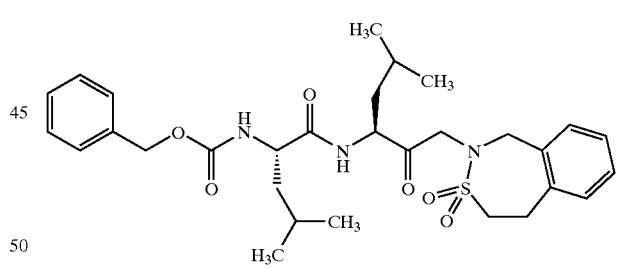

By the same procedure as described in example 14 using the compound prepared in reference example 26 in place of the compound prepared in reference example 7, the compound of the present invention having the following physical data was obtained.

TLC: Rf 0.70 (n-hexane:ethyl acetate=1:1);

NMR (CDCl$_3$): δ 7.42–7.13 (m, 9H), 6.33 (brd, J=6.9 Hz, 1H), 5.11 (s, 2H), 5.10 (m, 1H), 4.82–4.30 (br, 3H), 4.19 (m, 1H), 4.03–3.70 (br, 2H), 3.40–3.00 (m, 4H), 1.80–1.30 (m, 6H), 1.05–0.83 (m, 12H).

EXAMPLE 33(1)

N-[(3S)-5-methyl-2-oxo-1-(3,3-dioxo-1,2,4,5-tetrahydro-3,2-benzothiazepin-2-yl)-3-hexyl]-1-[(1R,2S)-2-benzoylaminocyclohexyl]carboxamide

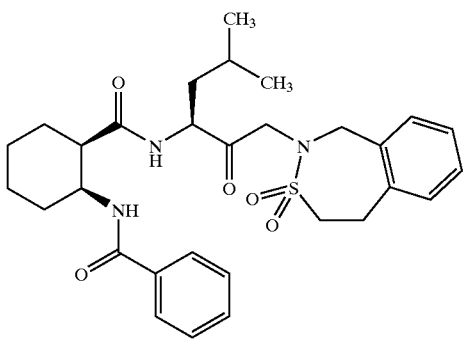

By the same procedure as described in example 1->example 2->example 3 using the compound prepraed in reference example 26 in place of 1,3,4,5-tetrahydro-2-benzazepine, the compound of the present invention having the following physical data was obtained.

TLC: Rf 0.42 (n-hexane:ethyl acetate=1:1);

NMR (DMSO-d$_6$): δ 8.12 (d, J=7.2 Hz, 1H), 7.83–7.70 (m, 3H), 7.57–7.10 (m, 7H), 4.60–4.12 (m, 4H), 3.90–3.50 (m, 2H), 3.40–3.07 (m, 4H), 2.72 (m, 1H), 2.11–1.08 (m, 11H), 0.67 (d, J=6.2 Hz, 3H), 0.53 (d, J=6.2 Hz, 3H).

REFERENCE EXAMPLE 27

2-(2,2-dimethoxyethylaminosulfonyl)nitrobenzene

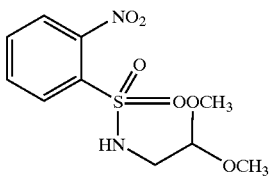

To a solution of 2,2-dimethoxyethylamine (2.61 g) in methylene chloride (100 ml) were added 2-nitrophenylsulfonylchloride (5.0 g) and diisopropylethylamine (5 ml) dropwise at −78° C. and the mixture was stirred for 10 minutes at room temperature. To the reaction mixture was added 1N hydrochloric acid and was extracted with chloroform. The organic layer was washed with a saturated aqueous solution of sodium chloride, dried over anhydrous sodium sulfate and was concentrated to give the title compound having the following physical data.

TLC: Rf 0.56 (chloroform:methanol=9:1);

NMR (CDCl$_3$): δ 8.20–8.10 (m, 1H), 7.92–7.88 (m, 1H), 7.82–7.70 (m, 2H), 5.65–5.50 (m, 1H), 4.37 (t, J=5.6 Hz, 1H), 3.32 (s, 6H), 3.23 and 3.20 (each d, J=5.4 Hz, each 1H).

REFERENCE EXAMPLE 28

2H,3H,4H,5H-benzo[f]-1,2,5-thiadiazepin-1,1-dione

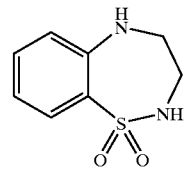

To a mixture of zinc (28.5 g) and acetic acid (100 ml) was added the compound prepared in reference example 27 (6.6 g) and the mixture was stirred for 3 hours at 80° C. The mixture was filtered and the filtrate was concentrated. The resiue was washed with chloroform to give the title compound (1.10 g) having the following physical data.

TLC: Rf 0.60 (chloroform:methanol=9:1).

EXAMPLE 34

(2S)-N-[(3S)-1-(1,1-dioxo-(3H,4H,5H-benzo[f]-1,2,5-thiadiazepin-2-yl))-5-methyl-2-oxo-3-hexyl]-4-methyl-2-benzyloxycarbonylaminopentanamide

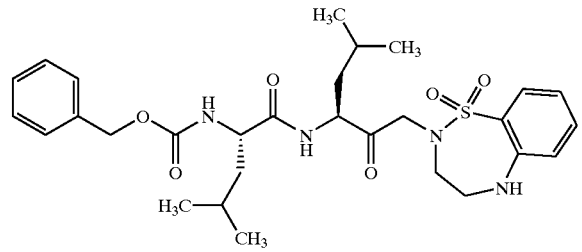

By the same procedure as described in example 14 using the compound prepared in reference example 28 in place of the compound prepared in reference example 7, the compound of the present invention having the following physical data was obtained.

TLC: Rf 0.40 (n-hexane:ethyl acetate=2:1);

NMR (CDCl$_3$): δ 7.79 (dd, J=7.8, 1.2 Hz, 1H), 7.42–7.29 (m, 6H), 6.97 (t, J=7.8 Hz, 1H), 6.82 (d, J=7.8 Hz, 1H), 6.40 (brd, J=7.8 Hz, 1H), 5.10 (m, 3H), 4.72 (m, 1H), 4.35 (br, 1H), 4.20 (m, 1H), 4.15 and 3.82 (each d, J=7.8 Hz, each 1H), 3.80–3.35 (m, 4H), 1.80–1.38 (m, 6H), 0.93 (d, J=6.3 Hz, 12H).

EXAMPLE 35–EXAMPLE 35(3)

By the same procedure as described in example 1->example 2->example 3 using corresponding compounds, the compounds of the present invention having the following physical data were obtained.

EXAMPLE 35

N-[(3S)-5-methyl-2-oxo-1-(2,3,4,5-tetrahydro-1H-1,4-benzodiazepin-4-yl)-3-hexyl]-(1R,2S)-2-benzoylaminocyclohexylcarboxamide

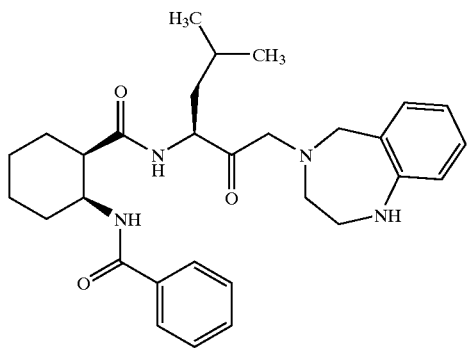

TLC: Rf 0.36 (chloroform:methanol=9:1);

NMR (CDCl₃): δ 7.84 and 7.76 (each d, totally 2H), 7.58–7.38 (m, 3H), 7.23 (m, 1H), 7.15–6.99 (m, 2H), 6.85–6.70 (m, 2H), 6.20–6.10 (m, 1H), 4.82–4.65 (m, 1H), 4.38–4.20 (m, 1H), 3.92–3.80 (m, 2H), 3.51–3.38 (m, 2H), 3.18–2.90 (m, 4H), 2.82–2.72 (m, 1H), 2.10–1.20 (m, 11H), 0.92–0.70 (m, 6H).

EXAMPLE 35(1)

N-[5-methyl-2-oxo-1-(1-methyl-2,3,4,5-tetrahydro-1H-1,4-benzodiazepin-4-yl)-3-hexyl]-(1R,2S)-2-benzoylaminocyclohexylcarboxamide

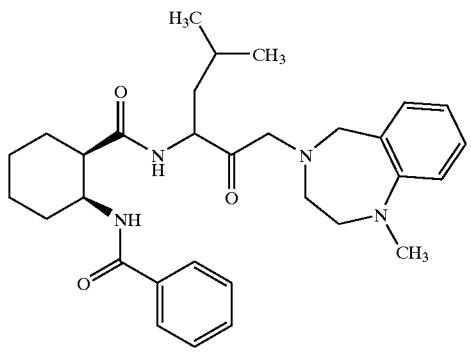

TLC: Rf 0.59 (chloroform:methanol=9:1);

NMR (CDCl₃): δ 7.86–7.73 (m, 2H), 7.58–7.17 (m, 5H), 7.10–7.01 (m, 1H), 6.94–6.80 (m, 2H), 6.21–6.11 (m, 1H), 4.82–4.67 (m, 1H), 4.37–4.22 (m, 1H), 3.91–3.77 (m, 2H), 3.40–3.30 (m, 2H), 3.03–2.85 (m, 7H), 2.82–2.71 (m, 1H), 2.20–1.23 (m, 11H), 1.05–0.73 (m, 6H).

EXAMPLE 35(2)

N-[S-methyl-2-oxo-1-(1-methyl-2,3,4,5-tetrahydro-1H-1,4-benzodiazepin-4-yl)-3-hexyl]-(1R,2S)-2-(4-fluorobenzoylamino)cyclohexylcarboxamide

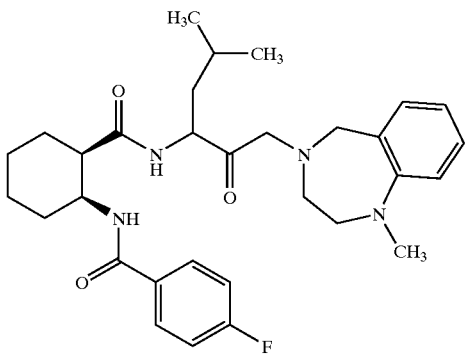

TLC: Rf 0.61 (chloroform:methanol=9:1);

NMR (CDCl₃): δ 7.90–7.72 (m, 2H), 7.54 and 7.33 (each brd, J=7.8 Hz, total 1H), 7.29–7.17 (m, 1H), 7.14–7.02 (m, 3H), 6.96–6.80 (m, 2H), 6.17 and 6.12 (each brd, J=7.8 Hz, total 1H), 4.83–4.68 (m, 1H), 4.32–4.20 (m, 1H)—, 3.90–3.79 (m, 2H), 3.43–3.32 (m, 2H), 3.10–2.80 (m, 7H), 2.78–2.69 (m, 1H), 2.13–1.20 (m, 11H), 1.08–0.73 (m, 6H).

EXAMPLE 35(3)

N-[(3S)-1-(1,1-dioxo-(3H,4H,5H-benzo[f]-1,2,5-thiadiazepin-2-yl))-5-methyl-2-oxo-3-hexyl]-(1R,2S)-2-benzoylaminocyclohexylcarboxamide

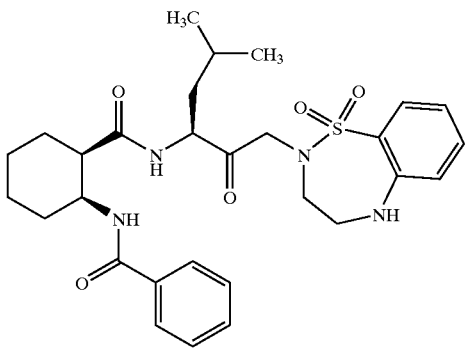

By the same procedure as described in example 1->example 2->example 3 using the compound prepared in reference example 28 in place of 1,3,4,5-tetrahydrobenzazepine, the title compound having the following physical data was obtained.

TLC: Rf 0.52 (ethyl acetate);

NMR (CDCl₃): δ 7.85–7.73 (m, 3H), 7.58–7.23 (m, 4H) 7.13 (brd, J=7.8 Hz, 1H), 6.97 (t, J=8.0 Hz, 1H), 6.82 (d, J=8.0 Hz, 1H), 6.14 (brd, J=7.4 Hz, 1H), 4.79 (m, 1H), 4.42–4.23 (m, 2H), 4.15 and 3.92 (each d, J=18.0 Hz, each 1H), 3.82–3.38 (m, 4H), 2.83–2.72 (m, 1H), 2.20–1.21 (m, 11H), 0.82 (d, J=6.2 Hz, 6H).

FORMULATION EXAMPLE

Formulation Example 1

The following components were admixed in a conventional method and punched out to give 100 tablets each containing 50 mg of active ingredient.

| | |
|---|---|
| N-[(3S)-5-methyl-2-oxo-1-(1,3,4,5-tetrahydro-2-benzazepin-2-yl)-3-hexyl]-1-[(1R,2S)-2-benzamidecyclohexyl]carboxamide | 5.0 g |
| carboxymethylcellulose calcium(disintegrating agent) | 0.2 g |
| magnesium stearate (lubricant) | 0.1 g |
| microcrystalline cellulose | 4.7 g |

Formulation Example 2

The following components were admixed in a conventional method. The solution was sterilized in conventional method, placed 5 ml portions into ampoules and freeze-dried in conventional method to give 100 ampoules each containing 20 mg of the active ingredient.

| | |
|---|---|
| N-[(3S)-5-methyl-2-oxo-1-(1,3,4,5-tetrahydro-2-benzazepin-2-yl)-3-hexyl]-1-[(1R,2S)-2-benzamidecyclohexyl]carboxamide | 2.0 g |
| mannitol | 20 g |
| distilled water | 500 ml |

What is claimed is:

1. A compound of formula (I),

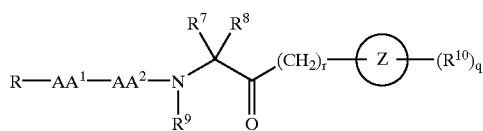

(I)

wherein R is
(i) hydrogen,
(ii) C1–8 alkyl,
(iii) CycA,
(iv) C1–8 alkyl substituted with a group selected from halogen atom, CycA, nitro, $CF_3$ and cyano,

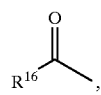

(v)

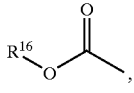

(vi)

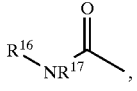

(vii)

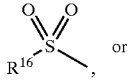

(viii) or

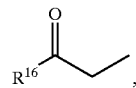

(ix)

CycA is mono-, bi- or tri-cyclic C3–15 carboring or mono-, bi- or tri-cyclic 3–15 membered heteroring comprising 1–4 of nitrogen, 1–2 of oxygen and/or 1 of sulfur;

$R^{16}$ is
(1) C1–8 alkyl,
(2) C2–8 alkenyl,
(3) C2–8 alkynyl,
(4) CycA or
(5) C1–8 alkyl, C2–8 alkenyl or C2–8 alkynyl substituted with a group selected from halogen, nitro, $CF_3$, cyano, CycA, $NR^{18}R^{19}$ and —NHC(O)-CycA;

$R^{17}$, $R^{18}$ and $R^{19}$ each independently are, hydrogen or C1–4 alkyl, $AA^1$ is
(i) a single bond, or

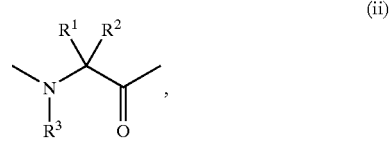

(ii)

wherein $R^1$ and $R^2$ are the same or different and represent
(i) hydrogen,
(ii) C1–8 alkyl,
(iii) CycA or
(iv) C1–8 alkyl substituted with 1–5 of group selected from the following (1)–(8):
(1) —$NR^{21}R^{22}$,
(2) —$OR^{23}$,
(3) —$SR^{24}$,
(4) —$COR^{25}$,
(5) —$NR^{26}CONR^{21}R^{22}$,
(6) guanidino,
(7) CycA,
(8) —$NR^{26}SO_2R^{21}$; or $R^1$ and $R^2$ are taken together to form C2–8 alkylene wherein one carbon atom may be replaced by oxygen, sulfur or —$NR^{20}$— and the alkylene may be substituted with —$NR^{21}R^{22}$ or —$OR^{23}$, $R^{20}$ is hydrogen, C1–4 alkyl, —COO—(C1–4 alkyl), phenyl or C1–4 alkyl substituted with phenyl, $R^{21}$, $R^{22}$, $R^{23}$, $R^{24}$ and $R^{26}$ are the same or different and represent hydrogen, C1–4 alkyl, phenyl or C1–4 alkyl substituted with phenyl, $R^{25}$ is C1–4 alkyl, phenyl, —$NR^{21}R^{22}$, wherein all symbols have the same meanings as above, —$OR^{23}$, wherein $R^{23}$ is the same meaning as above, or C1–4 alkyl substituted with phenyl, $R^3$ is hydrogen, C1–8 alkyl, phenyl or C1–8 alkyl substituted with phenyl or $R^3$ is taken together with $R^1$ to form C2–6 alkylene, wherein one carbon atom may be replaced by oxygen, sulfur or —NR$^{20}$— and the alkylene may be substituted with —NR$^{21}$R$^{22}$ or —OR$^{23}$, or when AA$^1$ is

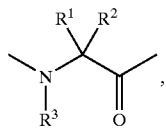

AA$^1$ and R may be taken together to form

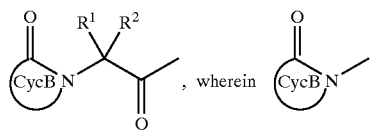, wherein is a 5–13 membered mono- or bi-cyclic heteroring and the other symbols have the same meanings as above, AA$^2$ is (i) a single bond, (ii)

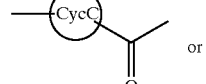

(iii)

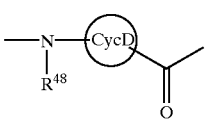

or (iv)

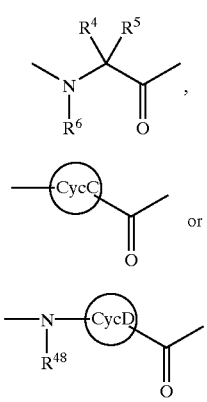

wherein R$^4$ and R$^5$ are the same or different and represent
(1) hydrogen,
(2) C1–8 alkyl,
(3) CycA or
(4) C1–8 alkyl substituted with 1–5 of group selected from the following (a)–(h):
(a) —NR$^{41}$R$^{42}$, (b) —OR$^{43}$, (c) —SR$^{44}$, (d) —COR$^{45}$, (e) —NR$^{46}$CONR$^{41}$R$^{42}$, (f) guanidino, (g) CycA, (h) —NR$^{46}$SO$_2$R$^{41}$; or R$^4$ and R$^5$ are taken together to form C2–8 alkylene, wherein one carbon atom may be replaced by oxygen, sulfur or —NR$^{40}$— and the alkylene may be substituted with —NR$^{41}$R$^{42}$ or —OR$^{43}$, R$^{40}$ is hydrogen, C1–4 alkyl, —COO—(C1–4 alkyl), phenyl or C1–4 alkyl substituted with phenyl, R$^{41}$, R$^{42}$, R$^{43}$, R$^{44}$ and R$^{46}$ are the same or different and represent hydrogen, C1–4 alkyl, phenyl or C1–4 alkyl substituted with phenyl, R$^{45}$ is C1–4 alkyl, phenyl, —NR$^{41}$R$^{42}$, wherein all symbols have the same meaning as above, —OR$^{43}$, wherein R$^{43}$ has the same meaning as above, or C1–4 alkyl substituted with phenyl, R$^6$ is hydrogen, C1–8 alkyl, phenyl or C1–8 alkyl substituted with phenyl or R$^6$ is taken together with R$^4$ to form C2–6 alkylene, wherein one carbon atom may be replaced by oxygen, sulfur or —NR$^{40}$— and the alkylene may be substituted with —NR$^{41}$R$^{42}$ or —OR$^{43}$, R$^{48}$ is hydrogen, C1–4 alkyl, phenyl or C1–4 alkyl substituted with phenyl or when AA$^1$ is a single bond, R$^{48}$ and R may be taken together to form C2–6 alkylene, wherein one carbon atom may be replaced by oxygen, sulfur or —NR$^{47}$—, wherein R$^{47}$ is hydrogen or C1–4 alkyl, CycC is a 3–17 membered mono- or bi-cyclic heteroring, CycD is a C3–14 mono- or bi-cyclic carboring or a 3–14 membered mono- or bi-cyclic heteroring, or AA$^2$ and AA$^1$ are taken together to form (i)

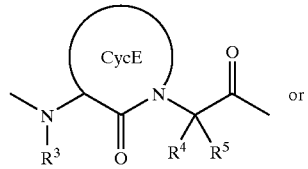 or (ii)

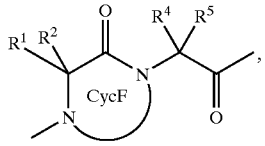, wherein CycE is a 4–18 membered mono- or bi-cyclic heteroring, CycF is a 5–8 membered monocyclic heteroring, and the other symbols have the same meanings as above, R$^7$ and R$^8$ are the same or different and represent
(i) hydrogen,
(ii) C1–8 alkyl,
(iii) CycA or
(iv) C1–8 alkyl substituted with 1–5 of group selected from the following (1)–(8);
(1) —NR$^{61}$R$^{62}$, (2) —OR$^{63}$, (3) —SR$^{64}$, (4) —COR$^{65}$, (5)—NR$^{66}$CONR$^{61}$R$^{62}$, (6) guanidino, (7) CycA, (8) —NR$^{66}$SO$_2$R$^{61}$, or R$^7$ and R$^8$ are taken together to form C2–8 alkylene, wherein one carbon atom may be replaced by oxygen, sulfur or —NR$^{60}$— and the alkylene may be substituted with —NR$^{61}$R$^{62}$ or —OR$^{63}$, R$^{60}$ is hydrogen, C1–4 alkyl, —COO—(C1–4 alkyl), phenyl or C1–4 alkyl substituted with phenyl, R$^{61}$, R$^{62}$, R$^{63}$, R$^{64}$ and R$^{66}$ are the same or different to represent hydrogen, C1–4 alkyl, phenyl or C1–4 alkyl substituted with phenyl, R$^{65}$ is C1–4 alkyl, phenyl, —NR$^{61}$R$^{62}$, wherein all symbols have the same meanings as above, —OR$^{63}$, wherein R$^{63}$ has the same meaning as above, or C1–4 alkyl substituted with phenyl, R$^9$ is hydrogen, C1–8 alkyl, phenyl or C1–8 alkyl substituted with phenyl or R$^9$ is taken together with R$^7$ to form C2–6 alkylene, wherein one carbon atom may be replaced by oxygen, sulfur or —NR$^{60}$— and the alkylene may be substituted with —NR$^{61}$R$^{62}$ or —OR$^{63}$, r is an integer of 1–4,

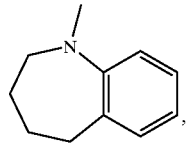 is

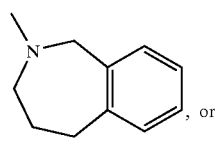, or

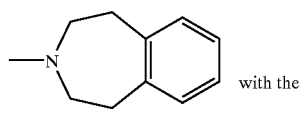 with the proviso that when r=1,

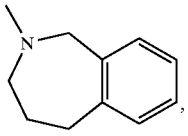 is not in the ring represented by (i), (ii) and (iii), one or two saturated carbon atom may be replaced by (1) oxygen,
(2) —S(O)$_s$— or
(3) —NR$^{83}$—, wherein s is 0 or an integer of 1–2, R$^{83}$ is
(a) hydrogen,
(b) C1–8 alkyl,
(c) CycA or
(d) C1–8 alkyl substituted with 1–5 of group selected from CycA, guanidino, —COR$^{68}$, —NR$^{69}$R$^{70}$, cyano and —P(O)(OR$^{75}$)$_2$, R$^{68}$ is C1–4 alkyl, phenyl or C1–4 alkyl substituted with phenyl, R$^{69}$ and R$^{70}$ are the same or different to represent hydrogen, C1–4 alkyl, phenyl or C1–4 alkyl substituted with phenyl, R$^{75}$ is hydrogen, C1–8 alkyl, phenyl or C1–4 alkyl substituted with 1–5 of phenyl, cyano or halogen, and the rings of (i), (ii) and (iii) may be fused with C5–8 carboring or a 5–8 membered heterering containing 1–2 of nitrogen, 1 of oxygen and/or 1 of sulfur, q is an integer of 0 or 1 to 5, R$^{10}$ is
(i) C1–8 alkyl,
(ii) C2–8 alkenyl,
(iii) C2–8 alkynyl,
(iv) halogen,
(v) CycA,
(vi) —COR$^{71}$,
(vii) —NR$^{72}$R$^{73}$,
(viii) —OR$^{74}$, or
(ix) C1–8 alkyl, C2–8 alkenyl, C2–8 alkynyl substituted with 1–5 of group selected from the following <1>–<7>:

<1> CycA, <2> guanidino, <3> —COR$^{71}$, <4> —NR$^{72}$R$^{73}$, <5> —OR$^{74}$, <6> cyano and <7> —P(O)(OR$^{82}$)$_2$, wherein R$^{82}$ is hydrogen, C1–8 alkyl, C1–4 alkyl substituted with 1–5 of phenyl, cyano or halogen, R$^{71}$ is
(1) C1–8 alkyl,
(2) CycA,
(3) —NR$^{72}$R$^{73}$,
(4) —OR$^{74}$ or
(5) C1–8 alkyl substituted with CycA, R$^{72}$ and R$^{73}$ are the same or different and represent
(1) hydrogen,
(2) C1–8 alkyl,
(3) CycA or
(4) C1–8 alkyl substituted with 1–5 of group selected from the following (a)–(f):
(a) CycA,
(b) guanidino,
(c) —NR$^{77}$R$^{78}$, wherein R$^{77}$ and R$^{78}$ are the same or different and represent hydrogen, C1–4 alkyl, phenyl or C1–4 alkyl substituted with phenyl,
(d) —OR$^{77}$, wherein R$^{77}$ has the same meaning as above,
(e) —COR$^{76}$, wherein R$^{76}$ is C1–4 alkyl, phenyl, —NR$^{77}$R$^{78}$, wherein all symbols have the same meanings as above, —OR$^{77}$, wherein R$^{77}$ has the same meaning as above, or C1–4 alkyl substituted with phenyl, and
(f) cyano;

R$^{74}$ is
(1) hydrogen,
(2) C1–8 alkyl,
(3) CycA, or
(4) C1–8 alkyl substituted with 1–5 of groups selected from the following (a)–(h), wherein one carbon atom may be replaced by oxygen, sulfur atom or —NR$^{84}$—;
(a) CycA,
(b) guanidino,
(c) —SiR$^{79}$R$^{80}$R$^{81}$, wherein R$^{79}$, R$^{80}$ and R$^{81}$ are the same or different to represent, C1–8 alkyl, phenyl or C1–8 alkyl substituted with phenyl,
(d) —NR$^{77}$R$^{78}$ wherein all symbols have the same meanings as above,
(e) —OR$^{77}$, wherein R$^{77}$ has the same meaning as above,
(f) —COR$^{76}$, wherein R$^{76}$ has the same meaning as above, (9) cyano, (h) —P(O)(OR$^{82}$)$_2$, wherein all symbols have the same meanings as above;

with the proviso that CycA in R, R$^1$, R$^2$, R$^4$, R$^5$, R$^7$, R$^8$, R$^{10}$, R$^{16}$, R$^{71}$, R$^{72}$, R$^{73}$, R$^{74}$, R$^{83}$ are the same or different, and CycA, CycB, CycC, CycD, CycE and CycF may be, each independently, substituted with 1–5 of R$^{27}$:

R$^{27}$ is (1) C1–8 alkyl,
(2) halogen,
(3) —NR$^{11}$R$^{12}$,
(4) —OR$^{13}$,
(5) C5–10 mono- or bi-cyclic carboring,
(6) nitro,
(7) CF$_3$,
(8) cyano,
(9) 5–10 membered mono- or bi-cyclic heteroring,
(10) —SR$^{14}$,
(11) —COR$^{15}$,
(12) oxo,
(13) —SO$_2$R$^{15}$,
(14) —OCF$_3$ or
(15) C1–8 alkyl substituted with 1–5 of group selected from the following (a)–(m):
(a) halogen,
(b) —NR$^{11}$R$^{12}$,
(c) —OR$^{13}$,
(d) C5–10 mono- or bi-cyclic carboring,
(e) nitro,
(f) CF$_3$,
(g) cyano,
(h) 5–10 mono- or bi-cyclic heteroring,
(j) —SR$^{14}$,
(k) —COR$^{15}$,
(l) —SO$_2$R$^{15}$,
(m) —OCF$_3$, wherein R$^{11}$ and R$^{12}$ are the same or different and represent, hydrogen, C1–4 alkyl, —COO—(C1–4 alkyl), phenyl or C1–4 substituted with phenyl, R$^{13}$ and R$^{14}$ are the same or different and represent, hydrogen, C1–4 alkyl, phenyl or C1–4 alkyl substituted with phenyl, R$^{15}$ is C1–4 alkyl, phenyl, —NR$^{11}$R$^{12}$, wherein all symbols have the same meanings as above, —OR$^{13}$, wherein R$^{13}$ has the same meaning as above, or C1–4 alkyl substituted with phenyl, or a non-toxic salt thereof.

2. The compound according to claim 1, wherein R is (i) hydrogen,
(ii) C1–8 alkyl,
(iii) CycA,
(iv) C1–8 alkyl substituted with CycA or nitro, (v)
, -continued (vi)
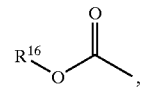, (vii)
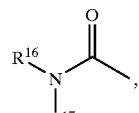, (viii)
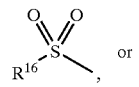 or (ix)
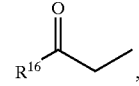, R$^{16}$ is
(1) C1–8 alkyl,
(2) C2–8 alkenyl,
(3) C2–8 alkynyl,
(4) CycA,
(5) C1–8 alkyl substituted with CycA or —NHC(O)-CycA,
(6) C2–8 alkenyl substituted with CycA,
(7) C2–8 alkynyl substituted with CycA, AA$^1$ is (i) a single bond, (ii)
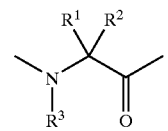

or taken together with R to represent (i)
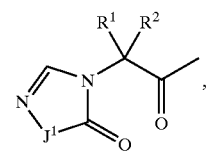, (ii)
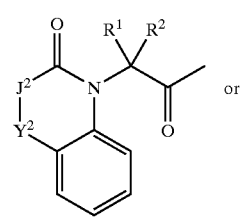 or (iii)
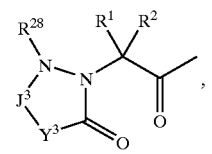, wherein J$^1$ is oxygen, sulfur, —NR$^{29}$—,
wherein R$^{29}$ is hydrogen, C1–4 alkyl, CycA or C1–4 alkyl substituted with CycA, C1–3 alkylene or C2–3 alkenylene, $J^2$ is a single bond or C1–2 alkylene, $Y^2$ is —N=CH—; —CH=N— or C1–2 alkylene, $J^3$ is carbonyl or C1–3 alkylene, $Y^3$ is C1–3 alkylene, oxygen or —NR$^{29}$—, wherein R$^{29}$ has the same meaning as above, $R^{28}$ is hydrogen, C1–4 alkyl, CycA or C1–4 alkyl substituted with CycA, or $R^{28}$ is taken together with $R^1$ to form C2–4 alkylene, and the other symbols have the same meanings as defined in claim 1, each ring may be substituted with 1–5 of $R^{27}$, $AA^2$ is (i) a single bond,

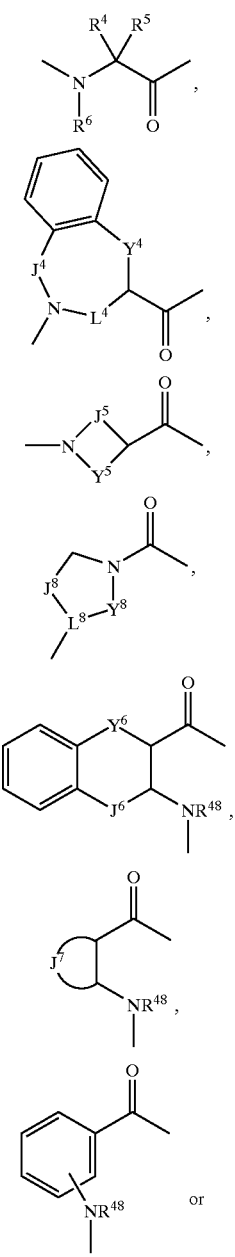

(ii)

(iii)

(iv)

(v)

(vi)

(vii)

(viii)

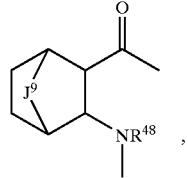

(ix)

wherein $J^4$, $Y^4$, $L^4$ are the same or different and represent a single bond or C1–3 alkylene, with the proviso that $J^4$, $Y^4$ and $L^4$ do not represent a single bond at the same time, $J^5$ is C1–6 alkylene, $Y^5$ is a single bond, C1–3 alkylene or —NR$^{67}$—, wherein R$^{67}$ is hydrogen, C1–4 alkyl, phenyl or C1–4 alkyl substituted with phenyl, $J^8$ is C1–5 alkylene, wherein one carbon atom may be replaced by oxygen, $Y^8$ is a single bond or C1–4 alkylene, $L^8$ is —N— or —CH—, $J^6$ and $Y^6$ are the same or different and represent a single bond or C1–3 alkylene, with the proviso that $J^6$ and $Y^6$ do not represent a single bond at the same time, $J^7$ is C1–6 alkylene, wherein one carbon atom may be replaced by oxygen, sulfur or —NR$^{67}$—, wherein R$^{67}$ has the same meaning as above, $J^9$ is C1–3 alkylene, oxygen, sulfur or —NR$^6$—, wherein R$^{67}$ has the same meaning as above, and each ring may be substituted with 1–5 of $R^{27}$, or $AA^2$ and $AA^1$ are taken together to form

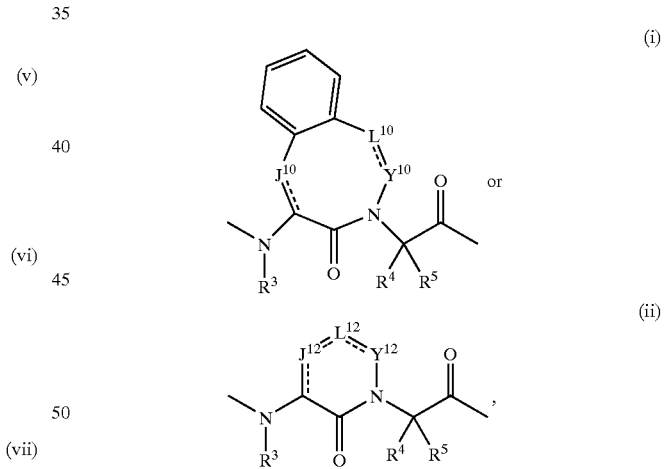

wherein ═══ is a single bond or a double bond, $J^{10}$ and $Y^{10}$ are the same or different and represent a single bond or C1–3 alkylene, $L^{10}$ is a single bond, C1–3 alkylene, —NR$^{57}$—, wherein R$^{57}$ is hydrogen, C1–4 alkyl, phenyl or C1–4 alkyl substituted with phenyl, —N═, oxygen or —S(O)$_p$—, wherein p is 0 or an integer of 1–2, $J^{12}$ and $Y^{12}$ are the same or different and represent a single bond or C1–3 alkylene, $L^{12}$ is C1–3 alkylene, —NR$^{57}$—, wherein R$^{57}$ has the same meaning as above, —N═, ═N—, oxygen or —S(O)$_p$—, wherein p has the same meaning as above, and the other symbols have the same meanings as defined in claim 1, and each ring may be substituted with 1–5 of R²⁷ and AA² and AA¹ are taken together to form

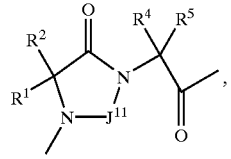

wherein J¹¹ is carbonyl or C2–4 alkylene and the other symbols have the same meanings as defined in claim 1, and R²⁷ in CycA is
(1) C1–8 alkyl,
(2) halogen,
(3) —NR¹¹R¹²,
(4) —OR¹³,
(5) phenyl,
(6) nitro,
(7) CF₃,
(8) cyano,
(9) tetrazole,
(10) —SR¹⁴,
(11) —COR¹⁵,
(12) oxo, or
(13) C1–8 alkyl substituted with 1–5 group selected from the following (a)–(k):
(a) halogen, (b) —NR¹¹R¹², (c) —OR¹³, (d) phenyl, (e) nitro, (f) CF₃, (g) cyano, (h) tetrazole, (j) SR¹⁴, or (k) COR¹⁵,
wherein all symbols have the same meanings as above, and R¹⁰ is
(i) C1–8 alkyl,
(ii) CycA,
(iii) —COR⁷¹ or
(iv) C1–8 alkyl substituted with CycA, guanidino, —COR⁷¹, —NR⁷²R⁷³ or —OR⁷⁴,
wherein all symbols have the same meanings as defined in claim 1,
or a non-toxic salt thereof.

3. The compound according to claim 2, wherein R is C1–8 alkyl, or C1–8 alkyl substituted with CycA or nitro,

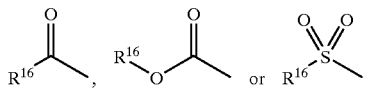

and AA¹ is a single bond, or

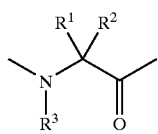

and AA² is a single bond,

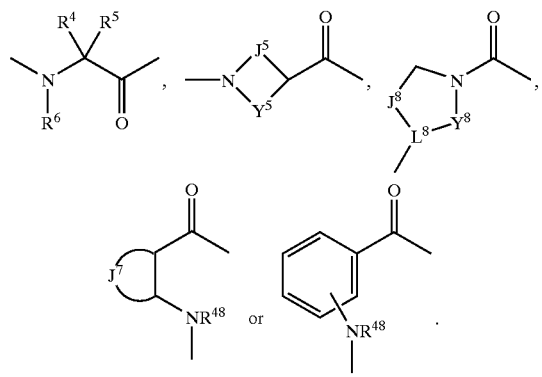

4. The compound according to claim 3, wherein R¹⁶ is C1–8 alkyl, C2–8 alkenyl, C2–8 alkynyl, CycA or C1–8 alkyl, C2–8 alkenyl or C2–8 alkynyl substituted with CycA, wherein CycA is mono- or bi-cyclic C5–10 carboaryl or partially or completely saturated one thereof, or mono- or bi-cyclic 5–10 membered heteroaryl containing 1–2 of nitrogen, 1–2 of oxygen and/or 1 of sulfur or partially or completely saturated one thereof, R¹ is hydrogen, C1–8 alkyl, phenyl, or C1–8 alkyl substituted with NH₂, C1–4 alkoxy, SH, SCH₃, phenyl, hydroxyphenyl, COOH, CONH₂, guanidino, imidazole or indole and R² is hydrogen or R¹ and R² are taken to form C3–6 alkylene, R³ is hydrogen or C1–4 alkyl or R³ and R¹ are taken together to form C2–4 alkylene, AA² is a single bond,

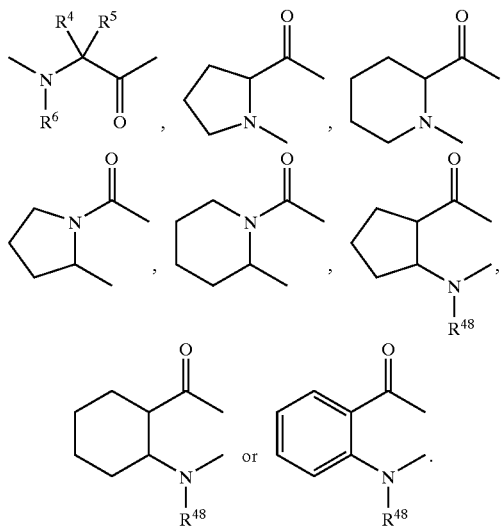

R⁴ is hydrogen, C1–8 alkyl, phenyl, or C1–8 alkyl substituted with NH₂, C1–4 alkoxy, SH, SCH₃, phenyl, hydroxyphenyl, COOH, CONH₂, guanidino, imidazole or indole and R⁵ is hydrogen or R⁴ and R⁵ are taken together to form C3–6 alkylene, R⁶ is hydrogen or C1–4 alkyl or R⁶ and R⁴ are taken together to form C2–4 alkylene, R⁴⁸ is hydrogen or C1–4 alkyl, R⁷ is hydrogen, C1–8 alkyl, phenyl, or C1–8 alkyl substituted with NH₂, C1–4 alkoxy, SH, SCH₃, phenyl, hydroxyphenyl, COOH, CONH$_2$, guanidino, imidazole or indole and R$^8$ is hydrogen or R$^7$ and R$^8$ are taken together to form C3–6 alkylene, R$^9$ is hydrogen or C1–4 alkyl or R$^9$ and R$^7$ are taken together to form C2–4 alkylene, or a non-toxic salt thereof.

5. The compound according to claim 1, wherein R$^{16}$ is C1–8 alkyl, C2–8 alkenyl or C2–8 alkynyl substituted with a group selected from halogen, nitro, CF$_3$, cyano and NR$^{18}$R$^{19}$, or a non-toxic salt thereof.

6. The compound according to claim 1, wherein R$^{16}$ is (1) CycA containing 1–5 of substituent R$^{27}$ or:

(2) C1–8 alkyl, C2–8 alkenyl or C2–8 alkynyl substituted with CycA containing 1–5 of substituent R$^{27}$, wherein at least one of R$^{27}$ included in (1) and (2) is selected from (i) C5–10 mono- or bi-cyclic carboring, (ii) 5–10 membered mono- or bi-cyclic heteroring, (iii) —SO$_2$R$^{15}$, (iv) —OCF$_3$ and (v) C1–8 alkyl substituted with 1–5 of group selected from (a) halogen, (b) —NR$^{11}$R$^{12}$, (c) —OR$^{13}$, (d) C5–10 mono- or bi-cyclic carboring, (e) nitro, (f) CF$_3$, (g) cyano, (h) 5–10 membered mono- or bi-cyclic heteroring, (j) —SR$^{14}$, (k) —COR$^{15}$, (l) —SO$_2$R$^{15}$ and (m) —OCF$_3$, wherein at least one substituent thereof is C5–10 mono- or bi-cyclic carboring, 5–10 membered mono- or bi-cyclic heteroring, —SO$_2$R$^{15}$ and —OCF$_3$, or a non-toxic salt thereof.

7. The compound according to claim 1, wherein AA$^1$ is a single bond and R$^{48}$ and R are taken together to form C2–6 alkylene, wherein one carbon atom may be replaced by —NR$^{47}$—, wherein R$^{47}$ is the same meaning as defined in claim 1, oxygen or sulfur, or a non-toxic salt thereof.

8. The compound according to claim 1, wherein

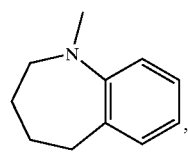
(i)

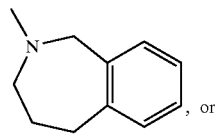
, or
(ii)

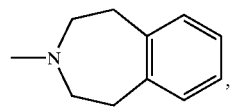
,
(iii)

with the proviso that when r=1, (z) is not

-continued

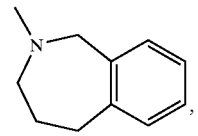
(ii)

in the rings (i), (ii), and (iii), one or two saturated carbon atom may be replaced by (1) oxygen, (2) —S(O)$_s$— or (3) —NR$^{83}$—, wherein all symbols have the same meanings as defined in claim 1, which may be fused with C5–8 carboring or 5–8 membered heteroring containing 1–2 of nitrogen, 1 of oxygen and/or 1 of sulfur.

9. The compound according to claim 1, wherein R$^{10}$ is C2–8 alkenyl, C2–8 alkynyl or C2–8 alkenyl or C2–8 alkynyl substituted with 1–5 of group selected from CycA, guanidino, —COR$^{71}$, —NR$^{72}$R$^{73}$, —OR$^{74}$, cyano and —P(O)(OR$^{82}$)$_2$, or a non-toxic salt thereof.

10. The compound according to claim 1, wherein

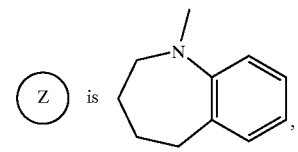

or a non-toxic salt thereof.

11. A compound according to claim 1, wherein

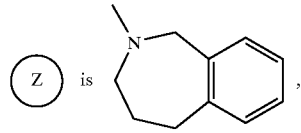

or a non-toxic salt thereof.

12. A compound according to claim 1, wherein

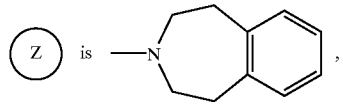

or a non-toxic salt thereof.

13. The compound according to claim 1, which is

(74) (3S)-3-amino-1-(1-benzyl-2,3,4,5-tetrahydro-1H-1,4-benzodiazepin-4-yl)-5-methyl-2-heptanone,

(75) (2S)-N-[(3S)-5-methyl-2-oxo-1-(1-benzyl-2,3,4,5-tetrahydro-1H-1,4-benzodiazepin-4-yl)-3-hexyl]-4-methyl-2-benzyloxycarbonylaminopentanamide,

(76) N-[(3S)-1-(1-benzyl-2,3,4,5-tetrahydro-1H-1,4-benzodiazepin-4-yl)-5-methyl-2-oxo-3-hexyl]-1-cyclohexylcarboxamide,

(77) N-[(3S)-1-(1-benzyl-2,3,4,5-tetrahydro-1H-1,4-benzodiazepin-4-yl)-5-methyl-2-oxo-3-hexyl]-3-cyclopentylpropanamide,

(78) N-[(3S)-1-(1-benzyl-2,3,4,5-tetrahydro-1H-1,4-benzodiazepin-4-yl)-5-methyl-2-oxo-3-hexyl]-1-[(1R,2S)-2-benzoylaminocyclohexyl]carboxamide,

(79) N-[(3S)-1-(1-benzyl-2,3,4,5-tetrahydro-1H-1,4-benzodiazepin-4-yl)-5-methyl-2-oxo-3-hexyl]-2-benzyloxybenzamide,

(80) (2S)-N-[(3S)-1-(1-ethoxycarbonylmethyl-2,3,4,5-tetrahydro-1H-1,4-benzodiazepin-4-yl)-5-methyl-2-oxo-3-hexyl]-2-benzyloxycarbonylamino-4-methylpentanamide,

(81) (2S)-N-[(3S)-5-methyl-1-(1-methyl-2,3,4,5-tetrahydro-1H-1,4-benzodiazepin-4-yl)-2-oxo-3-hexyl]-2-benzyloxycarbonylamino-4-methylpentanamide,

(82) (2S)-N-[(3S)-5-methyl-2-oxo-1-(1-(3-phenylpropyl)-2,3,4,5-tetrahydro-1H-1,4-benzodiazepin-4-yl)-3-hexyl]-2-benzyloxycarbonylamino-4-methylpentanamide,

(83) (2S)-N-[(3S)-5-methyl-2-oxo-1-(1-phenethyl-2,3,4,5-tetrahydro-1H-1,4-benzodiazepin-4-yl)-3-hexyl]-2-benzyloxycarbonylamino-4-methylpentanamide,

(84) (2S)-N-[(3S)-5-methyl-1-(1-isopropyl-2,3,4,5-tetrahydro-1H-1,4-benzodiazepin-4-yl)-2-oxo-3-hexyl]-2-benzyloxycarbonylamino-4-methylpentanamide,

(85) (2S)-N-[5-methyl-1-(1-carboxymethyl-2,3,4,5-tetrahydro-1H-1,4-benzodiazepin-4-yl)-2-oxo-3-hexyl]-2-benzyloxycarbonylamino-4-methylpentanamide,

(86) (2S)-N-[(3S)-5-methyl-2-oxo-1-(2,3,4,5-tetrahydro-1H-1,4-benzodiazepin-4-yl)-3-hexyl]-2-benzyloxycarbonylamino-4-methylpentanamide,

(87) (2S)-N-[(3S)-1-(1-aminocarbonylmethyl-2,3,4,5-tetrahydro-1H-1,4-benzodiazepin-4-yl)-5-methyl-2-oxo-3-hexyl]-2-benzyloxycarbonylamino-4-methylpentanamide,

(88) (2S)-N-[1-(1-(2-hydroxyethyl)-2,3,4,5-tetrahydro-1H-1,4-benzodiazepin-4-yl)-5-methyl-2-oxo-3-hexyl]-2-benzyloxycarbonylamino-4-methylpentanamide,

(89) (2S)-N-[(3S)-1-(1-cyanomethyl-2,3,4,5-tetrahydro-1H-1,4-benzodiazepin-4-yl)-5-methyl-2-oxo-3-hexyl]-2-benzyloxycarbonylamino-4-methylpentanamide,

(90) (2S)-N-[(3S)-1-(2,3,4,5-tetrahydro-1,4-benzoxazepin-4-yl)-5-methyl-2-oxo-3-hexyl]-2-benzyloxycarbonylamino-4-methylpentanamide,

(91) N-[(3S)-5-methyl-2-oxo-1-(2,3,4,5-tetrahydro-1,4-benzoxazepin-4-yl)-3-hexyl]-1-[(1R,2S)-2-benzoylaminocyclohexyl]carboxamide,

(92) (2S)-N-[(3S)-5-methyl-2-oxo-1-(2,3,4,5-tetrahydro-1,4-benzothiazepin-4-yl)-3-hexyl]-2-benzyloxycarbonylamino-4-methylpentanamide,

(93) N-[(3S)-5-methyl-2-oxo-1-(2,3,4,5-tetrahydro-1,4-benzothiazepin-4-yl)-3-hexyl]-1-[(1R,2S)-2-benzoylaminocyclohexyl]carboxamide,

(94) (2S)-N-[(3S)-5-methyl-2-oxo-1-(1,1-dioxo-2,3,4,5-tetrahydro-1,4-benzothiazepin-4-yl)-3-hexyl]-2-benzyloxycarbonylamino-4-methylpentanamide,

(95) N-[(3S)-5-methyl-2-oxo-1-(1,1-dioxo-2,3,4,5-tetrahydro-1,4-benzothiazepin-4-yl)-3-hexyl]-1-[(1R,2S)-2-benzoylaminocyclohexyl]carboxamide,

(96) (2S)-N-[(3S)-5-methyl-2-oxo-1-(3,3-dioxo-1,2,4,5-tetrahydro-3,2-benzothiazepin-2-yl)-3-hexyl]-2-benzyloxycarbonylamino-4-methylpentanamide,

(97) N-[(3S)-5-methyl-2-oxo-1-(3,3-dioxo-1,2,4,5-tetrahydro-3,2-benzothiazepin-2-yl)-3-hexyl]-1-[(1R,2S)-2-benzoylaminocyclohexyl]carboxamide,

(98) (2S)-N-[(3S)-1-(1,1-dioxo(3H,4H,5H-benzo[f]1,2,5-thiadiazepin-2-yl))-5-methyl-2-oxo-3-hexyl]-4-methyl-2-benzyloxycarbonylaminopentanamide,

(99) N-[(3S)-5-methyl-2-oxo-1-(2,3,4,5-tetrahydro-1H-1,4-benzodiazepin-4-yl)-3-hexyl]-(1R,2S)-2-benzoylaminocyclohexylcarboxamide, (100) N-[5-methyl-2-oxo-1-(1-methyl-2,3,4,5-tetrahydro-1H-1,4-benzodiazepin-4-yl)-3-hexyl]-(1R,2S)-2-benzoylaminocyclohexylcarboxamide, (101) N-[5-methyl-2-oxo-1-(1-methyl-2,3,4,5-tetrahydro-1H-1,4-benzodiazepin-4-yl)-3-hexyl]-(1R,2S)-2-(4-fluorobenzoylamino)cyclohexylcarboxamide, or (102) N-[(3S)-1-(1,1-dioxo(3H,4H,5H-benzo[f]1,2,5-thiadiazepin-2-yl))-5-methyl-2-oxo-3-hexyl]-(1R,2S)-2-benzoylaminocyclohexylcarboxamide, or a non-toxic salt thereof.

14. The compound according to claim 1, which is (1) (3S)-3-(t-butoxycarbonylamino)-5-methyl-1-(2,3,4,5-tetrahydro-1H-1-benzazepin-1-yl)hexan-2-one, (2) (3S)-3-amino-5-methyl-1-(2,3,4,5-tetrahydro-1H-1-benzazepin-1-yl)hexan-2-one, (3) N-[(3S)-5-methyl-2-oxo-1-(2,3,4,5-tetrahydro-1H-1-benzazepin-1-yl)-3-hexyl]-1-[(1R,2S)-2-benzoylaminocyclohexyl]carboxamide, (4) (2S)-N-[(3S)-5-methyl-2-oxo-1-(2,3,4,5-tetrahydro-1H-1-benzazepin-1-yl)-3-hexyl]-4-methyl-2-benzyloxycarbonylaminopentanamide, (5) N-[(3S)-5-methyl-2-oxo-1-(2,3,4,5-tetrahydro-1H-1-benzazepin-1-yl)-3-hexyl]-1-cyclohexylcarboxamide, (6) N-[(3S)-5-methyl-2-oxo-1-(2,3,4,5-tetrahydro-1H-1-benzazepin-1-yl)-3-hexyl]-4-benzyloxybenzamide, (7) N-[(3S)-5-methyl-2-oxo-1-(2,3,4,5-tetrahydro-1H-1-benzazepin-1-yl)-3-hexyl]-3-benzyloxybenzamide, (8) N-[(3S)-5-methyl-2-oxo-1-(2,3,4,5-tetrahydro-1H-1-benzazepin-1-yl)-3-hexyl]-2-benzyloxybenzcarboxamide, (9) N-[(3S)-5-methyl-2-oxo-1-(2,3,4,5-tetrahydro-1H-1-benzazepin-1-yl)-3-hexyl]-1-[(1S,2R)-2-benzoylaminocyclohexyl]carboxamide,

(10) N-[(3S)-5-methyl-2-oxo-1-(2,3,4,5-tetrahydro-1H-1-benzazepin-1-yl)-3-hexyl]benzamide,

(11) N-[(3S)-5-methyl-2-oxo-1-(2,3,4,5-tetrahydro-1H-1-benzazepin-1-yl)-3-hexyl]-3-cyclopentylpropanamide,

(12) N-[(3S)-5-methyl-2-oxo-1-(2,3,4,5-tetrahydro-1H-1-benzazepin-1-yl)-3-hexyl]cinnamide,

(13) N-[(3S)-5-methyl-2-oxo-1-(2,3,4,5-tetrahydro-1H-1-benzazepin-1-yl)-3-hexyl]benzenesulfonamide, or

(14) (2S)-N-[(3S)-5-methyl-2-oxo-1-(2,3,4,5-tetrahydro-1,5-benzoxazepin-5-yl)-3-hexyl]-2-benzyloxycarbonylamino-4-methylpentanamide or a non-toxic salt thereof.

15. A composition comprising the compound of formula (I) described in claim 1, or a non-toxic salt thereof, and a pharmaceutically acceptable carrier.

16. A method for inhibiting cysteine protease comprising administering to a subject and effective amount of the compound of formula (I) described in claim 1, or a non-toxic salt thereof.

17. The method according to claim 16, wherein said cysteine protease is cathepsin K, cathepsin S, cathepsin L, cathepsin B, cathepsin H, calpain or caspase-1.

18. A method for treatment of bone resorption diseases, comprising administering to a subject an effective amount of the compound of formula (I) described in claim 1, or a non-toxic salt thereof.

* * * * *

UNITED STATES PATENT AND TRADEMARK OFFICE
CERTIFICATE OF CORRECTION

| | | |
|---|---|---|
| PATENT NO. | : 7,008,938 B2 | Page 1 of 1 |
| APPLICATION NO. | : 10/901263 | |
| DATED | : March 7, 2006 | |
| INVENTOR(S) | : Kazuyuki Ohmoto et al. | |

It is certified that error appears in the above-identified patent and that said Letters Patent is hereby corrected as shown below:

Title Page, Item (73) please delete "Nokia Corporation, Espoo (FI)" and insert --ONO Pharmaceutical Co., Ltd.--

Signed and Sealed this

Eighth Day of June, 2010

David J. Kappos
*Director of the United States Patent and Trademark Office*